United States Patent
Orser

(10) Patent No.: US 9,517,265 B2
(45) Date of Patent: Dec. 13, 2016

(54) METHODS FOR THE PREVENTION AND/OR TREATMENT OF MEMORY IMPAIRMENT

(71) Applicant: The Governing Council of the University of Toronto, Toronto (CA)

(72) Inventor: Beverley A. Orser, Toronto, CA (US)

(73) Assignee: The Governing Council of the University of Toronto, Toronto, Ontario (CA)

( * ) Notice: Subject to any disclaimer, the term of this patent is extended or adjusted under 35 U.S.C. 154(b) by 0 days.

(21) Appl. No.: 13/867,470

(22) Filed: Apr. 22, 2013

(65) Prior Publication Data

US 2013/0302352 A1    Nov. 14, 2013

Related U.S. Application Data

(63) Continuation of application No. PCT/CA2011/001173, filed on Oct. 21, 2011.

(60) Provisional application No. 61/406,034, filed on Oct. 22, 2010.

(51) Int. Cl.
| | |
|---|---|
| A61K 39/395 | (2006.01) |
| A61K 31/00 | (2006.01) |
| A61K 31/53 | (2006.01) |
| A61K 31/551 | (2006.01) |
| C07K 16/28 | (2006.01) |
| A61K 31/5517 | (2006.01) |

(52) U.S. Cl.
CPC ........... *A61K 39/3955* (2013.01); *A61K 31/53* (2013.01); *A61K 31/551* (2013.01); *A61K 31/5517* (2013.01); *C07K 16/286* (2013.01)

(58) Field of Classification Search
None
See application file for complete search history.

(56) References Cited

PUBLICATIONS

Chambers et al. 2003, J. Med. Chem., 46:2227-40.*
Atack et al. Neuropharmacology, 2006, 51:1023-9.*
Navarro et al., 2002, Progress in Neuro-Psychopharm & Biol. Psychiatry, 26:1389-92.*
Matsushita et al., Progress in Neuro-Psychopharmacol., 1988, 12(6):951-66.*
Perio et al., Psychopharmacol., 1989, 97:262-8.*
Prather et al., Neuropharmacology, 1992,31(3):299-306.*
Galliani et al., Med. Sci. Res., 1991, 19:441-2.*
Miller et al., Br. J. Pharmacol., 1992, 107(1):78-86.*
Jackson et al, European J. Pharmacol., 1992, 221(2-3):199-203.*
Kawasaki et al., GABA:Receptors, Transporters and Metabolism, 1996:259-66, ed. By Tanaka and Ng. G. , Bowery, Birkhauser Verlag Basel/Switzerland.*
Martin, L. (2009) University of Toronto. The regulatory properties of α5 subunit-containing γ-aminobutyric acid subtype A receptors in learning and synaptic plasticity.
Martin, L.J., Oh, G.H. & Orser, B.A. Etomidate targets α5 γ-aminobutyric acid subtype a receptors to regulate synaptic plasticity and memory blockade. Anesthesiology 111, 1025-1035 (2009).
Atack, J. et al. (2009) The Journal of Pharmacology and Experimental Therapeutics, 331:470-483. In Vitro and in Vivo Properties of 3-tert-Butyl-7-(5-methylisoxazol-3yl)-2-(1-methyl-1H-1,2,4-triazol-5ylmethoxy)-pyrazolo[1,5-d]-[1,2,4] triazine (MRK-016), a GABAA Receptor α5 Subtype-Selective Inverse Agonist.
Serantes, R., et al. Interleukin-1βenhances GABAA receptor cell-surface expression by a phosphatidylinositol 3-kinase/Akt pathway: relevance to sepsis-associated encephalopathy. J Biol Chem 281, 14632-14643 (2006).
Garcia, Paul S., et al. "General Anesthetic Actions on GABA$_A$ Receptors," *Current Neuropharmacology*, 2010, 8, 2-9.
Nelson, L. E., et al. "The sedative component of anesthesia is mediated by GABA$_A$ receptors in an endogenous sleep pathway," *nature neuroscience*, vol. 5 No. 10, Oct. 2002.

* cited by examiner

*Primary Examiner* — Olga N Chernyshev
(74) *Attorney, Agent, or Firm* — Lathrop & Gage LLP

(57) ABSTRACT

The present invention relates to methods for the prevention and/or treatment of memory impairment and for improving memory and particularly to methods for the prevention and/or treatment of memory impairment and improving memory comprising administering an agent that decreases activity of a GABA$_A$ receptor. The present invention also relates the use of an agent that decreases activity of a GABA$_A$ receptor for preventing or treating a memory deficit and for improving memory.

30 Claims, 48 Drawing Sheets

A  Mouse Hippocampal Slice Biotinylation

B

A WT

B *Gabra5-/-*

Treatment with TNF-α and IL-6 does not affect the tonic current. The tonic current was not changed by treatment of the cultured hippocampal neurons for 20 min with TNF-α (A) and IL-6 (10 ng ml$^{-1}$) (B). $n = 10 - 14$, one-way ANOVA $F_{2,36} = 0.05$, $P = 0.95$ for A; $n = 5$, $P = 0.63$, Student's $t$ test for B. N.S.: non-significant result.

The PI3K inhibitor blocks the IL-1β-induced reduction of GABA-evoked peak currents. The inhibitory effects of IL-1β (20 ng ml$^{-1}$) on the peak current evoked by GABA (10 μM) were abolished by treating the neurons with the PI3K inhibitor LY294,002 (LY, 20 μM). LY294,002 alone had no effect on the GABA-evoked peak responses. $n = 6 - 11$, one-way ANOVA $F_{3,37} = 85.41$, $P < 0.0001$, Dunnett's post hoc compared to control *** $P < 0.001$.

METHODS FOR THE PREVENTION AND/OR TREATMENT OF MEMORY IMPAIRMENT

FIELD OF THE INVENTION

The present invention relates to methods for the prevention and/or treatment of memory impairment and particularly to methods for the prevention and/or treatment of memory impairment comprising administering an agent that decreases activity of a $GABA_A$ receptor.

BACKGROUND OF THE INVENTION

Modern anesthetic drugs have revolutionized medical care, and their use is increasing as the population ages[1]. Each year, more than 234 million surgical procedures necessitating general anesthesia are performed worldwide, yet surprisingly little is known about how these drugs work. Anesthetics cause a constellation of behavioural effects, including sedation, immobility, and memory blockade, which together allow the patient to tolerate the surgical trauma[2]. Memory blockade is an essential component of the anesthetic state.

Most patients, and even most physicians, assume that cognitive function rapidly returns to its normal preoperative state once an anesthetic has been metabolized[15, 16]. Unfortunately, many patients who undergo major surgery experience a marked deterioration in cognitive performance after the operation, a condition known as postoperative cognitive dysfunction (POCD)[2-6, 17]. For reasons that are not understood, many patients experience postoperative memory deficits that persist long after the anesthetic has been metabolize[2-6]. Large clinical trials have shown that cognitive dysfunction is present in over 25% of patients at the time of discharge and in 10% at 3 months after surgery[3].

Both the anesthetic and the surgery contribute to postoperative memory deficits. We and others have shown that anesthesia without surgery impairs learning, even days after administering the anesthetic[7, 25]. Similarly, surgery alone, performed under local or regional anesthesia, causes persistent memory deficits in human patients and laboratory animals[3, 19]. Clinical and animal studies have indicated that the most vulnerable cognitive domains, explicit memory and spatial memory, are dependent on the hippocampus[20-24].

The cause of postoperative/pos-anesthetic memory impairment is unknown, and the expected risk factors, such as hypoxia and low blood pressure, do not correlate with the condition[7]. Post-anesthetic memory deficits represent an undesirable and poorly understood adverse effect. Such mental deficits after anesthetic/surgery are associated with a reduction in quality of life, premature retirement, an increase in the rate of admission to long-term care facilities, and premature death[18, 19]. Most importantly, there are no known treatments or prevention strategies.

Therefore, a need exists to provide prevention and/or treatment for memory impairment caused by anesthesia, surgery and/or inflammation.

SUMMARY OF THE INVENTION

It is an object of the present invention to provide prevention and/or treatment for memory impairment.

It is another object of the present invention to provide prevention and/or treatment for memory impairment caused by anesthesia.

It is another object of the present invention to provide prevention and/or treatment for memory impairment caused by surgery.

It is another object of the present invention to provide prevention and/or treatment for memory impairment caused by inflammation.

In accordance with an aspect of the present invention, there is provided a method for preventing or treating a memory deficit, the method comprising administering an agent that decreases activity of a $GABA_A$ receptor.

In accordance with an aspect, the agent is administered after the memory deficit occurs. In another aspect, the agent is administered before the memory deficit occurs. In yet another aspect, the agent is administered while the memory deficit is occurring.

In accordance with an aspect, the memory deficit is induced by administration of an anesthetic. In an aspect, anesthetic is administered during surgery. In another aspect, the memory deficit is induced by inflammation. In yet another aspect, the memory deficit is induced by interleukin-1β (IL-1β).

In accordance with an aspect, the memory deficit is short-term memory loss. In another aspect, the memory deficit is long-term memory loss.

In accordance with an aspect, the $GABA_A$ receptor is an α5$GABA_A$ receptor.

In accordance with an aspect, the agent decreases activity of the $GABA_A$ receptor by binding to the $GABA_A$ receptor. In an aspect, the agent is an inverse agonist. In an aspect, the agent is an inverse agonist selective for the α5$GABA_A$ receptor. In an aspect, the agent is selected from the group consisting of L-655,708, MRK-016, Ro-4938581, α5IA, pyridazines, TB-21007, PWZ-029 and combinations thereof. In an aspect, the agent is L-655,708. In an aspect, the agent is MRK-016. In an aspect, the agent is an antibody. In an aspect the agent is an antibody specific for the α5$GABA_A$ receptor. In another aspect, the agent is an antagonist. In yet another aspect, the agent is an antagonist specific for the α5$GABA_A$ receptor.

In accordance with an aspect, the agent decreases activity of the $GABA_A$ receptor by inhibiting agonist interaction with the $GABA_A$ receptor. In an aspect, the agent inhibits interaction of IL-1β with the $GABA_A$ receptor. In another aspect, the agent reduces inflammation- or surgery-induced increases in IL-1β expression and/or activity.

In accordance with another aspect of the present invention, there is provided a use of an agent that decreases activity of a $GABA_A$ receptor for preventing and/or treating a memory deficit.

In accordance with another aspect of the present invention, there is provided a use of an agent that decreases activity of a $GABA_A$ receptor in the manufacture of a medicament for preventing and/or treating a memory deficit.

In accordance with an aspect, the agent is for use after the memory deficit occurs. In accordance with another aspect, the agent is for use before the memory deficit occurs. In accordance with yet another aspect, the agent is for use while the memory deficit is occurring.

In accordance with an aspect, the memory deficit is induced by use of an anesthetic. In an aspect, the anesthetic is for use during surgery. In accordance with another aspect, the memory deficit is induced by inflammation. In accordance with yet another aspect, the memory deficit is induced by IL-1β.

In accordance with an aspect, the memory deficit is short-term memory loss. In another aspect, the memory deficit is long-term memory loss.

In accordance with an aspect, the $GABA_A$ receptor is an $\alpha 5GABA_A$ receptor.

In accordance with an aspect, the agent decreases activity of the $GABA_A$ receptor by binding to the $GABA_A$ receptor. In an aspect, the agent is an inverse agonist. In an aspect, the agent is an inverse agonist selective for the $\alpha 5GABA_A$ receptor. In an aspect, the agent is selected from the group consisting of L-655,708, MRK-016, Ro-4938581, $\alpha 5IA$, pyridazines, TB-21007, PWZ-029 and combinations thereof. In an aspect, the agent is L-655,708. In an aspect, the agent is MRK-016. In an aspect, the agent is an antibody. In an aspect the agent is an antibody specific for the $\alpha 5GABA_A$ receptor. In another aspect, the agent is an antagonist. In yet another aspect, the agent is an antagonist specific for the $\alpha 5GABA_A$ receptor.

In accordance with an aspect, the agent decreases activity of the $GABA_A$ receptor by inhibiting agonist interaction with the $GABA_A$ receptor. In an aspect, the agent inhibits interaction of IL-1β with the $GABA_A$ receptor. In another aspect, the agent reduces inflammation- or surgery-induced increases in IL-1β expression and/or activity.

In accordance with an aspect of the present invention, there is provided a method for improving memory, the method comprising administering an agent that decreases activity of a $GABA_A$ receptor.

In accordance with an aspect, memory is improved following administration of an anesthetic. In an aspect, the anesthetic is administered during surgery. In an aspect, the agent is administered before, during and/or after administration of the anesthetic. In another aspect, memory is improved following an inflammatory reaction. In an aspect, the agent is administered before, during and/or after occurrence of the inflammatory reaction. In yet another aspect, memory is improved following an increase in IL-1β expression and/or activity. In an aspect, the agent is administered before, during and/or after the increase in IL-1β expression and/or activity.

In accordance with an aspect, the memory is short-term memory. In another aspect, the memory is long-term memory.

In accordance with an aspect, the $GABA_A$ receptor is an $\alpha 5GABA_A$ receptor.

In accordance with an aspect, the agent decreases activity of the $GABA_A$ receptor by binding to the $GABA_A$ receptor. In an aspect, the agent is an inverse agonist. In an aspect, the agent is an inverse agonist selective for the $\alpha 5GABA_A$ receptor. In an aspect, the agent is selected from the group consisting of L-655,708, MRK-016, Ro-4938581, $\alpha 5IA$, pyridazines, TB-21007, PWZ-029 and combinations thereof. In an aspect, the agent is L-655,708. In an aspect, the agent is MRK-016. In an aspect, the agent is an antibody. In an aspect the agent is an antibody specific for the $\alpha 5GABA_A$ receptor. In another aspect, the agent is an antagonist. In yet another aspect, the agent is an antagonist specific for the $\alpha 5GABA_A$ receptor.

In accordance with an aspect, the agent decreases activity of the $GABA_A$ receptor by inhibiting agonist interaction with the $GABA_A$ receptor. In an aspect, the agent inhibits interaction of IL-1β with the $GABA_A$ receptor. In another aspect, the agent reduces inflammation- or surgery-induced increases in IL-1β expression and/or activity.

In accordance with another aspect of the present invention, there is provided a use of an agent that decreases activity of a $GABA_A$ receptor for improving memory.

In accordance with another aspect of the present invention, there is provided a use of an agent that decreases activity of a $GABA_A$ receptor in the manufacture of a medicament for improving memory.

In accordance with an aspect, memory is improved following use of an anesthetic. In an aspect, the anesthetic is for use during surgery. In an aspect, the agent is for use before, during and/or after use of the anesthetic. In another aspect, memory is improved following an inflammatory reaction. In an aspect, the agent is for use before, during and/or after occurrence of the inflammatory reaction. In yet another aspect, memory is improved following an increase in IL-1β expression and/or activity. In an aspect, the agent is for use before, during and/or after the increase in IL-1β expression and/or activity.

In accordance with an aspect, the memory is short-term memory. In another aspect, memory is long-term memory.

In accordance with an aspect, the $GABA_A$ receptor is an $\alpha 5GABA_A$ receptor.

In accordance with an aspect, the agent decreases activity of the $GABA_A$ receptor by binding to the $GABA_A$ receptor. In an aspect, the agent is an inverse agonist. In an aspect, the agent is an inverse agonist selective for the $\alpha 5GABA_A$ receptor. In an aspect, the agent is selected from the group consisting of L-655,708, MRK-016, Ro-4938581, $\alpha 5IA$, pyridazines, TB-21007, PWZ-029 and combinations thereof. In an aspect, the agent is L-655,708. In an aspect, the agent is MRK-016. In an aspect, the agent is an antibody. In an aspect the agent is an antibody specific for the $\alpha 5GABA_A$ receptor. In another aspect, the agent is an antagonist. In yet another aspect, the agent is an antagonist specific for the $\alpha 5GABA_A$ receptor.

In accordance with an aspect, the agent decreases activity of the $GABA_A$ receptor by inhibiting agonist interaction with the $GABA_A$ receptor. In an aspect, the agent inhibits interaction of IL-1β with the $GABA_A$ receptor. In another aspect, the agent reduces inflammation- or surgery-induced increases in IL-1β expression and/or activity.

DETAILED DESCRIPTION OF THE PREFERRED EMBODIMENTS

The data presented herein support our claim that drugs, particularly inverse agonists that inhibit $GABA_A$ receptor activity, can be used to both prevent and treat cognitive disorders that arise a consequence of excessive activation of $GABA_A$ receptors. Excessive activation of $GABA_A$ receptors can result from either an exposure to drugs such as anesthetics or benzodiazepines or from pathological conditions such as severe inflammation or sepsis.

The studies presented herein surprisingly indicate that cognitive deficits persist long after the initial exposure to GABAergic drugs or pathophysiological process. In other words, marked activation of $GABA_A$ receptors, even for a limited time period, leads to long-term cognitive deficits. These results show that these deficits can be reversed by inverse agonists that target $GABA_A$ receptors.

These results are important because cognitive deficits exhibited by laboratory animals are consistent with the cognitive deficits observed in patients after anesthesia surgery or after serious medical illness. Furthermore, accumulating evidence indicates that the immature or young brain is particularly vulnerable to long-lasting cognitive dysfunction after exposure to anesthetic drugs. Thus, the present invention has therapeutic utility in both the young and the aging brain. Further, while our studies of animal behaviour have focused primarily on memory performance, inverse agonists that target $\alpha 5GABA_A$ receptors and other subtypes of GABA$_A$ receptors will have utility in reversing deficits in other cognitive domains such as executive function or levels of consciousness.

Data obtained from studies disclosed herein demonstrate that, inter alia: (1) the inverse agonist L-655,708 that preferentially targets α5GABA$_A$ receptors reverses memory deficits when administered 24 h after exposure to the anesthetic isoflurane; and (2) long-term memory deficits are observed after treatment with both isoflurane and sevoflurane. These studies show that recognition memory is impaired 24 hours after exposure to either isoflurane or sevoflurance anesthesia. The memory deficits were unexpected based on drug pharmacokinetics as it occurs at a time when the drug has been eliminated. Treatment with L-655,708 after exposure to the anesthetic reverses the memory deficit after isoflurane.

Data also obtained from studies disclosed herein, demonstrate that, inter alia: (1) MRK-016A, a second inverse agonist that targets α5GABA$_A$ receptors, but having different structural properties than L-655,708, reverses memory deficits associated with inflammation; (2) the inverse agonist, MRK-016 blocks the tonic inhibitory current in hippocampal neurons from mice; and (3) the inverse agonist L-655,708 reverses the sevoflurane-induced increase in tonic inhibitory conductance generated by GABA$_A$ receptors.

Short-term Memory Impairment After Isoflurane in Mice is Prevented by the α5 γ-Aminobutyric Acid Type A Receptor Inverse Agonist L-655,708

Memory blockade is an essential component of the anesthetic state. However, post-anesthetic memory deficits represent an undesirable and poorly understood adverse effect. Inhibitory α5 subunit-containing γ-aminobutyric acid subtype A (α5GABA$_A$) receptors are known to play a critical role in memory processes and are highly sensitive to positive modulation by anesthetics. We postulated that inhibiting the activity of α5GABA$_A$ receptors during isoflurane anesthesia would prevent memory deficits in the early post-anesthetic period.

Mice were pretreated with L-655,708, an α5GABA$_A$ receptor-selective inverse agonist, or vehicle. They were then exposed to isoflurane for 1 h (1.3% or 1 minimum alveolar concentration or air/oxygen control). Then, either 1 or 24 h later, mice were conditioned in fear-associated contextual and cued learning paradigms. In addition, the effect of L-655,708 on the immobilizing dose of isoflurane was studied. Motor co-ordination, sedation, anxiety and the concentration of isoflurane in the brain at 5 min, 1 h and 24 h post-isoflurane, were also examined.

Motor and sensory function recovered within minutes after termination of isoflurane administration. In contrast, a robust deficit in contextual fear memory persisted for at least 24 h. L-655,708 completely prevented memory deficits without changing the immobilizing dose of isoflurane. Trace concentrations of isoflurane were measured in the brain 24 h after treatment.

Memory deficits occurred long after the sedative, analgesic and anxiolytic effects of isoflurane had subsided. L-655,708 prevented the memory deficit, suggesting an isoflurane interaction at α5GABA$_A$ receptors contributes to memory impairment during the early post-anesthesia period.

The Role of GABA$_A$ Receptors in Postoperative Memory Loss

Each year, more than 234 million patients undergo anesthesia and surgery worldwide. It is widely assumed that cognitive function rapidly returns to baseline in the early postoperative period. However, postoperative cognitive dysfunction, particularly long-term memory loss, is a frequent but poorly understood neurological complication after surgery. Postoperative memory loss is associated with a reduction in quality of life, early retirement, as well as premature death.

Our goal is to understand the mechanisms underlying postoperative memory deficits and to develop treatment and prevention strategies. In our studies, we identified a "memory-blocking" receptor that, when activated, prevents the formation of new memories. Overactivation of these receptors disrupts communication in a region of the brain that regulates memory processes. General anesthetics can cause such overactivation, leading to profound memory blockade.

The prolonged time course of postoperative memory loss prompted us to look for an endogenous factor that activates the memory-blocking receptors. We determined that one of the most important pro-inflammatory cytokines, interleukin 1 β (IL-1β), increases receptor activity. This result is exciting because IL-1β causes memory deficits, via mechanisms that up until now remained unclear. Also, the levels of IL-1β in the brain increase after surgery. Thus, we hypothesize that IL-1β increases the activity of memory-blocking receptors, thereby causing postoperative memory deficits.

Using a mouse model, we will determine how IL-1β increases the activity of memory-blocking receptors. We will also determine whether inhibiting these receptors reduces the severity and/or incidence of postoperative memory deficits. If so, we anticipate developing a strategy for preventing postoperative cognitive dysfunction. Our results have implications for the memory loss associated with anesthesia and inflammatory disease.

Inflammation-Induced Memory Impairment is Mediated by an Increase in Tonic GABAergic Inhibition Acute and chronic systemic inflammation is associated with deficits of learning and memory through mechanisms that remain poorly understood. Direct evidence linking increased inhibitory neurotransmission to the pathogenesis of inflammation-induced memory deficits is currently lacking. Here, we show that a subtype of the γ-aminobutyric acid type A receptors containing the α5 subunit (α5GABA$_A$Rs) is required for disruption of synaptic plasticity and memory behavior by the key pro-inflammatory cytokine interleukin-1β (IL-1β). Using a mouse model, we find that memory loss caused by IL-1β can be reversed by either genetic or pharmacological methods that specifically inhibit α5GABAARs. Our in vitro studies show that IL-1β increases α5GABA$_A$R activity via activation of the p38 MAPK-dependent signaling pathway. IL-1β also increases surface expression of α5GABA$_A$Rs. The increase in α5GABA$_A$R activity caused by IL-1β reduces synaptic plasticity in the CA1 region of the hippocampus. Together, these findings identify a small subset of GABA$_A$ receptors that is expressed predominantly within the hippocampus as critical downstream effectors of IL-1β signaling. Thus, α5GABA$_A$Rs are potential targets for therapies aimed at reversing inflammation-induced memory deficits.

Inhibition of α5GABA$_A$ Receptors Restores Recognition Memory after General Anesthesia. Treatment for Memory Deficits in the Early Postoperative Period General anesthetics cause cognitive deficits that persist much longer than would be expected on the basis of their pharmacokinetics. The cellular mechanisms underlying these postanesthetic cognitive deficits remain unknown. γ-Aminobutyric acid type A (GABA$_A$) receptors are principal targets for most anesthetics. In particular, the α5GABA$_A$ receptor subtype has been implicated in acute memory blockade during anesthesia and memory deficits in the early postoperative period. Here, we used an object recognition task to determine whether working memory and short-term recognition memory are equally impaired after isoflurane anesthesia, whether memory deficits resolve spontaneously, and whether deficits can be reversed by inhibiting α5GABA$_A$ receptors. We also sought to determine whether the expression of α5GABA$_A$ receptors is necessary for the development of memory dysfunction after isoflurane. Finally, the effect sevoflurane, on short-term memory was also studied.

Wild-type and α5GABA$_A$ receptor null-mutant (Gabra5−/−) mice were treated with isoflurane (1.3%; 1 MAC), sevoflurane (2.3%; 1 MAC) or vehicle gas for 1 h. Memory performance was assessed with a novel object recognition task, either 24 or 72 h later. Working memory and short-term memory were tested 1 min and 1 h after training, respectively. To determine whether inhibition of α5GABA$_A$ receptors reverses memory deficits, a subset of mice were treated with L-655,708 at 24 h after isoflurane 30 min before behavioral training.

In wild-type mice, a brief exposure to isoflurane impaired short-term but not working recognition memory at 24 h. Short-term memory deficits were fully reversed by L-655,708 and resolved spontaneously by 72 h. Gabra5−/− mice showed no memory deficits 24 h after isoflurane. Sevoflurane also caused memory deficits 24 h after anesthesia.

Inhaled anesthetics cause deficits in recognition memory for 24 h. This proof-of-concept study shows that α5GABA$_A$ receptors are necessary for the development of postanesthetic deficits in recognition memory and that these receptors can be targeted to restore memory even after the anesthetic has been eliminated.

MRK-016, an Inverse Agonist that has Different Structural Properties than L-655,708 Blocks the Tonic Inhibitory Current in Hippocampal Neurons from Mice.

We examined the effects of L-655,708 on the tonic current evoked by an application of GABA in the absence or presence of MRK-016. MRK-016 is a GABA$_A$ receptor inverse agonist selective for the α5-subtype (EC50=3 nM) having the following chemical name: 3-(1,1-Dimethylethyl)-7-(5-methyl-3-isoxazolyl)-2-[(1-methyl-1H-1,2,4-triazol-5-yl)methoxy]-pyrazolo[1,5-d][1,2,4]triazine and the following chemical structure:

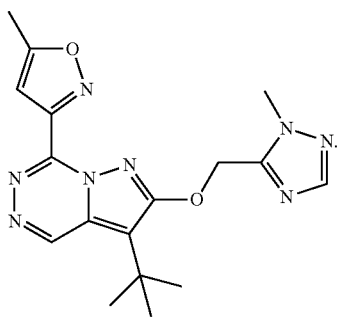 [SMILES: Cc1cc(-c2nncc3c(C(C)(C)C)c(OCc4ncnn4C)nn23)no1]

MRK-016 inhibited the tonic current as evidenced by the change in holding current which reflects the inhibition of all GABA$_A$ receptors.

A Second Inverse Agonist that Preferentially Targets α5GABA$_A$ Receptors but has Different Structural Properties than L-655,708 (MRK-016) Reverses Memory Deficits Associated with Inflammation.

We have determined that IL-1β-induced impairment of contextual fear memory can be reversed by pharmacological inhibition of α5GABA$_A$ receptors by the inverse agonist MRK-016. Fear conditioning was performed after injection of IL-1β in both wild-type (WT) and α5GABA$_A$ receptor knock out (Gabra5−/−) mice. MRK-016 restored freezing scores for contextual fear memory to control values when it was co-administered with IL-1β and it did not affect freezing to a conditioned tone stimulus.

The Inverse Agonist L-655,708 Reverses the Anesthetic-Induced Increase in Tonic Inhibitory Conductance Generated by GABA$_A$ Receptors.

GABA$_A$ receptors in the hippocampus generate a tonic inhibitory conductance that is highly sensitive to anesthetics. Our in vitro electrophysiological data show that the α5GABA$_A$ receptor inverse agonist, L-655,708 reverses enhancement of the tonic current by the inhaled anaesthetics isoflurane and desflurane.

Other and further advantages and features of the invention will be apparent to those skilled in the art from the following detailed description thereof, taken in conjunction with the accompanying drawings.

BRIEF DESCRIPTION OF THE DRAWINGS

The present invention will be further understood from the following detailed description with reference to the drawings in which:

FIG. 5B illustrates the effect of isoflurane according to the amount of time spent in the open arms region of the elevated plus maze in Example 1.

FIG. 5C illustrates the effect of isoflurane according to the amount of time spent in the center region of the elevated plus maze in Example 1.

FIG. 5D illustrates the effect of isoflurane according to the time required to cross the elevated beam in Example 1.

FIG. 5E illustrates the effect of isoflurane according to the number of times the hind foot slipped while crossing an elevated beam in Example 1.

FIG. 5F illustrates the effect of isoflurane according to the latency to flick tail away from a hot water bath in Example 1.

FIG. 7A illustrates that synaptic receptors are typically composed of $\alpha1\beta2\gamma2$ subunits whereas extrasynaptic $GABA_A$ receptors typically contain the $\alpha5$ subunit in pyramidal neurons. FIG. 7B illustrates that the tonic current is revealed by an application of the $GABA_A$ receptor antagonist bicuculline in wild-type (WT) but not Gabra5−/− hippocampal neurons.

FIG. 8A illustrates the results of injecting Wild-type (WT) and Gabra5−/− mice with the $\alpha5GABA_AR$ inverse agonist, L-655,708 30 minutes prior to training with the trace fear memory paradigm. FIG. 8B illustrates the results of treating WT mice with etomidate or etomidate plus L-655,708, 30 min prior to training.

FIG. 9A provides a schematic drawings showing synaptic events, miniature inhibitory postsynaptic currents (mIPSCs), and tonic current before and during application of midazolam or propofol. FIG. 9B illustrates the relationship between midazolam and propofol concentrations and the charge transfer associated with mIPSCs and tonic current.

FIGS. 10A and 10B illustrate that low and high frequency stimulation, respectively, induces similar plastic responses in both Gabra5−/− and wild-type (WT) slices. FIG. 10C illustrates that lack of $\alpha5GABA_ARs$ is associated with a lower threshold for synaptic potentiation when slices are stimulated with an intermediate—but not a low- or high-frequency stimulation protocol. FIG. 10D illustrates the relationship for stimulus intensity versus synaptic potentiation or depression.

FIG. 11A illustrates the timeline of the experiments wherein mice were injected with L-655,708 or vehicle 30 min prior to exposure to 1 h of isoflurane followed by training in the fear conditioning paradigm twenty-four hours later. FIG. 11B illustrates short-term memory impairment (tested 30 min after training) by isoflurane and its prevention by pre-emptive treatment with L-655,708. FIG. 11C illustrates long-term memory impairment (tested 24 h after training) after isoflurane and its prevention by pre-emptive treatment with L-655,708.

FIG. 12A illustrates the object recognition paradigm. FIG. 12B illustrates the results from exposing mice to isoflurane for 1 h followed by studying with the novel object recognition task 24 hours later and administering L-655,708 30 min prior to the presentation of the novel objects.

FIG. 13A illustrates typical confocal images showing immunofluorescence staining of $GABA_A$ receptor $\beta2/3$ subunits in lung tissues from control and IL-13-treated mice. FIG. 13B illustrates the summary of the immunofluorescence density of $\beta2/3$ subunits in lung tissues following IL-13 treatment.

FIG. 15A illustrates that both IL-1$\beta$ and etomidate increased the amplitude of the tonic current and that the combination of IL-1$\beta$ plus etomidate produced a supra-additive increase in the tonic current. FIG. 15B illustrates the comparison of the measured "new" current evoked by the combination of etomidate and IL-1$\beta$ to the theoretical sum of the "new" current.

FIG. 16A illustrates that in the absence of an immune response, the type 1 IL-1 receptor is inactive and the number of $\alpha5GABA_A$ receptors is limited. FIG. 16B illustrates that an inflammatory response increases the production of IL-1$\beta$ which increases the number of $\alpha5GABA_A$ receptors expressed on the cell surface, which in turn, increases chloride influx causing neuronal hyperpolarization and inhibition of long-term synaptic plasticity (LTP) and memory. FIG. 16C illustrates that anesthetics enhance $\alpha5GABA_A$ receptor activity directly by positive allosteric modulation, thereby increase channel opening and chloride influx causing an inhibition of LTP and memory. FIG. 16D illustrates that IL-1$\beta$ potentiates the effects of anesthetics by increasing the number of $\alpha5GABA_A$ receptors, causing profound memory impairment.

FIG. 17A illustrates that pre-treatment of the neurons with IL-1$\beta$ increased the amplitude of the tonic current as revealed by the application of bicuculline. FIG. 17B illustrates that treatment of the cultures with the IL-1 receptor antagonist, IL-1ra, reversed the IL-1$\beta$-induced increase in the tonic current.

FIG. 18A illustrates the miniature postsynaptic currents (mIPSCs) recorded from hippocampal neurons grown in primary cultures and that treatment of the neurons with IL-1$\beta$ inhibited mIPSC, and this effect was blocked by IL-1ra. FIG. 18B illustrates that IL-1$\beta$ reduced both the amplitude and frequency of mIPSCs.

FIG. 19A illustrates an increase in tonic current in co-cultured hippocampal neuron and cortical microglia exposed to the endotoxin, LPS (to induce the production of IL-1$\beta$) prior to recording from the neurons and that this was blocked by treating the co-cultures with the IL-1 receptor antagonist, IL-1ra. FIG. 19B illustrates that treatment with LPS did not modify the tonic current recorded in neurons hat were cultured alone, in the absence of microglia, suggesting that the microglia were the source of IL-1$\beta$ induced by LPS.

FIG. 20A illustrates the assessment of $GABA_A$ receptor expression using an antibody directed against $\beta2$ and $\beta3$ subunits after the treatment of the neurons with IL-1$\beta$ or vehicle for 1 h prior to immunostaining. FIG. 20B illustrates immunostaining with an anti-$\alpha5$ subunit antibody.

FIG. 21A illustrates the biotiynilation method used to determine whether the protein of interest is expressed on the neuronal surface. FIG. 21B illustrates the expression of $\alpha5$ subunit in IL-1$\beta$-treated hippocampal slices treated with IL-1$\beta$ prior to biotinylation, followed by Western blotting, as a percentage of expression compared to control slices.

FIG. 22A illustrates that IL-1β enhanced the current evoked by a low concentration of GABA which was blocked by inhibiting p38 MAPK, with bath application of SB203580. FIG. 22B illustrates that SB203580 blocked the enhancement by IL-1β and that SB203580 applied in the absence of IL-1β had no effect on the tonic current. FIG. 22C illustrates the differential effects of IL-1β on extrasynaptic and synaptic $GABA_A Rs$, and the different kinases involved in these effects.

FIG. 23A illustrates that LTP was reduced in LPS-treated WT mice. FIG. 23B illustrates that LTP was not reduced in LPS-treated Gabra5−/− mice.

FIG. 24A illustrates that LPS injection impaired contextual fear conditioning in wild-type (WT) mice. FIG. 24B illustrates that LPS injection did not impair contextual fear conditioning in Gabra5−/− mice. FIG. 24C illustrates that LPS injection did not impair amygdala-dependent auditory fearing conditioning in WT mice. FIG. 24D illustrates that that LPS injection did not impair amygdala-dependent auditory fearing conditioning in Gabra5−/− mice (C, D).

FIG. 25A illustrates the determination of equi-effective concentrations of IL-1β and etomidate measured by constructing dose-response plots under voltage-clamp conditions. FIG. 25B illustrates the isobologram for 50% of the maximum effect produced by IL-1β and etomidate.

FIG. 27A illustrates that surgery induces an impairment of contextual fear memory, and this effect could be blocked by IL-1 receptor antagonist injected before surgery. FIG. 27B illustrates that the amygdala-dependent auditory-cued test was not affected by surgery or the interleukin-1 receptor antagonist.

FIG. 29A illustrates that the tonic current was increased by exogenous IL-1β as revealed by the $GABA_A R$ competitive antagonist bicuculline. FIG. 29B illustrates the concentration-dependent effects of IL-1β on the tonic current density. FIG. 29C provides a representative recording showing the tonic currents revealed by Bic or by the inverse agonist for $α5GABA_A Rs$, L-655,708. FIG. 29D illustrates that $α5GABA_A Rs$ are necessary for the enhancing effects of IL-1β on the tonic current. FIG. 29E illustrates that the tonic current was increased by treating neuron and microglia co-cultures with the endotoxin LPS.

FIG. 31A illustrates that $GABA_A R$-mediated mIPSCs were inhibited by pre-treatment with IL-1β, and this effect could be blocked by IL-1ra. FIG. 31B provides traces averaged from 314-474 individual mIPSCs. FIG. 31C provide cumulative amplitude and frequency distributions of mIPSCs showing that the amplitude was inhibited by IL-1β, an effect abolished by IL-1ra and that the frequency of mIPSCs was not affected by IL-1β. FIG. 31D illustrates that the peak response evoked by application of GABA, which is generated by synaptic $GABA_A Rs$, was inhibited by pre-perfusion with IL-1β, and this effect could be blocked by IL-1ra.

FIG. 32A illustrates that IL-1β-induced enhancement of tonic current was blocked by co-application of IL-1ra and that treatment with an inhibitor of p38 MAPK, SB203,580 abolished the enhancing effects of IL-1β. FIG. 32B illustrates that the peak response evoked by application of GABA was inhibited by pre-perfusion with IL-1β, and this effect could be blocked by a PI3K inhibitor, wortmannin and that the p38 MAPK inhibitor SB203,580 did not block the inhibitory effects of IL-1β on the evoked peak response. FIG. 32C illustrates that surface expression of the α5 subunit was increased in hippocampal slices that had been treated with IL-1β. FIG. 32D illustrates that surface expression of the α1 subunit was not increased after IL-1β treatment.

FIGS. 33A, 33B and 33C illustrate that the enhancing effects of IL-1β on the tonic current were not blocked by SB202,474, an inactive analog of the p38 MAPK inhibitor SB203,580 or the JNK antagonist SP600,125 or the PI3K antagonist LY294,002, respectively.

FIG. 35A illustrates that injection of LPS inhibited LTP in WT mice. FIG. 35B illustrates that injection of LPS did not affect LTP in Gabra5−/− mice.

FIG. 36A illustrates that long-term potentiation (LTP) was induced by theta burst stimulation (TBS) in wild-type (WT) mice. FIG. 36B illustrates that incubation of slices with IL-1ra abolished the LPS-induced impairment of LTP in WT mice. FIG. 36C provides quantified data for results shown in FIG. 36A. FIGS. 36D and 36E illustrate that LTP in Gabra5−/− mice was not affected by injection of LPS.

FIG. 37A illustrates that IL-1β reduced freezing scores for contextual fear memory in WT but not Gabra5−/− mice. FIG. 37B illustrates that cued fear memory to a conditioned tone stimulus was not affected by IL-1β in either WT or Gabra5−/− mice. FIG. 37C illustrates that L-655,708 restored freezing scores for contextual fear memory to control values when it was co-administered with IL-1β, and it did not affect freezing to a conditioned tone stimulus.

FIG. 38A illustrates that LPS reduced freezing scores for contextual fear memory in WT mice, but not in Gabra5−/− mice. FIG. 38B illustrates that cued fear memory to a conditioned tone stimulus was not affected by LPS in WT or Gabra5−/− mice.

FIG. 40A illustrates time spent with novel and familiar objects during testing. FIG. 40B illustrates the discrimination ratios (time spent with novel object/time spent with both objects) of control and isoflurane-treated mice. FIG. 40C illustrates time spent exploring identical sample objects during training.

FIG. 41A illustrates time spent with novel and familiar objects during testing. FIG. 41B illustrates the discrimination ratios (time spent with novel object/time spent with both objects) of control and isoflurane-treated mice. FIG. 41C illustrates time spent exploring identical sample objects during training.

FIG. 42A illustrates time spent with novel and familiar objects during testing. FIG. 42B illustrates discrimination ratios (time spent with novel object/time spent with both objects) of control, L-655,708, and isoflurane+L-655,708 groups. FIG. 42C illustrates time spent exploring identical sample objects during training.

FIG. 43A illustrates time spent with novel and familiar objects during testing. FIG. 43B illustrates the discrimination ratios (time spent with novel object/time spent with both objects) of control and isoflurane-treated mice. FIG. 43C illustrates time spent exploring identical sample objects during training.

FIG. 44A illustrates time spent with novel and familiar objects during testing. FIG. 44B illustrates the discrimination ratios (time spent with novel object/time spent with both objects) of all groups. FIG. 44C illustrates time spent exploring identical sample objects during training.

FIG. 45A illustrates time spent with novel and familiar objects during testing. FIG. 45B illustrates the discrimination ratio (time spent with novel object/time spent with both objects). FIG. 45C illustrates time spent exploring identical sample objects during training.

DETAILED DESCRIPTION OF THE PREFERRED EMBODIMENTS

Figure 1:
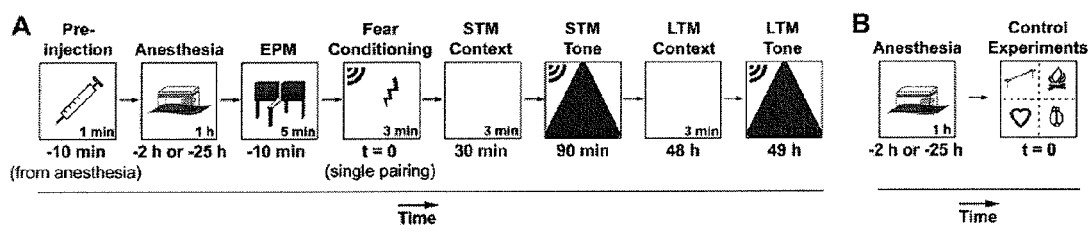
FIG. 1A is a scheme summarizing the time course of the experimental procedure for the treatment experiments in Example 1.
FIG. 1B is a scheme summarizing the time course of the experimental procedure for the control experiments in Example 1.

Further details of the preferred embodiments of the present invention are illustrated in the following examples which are understood to be non-limiting.

Example 1

Short-Term Memory Impairment after Isoflurane in Mice is Prevented by the α5 γ-Aminobutyric Acid Type A Receptor Inverse Agonist L-655,708

It has been widely assumed that the neurodepressive effects of general anesthetics dissipate rapidly and that cognitive faculties promptly return to baseline once the anesthetic has been eliminated. However, observational studies of patients who have undergone cardiac and non-cardiac procedures have shown that cognitive decline is present in 31% to 47% of patients at the time of hospital discharge and in 10% of patients at 3 months.[1-3] The highest incidence of memory impairment occurs in the early post-anesthetic period. For example, 47% of elderly patients who underwent general anesthesia for minor surgical procedures exhibit memory deficits for at least 24 h.[4] Declarative or explicit memory, which refers to memory for facts, objects, places and events, is particularly vulnerable.[1,2,5] The underlying mechanisms, severity and time course for recovery of memory deficits in the early post-anesthetic period remain poorly understood. We postulated that inhibiting the activity of α5GABA$_A$ receptors during isoflurane anesthesia would prevent memory deficits in the early post-anesthetic period.

In clinical studies, it is not possible to disentangle the effects of anesthetics from other factors that impair memory such as inflammation, analgesic drugs and concurrent disease.[6,7] Consequently, animal models are required to identify susceptible cognitive domains and the mechanisms underlying memory deficits after exposure to general anesthetics. The hippocampus is required for several forms of explicit memory and the temporal stages of explicit memory strongly parallel the stages of synaptic plasticity in the hippocampus.[8] In addition, the acute memory blocking effects of anesthetics parallel the inhibition of synaptic plasticity in the hippocampus.[9]

The current study used a well-characterized behavioral model of hippocampus-dependent fear-associated learning to study the mechanisms underlying "short-term" and "long-term" memory deficits after exposure to an inhaled anesthesia. Within the current context of the study, short-term memory refers to memory that lasts for minutes whereas long-term memory lasts for hours or days. Both early and late forms of memory were studied as they are known to depend on different neurotransmitter receptors, intracellular signaling pathways and regulators of gene expression.[8,10-12]

Specifically, short-term memory involves changes in the strength of preexisting synaptic connections and modulation of existing proteins. Long-term memory requires gene transcription, the production of new proteins, restructuring of synapses and growth of new synaptic connections.[8] The goal of the current study was to determine whether brief exposure to a general anesthetic produces deficits in short-term and long-term memory. We also sought to develop a pharmacological strategy to prevent memory deficits based on anesthetic interactions at a receptor that plays a central role in memory pathways.

Most anesthetics cause deficits in memory and synaptic plasticity, at least in part, by increasing the activity of inhibitory γ-aminobutyric acid subtype A (GABA$_A$) receptors.[13] GABA$_A$ receptors are heteromeric complexes composed of multiple subunits (α1-6, β1-3, γ1-3, δ, ε, θ, π, ρ1-3). In particular, the activity of GABA$_A$ receptors containing the α5 subunit (α5GABA$_A$ receptors) regulate synaptic plasticity and hippocampus-dependent memory.[6,7,14,15] α5GABA$_A$ receptors set the threshold for the induction of plasticity in pyramidal neurons by attenuating excitatory input.[9] Memory blockade during anesthesia has been attributed, in part, to increased α5GABA$_A$ receptor activity.[9,16,17] In the current study, we first sought to characterize memory deficits in the post-anesthetic period and determine whether such deficits were dissociated from impairment of motor function, anxiolysis and nociception. Next, we tested the hypothesis that inhibiting α5GABA$_A$ receptor activity during anesthesia prevents memory deficits in the early post-anesthetic period. Specifically, we tested whether L-655,708, an inverse agonist with high selectivity for α5GABA$_A$ receptors, prevented memory deficits that occurred after isoflurane anesthesia.[18] L-655,708 has the following chemical structure:

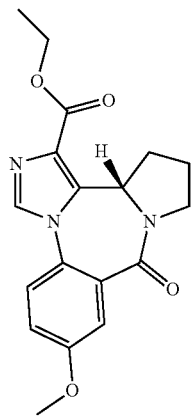 [SMILES: CCOC(=O)c1ncn2c1[C@@H]1CCCN1C(=O)c1cc(OC)ccc1-2]

Short-term memory (studied 30 min after conditioning) and long-term memory (studied 2 days after conditioning) were measured after 1 h exposure to isoflurane. The results show that mice rapidly recovered motor co-ordination, locomotion and nociception after exposure to isoflurane; however, a deficit in contextual fear memory that persisted for up to 24 h could be prevented by pretreatment with L-655,708.

Materials and Methods

Mice were pretreated with L-655,708, an α5GABA$_A$ receptor-selective inverse agonist, or vehicle and were then exposed to isoflurane for 1 h (1.3% or 1 minimum alveolar concentration or air/oxygen control). One h or 24 h later, mice were conditioned in fear-associated contextual and cued learning paradigms. In addition, the effect of L-655,708 on the immobilizing dose of isoflurane was studied. Motor co-ordination, sedation, anxiety and the concentration of isoflurane in the brain at 5 min, 1 h and 24 h post-isoflurane, were also examined.

Animals

Animal care and experimental protocols were approved by the University of Toronto Animal Care Committee (Toronto, Ontario, Canada) and conformed to the guidelines set by the Canadian Council on Animal Care. Male and female adult (8 to 16 wk old) C57BL6/J mice (Charles River Laboratories, Saint-Constant, Canada) were studied. The mice were housed five to a cage with free access to Purina mouse chow (Nestlé Purina PetCare Company, Vevey, Switzerland) and tap water. The temperature (22° C.) and reverse light/dark cycle (lights on at 0700 h; lights off at 1900 h) of the room were controlled. To reduce variability in learning and memory performance and prevent acute stress reactions during conditioning, all mice were handled daily for 10 min each for a minimum of 1 wk before the behavioral experiments were started.[19] The experimenters who scored behavioral performance were blinded to the drug treatment groups. To avoid subjecting the mice to multiple tests, different groups of mice were used to study motor co-ordination, nociception, core-temperature during anesthesia, arterial blood gases, and the concentration of isoflurane in the brain. Anxiety levels were studied using the elevated plus maze in same group of mice that was used to study fear conditioning.

Isoflurane Anesthesia

Mice selected at random received either L-655,708 (0.7 mg/kg in 10% dimethyl sulfoxide 2 μL/g) or vehicle (10% dimethyl sulfoxide) by subcutaneous injection 10 min before exposure to isoflurane or vehicle gases. During isoflurane exposure, individual mice were placed in an air-tight acrylic glass chamber (27 cm wide×10 cm deep×10 cm high). The chamber was pre-flushed with the vehicle gas mixture (30% O$_2$ in air delivered at 1 L/min) that did or did not contain isoflurane. The desired concentration of isoflurane was set on the vaporizer as 1 minimum alveolar concentration (MAC) or 1.33% for C57BL6/J mice[20] and the concentrations of isoflurane, oxygen and carbon dioxide in the chamber were continuously analyzed with a commercial gas analyzer (Datex Ohmeda, Mississauga, Canada). To prevent hypothermia during anesthesia, the floor of the chamber was warmed with a heating blanket. During the recovery phase (after isoflurane or vehicle gas treatment), the mouse was taken from the gas chamber and placed in a second heated acrylic glass chamber for 45 min. The mouse was then either returned to its home cage and allowed to recover for 24 h (24-h groups) or taken to a holding cage in an adjacent room (1-h groups). For continuity and to ensure that the experimenter who performed the fear-conditioning studies was blinded to the treatment group, mice that were allowed to recover for 24 h were placed back in a heated for 45 min before the behavioral experiments. FIGS. 1A and 1B summarize the time course of the experimental procedures. In FIG. 1A, each stage of the experimental paradigm is represented by chronological boxes and cartoons. Relative time is indicated below the boxes (t=0, start of fear conditioning training). The duration of each stage is inset at the bottom left. Prior to fear conditioning, test subjects were injected with L-655,708 or vehicle and 10 min later anesthetized with 1.0 minimum alveolar concentration (MAC) isoflurane in 30% O2. Four groups of isoflurane-treated subjects were used (1 h recovery+L-655,708; 1 h recovery+vehicle; 24 h recovery+L-655,708; 24 h recovery+vehicle). Two oxygen-control group was used (1 h recovery+L-655,708; 1 h recovery+vehicle). 10 min prior to fear conditioning, subjects were examined in the elevated plus maze (EPM). Subjects were tested for short-term memory (STM) and long-term memory (LTM) of the context and tone. In FIG. 1B, control experiments: Balance beam, tail flick (fire), blood gas (heart) and isoflurane brain quantification (brain, dorsal view) experiments were performed independently from learning and memory experiments.

The sample size selected for the fear-associated memory studies was determined by an independent cohort of 14 mice (7 male and 7 female), which demonstrated a deficit in short-term contextual fear conditioning 24 h after exposure to isoflurane compared with oxygen-treated controls. In control subject, the mean freezing score was $\rho_o$=57.8% whereas the standard deviation was $\sigma_o$=23.0%. In mice treated with isoflurane and studied 24 h after the anesthetic was terminated, the freezing score was $\mu_1$=32.8% and the standard deviation was $\sigma_1$=20.8%. A sample size calculation, based on an $\alpha$ value of 0.05, a 1-$\beta$ value equal to 80% and using a one-tailed test indicated an n value of 10. The sample size was calculated using the formula from Fundamentals of Biostatistics by Bernard A. Rosner, Equation 8.27: $n=(z_{1-\alpha}+z_{1-\beta})^2(\sigma_o^2+\sigma_1^2)/(\mu_o-\mu_1)^2$.

L-655,708 Effects on MAC

Mice selected at random received either L-655,708 (0.7 mg/kg) or vehicle (10% dimethyl sulfoxide) by subcutaneous injection 10 min before exposure to isoflurane. The affinity of L-655,708 for $\alpha$5GABA$_A$ receptors is 50- to 100-fold greater than its affinity for $\alpha$1, $\alpha$2, and $\alpha$3 subunit-containing GABA$_A$ receptors.[18] All available inverse agonists for $\alpha$5GABA$_A$ receptors bind to other benzodiazepine-sensitive GABA$_A$ receptor subtypes, albeit at lower affinity, and modify receptor function at higher concentrations. The subtype selectivity of L-655,708 is attributed to a higher affinity for $\alpha$5GABA$_A$ receptors, as the efficacy of this compound is similar at the other GABA$_A$ receptor subtypes to which it binds.[18] Consequently, to ascribe an effect of L-655,708 to $\alpha$5GABA$_A$ receptors, a careful selection of the concentration is required. The concentrations of L-655,708 used in the current study were selected on the basis of in vivo binding data, pharmacokinetic analyses, and previous memory studies. We estimated that at 30 min after injection, L-655,708 at 0.7 mg/kg intraperitoneal would result in 60-70% occupancy of $\alpha$5GABA$_A$ receptors in vivo with limited binding to $\alpha$1, $\alpha$2, and $\alpha$3 subunit-containing GABA$_A$ receptors and no significant off-target behavioral effects such as sedation and motor impairment.[21]

The tail-clamp withdrawal assay was used to determine whether L-655,708 influenced the potency of isoflurane for prevention of a motor response to noxious stimulus.[22] After equilibration with isoflurane (1.1%), a hemostat was applied to the tail and the mouse was assessed for purposeful movement in response to the tail-clamp. The dose of isoflurane was adjusted by ~0.15%, either up or down depending on the response, and equilibrated for 15 min. This method was continued until the concentrations of isoflurane that prevented and produced movement were determined. The MAC value was calculated as the mean value of these two concentrations. Mice were treated in a heated chamber and the inspired concentration of isoflurane was continuously analyzed with a commercial gas analyzer (Datex-Ohmeda). These data were examined using procedures described in the Statistical Analysis section.

Core Temperature During Anesthesia

Rectal temperature was studied in a separate group of mice to ensure the temperature did not drop substantially during isoflurane anesthesia. Mice were placed in the airtight acrylic glass chamber for administration of the anesthetic; a rectal probe was inserted after the mice lost their righting reflex and rectal temperature was inserted to measure temperature between 5 min and 1 h. The rectal probe was not inserted prior to the 5 min mark to ensure the mice were adequately anesthetized and not discomforted.

Analysis of Blood Gases

Mice were anesthetized in an acrylic glass chamber, which was flushed with isoflurane (1 MAC in 30% O2) for either 1 h or 5 min, then placed in the supine position on a stereotactic frame. Isoflurane (1.0 MAC) was administered via a nose cone. A needle was carefully inserted into the heart and blood was extracted into a heparinized syringe. The collected blood was immediately placed on ice and transported to a blood gas analyzer (ABL 700 series, Radiometer, Copenhagen, Denmark).

Concentration of End-Tidal Isoflurane During Recovery

Immediately after isoflurane anesthesia, several mice were transferred to a heated recovery chamber and a sampling catheter was positioned as close as possible to the snout of each mouse. The concentration of isoflurane in the expired gas was measured until it could no longer be detected (about 7 min).

Isoflurane Concentration in Brain Tissue

Following a designated recovery time, mice were sacrificed by cervical dislocation. The brains were rapidly removed at room temperature and placed in a gas-tight syringe containing polytetrafluoroethylene beads. The whole brain was immediately crushed with two strokes of the plunger and the syringe was then sealed. Isoflurane was measured using gas chromatography as previously described.[23-25] This method uses headspace gas chromatography based on previous measurements of the gas-brain coefficient. The methods are similar to that described for measurement of inhaled anesthetics in blood.[26]

Fear-Conditioning Studies

Testing of memory function was performed using two fear-conditioning paradigms. These tests study the ability of mice to learn and remember an association between an aversive stimulus (foot shock) and non-aversive or neutral stimuli (environmental context or an auditory cue). Different groups of mice were used to study associated fear conditioning at 1 h and 24 h after the end of isoflurane (or vehicle treatment). Each mouse was introduced to the fear conditioning chamber (50 cm wide×15 cm deep×15 cm high, Process Control Fear Conditioning Monitor GmbH 303410, Technical & Scientific Equipment Systems Inc., Chesterfield, Mo.). The chamber was illuminated with an interior overhead light (50 lx) and was equipped with a stainless steel grid floor connected to a constant-current shock generator. Each mouse was allowed to explore the chamber for 3 min before presentation of a pulsating tone (80 dB, 3600 Hz) which persisted for 30 s. The tone was followed immediately by a mild foot shock (0.7 mA for 0.5 s). The mouse was allowed to explore the chamber for a further 30 s after the shock to study post-shock freezing.

Assessment of learning and memory was performed by measuring the amount of time the mouse demonstrated "freezing behavior," defined as a completely immobile posture, except for respiratory efforts. Freezing was scored using Observer software (Noldus Information Technology, Wagoningen, The Netherlands), by an experimenter who was blinded to the treatment groups. Before each new training session, the chamber was cleaned with 70% ethanol to mask and eliminate odors from the previous mouse. At the end of the experiment, the mouse was removed from the chamber and housed singly in a temporary cage located in a separate room until completion of the short-term memory testing, after which it was returned to its home cage.

Short-term memory for contextual learning was probed 30 min after training by re-exposed the mice to the same fear conditioning chamber for 3 mm. Long-term memory for contextual learning was studied 2 days (48 h) after conditioning by re-exposing the mice to the conditioning chamber. Short-term memory for cued learning was determined 90 min after training by first allowing the mice to explore a modified chamber scented with 5% acetic acid and containing a plastic floor and cardboard walls and then after 3 min, re-presenting the tone (2-Hz pulsating tone, 80 dB, 3600 Hz) for 3 min. Non-specific freezing was measured during the exploration of the novel chamber prior to presenting the tone. Freezing scores to study recall were measured during presentation of the tone. Long-term memory for cued learning was determined by introducing the mice into the modified chamber and presenting the tone 2 days (48 h) after conditioning.

Elevated Plus Maze

Anxiety levels were studied using an elevated plus maze consisting of an acrylic glass apparatus in the shape of a cross (45 cm long×7 cm wide, with a central region of 7 cm×7 cm). Two opposing arms were enclosed with opaque white plastic walls (28 cm high, closed arms), whereas the other two opposing arms were left open (open arms). Ten minutes before the mice were placed in the fear-conditioning chamber, they were observed for 5 min in the elevated plus maze. An observer blinded to treatment group recorded the position of each mouse on the maze using Observer software. The time spent in the center and in the open and closed arms were measured over 5 min. In addition, motor activity was quantified to study locomotion.

A 5 min interval was granted between the elevated plus maze test and the training in fear conditioning.

Tail Flick

Mice were gently held by the scruff and allowed free movement of the tail. The tip of the tail was inserted to about 1 cm depth into a beaker of water (49° C.). The latency for the mouse to remove its tail from the water was recorded and used as an indication of nociception.

Balance Beam

To determine whether motor coordination was impaired 1 h after exposure to isoflurane, mice were selected at random and a double cross-over study was undertaken using a separate group of mice. Mice were pretreated with isoflurane or vehicle for 1 h and then given 1 h to recover prior to experimentation on the balance beam. One hour after exposure to isoflurane or vehicle, the mice were placed on a wooden platform (15×15 cm) elevated 40 cm from the ground and attached to an identical elevated platform by a wooden beam 2 cm in diameter×1.2 m long. Indicators of motor coordination and mobility include the time for the mice to spontaneously cross the beam, and the number of times the hindfoot slipped off the beam. Average values of three repetitions for each mouse were reported. The mice were pre-trained on the apparatus 1 day before the experiment.

Statistical Analysis

All statistics were carried out using Statistica (Statsoft, Inc. Tulsa, Okla.) software on a standard personal computer. Groups examined in the elevated plus maze and fear conditioning were compared with a two-way ANOVA followed by Post hoc least significant difference tests, using exposure to isoflurane and pretreatment with L-655,708 as the two factors. The remaining experiments were compared with one-way ANOVA followed by Post hoc least significant difference tests, where the single factor was either exposure to isoflurane, pre-treatment with L-655,708 or recovery time follow isoflurane anesthesia. Differences between groups were considered statistically significant at $P<0.05$. All analysis were performed with two-tailed tests. When testing for effects of isoflurane, comparisons were made against the oxygen-treated group, and differences are represented in the figures using asterisks. When testing for effects of L-655,708, comparisons were made against the corresponding vehicle-treated groups, and differences are represented in the figures using daggers.

The dose-response plot of minimum alveolar concentration was fit by nonlinear regression analysis using Sigmaplot software (Systat Software Inc., San Jose, Calif.) to estimate the concentration that caused 50% of the maximum effect ($EC_{50}$): $Y=Control+(I_{max}-Control)/(1+10^{(Log\ EC50-X)\cdot Hill\ slope})$, where Y is the response, $I_{max}$ is the maximum response, and X is the logarithm of the concentration.

Results

Motor and sensory function recovered within minutes after termination of isoflurane administration. In contrast, a robust deficit in contextual fear memory persisted for at least 24 h. L-655,708 completely prevented memory deficits without changing the immobilizing dose of isoflurane. Trace concentrations of isoflurane were measured in the brain 24 h after treatment.

Mice were pretreated with L-655,708 or vehicle then exposed to isoflurane (1 MAC or vehicle for 1 h). After a 1 h or 24 h recovery period, mice were trained to associate a foot shock with the context of a chamber (contextual fear learning) and an audible tone which was presented immediately before the shock (cued fear conditioning).

Short-Term and Long-Term Memory after Isoflurane—Isoflurane Causes Impairment in Short-Term Memory and Long-Term Memory that is Prevented by Pre-Administration of L-655,708

Short-term memory for contextual learning was studied by re-introducing the mice into the training chamber 30 min after fear conditioning. Those trained 1 h after isoflurane exhibited a memory deficit as evidenced by lower freezing scores compared with oxygen-treated controls (54.6±5.9%, n=11 versus 82.8±4.31%, n=12; P=0.003; FIG. 2A). Mice trained 24 h after isoflurane also exhibited lower freezing scores compared with controls (51.6±8.0%, n=12; P=0.0008; FIG. 2A). Thus, a short-term contextual memory deficit after isoflurane persists for at least 24 h.

L-655,708 completely reversed the short-term memory deficit for contextual learning as freezing scores at 1 h and 24 h after isoflurane (75.5±8.6%, n=9; P=0.04 and 81.9±5.6%, n=12; P=0.001, respectively; FIG. 2A) were similar to oxygen-treated control mice. It is important to note that L-655-708 had no effect on freezing in the oxygen-treated mice, suggesting a generalized enhancement of memory does not account for prevention of the post-isoflurane memory deficits (FIG. 2A). Post-hoc analysis revealed a main effect of isoflurane ($F_{(2,61)}=3.9$, P=0.03), L-655,708 ($F_{(1,61)}=9.2$, P=0.004) and their interaction ($F_{(2,61)}=3.6$, P=0.03) whereas L-655,708 had no effect on oxygen-treated mice (80.1±6.4%, n=11; P=0.76; FIG. 2A).

Short-term memory of the auditory tone was studied by placing mice in a novel context and re-introducing the audible tone 90 min after conditioning. Mice trained 1 h after isoflurane had lower freezing scores relative to oxygen-treated controls (35.7±6.43%, n=11 versus 68.9±8.3%, n=12; P=0.002; FIG. 2B) consistent with a deficit in short-term memory for cued learning. Mice trained 24 h after isoflurane exhibited no significant memory deficit to auditory tone (49.1+8.8%, n=12, P=0.08; FIG. 2B). L-655,708 prevented the short-term memory deficit to the tone in mice trained 1 h after isoflurane (49.1+8.8%, n=12; P=0.03, FIG. 2B), but had no effect on auditory recall in mice conditioned 24 h after exposure to isoflurane. Analysis of cued memory at 90 min revealed a main effect of isoflurane ($F_{(2,61)}$=4.9, P=0.01), and L-655,708 ($F_{(1,61)}$=5.4, P=0.02), but not for the interaction ($F_{(2,61)}$=0.8, P=0.5).

Long-term memory for contextual memory after isoflurane was studied by reintroducing the mice into the conditioning chamber 2 days after fear conditioning. Mice trained 1 h after isoflurane showed lower freezing scores than oxygen-treated controls (36.4±26.9%, n=11; versus 63.7±6.5%, n=12; P=0.02; FIG. 2C). This memory deficit that was completely reversed by pretreatment with L-655,708 (72.3±4.9%, n=9; P=0.004, FIG. 2C). In mice trained 24 hr after exposure to isoflurane, memory was significantly improved by L-655,708 compared with vehicle-treated controls (75.2±8.3%, n=12; P=0.02) although mice trained 24 h after isoflurane revealed only a trend towards lower freezing scores compared with air/oxygen controls (48.9±8.6%, n=12; P=0.18). Analysis revealed a main effect of L-655,708 ($F_{(1,61)}$=9.6, P=0.003), but not of isoflurane ($F_{(2,61)}$=1.0, P=0.4), or the interaction ($F_{(2,61)}$=2.1, P=0.1).

Long-term memory for the auditory tone was studied 2 days after fear conditioning. Long-term memory was reduced in mice trained 1 h after isoflurane exposure (21.8±23.1%, n=11 versus 49.5±6.8%, n=12; P=0.02). Mice trained 24 h after isoflurane showed no significant reduction in freezing scores (41.2±31.2%, n=12; P=0.48; FIG. 2D). L-655,708 did not reverse the long-term deficit in cued fear conditioning in the mice trained 1 h after isoflurane exposure (41.7±7.3%, n=9; P=0.13).

In FIG. 2A, freezing behavior to the context studied at 30 min after training. In FIG. 2B, freezing behavior to the audible cue at 90 min after training. In FIG. 2C, freezing behavior to the context at 2 days after training. In FIG. 2D, freezing behavior to the audible cue at 2 days after training. (1 h O2, vehicle: n=12; 1 h O2, L-655,708: n=11; 1 h Iso, vehicle: n=11; 1 h Iso, L-655,708: n=9; 24 h Iso, vehicle: n=12; 24 h Iso, L-655,708: n=12.) *P<0.05 and P<0.01, *P<0.001 compared to oxygen-treated subjects, 1 h, vehicle; †P<0.05 and ††P<0.01 compared to vehicle control. O2=oxygen-treated, Iso=isoflurane-treated.

L-655,708 Effects on MAC and Hypnosis—L-655,708 does not Affect MAC in Mice

Figure 3:
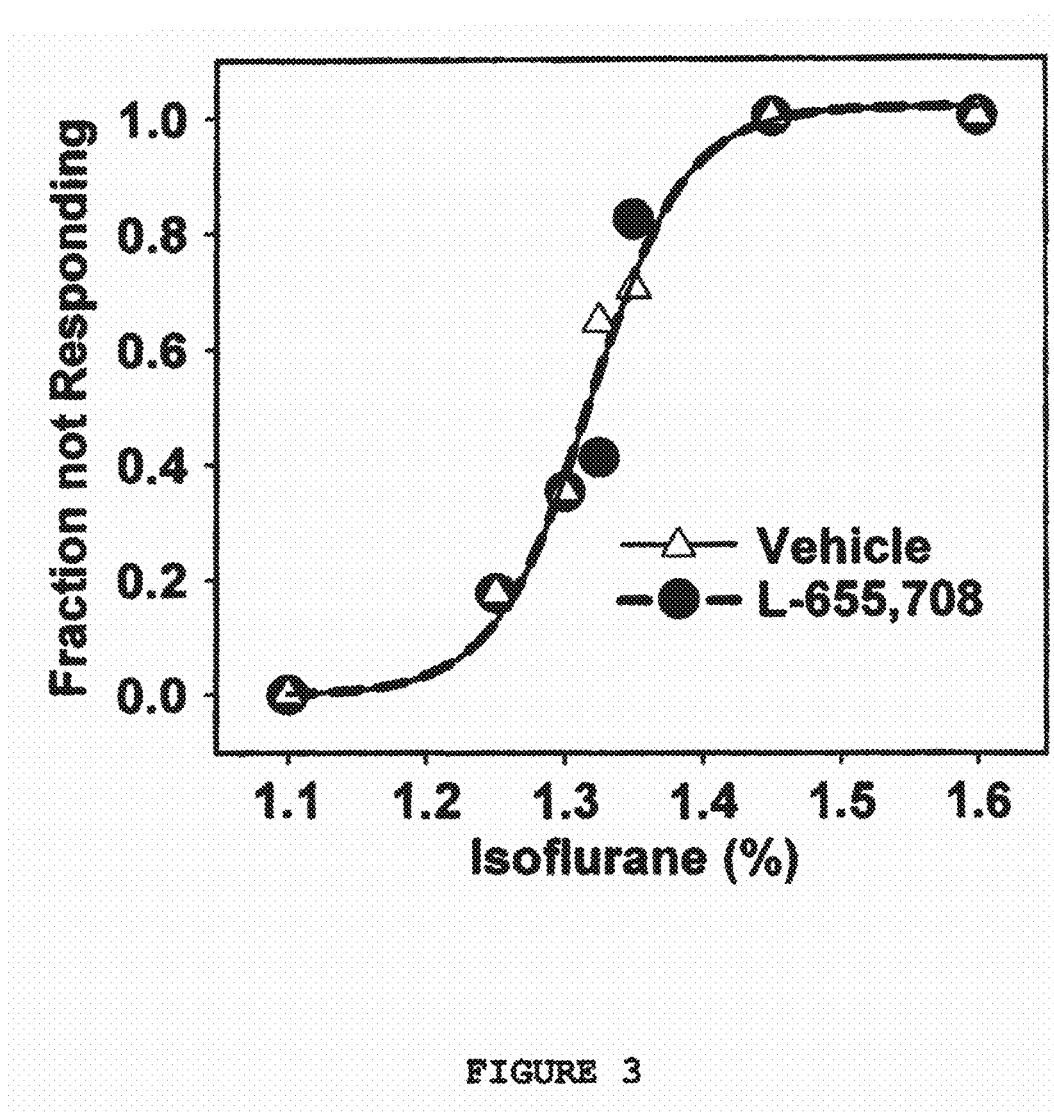
FIG. 3 illustrates the effect of pre-injection of L-655,708 on the minimum alveolar concentration (MAC) value of isoflurane in mice in Example 1.

It is possible that L-655,708 modified other components of the anesthetic state during isoflurane anesthesia including immobility and sedation. However, the tail-clamp assay showed that L-655,708 did not change the MAC value for isoflurane (FIG. 3). The immobilizing dose of isoflurane was similar in mice treated with L-655,708 (1.33±0.02, n=17) or vehicle (1.33±0.02, n=17, P>0.05). In addition, there was no significant difference in the time to self-right after the immobilizing dose of isoflurane was administered (vehicle: 153±26 s, L-655,708: 151±27 sec, n=9 for both groups, P>0.05). Thus, L-655,708 did not modify the "depth of anesthesia" as indicated by the immobilizing dose of isoflurane or the latency to recovery of the righting reflex following exposure to isoflurane.

In FIG. 3, pre-injection of L-655,708 did not alter the minimum alveolar concentration (MAC) value of isoflurane as measured using the tail-clamp assay when compared to vehicle-treated controls. Dose-response plots for the immobilizing dose of isoflurane revealed no difference in the EC50 values estimated from the fitted curves (mean±SEM, 1.32±0.048 versus 1.32±0.048, n=17 per group) for L-655,708-treated and vehicle-control mice, respectively.

L-655,708 does not Alter Baseline Freezing Scores—Isoflurane and L-655,708 do not Affect Baseline Freezing Behavior, Motor Function or Nociception in Mice.

The reduction in freezing scores observed 24 h after isoflurane was not associated with residual sedation or deficits in locomotion as evidenced by the lack of change in baseline freezing scores. Baseline freezing scores, measured during the training phase immediately before the presentation of the tone, were identical to controls studied 1 h after oxygen alone (n=12; FIG. 4A, Context), 1 h after isoflurane (n=11, P=1.0; FIG. 4A, Context) and 24 h after isoflurane (n=12; P=1.0; FIG. 4A, Context). No main effects were detected (isoflurane: $F_{(2,61)}$=0.8, P=0.4; L-655,708: $F_{(1,61)}$=3.2, P=0.08; isoflurane X L-655,708: $F_{(2,61)}$=0.8, P=0.4). It is also notable that L-655,708 did significantly increase freezing to context during training in oxygen-treated controls (n=11; P=1.0; FIG. 4A, Context), 1 h after isoflurane (n=9; P=0.11; FIG. 4A, Context), or 24 h after isoflurane (n=12; P=0.15; FIG. 4A, Context). Similarly, baseline freezing scores to the tone, measured during the training phase immediately before the delivery of the shock were not significantly different in oxygen-treated controls (n=12; FIG. 4A, Tone), 1 h isoflurane group (n=11; P=0.4; FIG. 4A, Tone), or the 24-h isoflurane group (n=12; P=1.0; FIG. 4A, Tone). In addition, L-655,708 alone did not alter the baseline motor activity, as no change in freezing to the yet unpaired tone was shown in oxygen-treated controls (n=11; P=0.4; FIG. 4A, Tone) at 1 h after isoflurane (n=9; P=0.4; FIG. 4A, Tone) and 24 h after isoflurane (n=12; P=0.12; FIG. 4A, Tone). Also, freezing scores measured immediately after the presentation of the foot shock did not differ between oxygen-treated subjects (n=12; FIG. 4A, After-Shock), subjects given 1 h to recovery from isoflurane anesthesia (n=11; P=0.79; FIG. 4A, After-Shock), or subjects given 24 h to recovery after isoflurane anesthesia (62.1.0; FIG. 4A, After-Shock).

Equally important, L-655,708 did not affect post-shock freezing in the oxygen group (n=12; P=0.8; FIG. 4A, After-Shock), 1 h isoflurane group (n=11; P=0.74; FIG. 4A, After-Shock), or 24 h isoflurane group (n=12; P=0.4; FIG. 4A, After-Shock), indicating that the ability of mice to sense the noxious stimulus was unaltered. Finally, isoflurane and L-655,708 did not promote non-specific freezing, as no differences in freezing to the modified context at 90 min were detected (isoflurane: $F_{(2,60)}$=3.7, P=0.03; L-655,708: $F_{(1,60)}$=1.7, P=0.2; isoflurane X L-655,708: $F_{(2,60)}$=0.9, P=0.4) between the three groups injected with vehicle (oxygen-treated, n=12; 1 h isoflurane, n=11; P=0.06; 24-h isoflurane, n=12; P=0.09; FIG. 4B) or L-655,708 (oxygen-treated, n=11; P=0.8; 1-h isoflurane, n=9; P=0.9; 24-h isoflurane, n=12; P=0.06; FIG. 4B). Similarly, no differences in freezing to the modified context after 2 days were detected (isoflurane: $F_{(2,61)}$=2.6, P=0.08; L-655,708: $F_{(1,61)}$=0.2, P=0.7; isoflurane X L-655,708: $F_{(2,61)}$=1.4, P=0.3) between the three groups injected with vehicle (oxygen-treated, n=12; 1-h isoflurane, n=11, P=0.7; 24-h isoflurane, n=12; P=0.07; FIG. 4B) or L-655,708 (oxygen-treated, n=11; P=0.7; 1-h isoflurane, n=9; P=0.6; 24-h isoflurane, n=12; P=0.1; FIG. 4B).

In FIG. 4A, baseline freezing before tone-shock pairing in the fear conditioning chamber prior to the tone (Context), during the tone (Tone), and immediately after delivery of the mild foot shock (After-Shock). In FIG. 4B, freezing in a modified context at the indicated time intervals after training. (1 h O2, vehicle: n=12; 1 h O2, L-655,708: n=11; 1 h Iso, vehicle: n=11; 1 h Iso, L-655,708: n=9; 24 h Iso, vehicle: n=12; 24 h Iso, L-655,708: n=12). 02=oxygen-treated, Iso=isoflurane-treated.

Anxiety in Isoflurane-Treated Mice—Other Effects of Isoflurane Subside by 1 h after Anesthesia General anesthetics modify a variety of behavioral end points that could confound studies of fear memory, including anxiety, motor coordination and nociception. Therefore, additional control experiments were performed to determine whether these behavioral end points were modified 1 h and 24 h after anesthesia. To measure anxiety, an elevated plus maze trial was performed 10 min before the training phase of fear conditioning. In this task, performance was similar in all groups indicating that anxiety was not effected (for example, time spent in closed arms: isoflurane: $F_{(1,63)}=2.0$, P=0.2; L-655,708: $F_{(1,63)}=1.2$, P=0.3; isoflurane X L-655,708: $F_{(2,60)}=0.06$, P=0.8; FIGS. 5A, 5B, 5C). In the elevated plus maze, the total number of visits to the middle area (the standard measure of activity in the elevated plus maze) was not statistically different for any of the groups (1 h $O_2$, vehicle: mean=17.2±2.7; 1 h $O_2$, L-655,708: mean=19.5±8.5, p=0.97; 1 h Iso, vehicle: mean=19.9±4.6, p=1.0; 1 h Iso, L-655,708: mean=17.3±7.0, p=0.99; 24 h Iso, vehicle: mean=18.1±5.3, p=1.0; 24 h Iso, L-655,708: mean=13.6±7.1, p=0.71) suggesting that sedative effects of isoflurane did not confound studies of memory.

Though we did observe a decrease in time spent in the open arm for mice given 24 h to recover from isoflurane and pretreated with L-655,708, there was no associated change in the time spent in the closed arms or was there a reduction in the total number of crossings. Moreover, since neither isoflurane, nor L-655,708 had any effect on anxiety on their own, and in combination they had no effect when mice we allowed to recovery from isoflurane for only 1 hr prior to experimentation, differences in anxiety cannot account for the observed isoflurane-induced memory impairment and prevention by L-655,708.

In FIGS. 5A-C, amount of time spent in the indicated region of the elevated plus maze. (O2, 1 h, vehicle: n=12; 02, 1 h, L-655,708: n=11; Iso, 1 h, vehicle: n=11; Iso, 1 h, L-655,708: n=9; Iso, 24 h, saline: n=12; Iso, 24 h, L-655, 708: n=12).

Motor Performance and Nociception in Isoflurane-Treated Mice

In a separate group of mice, motor coordination and the agility of mice was studied with a balance beam test 1 h after exposure to isoflurane or vehicle. No differences were observed between treatment groups for either the crossing times (vehicle n=12, isoflurane n=12; F(1.22)=0.1, P=0.70; FIG. 5D) or the number of foot slips (vehicle n=12, isoflurane n=12; F(1.22)=0.004, P=0.84; FIG. 5E).

Non-associative fear learning is correlated with the intensity of the electric shock[27] and it was therefore important to ensure that all groups perceived the same strength of stimulus. Thus, nociception was studied in a separate group of mice using the tail flick assay 1 h after exposure to isoflurane or vehicle. No differences were detected in the latency to tail flick (vehicle n=12 isoflurane n=12; $F_{(1,22)}=0.007$, P=0.94; FIG. 5F), a result consistent with the observation that all groups had similar freezing scores after receiving the foot-shock.

In FIG. 5D, time required to cross the elevated beam. In FIG. 5E, number of times the hind foot slipped while crossing an elevated beam. In FIG. 5F, latency to flick tail away from a hot water bath. (n=6 per group). *P<0.05 compared to O2, 1 h, saline. O2=oxygen-treated, Iso=isoflurane-treated.

Blood Gas Analysis—Isoflurane Pharmacokinetics

Since inhaled anesthetics depress respiration, one could argue hypoxic brain injury contributed to deficits in hippocampus-dependent memory performance in the experimental paradigm. To ensure that hypoxia was not a contributing factor, arterial blood gases were analyzed in separate groups of mice following isoflurane anesthesia (1 MAC in 30% $O_2$) for 1 h or 5 min. Hypoxia did not occur (Table 1). In addition, similar values for pH, concentration of bicarbonate, and partial pressure of carbon dioxide and oxygen were obtained (Table 1).

TABLE 1

Blood Gas Analysis for Mice Anesthetized with Isoflurane for 5 versus 60 min

| Measure | 5 min (n = 6) | 60 min (n = 6) | P Value |
|---|---|---|---|
| pH | 7.28 ± 0.02 | 7.23 ± 0.08 | 0.51 |
| pCO$_2$ (mmHg) | 48.6 ± 2.02 | 54.2 ± 12.3 | 0.41 |
| pO$_2$ (mmHg) | 142 ± 16 | 193 ± 31 | <0.001 |
| HCO$_3$ (M) | 22.0 ± 0.8 | 21.9 ± 2.5 | 0.78 |

Isoflurane Concentration in the Brain 1 h and 24 h after Anesthesia

The true clearance rate of isoflurane from the mammalian brain remains unknown. At least two rates of clearance have been observed, including one for clearance from the blood and the other for clearance from tissues, particularly those with high fat content.[28] The concentrations of isoflurane have not been previously measured in mice 24 h after treatment and are commonly assumed to be negligible. Thus, we measured the concentration of isoflurane in the brains of mice 1 h and 24 h after isoflurane anesthesia using gas chromatography. In addition, as a positive control, the concentration of isoflurane in the brain was measured 5 min after treatment. The isoflurane concentration in the brain was several times higher at 5 min after treatment than at 1 h after treatment as predicted (5 min: 0.814±0.194%, n=4; 1 h: 0.034±0.012%, n=6; P=0.0007; FIG. 6A). Surprisingly at 24 h, residual concentrations of isoflurane were detected in 5 of 6 brains (0.0095±0.0006%, n=6; P=0.0005; FIG. 6A). Of these five brains, two showed higher concentrations (0.0222%, 0.0311%) than the other three (0.0006%, 0.0012%, and 0.0019%). One brain had zero detectable isoflurane. Similarly, no isoflurane was detected in the brains of mice exposed to vehicle alone (n=4). The limit of isoflurane detection is approximately 0.0001%. The concentration of isoflurane in expired gas, measured immediately after the mice were removed from the chamber, decreased to an undetectable level within 7 min (FIG. 6B). Not surprisingly, the ability to detect isoflurane in the expired gas failed to correlate with the detection of isoflurane in the brain, suggesting the existence of separate rates of clearance.

Core Temperature

Rectal temperature was 37.8±0.4° C., at 5 min after introducing the mice into the anesthetic chamber and was 37.8±0.4° C. at 1 h after induction (n=6 per group; $F_{(1,10)}=0.02$, P=1.0). The corresponding chamber temperatures were 33.6±0.4° C. and 33.4±0.5° C., respectively (n=6 pre group, $F_{(1,10)}=0.06$, P=0.8).

Discussion

The current study demonstrates a robust memory deficit for hippocampus-dependent learning that persists for at least 24 h after a relatively brief exposure to isoflurane anesthesia in healthy adult mice. The memory impairment was dissociated from other residual effects of isoflurane including analgesia, sedation, anxiolysis and motor impairment. Pretreatment with L-665,708 prevented deficits in short-term and long-term memory for contextual learning without altering baseline memory behavior or motor scores. Gas chromatographic analysis revealed undetectable or trace concentrations of isoflurane 24 h after anesthesia.

The detection of residual brain concentrations of isoflurane 24 h after anesthesia was unexpected as this time interval is generally considered to be a sufficient to avoid the confounding effects of residual anesthetic on neurobehavioral performance.[29] Isoflurane undergoes minimal biodegradation (less than 0.2% is metabolized) and nearly 100% of isoflurane can be recovered in expired gas.[30] The presence of trace levels of isoflurane raises the possibility that a direct effect of isoflurane on neuronal networks causes post-anesthetic memory deficits. However, the best available evidence from previous studies indicates that much higher concentrations of isoflurane are required to block fear-conditioned memory.[31,32] Isoflurane concentrations as high as 0.6% are required to impair the freezing response when administered during contextual fear learning.[31] Also, the threshold concentrations of four commonly used anesthetics that impaired memory performance in rats during fear conditioning were 0.2% for isoflurane, 0.3% for sevoflurane, 0.3% for halothane, and 0.44% for desflurane.[32] Isoflurane concentrations measured in the current study at 24 h after anesthesia were orders of magnitude lower than those shown to directly impair memory. Consequently, the isoflurane detected at 24 h most likely represent an incidental finding rather than the direct cause of memory impairment. Instead, post-anesthetic memory deficits more likely result from yet-to-be identified processes that were initiated during exposure to high, "anesthetic" drug doses. An alternative hypothesis is that the initial exposure to a high concentration of isoflurane (1MAC) pre-conditioned or primed the neuronal circuitry, rendering it sensitive to trace concentrations of isoflurane in the post-anesthetic period. These hypotheses cannot be resolved with the current data and are worthy of future study.

L-655,708 prevented memory impairment without altering performance in oxygen-treated controls. Inverse agonists, including L-655,708 have a negative and opposite effect to that of classical agonists (e.g. midazolam). Inverse agonists decrease channel opening whereas benzodiazepine agonists enhance channel opening.[33,34] The dose of L-665,708 used in the present study was carefully selected to preferentially inhibit $\alpha 5GABA_A$ receptors. In vitro electrophysiological and biochemical studies have confirmed that L-655,708 has a preference for $\alpha 5GABA_A$ receptors that is 107-fold, 61-fold and 54-fold greater than $GABA_A$ receptors containing the $\alpha 1$, $\alpha 2$ and $\alpha 3$ subunits, respectively.[18] In addition, L-655,708, preferentially inhibits $\alpha 5GABA_A$ receptor-mediated currents in the hippocampus.[35] L-655,708, administered at a dose of 1 mg/kg (intraperitoneal) has previously been shown to yield 64% receptor occupancy of the $\alpha 5GABA_A$ receptor but only 18% occupancy of $\alpha 1$, $\alpha 2$ and $\alpha 3$ subunit-containing $GABA_A$ receptors.[33] L-665,708 rapidly achieves its rapid peak dose (t=0.25 h)[34] and has a relatively short half-life (0.5 h), despite a low plasma clearance rate (19 mL/kg in a rat model). Following subcutaneous injection, concentrations in the brain mimic those in the plasma, which indicates no tendency for L-655,708 to remain in the brain.[34] Thus, we assumed that L-655,708 was cleared 24 h after administration. L-655,708 likely prevents $GABA_A$ receptor activation during the initial exposure to isoflurane. Consistent with this notion, are the results of a previous study that showed L-655,708 acts on $\alpha 5GABA_A$ receptors to prevent memory blockade by etomidate.[9] The memory protective effect of L-655,708 is attributed to reduced $\alpha 5GABA_A$ receptor activity, although effects on other $GABA_A$ receptor subtypes cannot be entirely ruled out.

Fear-conditioning studies offer temporal resolution that can distinguish between short-term and long-term memory.[36] In our study, short-term memory was more strongly affected by pretreatment with isoflurane than long-term memory, particular when the subjects were allowed 24 h to recover from anesthesia prior to fear conditioning training. These results are interesting, given that the mechanisms involved in short-term and long-term memory are beginning to be understood as molecularly distinct processes.[12,36-40] Persistent memory-impairing effects of isoflurane may be mediated by alterations in the early phases of plasticity, in line with recent evidence from mouse slice preparations.[9] Isoflurane blocks the induction phase of long-term potentiation, an effect that can be reversed by inhibiting $GABA_A$ receptors with the competitive antagonist bicuculline.[41] Similarly, increased activity of $\alpha 5GABA_A$ receptors by etomidate prevents the induction of long-term potentiation in the hippocampus, an effect that can be reversed by L-655,708.[9] Long-term memory is strongly correlated with the maintenance of long-term potentiation and protein synthesis processes that underlie long-lasting plasticity.[42] The behavioural data presented in this study suggest the underlying mechanisms of long-term memory may be less liable to isoflurane anesthesia. Still, inhaled anesthetics are known to modify immediate-early gene transcription in response to early learning events.[32, 43] Whether L-655,708 reverses the effects of isoflurane on synaptic plasticity and protein translation remains to be determined.

There are several potential limitations of the current study. One possibility is that an unknown fraction of isoflurane was lost from the brain during transfer to the closed Teflon syringes. However, others have used similar methods to measure and compare isoflurane concentrations in the brain and blood of rabbits.[25] Two rates of clearance for inhaled anesthetics have been observed, one for clearance from the blood and the other for clearance from tissues, particularly those with high fat content.[28] After 270 min of elimination following isoflurane (1.3% for 90 min), 96% of the isoflurane had left the brain.[28] Furthermore, the blood and brain results were comparable after 30 and 90 min, which indicate that negligible amounts of anesthetic were lost from the brain samples.[28] Thus, we expect that the concentrations of isoflurane measured in the current study accurately reflect brain concentrations.

Post-anesthesia memory deficits in humans and animal subjects likely differ in time course and severity, in part due to allometric scaling and pharmacokinetics. Indeed, mice ambulate within minutes after terminating the anesthetic, suggesting a more rapid recovery time compared to humans. Also, the management of anesthesia in clinical practice and animal studies differs in terms of monitoring, the impact of noxious stimuli and the strict management of hemodynamic and biochemical parameters.[44] Surgery and inflammation could exacerbate the severity or extend the time course of anesthesia-related memory deficits.[45] The current results should prompt clinical studies to determine the incidence, severity and functional impact of memory deficits in the early-post anesthetic period. Among elderly patients, the incidence of postoperative cognitive dysfunction 24 h after sevoflurane anesthesia for minor surgery has been estimated to be as high as 47%.[4] Also, patients who underwent isoflurane or propofol anesthesia for interventional neuroradiological procedures showed memory decline for up to 24 h relative to their preoperative performance.[46] The functional consequence of such deficits is unknown but may have practical significance. Patients may need to have explicit recall for important information or undertake cognitively demanding tasks soon after their procedures. In particular, patients who undergo only brief diagnostic or surgical procedures typically expect to recover their baseline level of memory the day after anesthesia.

Since inhibiting α5GABA$_A$ receptors could promote intraoperative awareness, it is of interest to determine whether inverse agonists can treat as well as prevent memory deficits in the early post-anesthetic period. Older generations of non-selective inverse agonists such as the β-carboline, methyl-6,7-dimethoxy-4-ethyl-beta-carboline-3-carboxylate or FG 7142 (ZK-31906), improve memory performance; however these agents have epileptogenic and anxiogenic properties.[47] L-655,708 and orally administered selective inverse agonists selective for the α5GABA$_A$ receptor were not convulsant, pro-convulsant or axiogenic in animal studies.[33,48] In human volunteers, pretreatment with an inverse agonist for α5GABA$_A$ receptors, α5IA, reversed memory impairment for word-list learning after the ingestion of ethanol.[48-51] Animal studies are currently underway to determine whether the administration of L-655,708 after anesthesia and fear conditioning can rescue, as well as prevent memory deficits in the early post-anesthetic period.

Conclusions

Memory deficits occurred long after the sedative, analgesic and anxiolytic effects of isoflurane had subsided. L-655,708 prevented the memory deficit, suggesting an isoflurane interaction at α5GABA$_A$ receptors contributes to memory impairment during the early post-anesthesia period.

Reference List for Example 1

1. Johnson T, Monk T, Rasmussen L S, Abildstrom H, Houx P, Korttila K, Kuipers H M, Hanning C D, Siersma V D, Kristensen D, Canet J, Ibanaz M T, Moller J T: Postoperative cognitive dysfunction in middle-aged patients. Anesthesiology 2002; 96: 1351-7
2. Moller J T, Cluitmans P, Rasmussen L S, Houx P, Rasmussen H, Canet J, Rabbitt P, Jolles J, Larsen K, Hanning C D, Langeron O, Johnson T, Lauven P M, Kristensen P A, Biedler A, van Beem H, Fraidakis O, Silverstein J H, Beneken J E, Gravenstein J S: Long-term postoperative cognitive dysfunction in the elderly ISPOCD1 study. ISPOCD investigators. International Study of Post-Operative Cognitive Dysfunction. Lancet 1998; 351: 857-61
3. Newman M F, Kirchner J L, Phillips-Bute B, Gayer V, Grocott H, Jones R H, Mark D B, Reyes J G, Blumenthal J A: Longitudinal assessment of neurocognitive function after coronary-artery bypass surgery. N Engl J Med 2001; 344: 395-402
4. Rohan D, Buggy D J, Crowley S, Ling F K, Gallagher H, Regan C, Moriarty D C: Increased incidence of postoperative cognitive dysfunction 24 hr after minor surgery in the elderly. Can J Anaesth 2005; 52: 137-42
5. Monk T G, Weldon B C, Garvan C W, Dede D E, van der Aa M T, Heilman K M, Gravenstein J S: Predictors of cognitive dysfunction after major noncardiac surgery. Anesthesiology 2008; 108: 18-30
6. Culley D J, Baxter M, Yukhananov R, Crosby G: The memory effects of general anesthesia persist for weeks in young and aged rats. Anesth Analg 2003; 96: 1004-9
7. Culley D J, Baxter M G, Yukhananov R, Crosby G: Long-term impairment of acquisition of a spatial memory task following isoflurane-nitrous oxide anesthesia in rats. Anesthesiology 2004; 100: 309-14
8. Kandel E R: The biology of memory: A forty-year perspective. J Neurosci 2009; 29: 12748-56
9. Martin L J, Zurek A A, MacDonald J F, Roder J C, Jackson M F, Orser B A: α5GABA$_A$ receptor activity sets the threshold for long-term potentiation and constrains hippocampus-dependent memory. J Neurosci 2010; 30:5269-82
10. Barondes S H, Cohen H D: Memory impairment after subcutaneous injection of acetoxycycloheximide Science 1968; 160: 556-7
11. Izquierdo L A, Barros D M, Vianna M R, Coitinho A, deDavid e Silva T, Choi H, Moletta B, Medina J H, Izquierdo I: Molecular pharmacological dissection of short- and long-term memory. Cell Mol Neurobiol 2002; 22: 269-87
12. Tully T, Preat T, Boynton S C, Del Vecchio M: Genetic dissection of consolidated memory in *Drosophila*. Cell 1994; 79: 35-47
13. Hemmings H C, Jr., Akabas M H, Goldstein P A, Trudell J R, Orser B A, Harrison N L: Emerging molecular mechanisms of general anesthetic action. Trends Pharmacol Sci 2005; 26: 503-10
14. Caraiscos V B, Elliott E M, You-Ten K E, Cheng V Y, Belelli D, Newell J G, Jackson M F, Lambert J J, Rosahl T W, Wafford K A, MacDonald J F, Orser B A: Tonic inhibition in mouse hippocampal CA1 pyramidal neurons is mediated by alpha5 subunit-containing gamma-aminobutyric acid type A receptors. Proc Natl Acad Sci USA 2004; 101: 3662-7
15. Hanning C D: Postoperative cognitive dysfunction. Br J Anaesth 2005; 95: 82-7
16. Cheng V Y, Martin L J, Elliott E M, Kim J H, Mount H T, Taverna F A, Roder J C, Macdonald J F, Bhambri A, Collinson N, Wafford K A, Orser B A: Alpha5GABAA receptors mediate the amnestic but not sedative-hypnotic effects of the general anesthetic etomidate. J Neurosci 2006; 26: 3713-20
17. Martin L J, Oh G H, Orser B A: Etomidate targets alpha5 gamma-aminobutyric acid subtype A receptors to regulate synaptic plasticity and memory blockade. Anesthesiology 2009; 111: 1025-35
18. Quirk K, Blurton P, Fletcher S, Leeson P, Tang F, Mellilo D, Ragan C I, McKernan R M: [3H]L-655,708, a novel ligand selective for the benzodiazepine site of GABAA receptors which contain the alpha 5 subunit. Neuropharmacology 1996; 35: 1331-5
19. Bailey K R, Rustay N R, Crawley J N: Behavioral phenotyping of transgenic and knockout mice: Practical concerns and potential pitfalls. Ilar J 2006; 47: 124-31
20. Ip D T, Gong, D., Sonner, J., Roder, J., Orser, B. A., Eger, E. I.: Increased sensitivity to pentobarbital and volatile anesthetics in GluR2 deficient mice. Anesth Analg 1999; 88: 5349
21. Atack J R, Pike A, Clarke A, Cook S M, Sohal B, McKernan R M, Dawson G R: Rat pharmacokinetics and pharmacodynamics of a sustained release formulation of the GABAA α5-selective compound L-655,708. Drug Metab Dispos 2006; 34: 887-93
22. Homanics G E, Ferguson C, Quinlan J J, Daggett J, Snyder K, Lagenaur C, Mi Z P, Wang X H, Grayson D R, Firestone L L: Gene knockout of the alpha6 subunit of the gamma-aminobutyric acid type A receptor: Lack of effect on responses to ethanol, pentobarbital, and general anesthetics. Mol Pharmacol 1997; 51: 588-96

23. Joo D T, Gong D, Sonner J M, Jia Z, MacDonald J F, Eger E I, 2nd, Orser B A: Blockade of AMPA receptors and volatile anesthetics: Reduced anesthetic requirements in GluR2 null mutant mice for loss of the righting reflex and antinociception but not minimum alveolar concentration. Anesthesiology 2001; 94: 478-88

24. Mihic S J, McQuilkin S J, Eger E I, 2nd, Ionescu P, Harris R A: Potentiation of gamma-aminobutyric acid type A receptor-mediated chloride currents by novel halogenated compounds correlates with their abilities to induce general anesthesia. Mol Pharmacol 1994; 46: 851-7

25. Strum D P, Johnson B H, Eger E I, 2nd: Elimination of anesthetics from rabbit brain. Science 1986; 234: 1586-8

26. Liu J, Laster M J, Taheri S, Eger E I, 2nd, Chortkoff B, Halsey M J: Effect of n-alkane kinetics in rats on potency estimations and the Meyer-Overton hypothesis. Anesth Analg 1994; 79: 1049-55

27. Kamprath K, Wotjak C T: Nonassociative learning processes determine expression and extinction of conditioned fear in mice. Learn Mem 2004; 11: 770-86

28. Wyrwicz A M, Conboy C B, Ryback K R, Nichols B G, Eisele P: In vivo 19F-NMR study of isoflurane elimination from brain. Biochim Biophys Acta 1987; 927: 86-91

29. Bekker A, Shah R, Quartermain D, Li Y S, Blanck T: Isoflurane preserves spatial working memory in adult mice after moderate hypoxia. Anesth Analg 2006; 102: 1134-8

30. Holaday D A, Fiserova-Bergerova V, Latto I P, Zumbiel M A: Resistance of isoflurane to biotransformation in man. Anesthesiology 1975; 43: 325-32

31. Rau V, Oh I, Laster M, Eger E I, 2nd, Fanselow M S: Isoflurane suppresses stress-enhanced fear learning in a rodent model of post-traumatic stress disorder. Anesthesiology 2009; 110: 487-95

32. Alkire M T, Gorski L A: Relative amnesic potency of five inhalational anesthetics follows the Meyer-Overton rule. Anesthesiology 2004; 101: 417-29

33. Atack J R, Bayley P J, Seabrook G R, Wafford K A, McKernan R M, Dawson G R: L-655,708 enhances cognition in rats but is not proconvulsant at a dose selective for alpha5-containing GABAA receptors. Neuropharmacology 2006; 51: 1023-9

34. Atack J R, Pike A, Clarke A, Cook S M, Sohal B, McKernan R M, Dawson G R: Rat pharmacokinetics and pharmacodynamics of a sustained release formulation of the GABAA alpha5-selective compound L-655,708. Drug Metab Dispos 2006; 34: 887-93

35. Casula M A, Bromidge F A, Pillai G V, Wingrove P B, Martin K, Maubach K, Seabrook G R, Whiting P J, Hadingham K L: Identification of amino acid residues responsible for the alpha5 subunit binding selectivity of L-655,708, a benzodiazepine binding site ligand at the GABA(A) receptor. J Neurochem 2001; 77: 445-51

36. Schafe G E, Nadel N V, Sullivan G M, Harris A, LeDoux J E: Memory consolidation for contextual and auditory fear conditioning is dependent on protein synthesis, PKA, and MAP kinase. Learn Mem 1999; 6: 97-110

37. Barondes S H: Cerebral protein synthesis inhibitors block long-term memory. Int Rev Neurobiol 1970; 12: 177-205

38. Peters M, Bletsch M, Catapano R, Zhang X, Tully T, Bourtchouladze R: RNA interference in hippocampus demonstrates opposing roles for CREB and PPlalpha in contextual and temporal long-term memory. Genes Brain Behav 2009; 8: 320-9

39. Saab B J, Georgiou J, Nath A, Lee F J, Wang M, Michalon A, Liu F, Mansuy I M, Roder J C: NCS-1 in the Dentate Gyms Promotes Exploration, Synaptic Plasticity, and Rapid Acquisition of Spatial Memory. Neuron 2009; 63: 643-56

40. Yin J C, Tully T: CREB and the formation of long-term memory. Curr Opin Neurobiol 1996; 6: 264-8

41. Simon W, Hapfelmeier G, Kochs E, Zieglgansberger W, Rammes G: Isoflurane blocks synaptic plasticity in the mouse hippocampus. Anesthesiology 2001; 94: 1058-65

42. Nguyen P V, Woo N H: Regulation of hippocampal synaptic plasticity by cyclic AMP-dependent protein kinases. Prog Neurobiol 2003; 71: 401-37

43. Ren Y, Zhang F J, Xue Q S, Zhao X, Yu B W: Bilateral inhibition of gamma-aminobutyric acid type A receptor function within the basolateral amygdala blocked propofol-induced amnesia and activity-regulated cytoskeletal protein expression inhibition in the hippocampus. Anesthesiology 2008; 109: 775-81

44. Loepke A W, McGowan F X, Jr., Soriano S G: CON: The toxic effects of anesthetics in the developing brain: The clinical perspective. Anesth Analg 2008; 106: 1664-9

45. Wan Y, Xu J, Ma D, Zeng Y, Cibelli M, Maze M: Postoperative impairment of cognitive function in rats: A possible role for cytokine-mediated inflammation in the hippocampus. Anesthesiology 2007; 106: 436-43

46. Munte S, Munte T F, Kuche H, Osthaus A, Herzog T, Heine J, Leuwer M, Piepenbrock S: General anesthesia for interventional neuroradiology: Propofol versus isoflurane. J Clin Anesth 2001; 13: 186-92

47. Mohler H, Rudolph U, Boison D, Singer P, Feldon J, Yee B K: Regulation of cognition and symptoms of psychosis: Focus on GABA(A) receptors and glycine transporter 1. Pharmacol Biochem Behav 2008; 90: 58-64

48. Chambers M S, Atack J R, Carling R W, Collinson N, Cook S M, Dawson G R, Ferris P, Hobbs S C, O'Connor D, Marshall G, Rycroft W, Macleod A M: An orally bioavailable, functionally selective inverse agonist at the benzodiazepine site of GABAA alpha5 receptors with cognition enhancing properties. J Med Chem 2004; 47: 5829-32

49. Chambers M S, Atack J R, Broughton H B, Collinson N, Cook S, Dawson G R, Hobbs S C, Marshall G, Maubach K A, Pillai G V, Reeve A J, MacLeod A M: Identification of a novel, selective GABA(A) alpha5 receptor inverse agonist which enhances cognition. J Med Chem 2003; 46: 2227-40

50. Dawson G R, Maubach K A, Collinson N, Cobain M, Everitt B J, MacLeod A M, Choudhury H I, McDonald L M, Pillai G, Rycroft W, Smith A J, Sternfeld F, Tattersall F D, Wafford K A, Reynolds D S, Seabrook G R, Atack J R: An inverse agonist selective for alpha5 subunit-containing GABAA receptors enhances cognition. J Pharmacol Exp Ther 2006; 316: 1335-45

51. Nutt D J, Besson M, Wilson S J, Dawson G R, Lingford-Hughes A R: Blockade of alcohol's amnestic activity in humans by an alpha5 subtype benzodiazepine receptor inverse agonist. Neuropharmacology 2007; 53: 810-20.

Example 2

The Role of $GABA_A$ Receptors in Postoperative Memory Deficits Memory and $\alpha 5 GABA_A$ Receptors Over the past 4 years, a new concept of how inhibitory transmission regulates learning and memory has emerged from our work. A tonic form of inhibition generated by extrasynaptic GABAA receptors (GABA$_A$Rs), rather than synaptic inhibition, prevents the formation of new memories (*J Neurosci* 2010). We found that this tonic inhibitory conductance is generated by a single receptor subtype known as α5GABA$_A$R, which is expressed predominantly in the hippocampus. This finding suggests that by selectively targeting α5GABA$_A$R function we can modify memory without causing the adverse effects associated with nonselective GABA$_A$R agonists (sedation, loss of consciousness) and antagonists (seizures, anxiety). Consistent with this postulate, we have confirmed that the anesthetic etomidate blocks the formation of new memory by up-regulating α5GABA$_A$Rs, as exemplified by the failure of etomidate to block memory in mice lacking these receptors (*J Neurosci* 2010; *Anesthesiology* 2009). Also, the memory-blocking properties of anesthetics can be dissociated from the other therapeutic effects of these drugs (sedation, analgesia, and hypnosis) based on pharmacogenetics (*J Neurosci* 2006). This dissociation is important because it helps to explain why some patients who have been given an anesthetic, and who appear to be unconscious, experience unintended explicit recall of surgical events, a phenomenon known as "intra-operative awareness" (*N Engl J Med* 2008). Our results have garnered attention from the public and the scientific community, as evidenced by invitations to write commentaries for high-profile journals, including *Scientific American* (2007) and *Trends in Neuroscience* (manuscript in preparation). We remain committed to translating our scientific discoveries into improvements in clinical outcomes, as evidenced by a clinical trial (*Pain Med* 2010) and review articles (*CMAJ* 2008; *Trends Pharmacol Sci* 2005; *Pharmacol Biochem Behav* 2008; *Anesthesiology*, under revision).

During previous studies we also examined, at the molecular and cellular levels, how α5GABA$_A$Rs regulate the networks in the hippocampus that subserve the formation of memory. We showed that α5GABA$_A$Rs set the threshold for the induction of long-term plasticity (*J Neurosci* 2010) and reduce neuronal excitability and the firing of action potentials via a shunting inhibition (*J Neurophysiol* 2007). During intense network stimulation, α5GABA$_A$Rs generate a slowly decaying inhibitory synaptic current, possibly because of spillover of transmitter from the synaptic cleft (*Neuropharmacology* 2010). Using tandem mass spectroscopy, we showed that native extrasynaptic GABA$_A$Rs in the hippocampus are composed primarily of α5β3γ2 subunits (*J Neurosci Res* 2009). Armed with this knowledge, we then studied recombinantly expressed α5β3γ2 subunits, showing that anesthetics act as powerful "supraagonists" to activate these receptors (manuscript in preparation).

Following another line of inquiry, we examined the role of extrasynaptic GABA$_A$Rs in acute pain processes. We showed that extrasynaptic δ subunit containing GABA$_A$Rs modulate acute nociception and are novel targets for non-opioid analgesics (*Pain*, under revision). Also, the analgesic properties of insulin (*Anesth Analg* 2004) could result from an increase in the potency of glycine at the glycine receptor caused by insulin's activation of tyrosine kinases (*Mol Pharmacol* 2007). Furthermore, nonsteroidal anti-inflammatory drugs increase the release of insulin from beta cells, which might contribute to the analgesic properties of these drugs (*Br J Pharmacol* 2007).

In another study, we provided the first in vitro evidence that the analgesic gabapentin activates extrasynaptic GABAARs (*Anesthesiology* 2006) possibly by increasing the production of neurosteroids (manuscript in preparation).

We showed that inflammation increases the expression and function of GABA$_A$Rs in the lung epithelium of mice and humans and identified a new strategy for the treatment of asthma (*Nat Med* 2007). Also, the activation of TRPM7 channels by low extracellular concentrations of calcium and magnesium triggers cell death (*Prot Natl Acad Sci USA* 2007). Conversely, impairment of hippocampus-dependent memory after ischemic neuronal injury is attenuated by inhibiting the TRPM7 channels (*Nat Neurosci* 2009).

Our long-term goal is to elucidate the molecular mechanisms of general anesthetics and to translate such knowledge to enhance patient care. Our recent studies focus on the memory-blocking properties of anesthetics, because memory deficits are present in over 25% of adult patients at the time of hospital discharge and in 10% at 3 months. Prolonged postoperative memory loss is associated with a reduction in quality of life, early retirement, and premature death. The mechanisms causing postoperative memory loss are unknown and there are no known strategies for treatment or prevention.

This study builds on our previous studies, in which we identified a "memory-blocking receptor" in the hippocampus that prevents the formation of new memories (*Proc Nayl Acad Sci USA* 2004; *J Neurosci* 2006; *J Neurophysiol* 2007; *J Neurosci* 2010). Specifically, GABA$_A$ receptors containing the α5 subunit (α5GABA$_A$ receptors) generate a tonic inhibitory conductance in hippocampal pyramidal neurons that prevents the induction of synaptic plasticity and the acquisition of new memory. The α5GABA$_A$ receptors are exquisitely sensitive to general anesthetics, which dramatically up-regulate their function, thereby causing profound memory blockade (*J Neurosci* 2004; *Anesthesiology* 2010). Inhibiting α5GABA$_A$ receptors during anesthesia, by either pharmacological or genetic interventions, prevents postoperative memory deficits, even though the dose of anesthetic that is required for surgery remains unchanged.

The prolonged time course of postoperative memory deficits prompted us to seek an endogenous regulator that enhances the activity of the memory-blocking receptor. For several reasons, we focused our search on the immune system. First, diseases and conditions that necessitate anesthesia, such as infection, cancer, and trauma often activate an inflammatory response. Second, the pro-inflammatory cytokine interleukin 1β (IL-1β) causes memory impairment through mechanisms that remain uncertain. Third, the levels of IL-1β in the hippocampus increase dramatically after surgery. Fourth, we showed that inflammation increases the expression of GABA$_A$ receptors in the lung (*Nat Med* 2007). Our exciting preliminary results show that IL-1β enhances a tonic inhibitory conductance in hippocampal pyramidal neurons that is likely generated by α5GABA$_A$ receptors. Furthermore, IL-1β and anesthetics appear to interact synergistically to up-regulate the function of α5GABA$_A$ receptors.

On the basis of the results summarized above, we propose the following general hypotheses: 1) IL-1β increases the activity of α5GABA$_A$ receptors, thereby causing memory deficits; and 2) the increase in activity of α5GABA$_A$ receptors caused by the synergistic interaction between IL-1β and anesthetics leads to profound memory loss. We will address these hypotheses with the following specific aims:

Aim 1: To identify the signalling pathways and mechanisms by which IL-1β increases the tonic inhibitory conductance in hippocampal pyramidal neurons.

Aim 2: To determine whether the increase in α5GABA$_A$ receptor activity caused by IL-1β impairs synaptic plasticity in vitro and memory in vivo.

Aim 3: To determine whether IL-1β and anesthetics interact synergistically to increase α5GABA$_A$ receptor activity, thereby enhancing the memory-blocking properties of anesthetics in vivo.

Aim 4: To determine whether inhibiting α5GABA$_A$ receptors attenuates postsurgical memory deficits in vivo. To address these questions, we will employ a variety of complementary approaches with animal models that include null mutant mice lacking the α5 subunit, and mice lacking the IL-1β receptors.

Insights regarding the regulation of α5GABA$_A$ receptors by IL-1β will have broad implications for the memory loss associated with anesthesia as well as for a variety of inflammatory diseases. Our results will have direct implications for dosing of anesthetics and for postoperative memory loss in patients at high risk for inflammation.

Our exciting results from the present studies determined that the same receptors that prevent the formation of new memories during general anesthesia contribute to undesirable persistent memory deficits in the postoperative period.

These studies build on our earlier studies, which were the first to identify a type of "memory-blocking receptor" that is expressed predominantly in the hippocampus[8,9]. We refer to these receptors as memory-blocking receptors because increasing their activity prevents the formation of new memory, whereas inhibiting them, by either genetic or pharmacological interventions, improves learning and memory performance for certain hippocampus-dependent tasks[9-13]. We also showed that anesthetics supra-enhance the activity of the memory-blocking receptors, thereby causing profound memory blockade[8,14]. Our present studies have determined that these receptors contribute to postoperative memory deficits and offer insights into the pathogenesis of many other memory disorders.

The proposed studies will focus on γ-aminobutyric acid (GABA) type A receptors (GABA$_A$Rs), which mediate the majority of inhibition in the brain[26,27]. Here, we briefly describe the properties of GABA$_A$Rs and our contributions to the field[2,8-11,14,25,28-34]. GABA$_A$Rs are chloride-permeable ion channels that are assembled from various classes of subunits (α1-6, β1-3, γ1-3, δ, ε, θ, π, and ρ1-3)[35,36]. They are categorized into two groups: synaptic GABA$_A$Rs, which consist predominantly of α1, β2, and γ2 subunits, and extrasynaptic GABA$_A$Rs, which consist of α5, β3, and γ2 subunits or, alternatively, α4 or α6, β2 or β3, and δ subunits[37,38].

Figure 7:
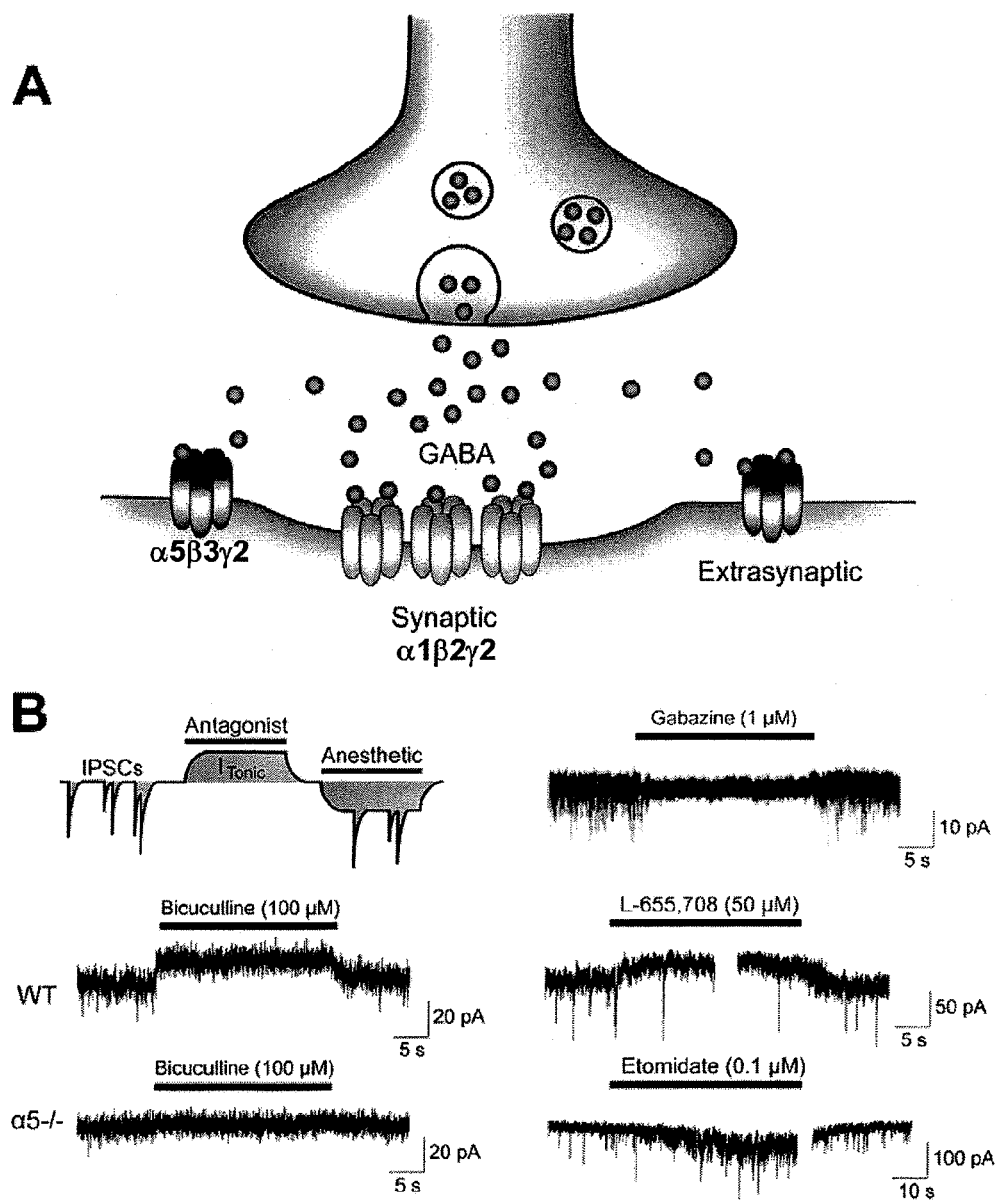
FIG. 7 illustrates the distinct pharmacological properties of extrasynaptic $GABA_A$ receptors.

Synaptic GABA$_A$Rs are transiently stimulated by near-saturating concentrations of GABA and generate transient postsynaptic potentials[37,39]. Extrasynaptic GABA$_A$Rs are activated by low ambient concentrations of GABA and generate a tonic inhibitory conductance that has distinct pharmacological properties (FIG. 7)[38,40-42]. FIG. 7 illustrates the distinct pharmacological properties of extrasynaptic GABA$_A$ receptors. FIG. 7A illustrates that synaptic receptors are typically composed of α1β2γ2 subunits whereas extrasynaptic GABA$_A$ receptors typically contain the α5 subunit in pyramidal neurons. FIG. 7B illustrates that the tonic current is revealed by an application of the GABA$_A$ receptor antagonist bicuculline in wild-type (WT) but not Gabra5−/− hippocampal neurons. Bicuculline blocks both the tonic and synaptic conductance. The GABA$_A$ receptor antagonist gabazine selectively inhibits the synaptic but not tonic current whereas the tonic current is selectively inhibited by the α5 subunit-selective inverse agonist, L-655,708. Low concentrations of the anesthetic etomidate selectively potentiate the tonic current.

Our previous studies were the first to identify an extrasynaptic GABAAR subtype that plays a pivotal role in learning and memory processes (PNAS 2004)[9]. These GABA$_A$Rs, which contain the α5 subunit (α5GABA$_A$Rs), are expressed predominantly in pyramidal neurons in the hippocampus[43,44]. We developed a method to isolate native α5GABA$_A$Rs and then used tandem mass spectroscopy to show that they are composed primarily of α5, β3, and γ2 subunits[29]. These extrasynaptic α5GABA$_A$Rs have biophysical properties quite different from those of the synaptic GABA$_A$Rs, which suggests that they serve distinct physiological roles.

Figure 8:
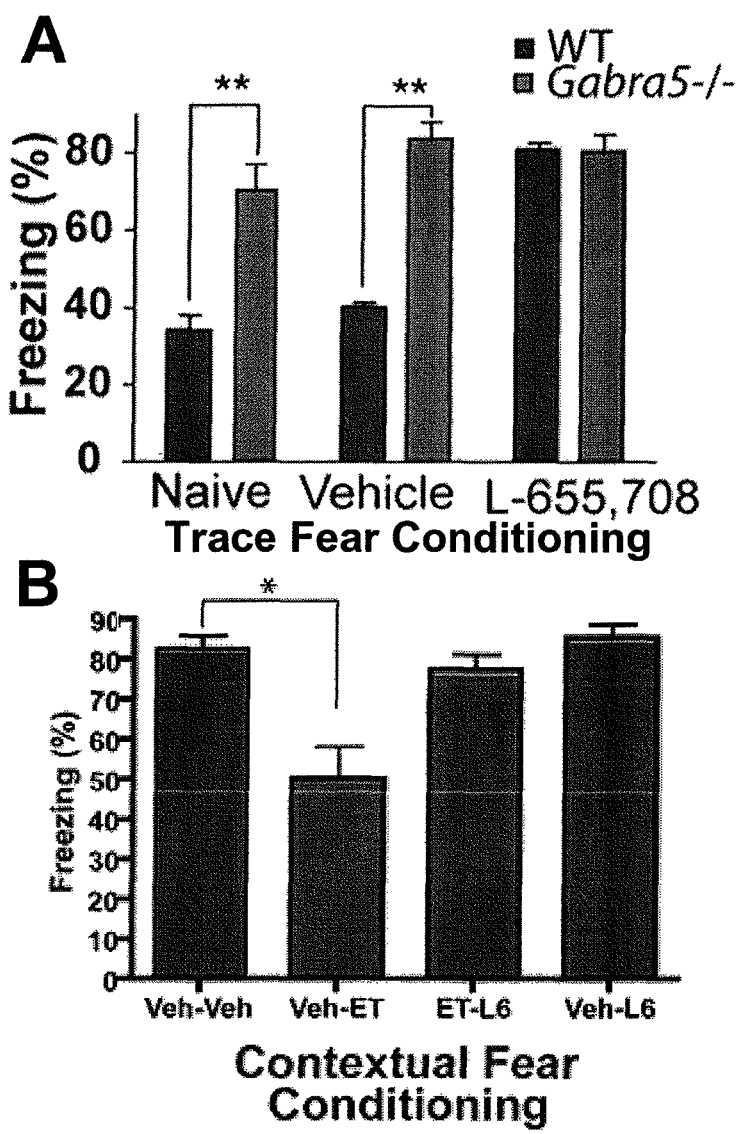
FIG. 8 illustrates that learning is modulated by $\alpha5$ $GABA_A$ receptor activity.

We have demonstrated that, for certain hippocampus-dependent tasks, mice lacking the α5 subunit (Gabra5−/−) exhibit better learning than wild-type (WT) controls[10,11]. Conversely, pharmacological inhibition of α5GABA$_A$Rs with the inverse agonist L-655,708 improves memory in WT mice (FIG. 8)[11]. FIG. 8 illustrates learning that is modulated by α5 GABA$_A$ receptor activity. In FIG. 8A WT and Gabra5−/− mice were injected with the α5 GABA$_A$R inverse agonist, L-655,708 (i.p.), 30 minutes prior to training with the trace fear memory paradigm. During the conditioning phase, each mouse was presented with an auditory tone which was followed 20 seconds later by a foot shock. The mouse learned to associate the conditioned (tone) and unconditioned (foot shock) stimuli despite the time or "trace" interval between the presentations. During testing, the tone was presented in a modified context. The Gabra5−/− mice exhibited higher freezing scores and therefore better memory recall when compared with WT mice. Similarly, WT mice treated with L-655,708 (1 mg/kg; i.p.) demonstrated increased freezing scores. In FIG. 8B mice were trained to associate a specific context with a foot shock. WT mice were treated with etomidate or etomidate plus L-655,708, 30 min prior to training. Etomidate reduced the freezing score whereas the co-administration of L-655,708 prevented the etomidate-induced memory deficit. Data are shown as mean±S.E.M. in all the figures.

Figure 9:
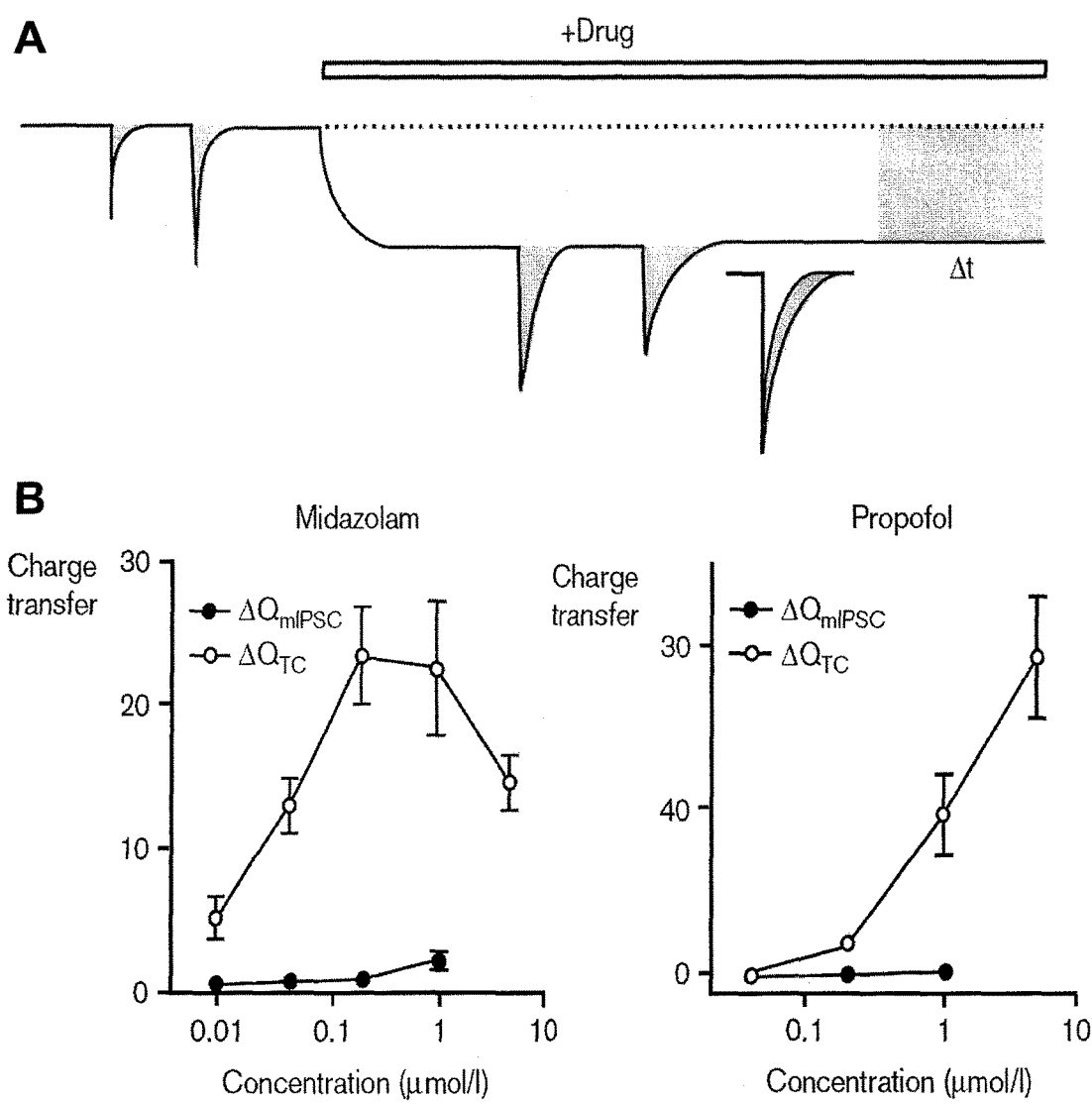
FIG. 9 illustrates a greater increase in the charge transfer associated with the tonic current compared to the synaptic current that is produced by midazolam and propofol.

Furthermore, α5GABA$_A$Rs are exquisitely sensitive to many classes of neurodepressive drugs, including benzodiazepines and anesthetics such as etomidate, propofol, and isoflurane[8,9,11,14,45]. These drugs "supra-enhance" the function of α5GABAARs beyond the normal physiological range (FIG. 9)[8], thereby impairing the formation of new memory (FIG. 8). FIG. 9 illustrates a greater increase in the charge transfer associated with the tonic current compared to the synaptic current that is produced by midazolam and propofol. FIG. 9A provide schematic drawings showing synaptic events, miniature inhibitory postsynaptic currents (mIPSCs), and tonic current before and during application of midazolam or propofol. The drugs enhance both tonic and synaptic currents. FIG. 9B illustrates the relationship between midazolam and propofol concentrations and the charge transfer associated with mIPSCs (closed circles) and tonic current (open circles). Midazolam and propofol produced a 7-21 fold and 6-33 fold greater increase in charge transfer for the tonic current than that for mIPSCs, respectively.

Figure 10:
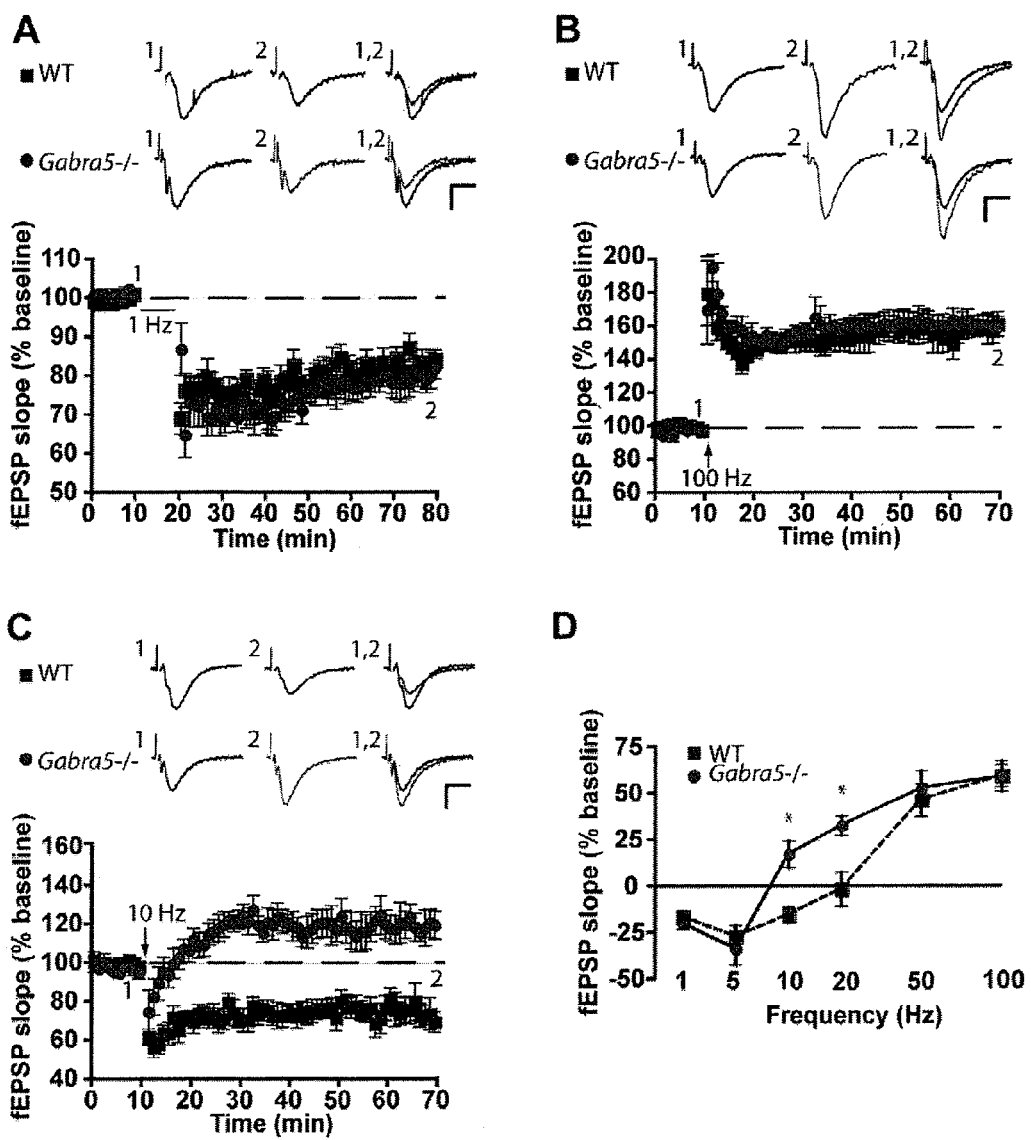
FIG. 10 illustrates $\alpha5$ $GABA_A$ receptor regulation of excitatory synaptic plasticity.

The mechanisms by which α5GABA$_A$Rs regulate the formation of new memories were examined by us in vitro. In one key study (J Neurosci 2010), we showed that α5GABA$_A$Rs play a role in modifying synaptic plasticity in the Schaeffer-collateral CA1 pathway by regulating the excitatory input required to induce long-term potentiation (LTP; FIG. 10)[28]. FIG. 10 illustrates α5 GABA$_A$ receptor regulation of excitatory synaptic plasticity. Low (FIG. 10A) and high (FIG. 10B) frequency stimulation induces similar plastic responses in both Gabra5−/− and wild-type (WT) slices. FIG. 10C illustrates that the lack of α5GABA$_A$Rs is associated with a lower threshold for synaptic potentiation when slices are stimulated with an intermediate—but not a low- or high-frequency stimulation protocol. Stimulation at 10 Hz for 1 min potentiates synaptic responses in Gabra5−/− but not WT slices. FIG. 10D illustrates the relationship for stimulus intensity versus synaptic potentiation or depression (n=8 slices/group). Sample traces are shown (black=pre-tetanus, blue or red=post-tetanus) above each figure for the times indicated by the numbers. Calibration: 0.5 mV, 5 ms. (* P<0.05). Notably, α5GABA$_A$Rs inhibit the induction of LTP when slices are simulated in the 10 Hz range, a frequency range that is associated with the acquisition of new memory in vivo[28,46,47]. In addition, α5GABA$_A$Rs cause a shunting inhibition that decreases the firing of action potentials[31].

Figure 11:
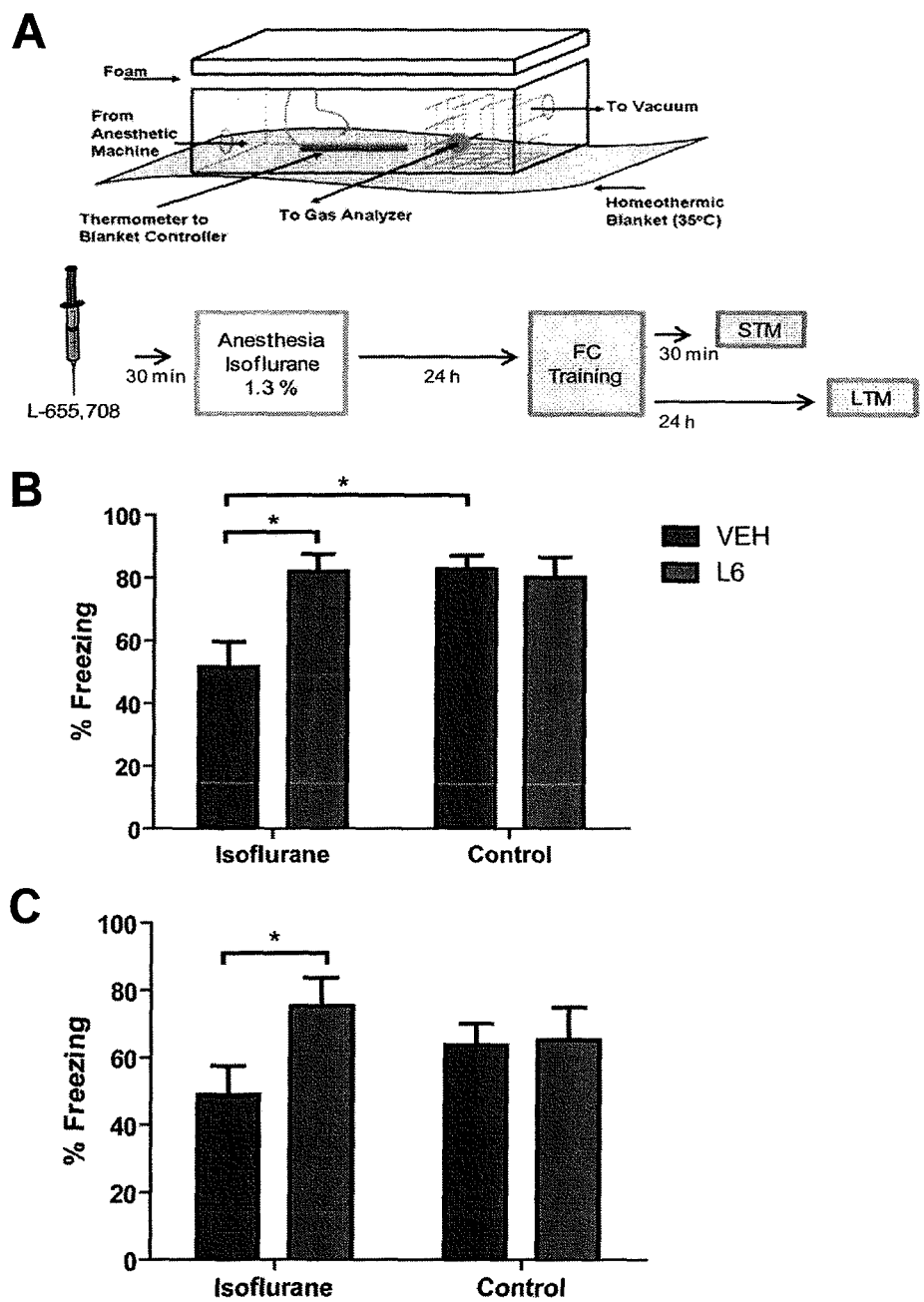
FIG. 11 illustrates L-655,708 reversal of memory impairment after isoflurane anesthesia.

Our more recent studies have shown that α5GABA$_A$Rs contribute to subtle memory deficits that persist long after initial exposure to a high dose of anesthetic[25]. A 1-hour exposure of C57Bl6/J mice to a standard dose of isoflurane (1.3% atm) caused memory deficits that persisted for at least 48 hours (FIG. 11). FIG. 11 illustrates L-655,708 reversal of memory impairment after isoflurane anesthesia. In FIG. 11A mice were exposed to 1 h of isoflurane (1.3% atm) in a heated, air-tight chamber. The timeline of the experiments is shown. Mice were injected with L-655,708 or vehicle 30 min prior to anesthesia. Twenty-four hours later, the mice were trained in the fear conditioning paradigm. FIG. 11B illustrates that short-term memory impairment (tested 30 min after training) was impaired by isoflurane. The impairment was prevented by pre-emptive treatment with L-655, 708. FIG. 11C illustrates that long-term memory impairment (tested 24 h after training) was impaired after isoflurane. This impairment was prevented by pre-emptive treatment with L-655,708. * P<0.05. Despite robust memory deficits, these mice behaved normally in other respects, with no evidence of sedation, analgesia, or motor impairment. Trace levels of isoflurane were detected in the brain for at least 24 hours after exposure to the standard dose of anesthetic.

Figure 12:
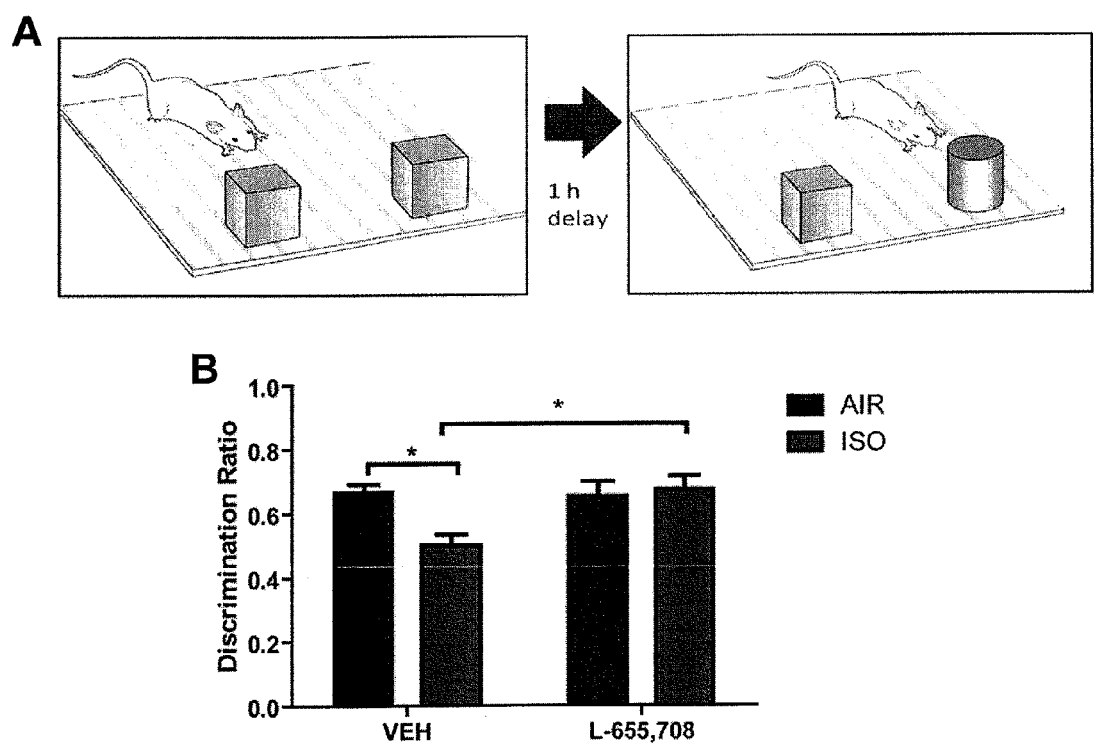
FIG. 12 illustrates L-655,708 reversal of isoflurane-induced memory deficits in Example 2.

In a preliminary study, a 1-hour exposure of WT mice to isoflurane caused memory deficits for object-recognition tasks[48] 24 hours later (FIG. 12). These memory deficits were reversed by treating the mice with L-655,708 on the day after anesthesia, 30 minutes before presentation of the novel objects (FIG. 12). FIG. 12A illustrates the object recognition paradigm is illustrated (modified from The Neurobiology of Learning and Memory, 2008). During the training phase, the mouse is exposed to two identical objects for 10 minutes. Following a one-hour delay, the mouse is presented with one familiar object and one novel object. Memory is assessed by comparing the preference (time spent) with the novel object when compared to the familiar object. The ratio of these values is the reported as the Discrimination Ratio. In FIG. 12B mice were exposed to isoflurane (1.3% atm) for 1 h then 24 hours later were studied with the novel object recognition task. The memory deficit observed in isoflurane-treated mice was reversed by L-655,708 (0.35 mg/kg) that was administered 30 min prior to the presentation of the novel objects (n=7 per group; *P<0.05). These results suggest that over-activation of α5GABA$_A$Rs contributes to profound memory blockade during general anesthesia and to persistent memory deficits in the early post-anesthetic period.

Postoperative Memory Deficits

Figure 13:
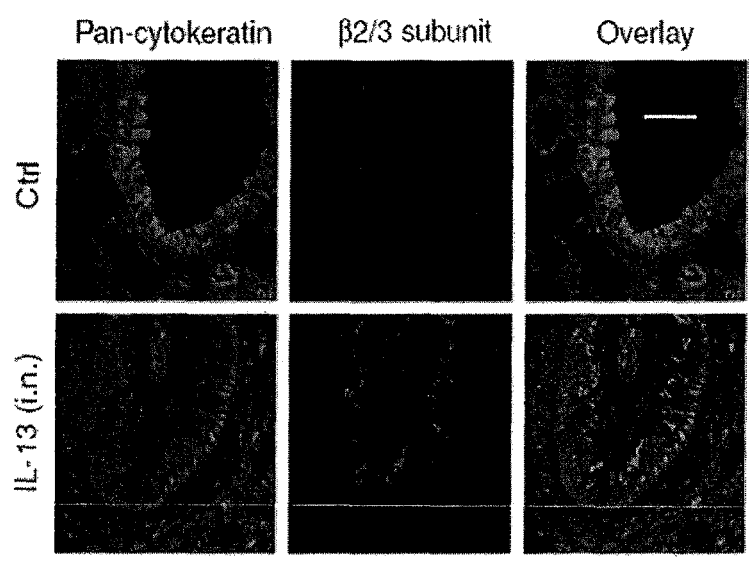
FIG. 13 illustrates the increase in immunostaining of the $GABA_A$ receptor $\beta2$ and $\beta3$ subunits by the inflammatory cytokine IL-13 in airway epithelial cells.
Figure 13:
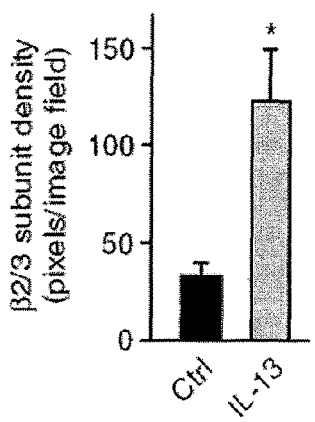

Given the persistence of postoperative memory deficits, we searched for an endogenous factor that up-regulates the function of α5GABA$_A$Rs. For several reasons, we focused our search on the immune system. First, diseases and conditions that necessitate surgery and anesthesia, such as infection, cancer, and trauma, often activate an inflammatory response[49]. Second, the pro-inflammatory cytokine interleukin 1β (IL-1β) causes memory impairment through mechanisms that are as yet uncertain[50-52]. Third, the levels of IL-1β in the hippocampus increase dramatically after surgery[53]. Fourth, we discovered that inflammation increases the expression of GABA$_A$ receptors in the lung (Nat Med 2007) (FIG. 13)[30]. FIG. 13 illustrates the increase in immunostaining of the GABA$_A$ receptor β2 and β3 subunits by the inflammatory cytokine IL-13 in airway epithelial cells. FIG. 13A illustrates typical confocal images showing immunofluorescence staining of GABA$_A$ receptor β2/3 subunits (red) in lung tissues from control and IL-13-treated mice. Scale bar, 20 mm. FIG. 13B provides a summary of the immunofluorescence density of β2/3 subunits in lung tissues demonstrating increased staining of β2/3 subunits following IL-13 treatment (* P<0.01). Although IL-1β is known to cause memory loss and impair synaptic plasticity, the key downstream effectors that can be targeted for therapeutic intervention have not been elucidated. Our exciting new results show that IL-1β enhances a tonic inhibitory conductance in hippocampal neurons that is putatively generated by α5GABA$_A$Rs.

Figure 14:
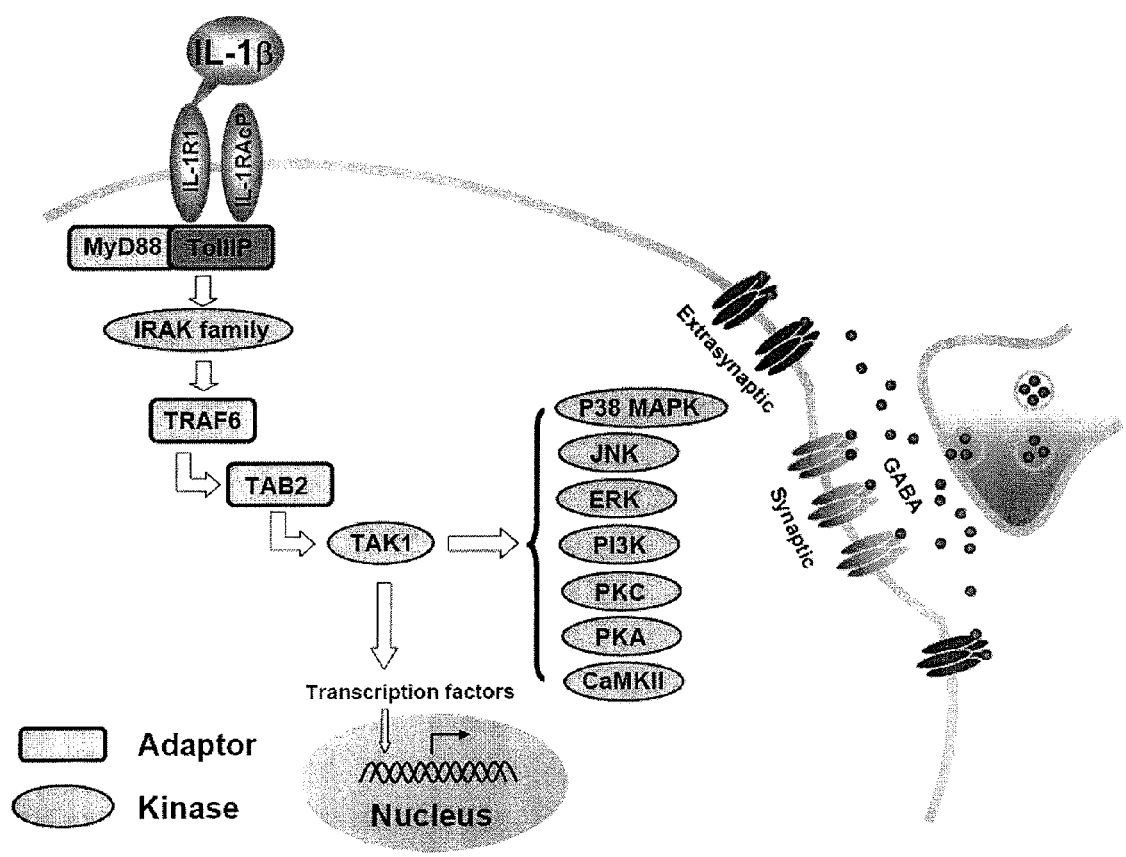
FIG. 14 illustrates the IL-1$\beta$ signalling pathways.

IL-1β is a pleiotropic cytokine that is produced in response to inflammation by a wide variety of immunocompetent cells in the periphery and by glia and neurons in the brain. The complex IL-1β signalling pathway is shown in FIG. 14[52,54,55]. IL-1β binds to and activates the type 1 IL-1 receptor (IL-1R1) which initiates the formation of a complex between IL-1R1 and the IL-1 receptor Accessory Protein (IL-1RAcP). The cytosolic proteins MyD88 (Myeloid Differentiation primary response gene-88) and IRAK family TollIP (Toll-IL-1β Interacting Protein) are recruited to the complex, where they function as protein adaptors and recruit IRAK (IL-1 Receptor-Associated Kinase), in turn. IRAK, a serine-threonine kinase, activates and recruits TRAF6 (TNF Receptor-Associated Factor-6) to the IL-1R1 complex. TRAF6 activates TGF-Beta-Activating Kinase-1 (TAK-1) via TAB2 (TAK1 Binding Protein), which further activates p38 MAPK, a host of cytosolic signaling facts and various transcription factors, such as nuclear factor-kappa B (NF-kB). The binding of IL-1ra (IL-1 receptor antagonist) prevents this signalling pathway by blocking the IL-1R1 receptor. Note that the naturally occurring IL-1 receptor antagonist (IL-1ra) blocks the actions of IL-1β by inhibiting the type 1 IL-1 receptor (IL-1R1), without activating cytosolic signalling[55-57].

Other studies support a role for IL-1β in the pathogenesis and persistence of postoperative memory deficits[58-60]. In patients who had undergone surgery, the incidence of poor cognitive outcome was higher among those with a polymorphism for IL-1β[61]. Given the putative causal role of IL-1β in the genesis of memory deficits after surgery, it might seem reasonable to simply block the IL-1R1 to prevent memory deficits. However, IL-1β contributes to host defense functions. Blocking the IL-1R1 would increase the risk of infection and inhibit healing of wounds[62]. Also, IL-1β plays a physiological role in memory processes, whereby low "physiological" basal levels promote memory. In contrast, the high levels of IL-1β that occur during inflammation cause memory loss[50,63,64]. Our goal is to identify a downstream effecter of IL-1β that can be targeted for therapeutic intervention.

Neuroinflammation and α5GABAARs

There are strong parallels between the inhibition of memory by IL-1β and α5GABA$_A$R-induced memory loss. The influence of IL-1β on memory impairment is specific to tasks that require normal functioning of the hippocampus, as evidenced by deficits in explicit recall in humans and impaired contextual fear memory and object recognition in animals that occur when the level of IL-1β increases[50,64]. Hippocampus-independent memory is typically spared from the effects of IL-1β[50]. Similarly, hippocampus-dependent memory is impaired, but hippocampusindependent memory is spared, when α5GABA$_A$Rs function is increased[11]. At the network level, IL-1β blocks the induction phase of long-term potentiation (LTP) of synaptic plasticity in the hippocampus[50].

Similarly, overactivation of α5GABA$_A$Rs blocks the induction but not the maintenance or consolidation of LTP$_{10}$. These parallels suggest that IL-1β and α5GABA$_A$Rs might work through common pathways to inhibit plasticity and impair memory.

Figure 15:
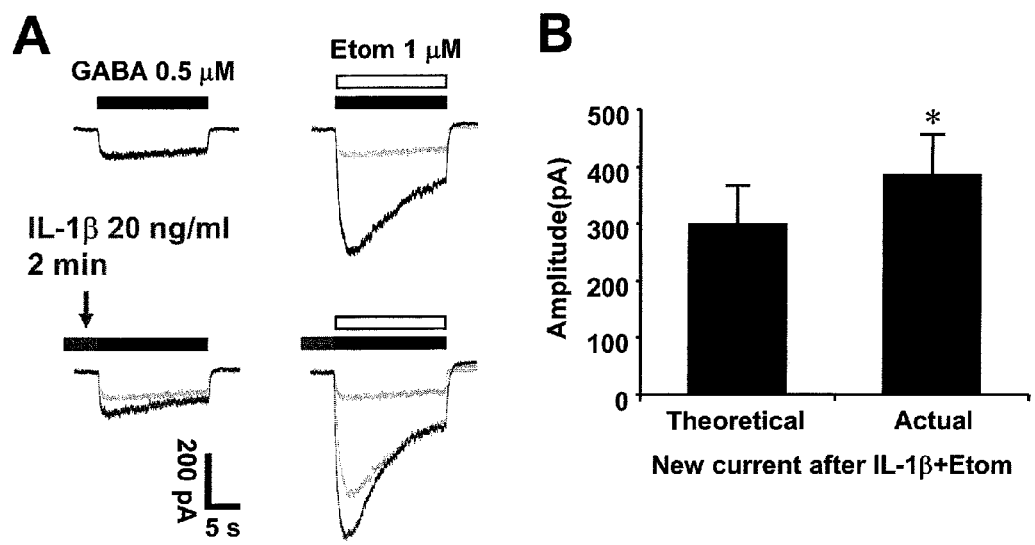
FIG. 15 illustrates the supra-additive enhancement of the tonic current by IL-1$\beta$ and etomidate in Example 2.

Our additional preliminary studies showed that IL-1β interacts synergistically with anesthetics to increase the tonic inhibitory current (FIG. 15). FIG. 15 illustrates the supra-additive enhancement of the tonic current by IL-1β and etomidate. The tonic current was evoked by applying GABA (0.5 μM) to cultured hippocampal pyramidal neurons. FIG. 15A illustrates that both IL-1β (20 ng/ml) and etomidate (1 μM) increased the amplitude of the tonic current. The combination of IL-1β plus etomidate produced a supra-additive increase in the tonic current. The baseline GABA-evoked current and etomidate-enhanced current are superimposed in grey for comparison. In FIG. 15C the measured "new" current evoked by the combination of etomidate and IL-1β was compared to the theoretical sum of the "new" current. The measured current was greater than the theoretical sum * $P<0.05$, Student's t-test, (n=5). The combination of IL-1β and the anesthetic etomidate produced a greater increase in current than the summed effects of each factor alone. This synergistic interaction suggests that IL-1β could potentiate the memory-blocking properties of anesthetics during surgery, as well as more subtle memory deficits caused by low residual levels of anesthetics in the early postoperative period. Thus, IL-1β and anesthetics appear to interact synergistically to enhance α5 GABA$_A$R activity, thereby potentiating the memory-blocking properties of the anesthetics.

Figure 16:
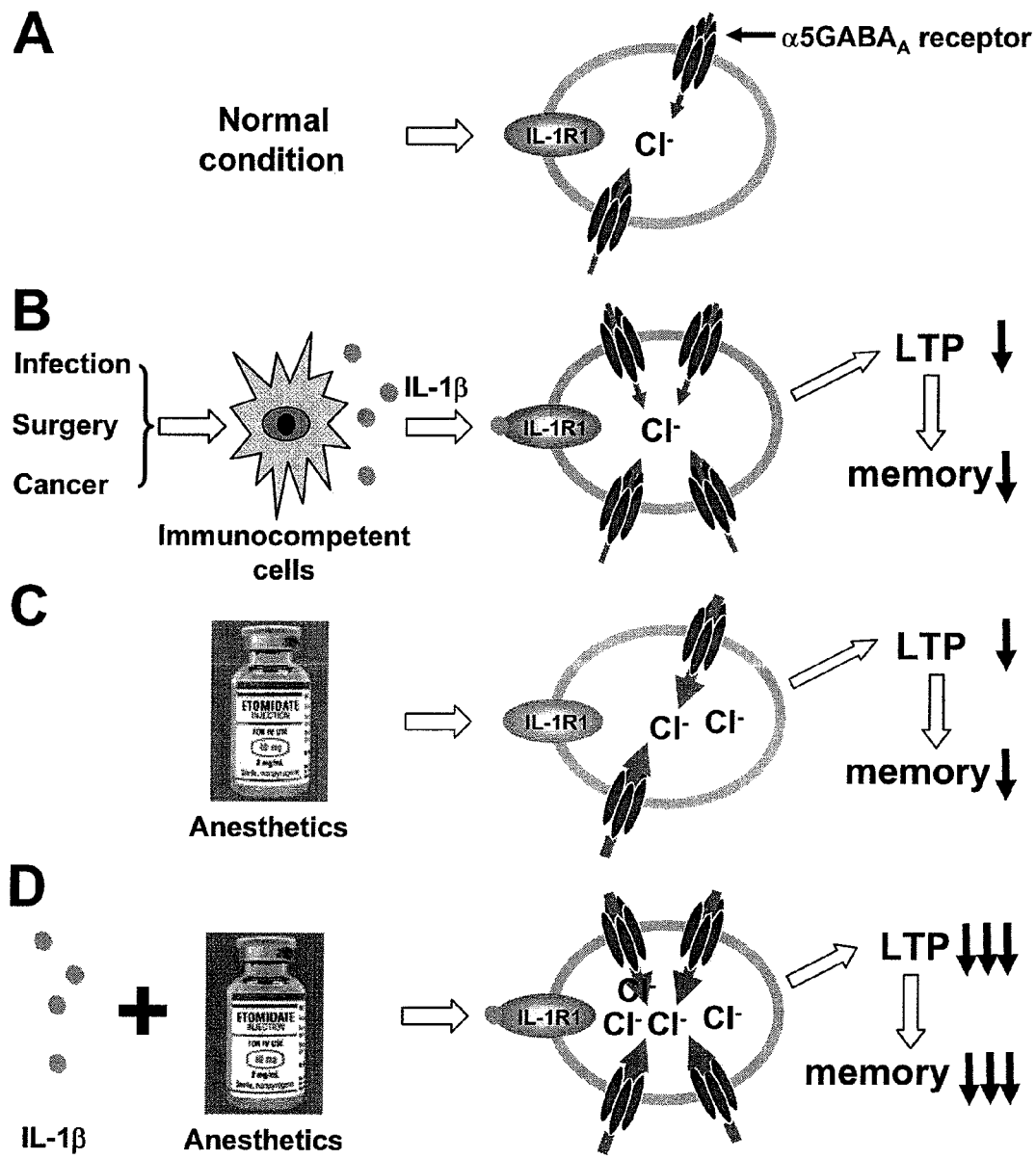
FIG. 16 illustrates the general hypotheses of IL-1$\beta$ action in Example 2.

On the basis of this evidence, we have formulated the following overall concept of postoperative memory deficits. Anesthetics directly enhance the activity of α5GABA$_A$Rs by positive allosteric modulation, whereas IL-1β indirectly increases the activity of these receptors by as-yet-unknown mechanisms. Furthermore, IL-1β exacerbates the memory-blocking effects of anesthetics both during surgery and in the early postoperative period (FIG. 16). FIG. 16 illustrates general hypotheses of IL-1β action. FIG. 16A illustrates that in the absence of an immune response, the type 1 IL-1 receptor is inactive and the number of α5GABA$_A$ receptors is limited. FIG. 16B illustrates that an inflammatory response increases the production of IL-1β which increases the number of α5 GABA$_A$ receptors expressed on the cell surface, which in turn, increases chloride influx causing neuronal hyperpolarization and inhibition of long-term synaptic plasticity (LTP) and memory. FIG. 16C illustrates that anesthetics enhance α5GABA$_A$ receptor activity directly by positive allosteric modulation, thereby increase channel opening and chloride influx causing an inhibition of LTP and memory. FIG. 16D illustrates that IL-1β potentiates the effects of anesthetics by increasing the number of α5GABA$_A$ receptors, causing profound memory impairment. Subsequently, the increased levels of IL-1β sustain the postoperative memory deficits by enhancing the function of α5GABA$_A$Rs.

Our proposed studies are important because if α5GABA$_A$Rs do indeed cause postoperative memory loss, drugs that inhibit these receptors could have an immense therapeutic impact. In fact, drugs that inhibit α5GABA$_A$ Rs are already being developed[65,66]. The restricted expression of α5GABA$_A$Rs in the brain contributes to the relative safety of these inhibitors, which lack the proconvulsant and anxiogenic properties of nonselective GABA$_A$R antagonists. In particular, the α5GABA$_A$R inverse agonists have been shown to improve memory performance in animals and humans without causing convulsions[13,67]. Thus, our results will lead to strategies to prevent or treat postoperative memory deficits.

Overall Strategy

First, we will determine how IL-1β increases α5GABA$_A$R function in vitro. Such information is important because IL-1β levels increase in a multitude of inflammatory disorders, not only in the context of surgery. It is important to identify the specific GABA$_A$R subtypes and intracellular signalling cascades that mediate the increase in tonic current by IL-1β for two specific reasons: first, this knowledge might allow us to target and disrupt the ion channel or regulatory factors and second, we might be able to predict the actions of other ligands that activate the same signaling pathway. We used a similar strategy to improve memory performance, by inhibiting the transient receptor potential melastatin 7 channel (TRPM7), which contributes to hypoxic neuronal death (*Nat Neurosci* 2009)[68]. Having established that IL-1β regulates α5GABA$_A$R function, we will examine the relevance of this interaction in the context of memory loss after anesthesia and surgery in vivo.

In addition, the specific source of IL-1β, the time course of the inflammatory response and the concentrations of anesthetics in the brain will also be investigated.

Hypotheses

On the basis of the results summarized above, we propose the following general hypotheses: 1) IL-1β increases the activity of α5GABA$_A$Rs, thereby causing memory deficits; and 2) the increase in activity of α5GABA$_A$Rs caused by the synergistic interaction between IL-1β and anesthetics leads to profound memory loss. We will test these hypotheses by addressing the following aims:

Aim 1: To identify the signalling pathways and mechanisms by which IL-1β increases the tonic inhibitory conductance in hippocampal pyramidal neurons.

Aim 2: To determine whether the increase in α5GABA$_A$R activity caused by IL-1β impairs synaptic plasticity in vitro and memory in vivo.

Aim 3: To determine whether IL-1β and anesthetics interact synergistically to increase α5GABA$_A$R activity, thereby enhancing the memory-blocking properties of anesthetics in vivo.

Aim 4: To determine whether inhibiting α5GABA$_A$Rs attenuates postsurgical memory deficits in vivo.

Research Plan

General Methods

We will perform complementary in vitro experiments (electrophysiology, immunocytochemistry, and Western blotting) and in vivo studies (behaviour) with mouse models. We have previously employed all of the proposed methods, as reported in our publications[30,53,58,69-73].

Animal Models

We will use genetically modified mice models, including mice with targeted deletion of the α5 gene (Gabra5−/−) and their 129/SvxC57BL/6 WT controls. The Gabra5−/− mice represent a valuable model, because they show minimal, if any, compensatory changes in other $GABA_AR$ subunits[74]. At the circuit level, α5−/− mice show no apparent alterations in baseline inhibitory or excitatory interactions in response to paired-pulse stimulation[28]. For a small number of in vitro experiments, C57BL6/J mice lacking the type 1 IL-1 receptor (IL-1R1 KO) will be obtained from Dr. Mervyn Maze. Neurons from the IL-1R1 KO mice will be studied in vitro; however, the mice themselves will not be used for in vivo studies because they demonstrate baseline alterations in memory behaviours and a complete absence of LTP in the CA1 region of hippocampus[63]. Littermates will be used for all of the behavioural experiments, and experimenters will be blinded to the genotype and treatment groups.

Cultured Neurons and Brain Slices

The culture model offers an assay with relatively high throughput. Hippocampal slices will be used to study network activity in the CA3-CA1 pathway. The influence of IL-1β modulation of the tonic current on basal excitatory and inhibitory neurotransmission will be determined. Experiments will be performed at 34° C. in hippocampal slices[75].

Recombinant Receptors

We will use human embryonic kidney 293 (HEK 293) cells that have been transiently transfected, by means of Lipofectamine 2000 (Invitrogen), with cDNAs encoding human $GABA_AR$ subunit isoforms and human IL-1R1.

Electrophysiology

Standard and perforated patch voltage-clamp and current-clamp recordings will be obtained to measure the tonic current, noise variance, miniature inhibitory postsynaptic currents (IPSCs), excitatory postsynaptic currents (EPSCs), paired-pulse facilitation (PPF), LTP, long-term depression (LTD), and the reversal potential for chloride ions (ECl). Perforated patch recordings will be obtained in cases where it is vital to avoid disrupting the cytosolic factors. α5$GABA_AR$ function will be evaluated by applying low concentrations of GABA (500 nM), mimicking the ambient levels of GABA in the brain[38] and measuring changes in holding current that occurs after various manipulations.

Cytokines

The IL-1β signalling pathway and the effect of the naturally occurring antagonist IL-1β are summarized in FIG. 14. Our experimental tools will include recombinant mouse IL-1β (IL-1β/IL-1F2 R&D Systems, Inc., City, Minn.) and IL-1ra, which functions as a competitive antagonist by preventing IL-1β from binding to the IL-1R1. Peripheral administration of IL-1β can signal to the brain by both blood and neural routes and will stimulate cytokine production, especially in the hippocampus[53,76,77]. In some experiments, IL-1β levels will be measured by ELISA kit strips.

Lipopolysaccharide-Induced Inflammation and Surgery

We will use two methods to increase the endogenous level of IL-1β: the widely studied lipopolysaccharide (LPS) model and a surgical method. LPS is a component of the cell wall of gram-negative bacteria that produces systemic and brain inflammation[78,79]. It will be administered by i.p. injection (125 μg/kg)[80,81]. We will not attempt to administer LPS (or IL-1β) directly into the brain because that approach requires anesthesia and surgery, which would confound the results. In addition, to surgically induce the production of IL-1β, tibial osteotomy will be performed under general anesthesia[82]. This standard orthopedic procedure consists of open tibial fracture (osteotomy) of the hind paw with intra-medullar fixation, performed under aseptic conditions as previously described[82]. Buprenorphine will be administered as an analgesic. This surgical model has been used by others[53] and was approved for use by at the ethic review panel of the Imperial College London, England.

Anesthetic Drugs

Two prototypic anesthetics, representing each of the two major classes of anesthetics, will be studied: etomidate (representing intravenously administered anesthetics) and isoflurane (representing inhalational anesthetics). Both drugs are widely used in clinical practice. We have extensively characterized their properties and actions on $GABA_ARs$[10,11,14,83].

Behavioural Assays

Several behavioural models have been developed to study hippocampus dependent memory, of which we will use two: fear conditioning, and novel-object recognition. In control experiments, we will study anxiety, nociception, motor function, and coordination (Table 2).

TABLE 2

Behavioural assays for the proposal.

| Cognitive Domain | Behavioural Assay | Protocol | Expected Outcome | References |
|---|---|---|---|---|
| Memory | Delayed Fear Conditioning | During training each mouse is placed in the fear conditioning chamber for 8 min. Following 3 min of habituation, a 20 s tone is presented. The last 2s of the tone are accompanied by a foot shock. Three tone-shock pairings are presented. Contextual fear memory is tested 24 h after training; the mouse is placed in the training context and freezing behavior is measured. Cued fear memory is measured 48 h after training, the mouse is placed in a modified context and the tone is presented. | Mice that display intact hippocampus-dependent memory exhibit freezing behavior in response to the context. Mice that exhibit intact hippocampous-independent memory exhibit freezing behavior in response to the tone | Jacobs et al. (2010) J Neurosci Methods 190 (2): 235-39. |
| | Object Recongnition | During training each mouse is presented with 2 identical objects in a familiar context for 10 min. Following a 1 h delay, the mouse is tested for 5 min. During testing a novel and a familiar, previously shown object are presented. The amount of time spent with each object is recorded. | Since mice exhibit an innate preference for novel objects, mice that remember the familiar object will spend a greater percentage of time with the novel object | Bevins R.A. & Besbeer J. (2006) Nat Protocols 1 (1): 130-11 |

TABLE 2-continued

Behavioural assays for the proposal.

| Cognitive Domain | Behavioural Assay | Protocol | Expected Outcome | References |
|---|---|---|---|---|
| Locomotor Activity | Open Field Test | Each mouse is habituated to a chamber (25 cm × 25 cm × 25 cm) 24 h prior to testing to minimize novelty-induced exploration and freezing. During testing the mouse is placed in the chamber for 10 min. The arena is divided into 25 individual squares and chamber of squares crossed is counted | If locomotor activity is unaffected by the treatment, the chamber of fields crossed should be similar in control and treated groups. | Ennaceur et al. (2006) Behav Brain Res 171(1): 26-49. |
| Anxiety | Elevated Plus Maze | Each mouse is placed in the centre of the maze that consists of 4 arms in the form of a plus. The maze has two open arms and two arms that are enclosed by walls 5 cm high and is raised 40 cm from the floor. The open arms are illuminated. Entries into the center and each of the arms are recorded over 5 min. | The test relies on the animal's inherent drives to explore novel areas and to avoid aversive features such as bright light, heigh and open spaces. Mice will tend to avoid the open arms. If the treatment is anxiolytic mice will spend more time in the open arms. An anxiogenic treatment will result in an time spent in the aversive open arms | Walf A. A. & Frye C.A. (2007) Nat Protocols 2 (2): 322-8. |
| Consciousness | Tail-Clamp | Anesthetic is administered 20 min prior to tail clamping. A painful stimulus is applied to the tail with a long hemostat for a maximum of 10 s. | A positive response (movement) is considered a gross movement of the head, extremeties or body. A negative response is considered immobility. | Gomez de Segura et al. (2009) Anesthesiology 110: 1138-8. |

Experimental Plan

Aim 1

To identify the signalling pathways and mechanisms by which IL-1β increases the tonic inhibitory conductance in hippocampal pyramidal neurons.

Rationale and Preliminary Data

It is well known that IL-1β impairs cognition and synaptic plasticity[50-52,64]; however, the specific contribution of extrasynaptic GABA$_A$Rs to these processes has never been studied. Other researchers have used several techniques to assess the effects of IL-1β on GABA$_A$R activity in general, with variable results. An increase in GABA$_A$R function caused by IL-1β was evidences by an increase in uptek of chloride in synaptosomes[84] and potentiation of GABA-evoked currents and bicuculline-sensitive hyperpolatization[85].

In contrast, exogenous IL-1β reduced currents evoked by high concentrations of GABA in hippocampal neurons and reduced IPSCs in CA3 pyramidal neurons[86,87]. These variable outcomes could result from the opposing effects of IL-1β on extrasynaptic and synaptic GABA$_A$Rs. Our initial hypothesis is that IL-1β preferentially increases the activity of extrasynaptic α5GABA$_A$Rs, rather than synaptic GABA$_A$Rs.

Figure 17:
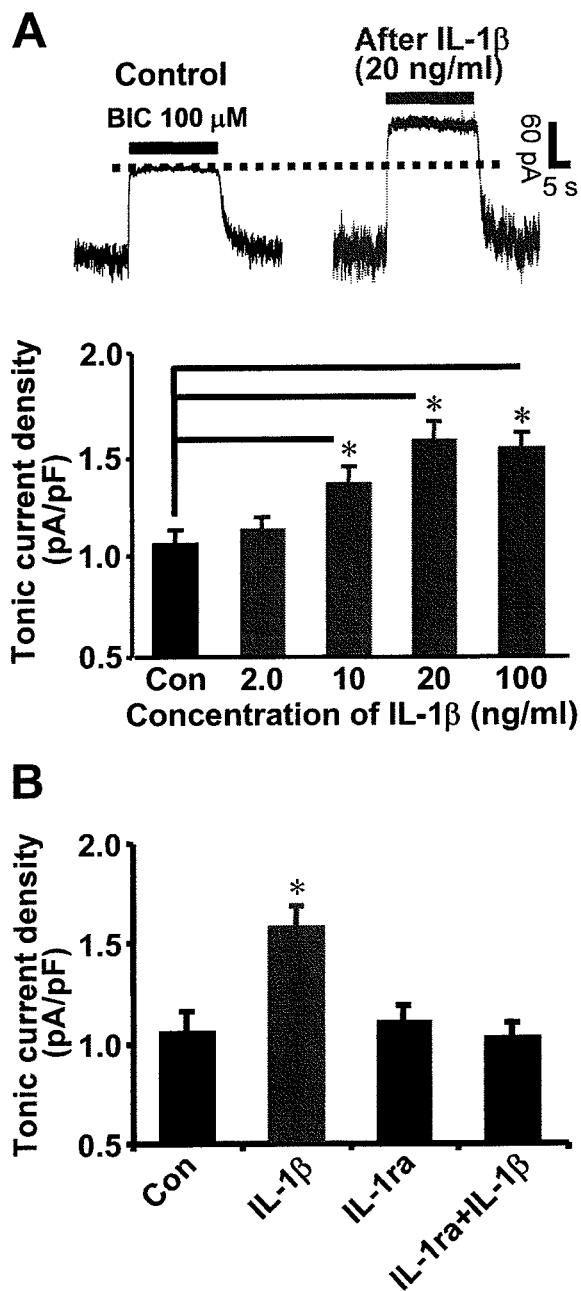
FIG. 17 illustrates the increase in tonic current by IL-1$\beta$ as recorded in hippocampal pyramidal neurons in Example 2.
Figure 18:
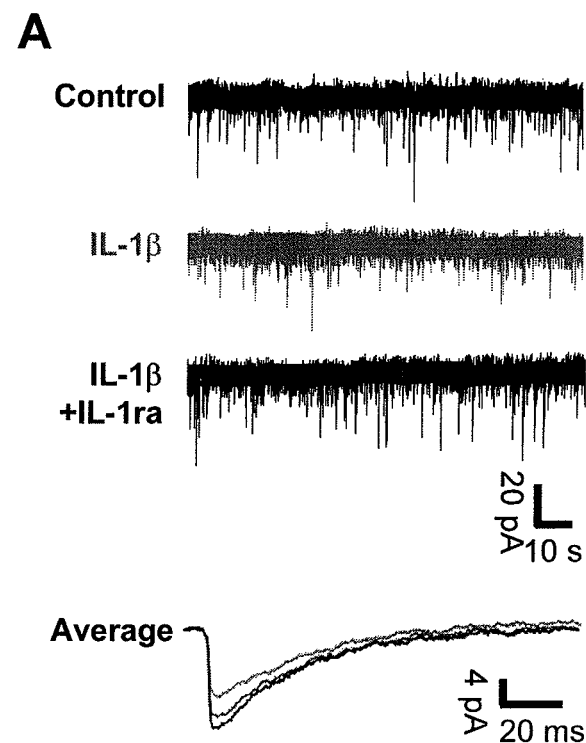
FIG. 18 illustrates IL-1$\beta$ inhibition of synaptic $GABA_A$ receptor currents in Example 2.
Figure 18:
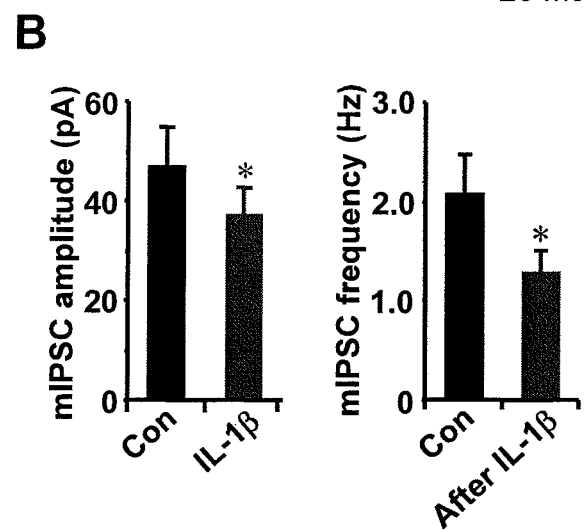

Our first objective in preliminary studies was to determine whether IL-1β, at concentrations comparable to those that occur during inflammatory states[50,88,89], increased a tonic current in pyramidal neurons. To test this hypothesis, we pretreated cultured hippocampal neurons with IL-1β (10-100 ng/ml) either 30 minutes or 12 hours before obtaining the recordings. The tonic current was increased (FIG. 17), whereas miniature IPSCs were modestly inhibited (FIG. 18). FIG. 17 illustrates the increase in tonic current by IL-1β as recorded in hippocampal pyramidal neurons. FIG. 17A (upper panel) illustrates that pre-treatment of the neurons with IL-1β (20 ng/ml for 30 min) increased the amplitude of the tonic current as revealed by the application of bicuculline (BIC 100 μM). The histogram in FIG. 17A (lower panel) shows the concentration-dependent effect of IL-1β on the tonic current. The extracellular solution contained GABA 0.5 μM, TTX 0.3 μM, CNQX 10 μM and DL-APV 40 μM. * P<0.05 compared with control, n=13-22. FIG. 17B illustrates that treatment of the cultures with the IL-1 receptor antagonist, IL-1ra, reversed the IL-1β-induced increase in the tonic current. FIG. 18 illustrates IL-1β inhibition of synaptic GABA$_A$ receptor currents. FIG. 18A illustrates miniature postsynaptic currents (mIPSCs) recorded from hippocampal neurons grown in primary cultures. Treatment of the neurons with IL-1β (20 ng/ml) for 20 min inhibited mIPSC, and this effect was blocked by IL-1ra. FIG. 18B illustrates that IL-1β reduced both the amplitude and frequency of mIPSCs. * P<0.05 compared with control, n=7. The increase in tonic current was the same whether neurons were pretreated for 30 minutes or 12 hours (data not shown). The enhancement by pretreatment with IL-1β was completely blocked by IL-1ra, which indicates that it resulted from activation of the IL-1R1[52,54,55]. IL-1ra alone had no effect on the tonic or synaptic currents (data not shown). Furthermore, no change in the tonic current occurred when IL-1β and GABA were applied together, which suggests that IL-1β acts by indirect mechanisms.

Next, to determine whether α5GABA$_A$Rs generate the IL-1β-enhanced tonic current, neurons were treated with the α5GABA$_A$R-preferring inverse agonist L-655,708 (20 nM). L-655,708 reduced the IL-1β-modulated tonic current by approximately 70% (69.2±4.4% of control, n=12; P<0.01). The residual tonic current might have resulted from incomplete block of α5GABA$_A$Rs by L-655,708 or from current generated by non-α5GABA$_A$R subtypes. These possibilities will be investigated in the proposed research. Finally, inflammation stimulates the production of other cytokines in the hippocampus, notably TNF-α and IL-6[90,91]. However, application of TNF-α (100 ng/ml) and IL-6 (10 ng/ml) did not change the amplitude of the tonic current (with TNF-α: 104.1%±12.1%, n=10; with IL-6: 96.3%±6.0% of control, n=5; P>0.05).

Figure 19:
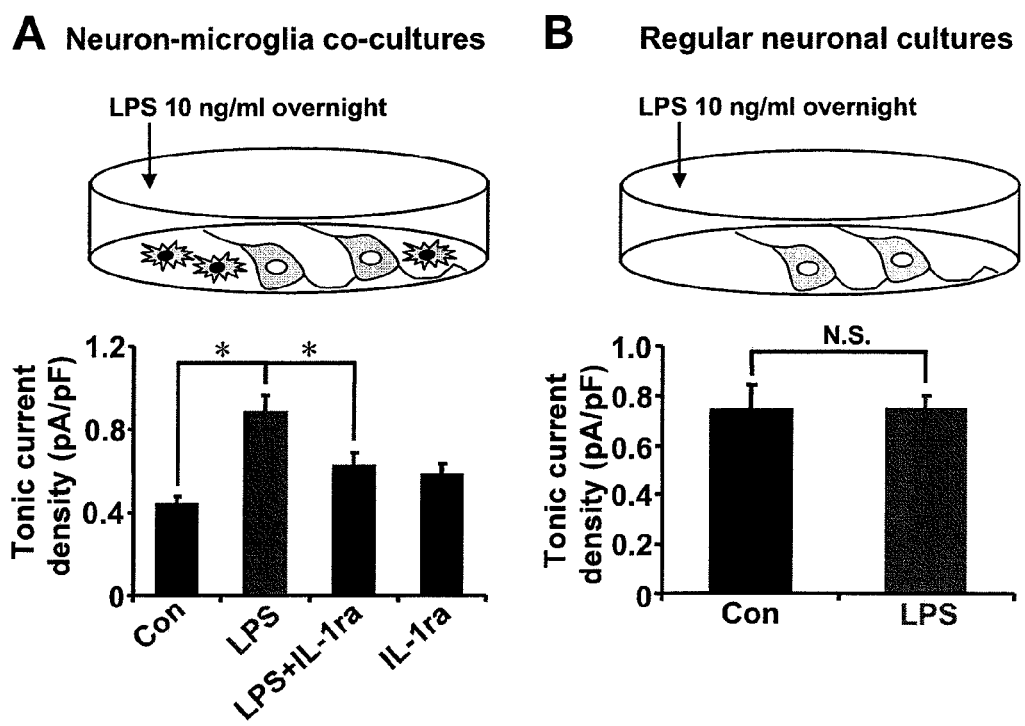
FIG. 19 illustrates LPS-induced increases in the tonic current recorded in hippocampal neurons grown in coculture with microglia in Example 2.

In additional studies, we sought to determine whether endogenous IL-1β, released from immunocompetent cells, increased the tonic current. We used a co-culture model, in which mouse cortical microglia and hippocampal neurons were cultured together and treated with LPS (10 ng/ml, 12 hours) (FIG. 19). FIG. 19 illustrates LPS-induced increases in the tonic current recorded in hippocampal neurons grown in coculture with microglia. In FIG. 19A hippocampal neuron and cortical microglia were co-cultured then exposed to the endotoxin, LPS (10 ng/ml) for 12 hours (to induce the production of IL-1β) prior to recording from the neurons. The tonic current was increased following LPS treatment and this effect was blocked by treating the co-cultures with the IL-1 receptor antagonist, IL-1ra. FIG. 19B illustrates that treatment with LPS (10 ng/ml, 12 hours) did not modify the tonic current recorded in neurons that were cultured alone, in the absence of microglia, suggesting that the microglia were the source of IL-1β induced by LPS. * P<0.05, n=10-19. The amplitude of the tonic current was increased in LPS-treated cocultured neurons, and this effect was blocked by IL-1ra. Notably, LPS did not modify the tonic current in neurons that were cultured alone (in the absence of microglia). The results summarized above support our hypothesis that inflammation produces IL-1β, which potentiates a tonic inhibitory conductance in pyramidal neurons.

Do α5GABA$_A$ Rs Generate the IL-1β-Enhanced Tonic Current?

We postulate that activation of α5GABA$_A$Rs is necessary for the IL-1β-dependent enhancement of the tonic current. We will test this directly by (a) treating α5−/− and WT neurons with IL-1β and measuring the tonic current, anticipating that IL-1β will not generate a tonic current in the α5−/− neurons; (b) applying L-655,708 to IL-1β-treated α5−/− and WT neurons, anticipating that the current will be reduced only in the WT neurons; (c) using a panel of subunit-selective pharmacological probes to confirm that the receptors are of α5β3γ2 subunits[9]; and (d) determining whether the enhancement of α5GABA$_A$Rs by a downstream component of the IL-1β signalling pathway is sufficient to increase the tonic current. Both IL-1β[92] and anisomycin[93] activate p38 mitogen-activated protein kinase (p38 MAPK), so we anticipate that anisomycin will have an effect similar to that of IL-1β in enhancing the tonic current in WT neurons, thus occluding the effects of IL-1β. In the highly unlikely event that IL-1β enhances a tonic current in α5−/− neurons, we will determine whether IL-1β modulates the only other major extrasynaptic GABA$_A$R subtype (δ subunit-containing GABA$_A$Rs), by recording from neurons obtained from δ subunit knock-out (Gabrad−/−) mice, which are available in our laboratory. However, we expect that the majority of the tonic current will be generated by α5GABA$_A$Rs and that such testing will therefore be unnecessary.

The miniature IPSCs were partially inhibited by IL-1β. We postulate that postsynaptic mechanisms, rather than a reduction in transmitter release, account for this inhibition. To test this postulate, we will (a) treat neurons with IL-1β in the absence and presence of IL-1ra to confirm that IL-1R1 mediates the inhibitory effects on synaptic inhibition; (b) record miniature IPSCs and current evoked by a high concentration of GABA (600 μM), anticipating that IL-1β will reduce the amplitude of both; and (c) perform nonstationary noise analysis of the miniature IPSCs to determine whether IL-1β changes the number of channels or channel conductance. In other studies, to confirm that the increase in tonic current caused by IL-1β is mediated by the IL-1R1, current will be recorded from IL-1R1 KO neurons. We anticipate that (a) the baseline tonic current and miniature IPSCs will be similar in WT and IL-1R1 KO neurons and (b) IL-1β will neither increase the tonic current nor inhibit miniature IPSCs in IL-1R1 KO neurons. If the results of these experiments match our predictions, they will show that IL-1β specifically increases the tonic but not the synaptic current in pyramidal neurons.

Finally, an important consideration when studying specific GABA$_A$R subtypes in the hippocampal neurons is the heterogeneity of the receptor populations. The pharmacological probes used to distinguish GABA$_A$R subtypes are not entirely selective[94]. To address this concern, HEK 293 cells will be transiently transfected with cDNAs encoding the human isoforms of the GABA$_A$R subunits and IL-1R1. We will study combinations of subunits intended to mimic extrasynaptic GABA$_A$Rs (α5β3γ2) or synaptic GABA$_A$Rs (α1β2γ2), as we have done previously[9,14]. We will examine (a) the potency and efficacy of IL-1β in modifying GABA-evoked current (by means of dose-response plots); (b) whether IL-1β modifies the potency of GABA; and/or (c) whether IL-1β modifies the gating and conductance properties of α5GABA$_A$Rs.

Does Enhancement of α5GABAARs by IL-1β Reduce Neuronal Excitability?

We postulate that the IL-1β-enhanced tonic GABA-activated current reduces neuronal excitability and the firing of action potentials in pyramidal neurons. We will test this hypothesis directly with current-clamp recordings from cultured neurons, employing procedures that will modify α5GABA$_A$Rs and the effects of IL-1β.

Specifically, we will (a) compare the effects of IL-1β on the firing of action potentials in α5−/− and WT neurons, predicting a minimal effect in the α5−/− neurons; (b) determine whether IL-1ra reverses the IL-1β-induced changes in firing; (c) treat neurons with IL-1β and determine whether L-655,708 (an inverse agonist that blocks the tonic current by 70%, data not shown) modifies current from α5−/− or WT neurons; (d) apply the GABAAR antagonist bicuculline to determine whether the effects of IL-1β on firing are blocked; (e) determine whether IL-1β alters ECl; and (e) determine, by means of perforated patch current-clamp recordings, whether IL-1β alters the resting membrane potential. We predict that IL-1β will hyperpolarize the neurons and reduce neuronal firing.

Does IL-1β Increase the Number or Function of α5GABAARs?

Figure 20:
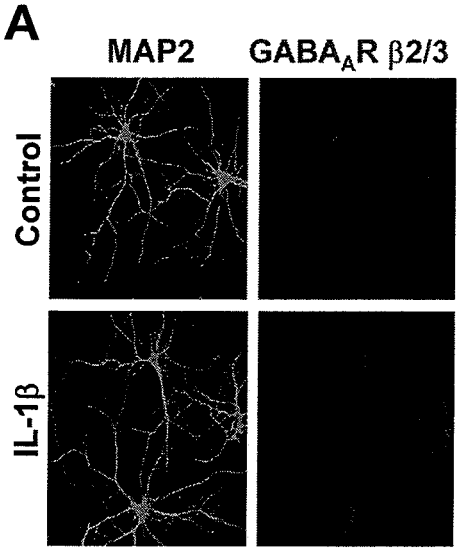
FIG. 20 illustrates increases in the expression of $GABA_A$ receptors by IL-1$\beta$ in cultured hippocampal neurons in Example 2.
Figure 20:
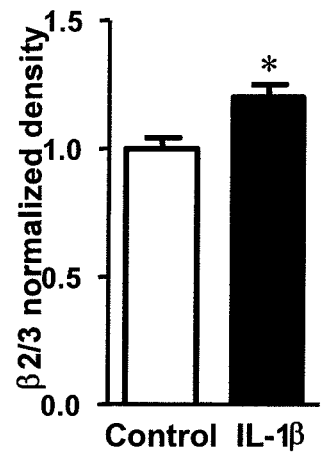
Figure 20:
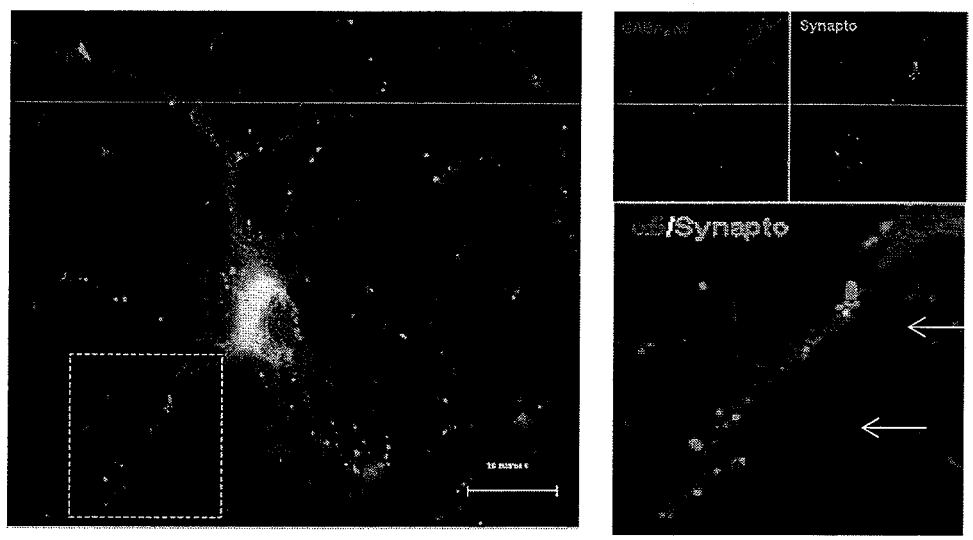
Figure 21:
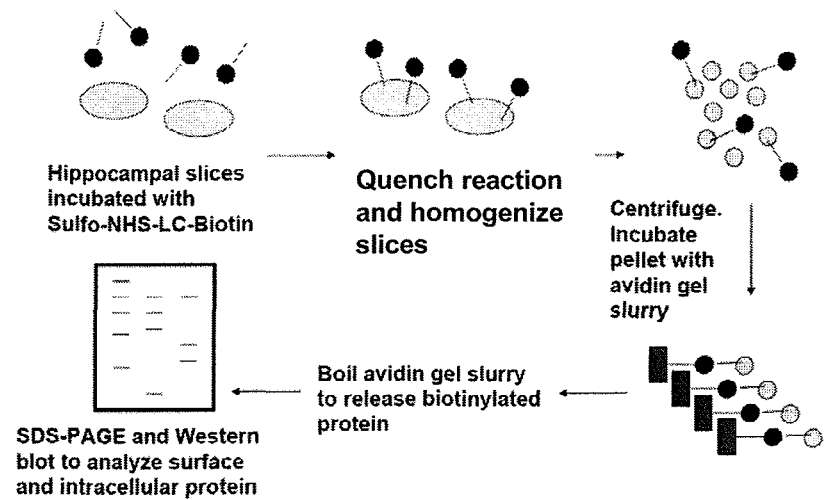
FIG. 21 illustrates increases in the cell surface expression of the $\alpha5$ subunit by IL-1$\beta$ in hippocampal slices in Example 2.
Figure 21:
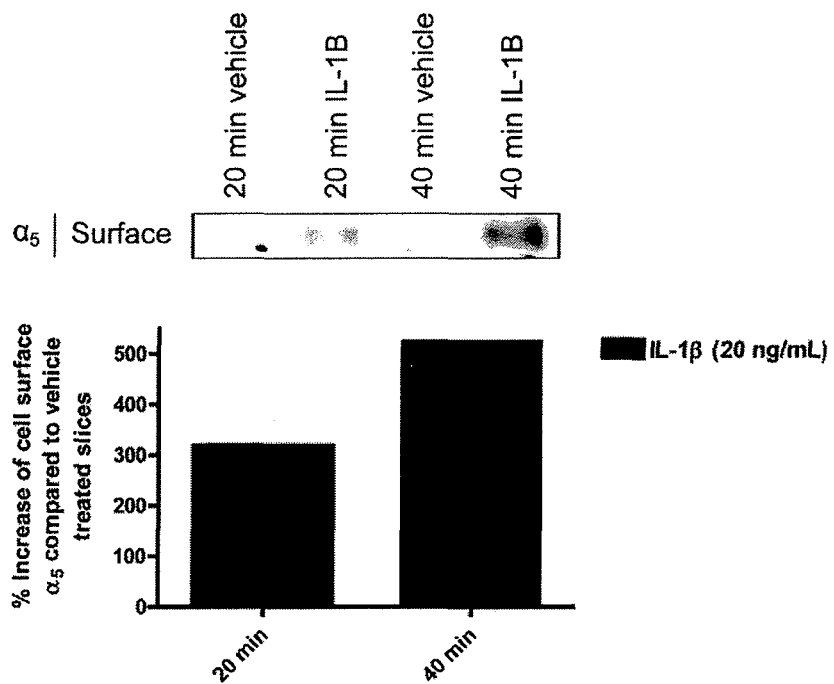

The increase in tonic current caused by IL-1β could result from an increase in either the number or the function of GABA$_A$Rs, or both. Given that extrasynaptic GABA$_A$Rs are highly mobile and given that the effects of IL-1β occur within minutes, we postulate that IL-1β increases the trafficking of α5GABA$_A$Rs to the plasma membrane, thereby increasing the tonic current[95-97]. The cytosolic regulatory factors that control the expression, translocation, and function of GABA$_A$R subunits are just beginning to be clearly understood. In preliminary testing of our hypothesis, cultured hippocampal neurons were stained with an antibody directed against the β2/3 subunits. FIG. 20 illustrates increases in the expression of GABA$_A$ receptors by IL-1β in cultured hippocampal neurons. In FIG. 20A GABA$_A$ receptor expression was assessed using an antibody directed against β2 and β3 subunits. The neurons were treated with IL-1β (20 ng/ml) or vehicle for 1 h prior to immunostaining. * P<0.05. The immunofluorescence increased in IL-1β- treated neurons, consistent with an increase in GABA$_A$Rs (FIG. 20A). In FIG. 20B immunostaining with an anti-α5 subunit antibody (red) shows puncta and some diffuse staining that does not co-localize with the synaptic marker synaptophysin (green) suggesting that α5 subunits are mainly present at extrasynaptic sites. We will use these methods to determine whether IL-1β treatment increases the expression or distribution of α5 subunits. Neurons from Gabra5−/− mice will be immunostained to confirm the selectivity of the anti-α5 subunit antibody. Immunostaining with anti-α5 antibodies (FIG. 20B) indicated the extrasynaptic location of the subunits. In other preliminary studies, biotynilation and Western blotting of hippocampal slices was used to show that IL-1β dramatically increases the surface expression of α5GABA$_A$Rs (FIG. 21). FIG. 21 illustrates increases in the cell surface expression of the α5 subunit by IL-1β in hippocampal slices. FIG. 21A illustrates the biotyinylation method used to determine whether the protein of interest is expressed on the neuronal surface. In FIG. 21B hippocampal slices were treated with IL-1β (20 ng/ml) for 20 or 40 min prior to biotinylation, followed by Western blotting (upper panel). The surface expression of α5 subunit in IL-1β-treated hippocampal slices was expressed as a percentage of expression compared to control slices. IL-1β produced a dramatic time-dependent increase in cell surface expression of the α5 subunit.

To further study whether IL-1β enhances the trafficking of extrasynaptic GABA$_A$Rs to the cell surface, we will (a) stain GABA$_A$Rs in hippocampal slices with antibodies directed against the α5 and β3 subunits (anti-α5 subunit antibody provided by Dr. Werner Sieghart); (b) stain α4 and 5 subunits; (c) stain synaptic GABA$_A$Rs with antibodies directed against α1, α2, and β2 subunits, anticipating that staining will be reduced in IL-1β-treated slices; and (d) treat slices with IL-1ra, which should prevent IL-1β-induced changes in staining. IL-1β is expected to increase α5GABA$_A$Rs only in the principal pyramidal neurons, not the inhibitory interneurons. To test this hypothesis, hippocampal slices will be immunostained and the CA1 and CA3 subfields probed, with particular attention to cell type-specific expression patterns. The interneurons will be identified by their morphology and positive staining for glutamate decarboxylase-67 (GAD-67). Staining of the α5 subunit is expected to increase in the pyramidal neurons but not the interneurons.

To determine whether IL-1β increases subunit protein levels in WT neurons, we will use Western blotting with antibodies directed against α5, α2, α1, β2, β3, δ, and γ subunits. We will (a) immunoblot IL-1β-treated α5−/− and WT slices with α5 antibody and (b) use a biotinylation assay to determine whether IL-1β increases α5GABA$_A$ Rs expressed on the cell surface, as described in FIG. 21[29,99]. The antibodies required for these experiments are already available in our laboratory. Because immunocompetent cells contain the machinery to increase production of GABA[100], we will also assess the level of GAD-67 by Western blotting (and immmunostaining). Finally, mRNA levels in slices will be probed with RT-PCR and microarrays to measure changes in the expression levels for a variety of subunits. It is already known that the MAPK pathways activate the binding of early growth factor 3 (Egr3) to an ERE site on a promoter that generates the α4 subunit[101,102]. A similar mechanism might promote the generation of α5 subunits. However, we expect to find that IL-1β primarily promotes the trafficking of nascent receptors to the cell surface rather than the production of new receptors.

Which Signalling Pathways Mediate the Enhancement of Tonic Current by IL-1β?

Figure 22:
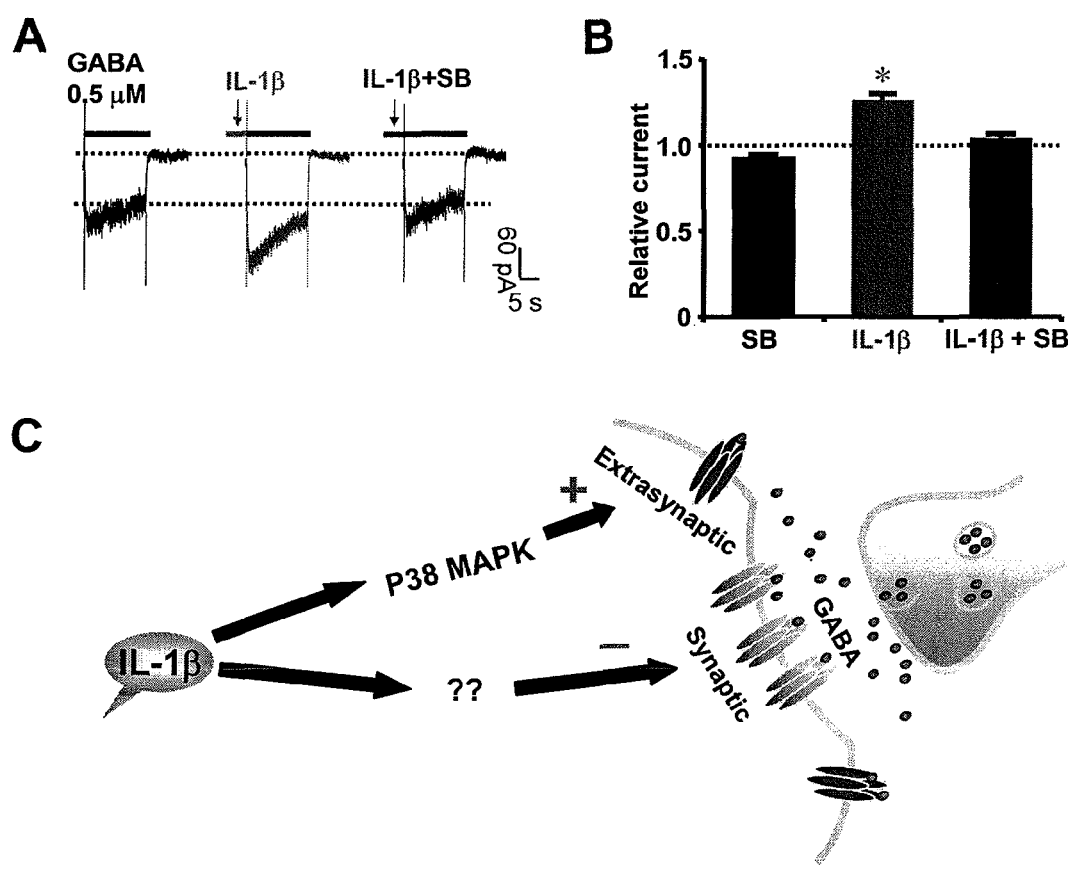
FIG. 22 illustrates that the intracellular signalling pathway mediating IL-1β enhancement of the tonic current involves p38 MAPK in Example 2.

Because IL-1β activates p38 MAPK and c-Jun N-terminal kinase (JNK)[52,54,55], we have assessed the role of these kinases in preliminary studies. The tonic current was recorded from IL-1β-treated neurons in the absence and presence of the p38 MAPK inhibitor SB203580. FIG. 22 illustrates the intracellular signalling pathway mediating IL-1β enhancement of the tonic current involves p38 MAPK. FIG. 22A illustrates that IL-1β (20 ng/ml) enhanced the current evoked by a low concentration of GABA (0.5 μM). The IL-1β-dependent enhancement was blocked by inhibiting p38 MAPK, with bath application of SB203580 (SB; 20 μM). FIG. 22B illustrates that the histogram shows that SB blocked the enhancement by IL-1β. SB applied in the absence of IL-1β had no effect on the tonic current. FIG. 22C provides schematic drawings showing the differential effects of IL-1β on extrasynaptic and synaptic GABA$_A$Rs, and the different kinases involved in these effects. It remains to be determined whether inhibition of synaptic current by IL-1β is mediated via similar signalling pathways (also see FIG. 18). The IL-1β-induced increase in tonic current was inhibited by SB203580 (FIG. 22) whereas an inhibitor of JNK (SP600125, 1 μM) did not modify the IL-1β-enhanced tonic current. Notably, SB203580 did not modify IL-1β inhibition of miniature IPSCs (data not shown). These results suggest that IL-1β works through two distinct pathways to modify synaptic and extrasynaptic receptors. Thus, we hypothesize that IL-1β activates p38 MAPK, which stimulates a signalling cascade to increase the trafficking of α5GABAARs to the cell surface.

Our working hypothesis is that IL-1β increases the translocation of nascent α5GABA$_A$Rs via post-translational modifications such as subunit phosphorylation. We will first assess downstream components in the p38 MAPK pathways, including Akt and PKC, as these factors phosphorylate the β subunit[51,96,103] and have been reported by the Moss laboratory to increase GABA$_A$R surface expression[104]. Akt is highly expressed in the hippocampus and is activated by multiple factors, including IL-1β[51]. Also, the Moss laboratory has shown that PKC increases trafficking of extrasynaptic receptors to the surface[104]. To identify the contributions of Akt and PKC, we will use inhibitors and activators of these and other kinases, as listed in Table 3.

TABLE 3

Potential kinases modulated by IL-1β.

| Protein kinases | Inhibitors | Activators | References |
| --- | --- | --- | --- |
| AKI | 1. API-2<br>2. SH-5<br>3. In-DEBC hydrochloride<br>4. FPA 124 | 1. myr-Akt1.ER*<br>(conditionally active form of Akt1)<br>2. YS-19 monohydrate | Serantes et al. (2006) J Biol Chem 281, 14632<br>Thimumaiah et al (2005) J Biol Chem 36, 31924 |
| PKC | 1. Calphostin C<br>2. Chelerythine chloride | 1. Phorbol 12-myristate 13-acetate | Palma et al. (2005) PNAS 102, 1667<br>Chan et al (2003) J Biol Chem 278, |

TABLE 3-continued

Potential kinases modulated by IL-1β.

| Protein kinases | Inhibitors | Activators | References |
|---|---|---|---|
| | 3. Go6850<br>4. Bisindolylmaleimide 1 | 2. Bryostatin<br>3. PKC fragment (530-558)<br>4. SC-10 | 20453<br>An et al (2006) J Photochem Photobiol B 85, 92 |
| PKA | 1. H89<br>2. Rp-8-Br-cAMP<br>3 KT 5720<br>4. PKI 14-22 amide | 1. 8-Bromo-cAMP<br>2. Adenosine 3',5'-cyclic monophosphate | Palma, et al. (2005) PNAS 102, 1667<br>Yamada et al (2006) Pathobiology 73, 1<br>Chow et al (1998) J. Neurochem 70, 2606 |
| CaMKII | 1. KN-62<br>2. KN-93<br>3. CK59 | | Hidaka and Yokokuro (1996) Adv Pharmacol 36, 193<br>Anderson et al (1998) Pharmacol Exp Ther 287, 996 |

The concentration of IL-1β selected for these studies will be based on the best available evidence but may not mimic in vivo concentrations exactly. In addition, the cytosolic factors that mediate IL-1β signalling may be altered in cultured neurons relative to neurons in the intact hippocampus. We appreciate that the increase in surface expression of the α5 subunit in slices was much greater than that expected on the basis of current recordings obtained from cultured neurons. We will determine, by means of cell-attached and perforated patch recordings, whether these differences are due to dialysis of the cell contents. Alternatively, it is possible that not all α5 subunits contribute to functional channels. To address these caveats, several of the experiments described below will examine the effects of endogenous IL-1β in ex vivo brain slices.

Aim 2

To determine whether the increase in α5GABA$_A$ receptor activity caused by IL-1β impairs synaptic plasticity in vitro and memory in vivo.

Does IL-1β Act Via α5GABA$_A$ Rs to Impair Plasticity?

The exact neurobiological mechanisms that subserve memory remain to be fully elucidated; nevertheless, one proposed mechanism, Hebbian synaptic plasticity, has already received considerable attention[105]. LTP or strengthening of synaptic connectivity is thought to underlie the formation of memory[106]. IL-1β could influence any of several molecular processes that regulate synaptic plasticity[50]. The key question is whether α5GABA$_A$Rs underlie the predominant effect of IL-1β on plasticity. Our working hypothesis is that IL-1β acts via α5GABA$_A$Rs to inhibit LTP. In preliminary work to test this hypothesis, α5−/− and WT mice were treated with LPS (125 μg/kg, i.p.). After 3 hours, the mice were sacrificed and the hippocampi harvested. Extracellular field recordings were obtained with a recording electrode placed in the stratum radiatum of the CA1 subfield. The Schaffer collaterals were stimulated with a theta burst protocol[107].

Figure 23:
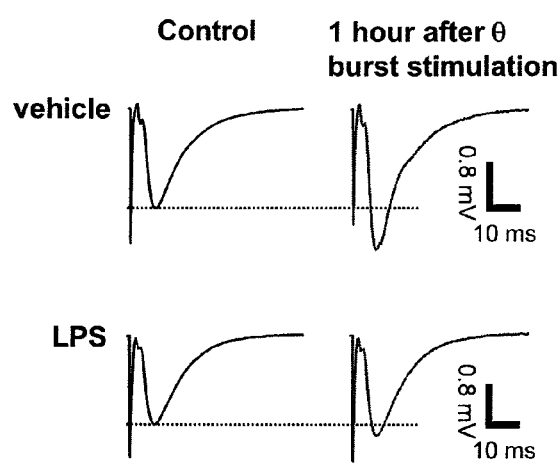
FIG. 23 illustrates that long-term potentiation of excitatory field potentials is reduced by LPS-treatment in wild-type (WT) mice but not Gabra5−/− mice in Example 2.
Figure 23:
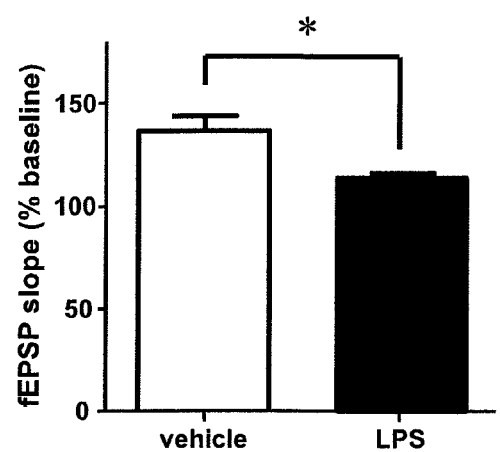
Figure 23:
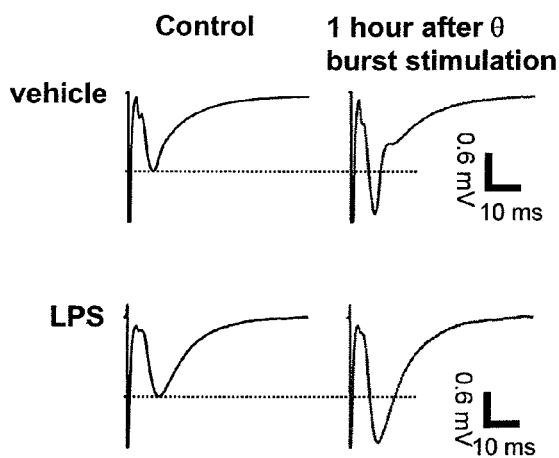
Figure 23:
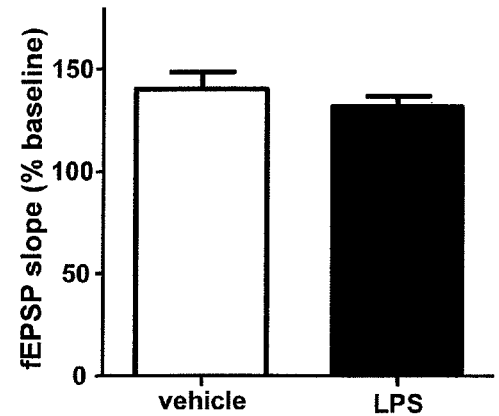

Consistent with our working hypothesis, LTP was induced in LPS-treated α5−/− slices but not in WT slices (FIG. 23). FIG. 23 illustrates that long-term potentiation of excitatory field potentials is reduced by LPS-treatment in WT mice but not Gabra5−/− mice. Mice were treated with LPS (125 mg/kg) and 3 hours later hippocampal slices were prepared. Field excitatory postsynaptic potentials (fEPSPs) were recorded in the CA1 stratum radiatum for one hour after θ burst stimulation to the Schaffer collaterals. LTP was assessed during last 5-min of the recordings. LTP was reduced in LPS-treated WT mice (FIG. 23A) but not Gabra5−/− mice (FIG. 23B) * P<0.05, unpaired t test, n=6-12. The role of α5GABA$_A$Rs in IL-1β-induced inhibition of LTP will be studied further, along with possible IL-1β-induced changes in baseline excitatory and inhibitory synaptic transmission and PPF. Two strategies will be used to increase IL-1β levels: exogenous IL-1β will be applied to slices, and LPS will be administered to mice before the slices are harvested. Schaeffer collaterals will be stimulated at several frequencies, as described previously[28]. We will (a) compare baseline IPSCs, EPSCs, tonic current, IPSPs, EPSP and PPF, in α5−/− and WT slices treated with IL-1β or vehicle (b) compare LTP in α5−/− and WT slices, anticipating that LTP will be attenuated in the WT but not the α5−/− slices; (c) treat slices with IL-1ra, which is expected to reverse the IL-1β-induced inhibition of LTP in WT slices; (d) treat slices with L-655,708, which is expected to reverse the IL-1β-induced inhibition of LTP in WT slices; (e) treat slices with bicuculline, which should block all effects of IL-1β in both genotypes; and (f) measure the resting membrane potential, which is expected to be hyperpolarized by LPS treatment or administration of exogenous IL-1β. We expect that together, the results of these experiments will show that IL-1β up-regulates α5GABA$_A$Rs, in a manner similar to that of anesthetics[11,28], thereby inhibiting the LTP evoked by a wide range of stimulation frequencies.

Does IL-1β Act Via α5GABA$_A$ Rs to Impair Memory?

Figure 24:
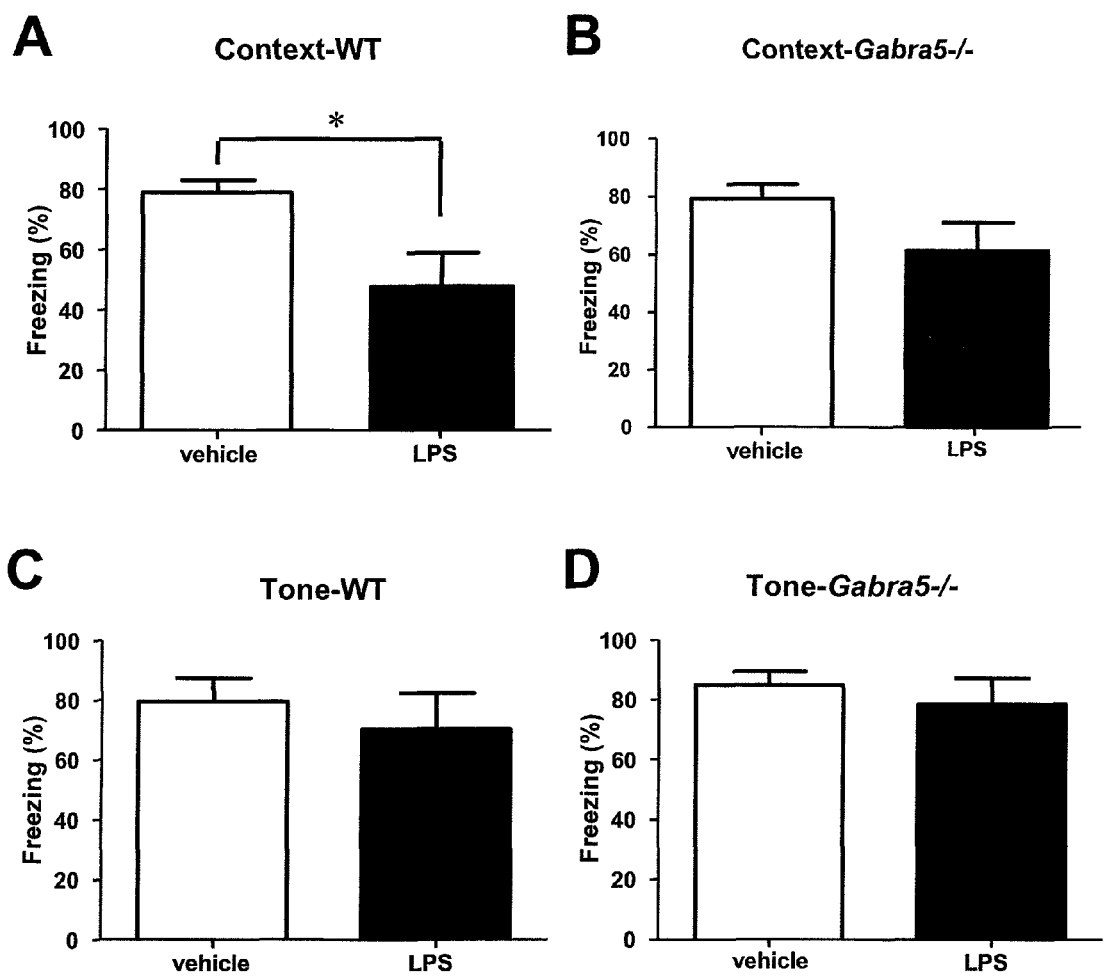
FIG. 24 illustrates that LPS impairment of hippocampus-dependent memory is reduced in Gabra5−/− mice in Example 2.

We postulate that high levels of IL-1β prevent the formation of new memories by up-regulating α5GABA$_A$R function. This hypothesis was tested in preliminary studies by administering LPS (125 μg/kg, i.p.) to 3-month-old male α5−/− and WT mice. Three hours later, the mice underwent fear conditioning for auditory and contextual cues, and memory performance was assessed the following day. As anticipated, freezing scores were lower in WT mice than in α5−/− mice (FIG. 24). FIG. 24 illustrates that LPS impairment of hippocampus-dependent memory is reduced in Gabra5−/− mice. LPS injection (125 μg/kg, i.p.) impaired contextual fear conditioning in wild-type (WT) mice (FIG. 24A), but not in Gabra5−/− mice (FIG. 24B). LPS injection did not impair amygdala-dependent auditory fearing conditioning in WT or Gabra5−/− mice (FIGS. 24C and 24D). * P<0.05, unpaired t test, n=6-7. Auditory-cued fear learning (amygdala-dependent), was similar in the two genotypes. To confirm that IL-1β blocks the formation of new memories via up-regulation of α5GABAARs, we will (a) administer IL-1ra after LPS, anticipating that it will reverse the memory deficit; (b) administer exogenous IL-1β to α5−/− and WT mice and assess memory performance; and (c) determine whether preemptive pretreatment with L-655,708 before fear conditioning prevents IL-1β-induced memory deficits. A separate cohort of mice will be euthanized at the same time as those used in the behavioural studies, to test the assumption that the levels of IL-1β in the hippocampus are similar in all treatment groups. LPS and exogenous IL-1β are expected to increase the level of IL-1β in the hippocampus.

IL-1β may influence other important processes that contribute to the consolidation of memory, such as synaptic scaling[108] and adult neurogenesis[109-111]. These processes will be pursued if the results fail to meet our expectations. Also, LPS may produce additional cytokines that impair cognition; however, we will focus on IL-1β because this cytokine plays the predominant role in postoperative cognitive dysfunction'. In the unlikely event that IL-1ra does not antagonize the memory deficits, we will study the role of TNF-α and IL-6 on α5GABAAR-dependent memory dysfunction[90,91].

Aim 3

To determine if IL-1β and anesthetics interact synergistically to increase α5GABA$_A$ receptor activity, thereby enhancing the memory-blocking properties of anesthetics in vivo.

Rationale and Preliminary Data

Various anesthetics cause a concentration-dependent increase in GABA$_A$R activity through the mechanism of positive allosteric modulation[10,14]. In contrast, IL-1β appears to increase the number of GABA$_A$Rs expressed in the cell membrane[51]. The combination of these effects could produce several outcomes; however, we hypothesize that IL-1β and anesthetics interact synergistically to increase α5GABA$_A$R function. The pharmacological studies described below are important because their results will have direct clinical implications. If our hypothesis is correct, lower doses of anesthetic should be administered to patients who are at increased risk for inflammation. Also, the enhancement of anesthetic potency by IL-1β could explain the apparently greater depth of anesthesia scores in high-risk patients, as revealed by encephalogram-based monitors[112-114]. Our preliminary studies, which examined the interaction between etomidate and IL-1β in modifying the tonic current, revealed a supra-additive effect (FIG. 15). Specifically, the increase in current produced by the combination of IL-1β and etomidate was greater than the theoretical sum of each compound alone. Thus, we predict that IL-1β will greatly increase the memory-blocking properties of the anesthetic.

Do IL-1β and Anesthetic Interact Synergistically to Increase α5GABA$_A$ Rs Activity In Vitro?

Figure 25:
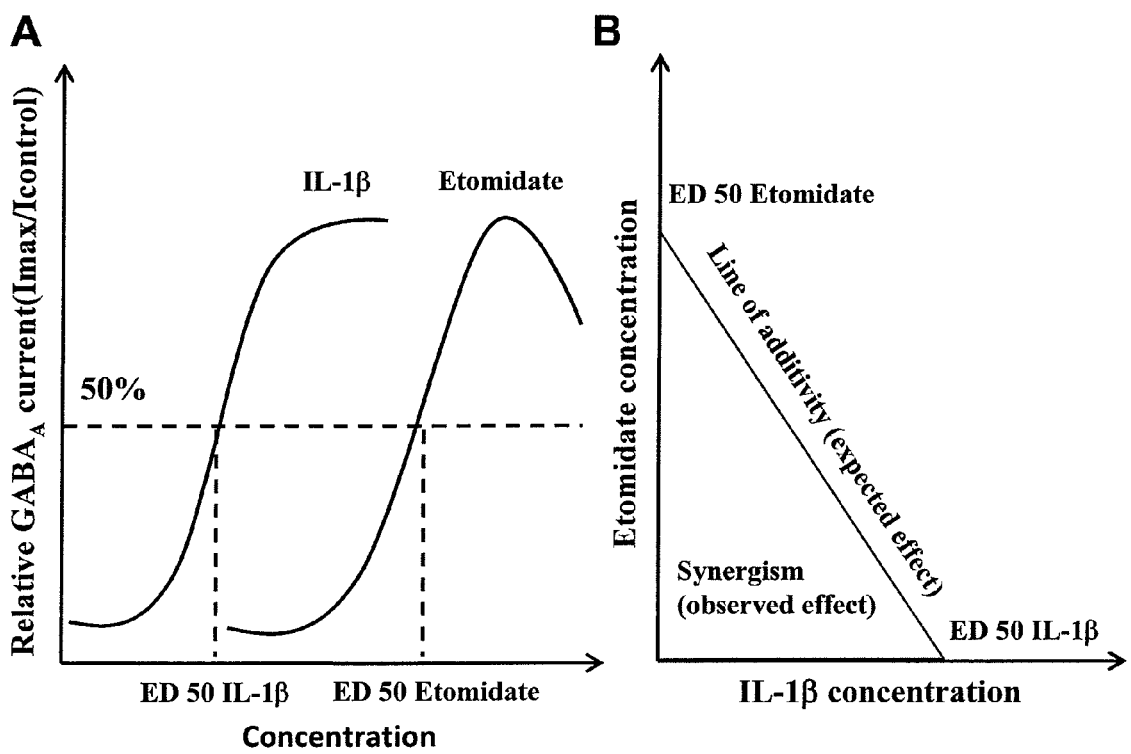
FIG. 25 illustrates isobolographic analysis of the interaction between IL-1β and etomidate for enhancement of $α5GABA_A$ receptor function in Example 2.

Following from the preliminary results described above, we will perform an isobolographic analysis (a quantitative method that is widely used to evaluate drug combinations[115,116]) to confirm the presence of a synergistic interaction between IL-1β and α5GABA$_A$Rs, as we have done previously (FIG. 25)[34]. FIG. 25 illustrates isobolographic analysis of the interaction between IL-1β and etomidate for enhancement of α5GABA$_A$ receptor function. In FIG. 25A the isobolographic analysis first requires the determination of equi-effective concentrations of IL-1β and etomidate (e.g. 50% of the maximum tonic current). These concentrations will be measured by constructing dose-response plots under voltage-clamp conditions. Combination of drugs that produce the same effects are determined. In FIG. 25B synergism is indicated by pairs of concentrations which fall below the line of additivity and are contained within the region bounded by the line and the coordinate axes. The isobologram for 50% of the maximum effect produced by IL-1β and etomidate is shown for illustrative purposes. The straight line that connects the intercept points represents the line of additivity. Next, because hippocampal neurons contain heterogeneous GABA$_A$R subtypes, we will confirm that α5β3γ2 receptors are synergistically modulated by IL-1β and anesthetics. Receptors will be expressed in HEK cells that are also co-transfected with IL-1R1 cDNA. Concentration-response plots for enhancement of a GABA-evoked tonic current (EC10) by IL-1β, anesthetics, and the combination of IL-1β and anesthetics will be studied. We expect to confirm a synergistic interaction for "extrasynaptic" GABA$_A$Rs in vitro.

Does IL-1β Increase the Potency of Anesthetics for Memory Blockade?

Figure 26:
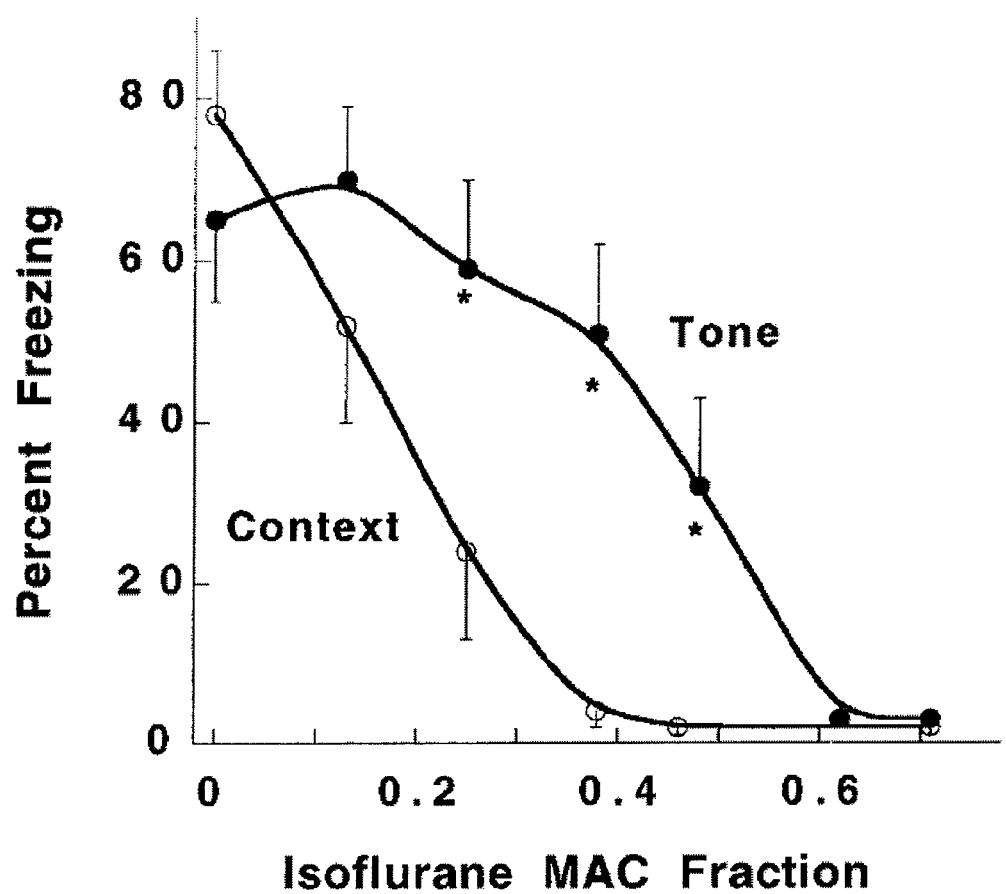
FIG. 26 illustrates the effect of isoflurane on fear conditioned responses.

Given the supra-additive interaction between IL-1β and α5GABA$_A$Rs in vitro, we predict that IL-1β will markedly increase the memory-blocking properties of anesthetics in vivo. To assess the behavioural consequences of this synergistic interaction, we will use classical fear-associated memory paradigms (FIG. 26)[71]. FIG. 26 illustrates the effect of isoflurane on fear conditioned responses. Mice were trained to associate the presentation of a tone and a particular environment (context) with a foot shock. Fear of both the tone and context was assessed by studying freezing behaviour. Freezing scores were expressed as the percent of time freezing in response to context or tone (mean±SEM, n=8 per group). Each mouse was trained in the presence of a single concentration of isoflurane. Freezing in response to the tone or context differed at 0.25, 0.38, and 0.48 MAC, suggesting isoflurane more potently inhibits brain structures involved in contextual learning (* P<0.05 between corresponding concentration groups). Etomidate dose-response plots for the inhibition of contextual and auditory fear will be generated in mice treated with (a) LPS or vehicle or (b) exogenous IL-1β or vehicle. The doses of LPS and IL-1β will be carefully selected to cause minimal changes in memory performance on their own. Despite the modest effect, LPS and IL-1β are expected to markedly shift the plot of anesthetic potency to the left. To test whether α5GABA$_A$Rs contribute to the enhanced sensitivity, we will (a) construct anesthetic concentration-response plots for LPS-treated α5−/− and WT mice, anticipating no IL-1β-dependent change in potency for the α5−/− mice; and (b) determine whether the shift in concentration-response plots for etomidate in WT but not α5−/− mice will be reversed with IL-1ra. As negative controls, the potency of etomidate for immobilization and sedative effects (which do not depend on α5GABA$_A$Rs) will be tested.

The levels of IL-1β after LPS treatment or administration of exogenous IL-1β may differ from those that occur after surgery. Thus, the studies described below will examine the contribution of IL-1β to postoperative memory loss.

Aim 4

To determine whether inhibiting α5GABA$_A$ receptors attenuates postsurgical memory deficits in vivo.

Rationale and Preliminary Data

Figure 27:
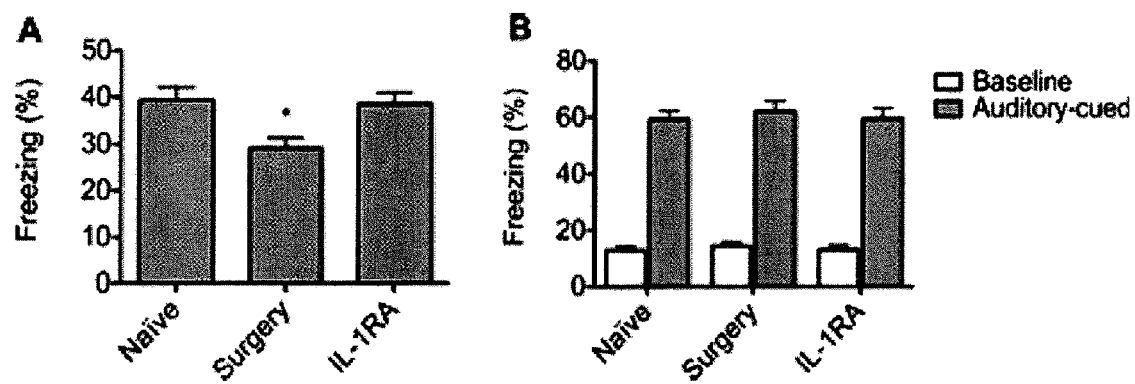
FIG. 27 illustrates prevention of postsurgical impairment of contextual but not auditory-cued memory by the interleukin-1 receptor antagonist.

A standard mouse model of orthopedic surgery[53,82] was used to show that postoperative memory deficits correlate with the activation of innate immune cells (a process referred to as reactive microgliosis) and with increased levels of IL-1β in the hippocampus. Following tibial osteotomy, mice exhibited memory deficits for contextual and trace fear conditioning (hippocampus-dependent tasks) but not auditorycued memory and hippocampus-independent tasks. The deficits persisted for the duration of the study (3 days after surgery; FIG. 27). FIG. 27 illustrates prevention of postsurgical impairment of contextual but not auditory-cued memory by the interleukin-1 receptor antagonist. Mice were trained on delayed fear conditioning protocol prior to surgery. Mice were injected either with vehicle or interleukin-1 receptor antagonist prior to surgery. Mice were tested for contextual fear memory (FIG. 27A) and auditory cued fear memory (FIG. 27B) 3 days after surgery. FIG. 27A illustrates that surgery could induce an impairment of contextual fear memory, and this effect could be blocked by IL-1 receptor antagonist injected before surgery. (* P<0.05). FIG. 27B illustrates that amygdala-dependent auditory-cued test was not affected by surgery or the interleukin-1 receptor antagonist. n=30 per group. Surgery increased the levels of the cytokines IL-1β, IL-6, and TNF-α, with IL-1β showing the greatest and most sustained increase. More importantly, no memory deficits were detected in mice that had been pretreated with IL-1ra and in IL-1R1 KO mice[53]. These studies showed that IL-1β plays a pivotal role in postsurgical memory deficits.

Does Inhibition of α5GABA$_A$Rs Attenuate Postoperative Memory Deficits?

Figure 28:
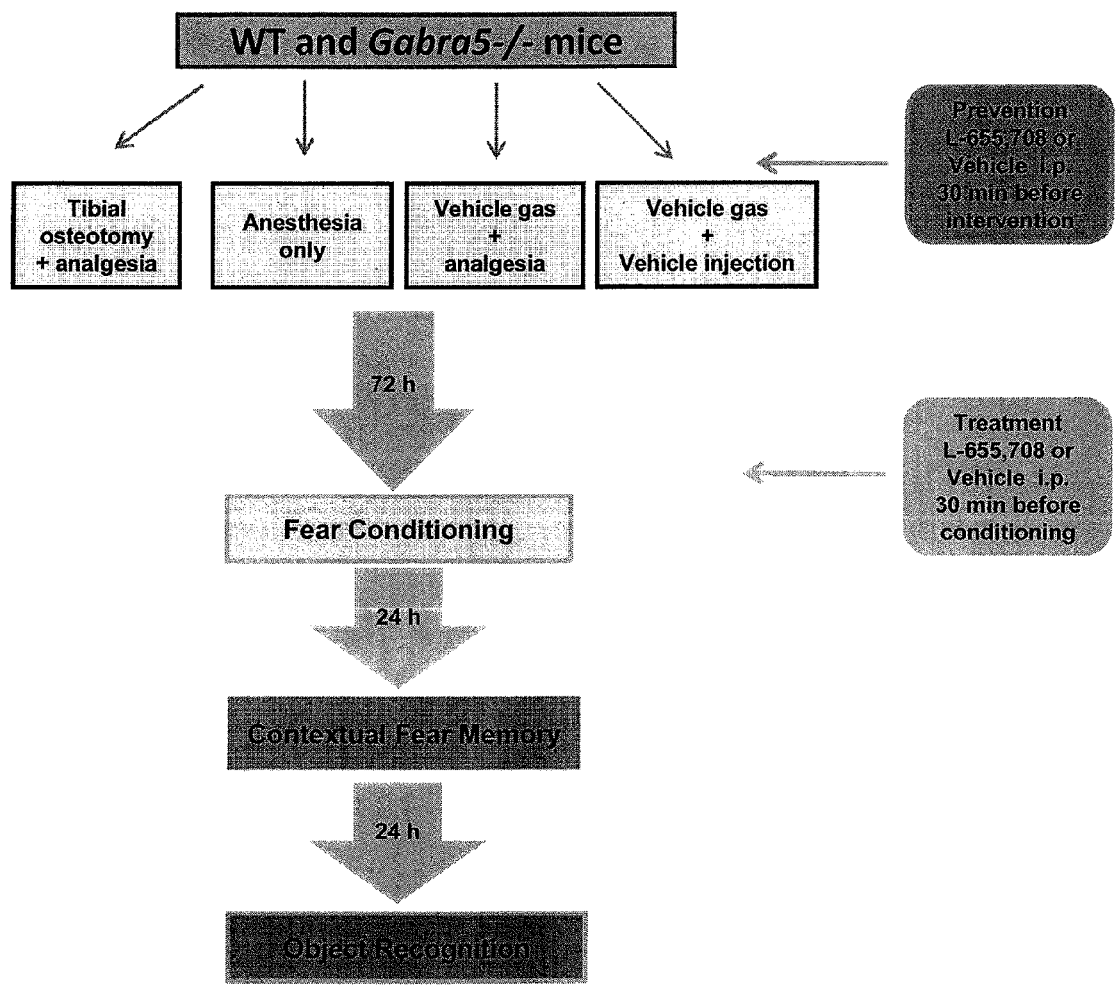
FIG. 28 illustrates the Aim 4 experimental design in Example 2 to determine whether inhibiting $α5GABA_A$ receptor activity attenuate postoperative memory deficits.
Figure 29:
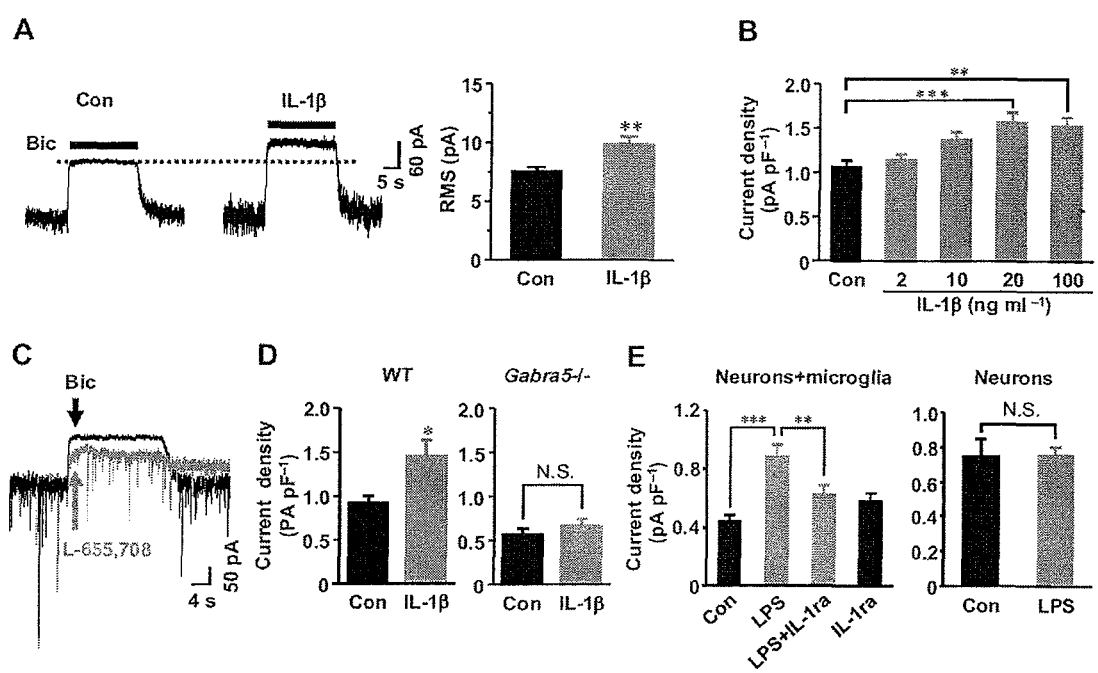
FIG. 29 illustrates that IL-1β increases the tonic current generated by $α5GABA_A Rs$ in cultured hippocampal neurons in Example 3.
Figure 30:
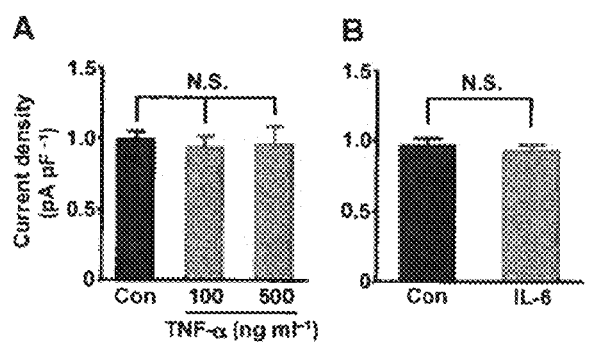
FIG. 30 illustrates that treatment with TNF-α (FIG. 30A) and IL-6 (FIG. 30B) does not affect the tonic current in Example 3.
Figure 31:
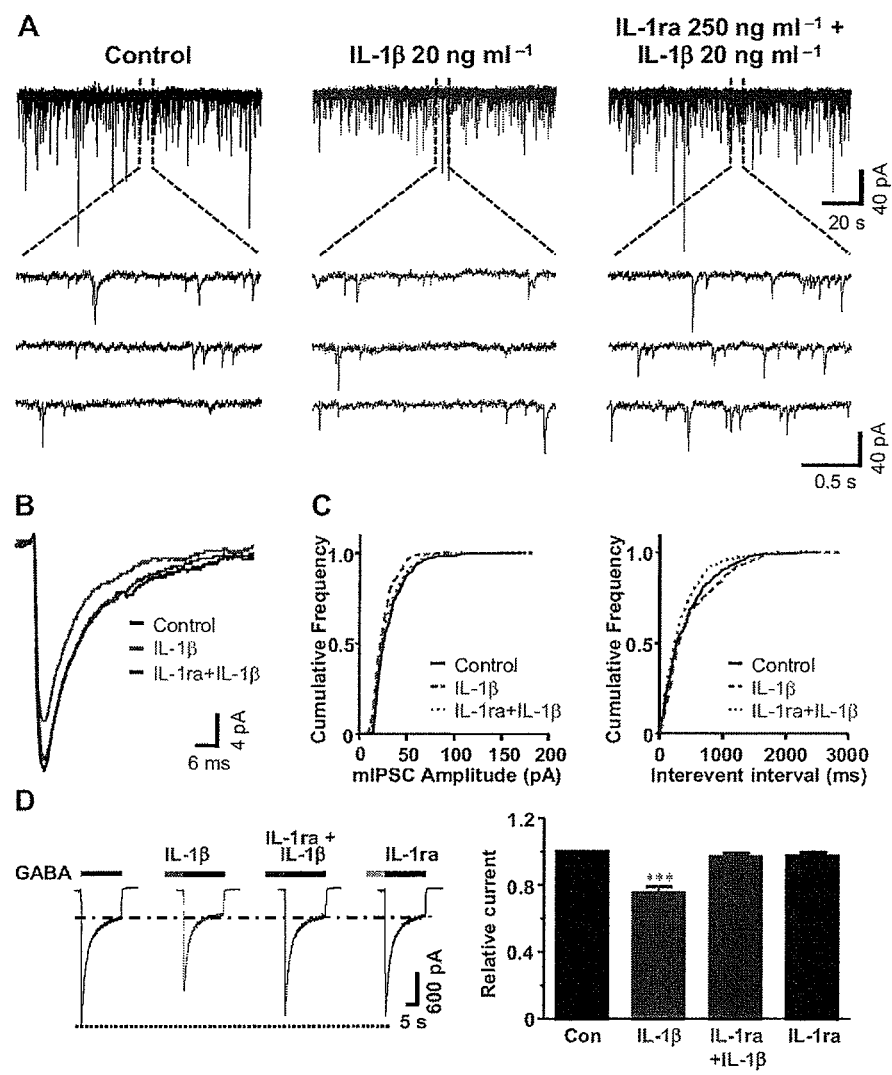
FIG. 31 illustrates that IL-1β decreases the amplitude of inhibitory synaptic currents in cultured hippocampal neurons in Example 3.
Figure 32:
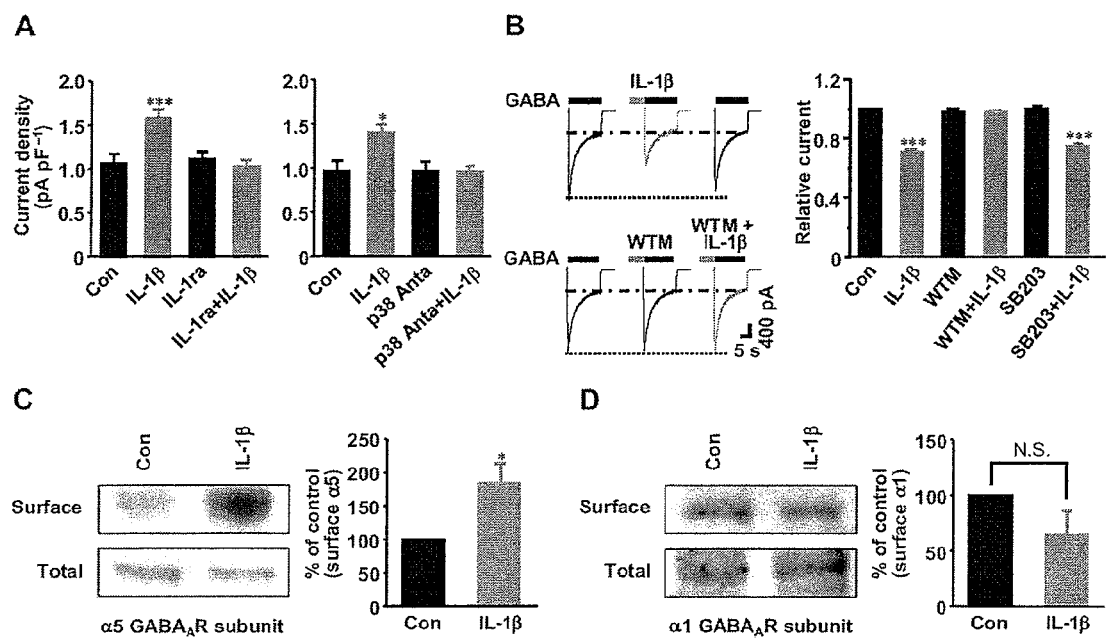
FIG. 32 illustrates that IL-1β modulates tonic and synaptic inhibitory currents through different signaling pathways in Example 3.
Figure 33:
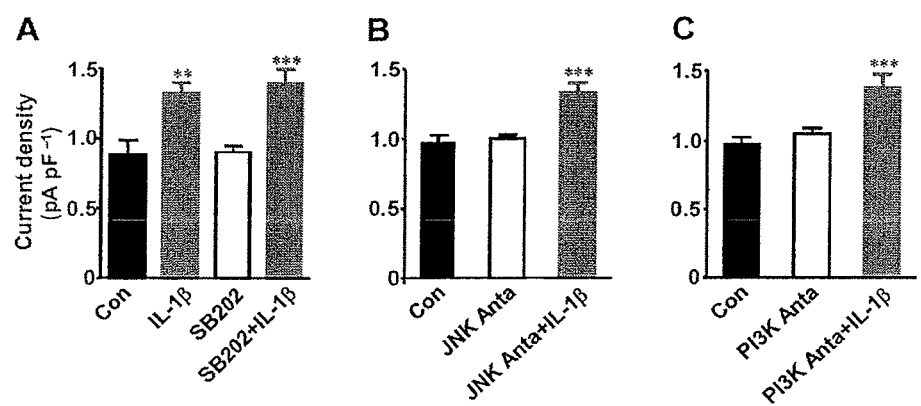
FIG. 33 illustrates that JNK- and PI3K-dependent pathways do not contribute to IL-1β-induced enhancement of tonic current in Example 3.
Figure 34:
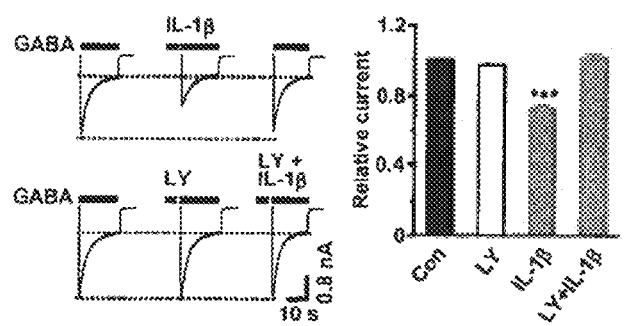
FIG. 34 illustrates that the PI3K inhibitor LY294,002 blocks the IL-1β-induced reduction of GABA-evoked peak currents in Example 3.
Figure 35:
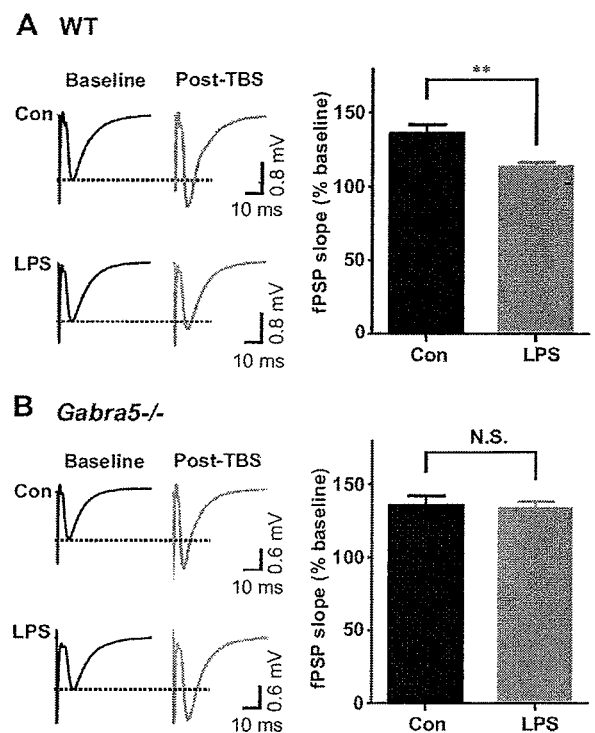
FIG. 35 illustrates that LPS-induced inflammation impairs long-term potentiation in WT but not Gabra5−/− mice in Example 3.
Figure 36:
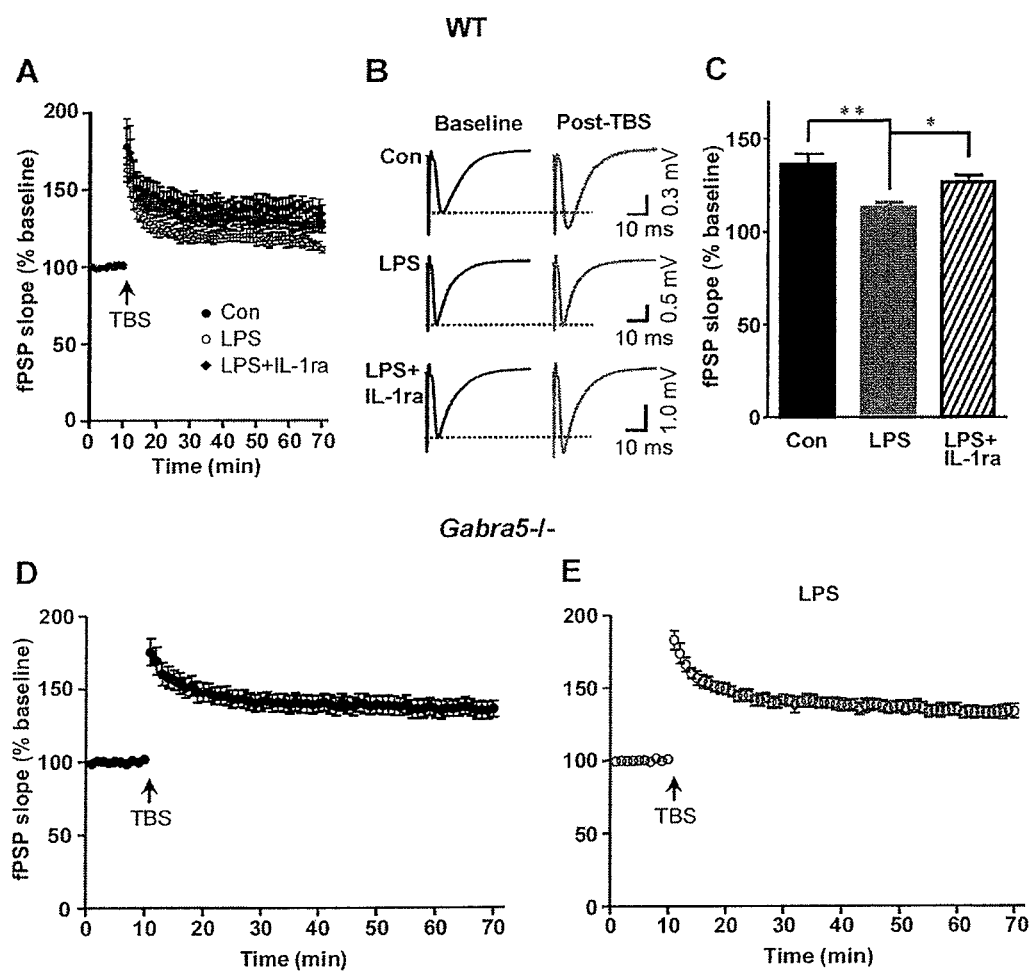
FIG. 36 illustrates that endogenous IL-1β release induced by injection of LPS inhibits long-term potentiation in slices from wild-type mice in Example 3.
Figure 37:
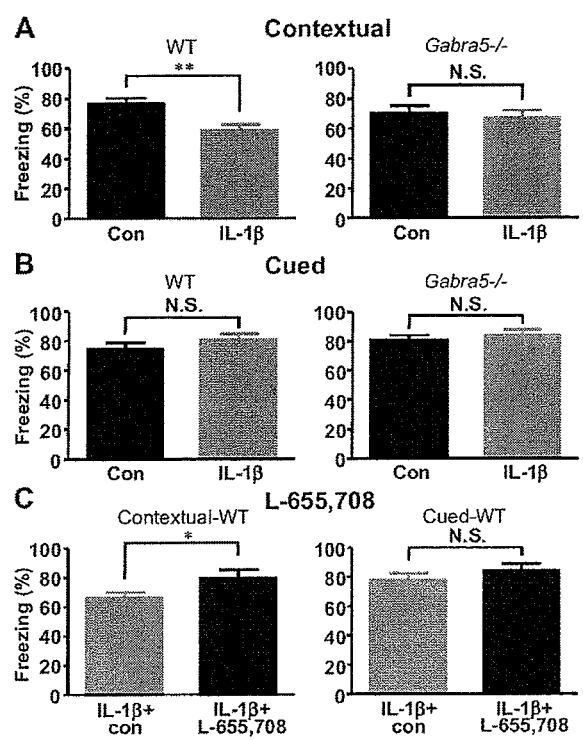
FIG. 37 illustrates that IL-1β-induced impairment of contextual fear memory is absent in Gabra5−/− mice and can be prevented by pharmacological inhibition of $α5GABA_A Rs$ with L-655,708 in WT mice in Example 3.
Figure 38:
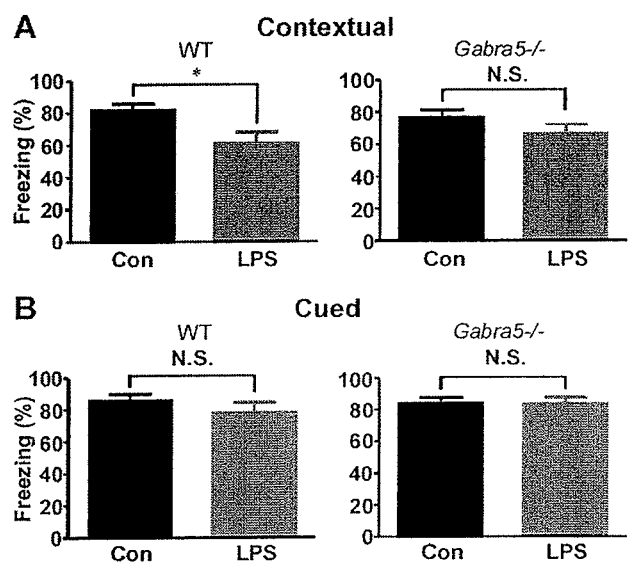
FIG. 38 illustrates that systemic inflammation induced by LPS impairs hippocampus-dependent memory in wild-type but not in Gabra5−/− mice in Example 3.
Figure 39:
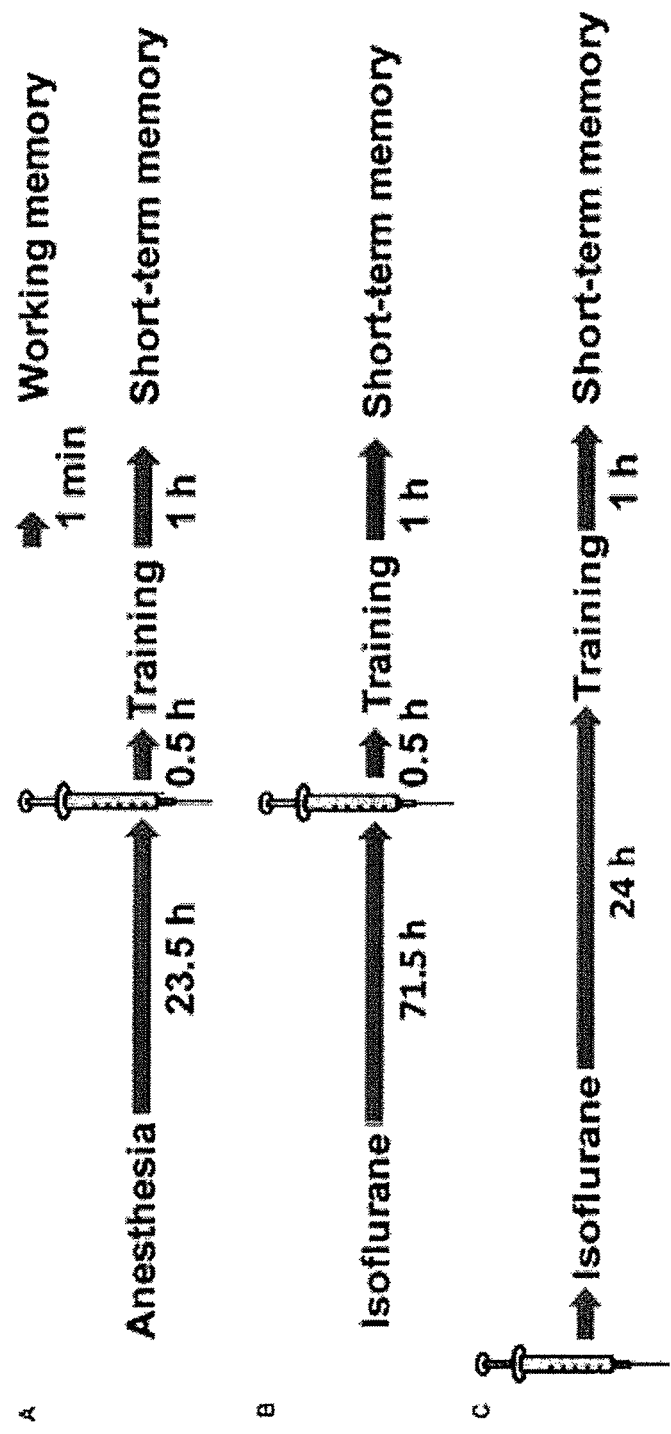
FIG. 39A illustrates the timeline of experimental treatment in which wild-type and Gabra5−/− mice were trained on the object recognition paradigm 24 h after anesthesia in Example 4.
FIG. 39B illustrates the timeline of experimental treatment in which wild-type mice were tested 72 h after isoflurane in Example 4.
FIG. 39C illustrates the time of experimental treatment in which wild-type and Gabra5−/− mice received injections of L-655,708 or vehicle 10 min prior to anesthesia in Example 4.
Figure 40:
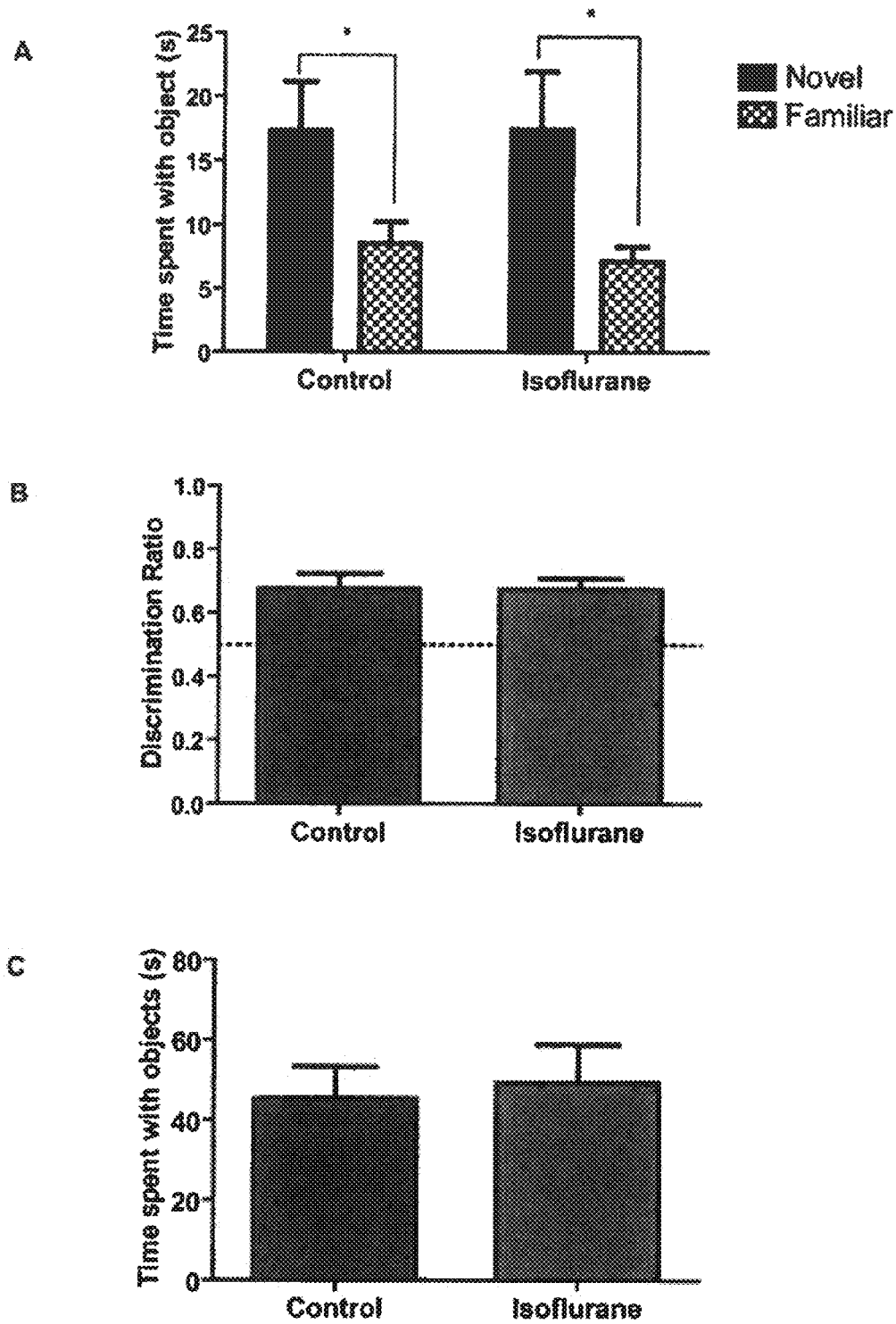
FIG. 40 illustrates the training of mice on the object recognition paradigm and testing 1 min after training one day after isoflurane exposure in Example 4.
Figure 41:
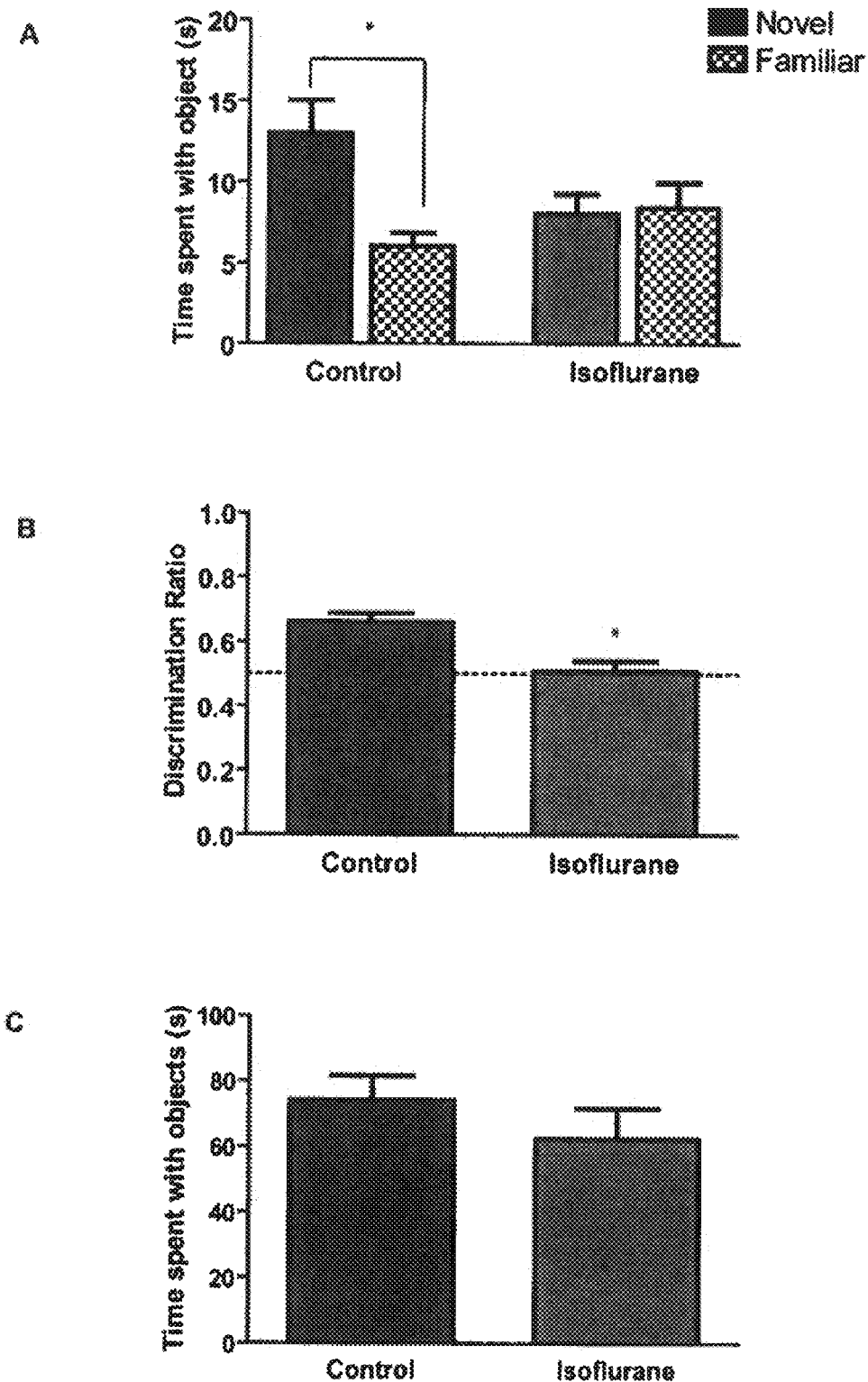
FIG. 41 illustrates the training of mice on the object recognition paradigm and testing 1 h later one day after isoflurane exposure in Example 4.
Figure 42:
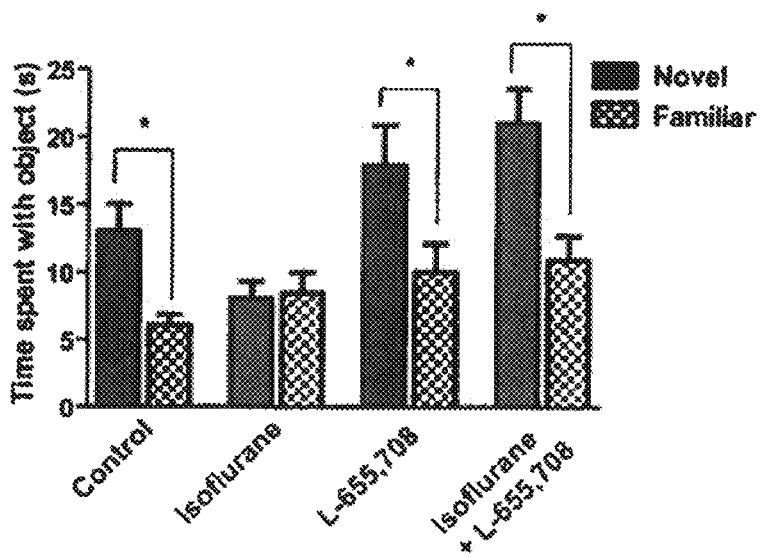
FIG. 42 illustrates training of mice on the object recognition paradigm 24 h after anesthesia and testing of short-term memory 1 h after training in Example 4.
Figure 42:
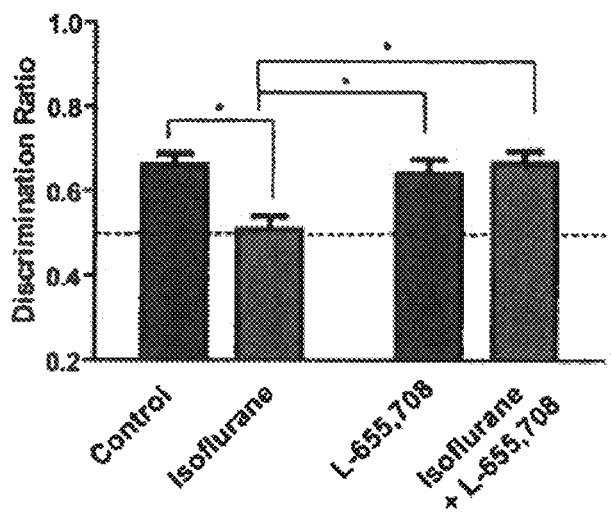
Figure 42:
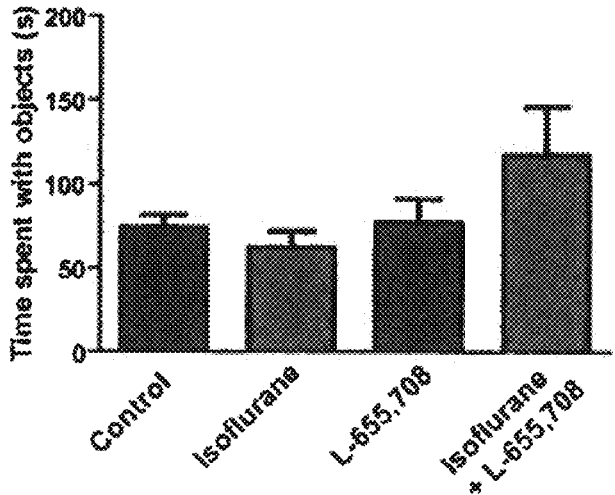
Figure 43:
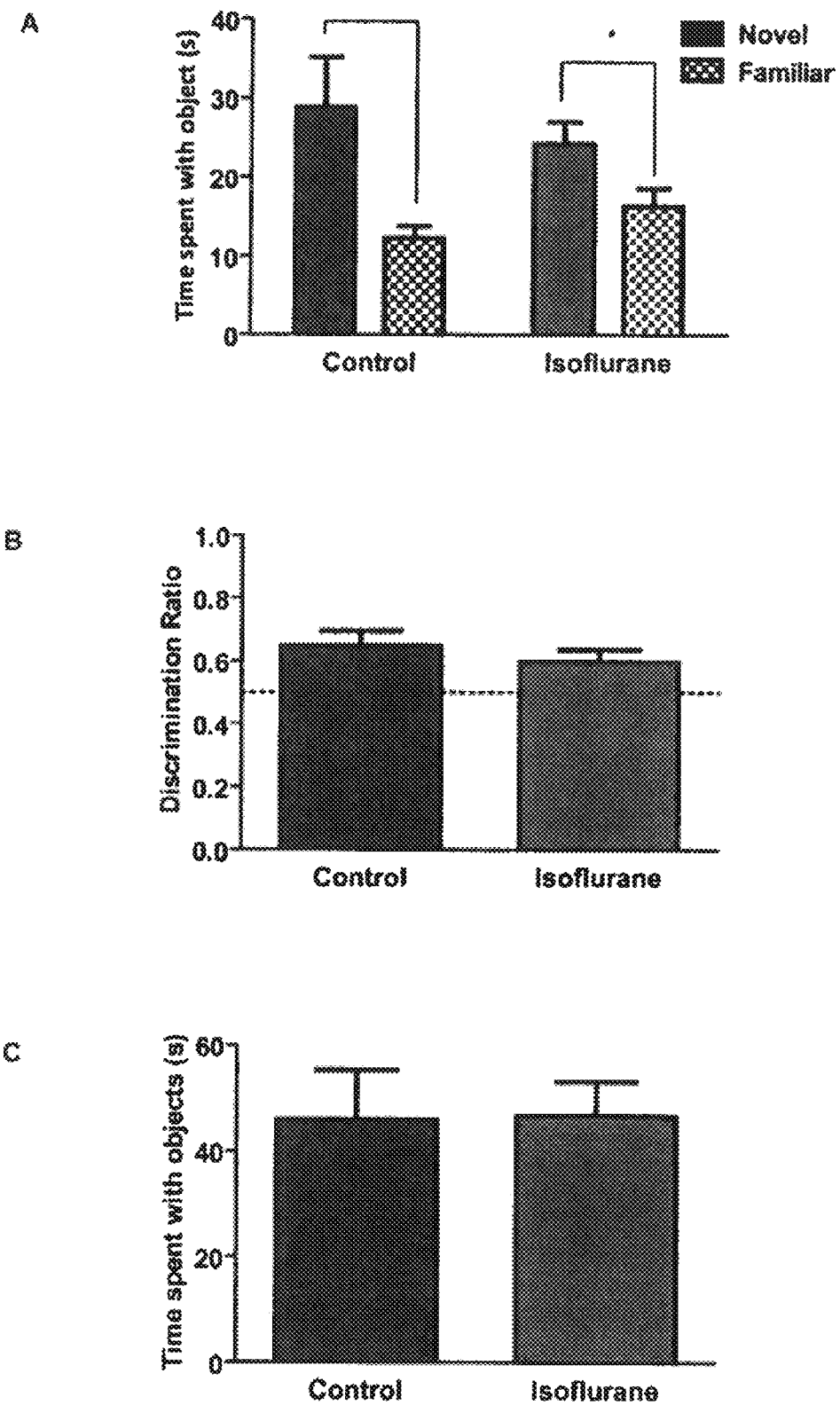
FIG. 43 illustrates training of mice on the object recognition paradigm 72 h after anesthesia and testing of short-term memory 1 h after training in Example 4.
Figure 44:
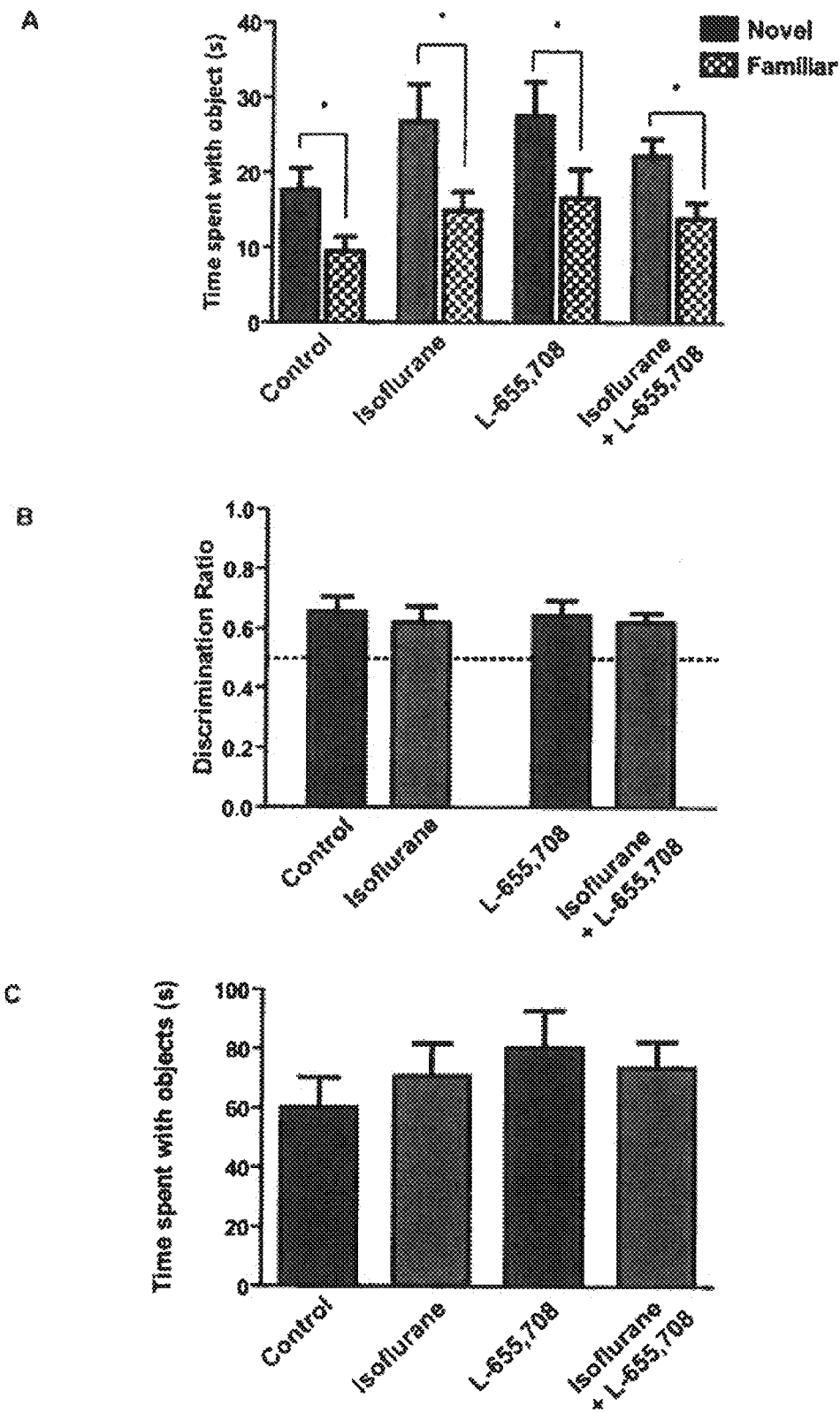
FIG. 44 illustrates training of mice on the object recognition paradigm 24 h after anesthesia and testing of short-term memory 1 h after training in Example 4.
Figure 45:
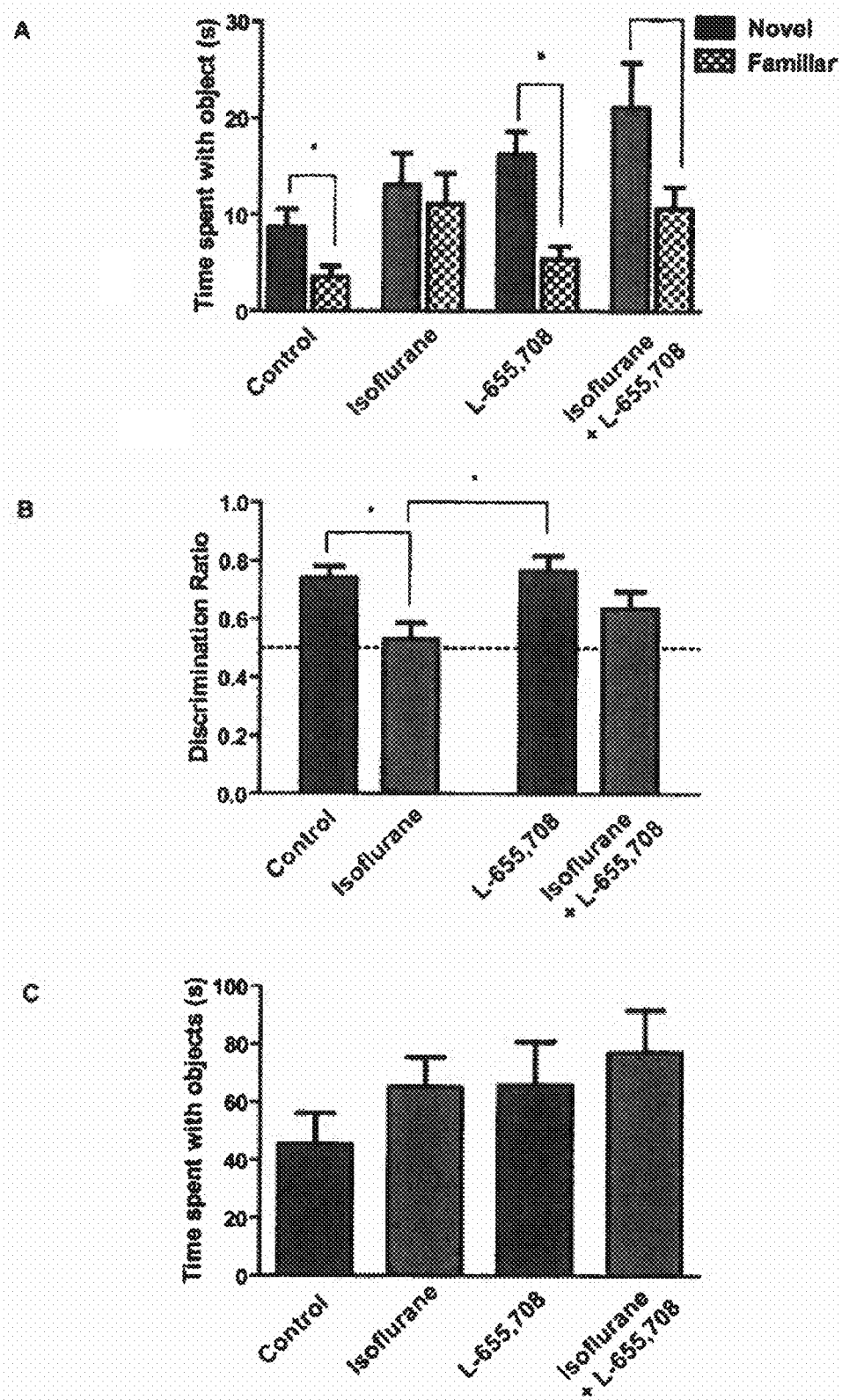
FIG. 45 illustrates training of mice on the object recognition paradigm 24 h after anesthesia and testing of short-term memory 1 h after training in Example 4.

We hypothesize that surgery increases the level of IL-1β, which in turn increases α5GABA$_A$R activity, causing deficits in the formation of memory during the postoperative period. The ability to form new memory will be assayed in mice following tibial osteotomy performed under isoflurane anesthesia, and the results will be compared with those for control animals that have not undergone surgery (FIG. 28). FIG. 28 illustrates the Aim 4 experimental design. The study will determine whether inhibiting α5GABA$_A$ receptor activity attenuate postoperative memory deficits. Wild-type (WT) and Gabra5−/− mice will be assigned to one of four groups: (1) Tibial osteotomy under isoflurane anesthesia with postoperative analgesia, (2) Isoflurane anesthesia only, (3) Vehicle gas and post-operative analgesia, (4) Vehicle gas and vehicle injection. Mice in the "prevention" group will be pretreated with L-655,708 or vehicle. Three days (72 h) after surgery, mice will be trained on the fear conditioning paradigm. Contextual fear memory will be assessed 24 h after training. The next day (120 h after surgery), novel object recognition memory will be assessed. Mice in the "treatment" group will be treated with L-655,708 or vehicle 30 min prior to training on the fear conditioning task. The following nonsurgical control groups will also be studied: 1) those receiving anesthesia and analgesia; 2) vehicle gas and analgesia; 3) vehicle gas and saline injection. Memory will be tested with two hippocampusdependent assays. Fear conditioning to context will be tested on postoperative day 3, and memory testing on postoperative day 4. Memory will also be assessed by novel-object recognition on postoperative day 548. The novelty preference paradigm evaluates episodic memory and depends on the innate motivation of experimental subjects to explore novel objects in preference to familiar objects.

This task will be used because loss of non-aversive episodic memory is the most common deficit observed in patients who have undergone surgery[2-6]. The disruption of episodic memory also characterizes many memory disorders associated with inflammation[117,118]. These experiments are designed to study both the prevention and the treatment of postsurgical memory deficits. We will test (a) whether the deficit in memory performance is greater in WT than in α5−/− mice, (b) whether preemptive administration of L-655,708 (i.p.) or vehicle 30 minutes before surgery attenuates memory loss in α5−/− and WT mice, and (c) whether treatment with L-655,708 after surgery reverses memory loss. To test whether the levels of IL-1β are similar in all treatment groups, IL-1β will be measured with ELISA on postoperative days 3 and 7. To test whether surgery increases the expression of α5GABA$_A$Rs, ex vivo brain slices will be harvested on day 3, and the slices will be immunostained.

The transcription (mRNA) and expression of GABA$_A$R subunits and GAD-67 will also be assessed with Western blotting. We anticipate that the results from these studies will provide the first evidence that inhibiting α5GABA$_A$Rs with L-655,708 reverses memory deficits after surgery.

Postoperative cognitive deficits can persist for weeks, whereas our studies will examine memory deficits over days. Memory performance will be assessed weeks after surgery in future experiments.

Future Directions

Our preliminary results raise many questions that merit future study beyond the scope of the current study. For example, the source of IL-1β is of great interest, as are the changes in IL-1β levels in the perioperative period. Also, the interplay between GABA, anesthetics, and the immune response requires further study as GABA$_A$R agonists may modify the immune responses[119,120].

Significance of the Studies

Memory dysfunction is the most frequent and most debilitating symptom associated with POCD. We anticipate that our results will foster a conceptual leap in our collective understanding of the pathogenesis of postoperative memory loss. The current understanding is that something "bad" happens during anesthesia that triggers long-lasting memory deficits. Our results will elucidate a specific mechanism whereby postoperative memory deficits result from the activation of memory-blocking receptors by neuroinflammatory processes. The vital importance of good cognition in overcoming life-threatening illness is just beginning to be understood. The proposed preclinical studies will establish a foundation for clinical trials aiming to reduce the serious morbidity and mortality associated with postoperative memory deficits.

Reference List for Background of the Invention and Example 2

1. Weiser, T. G., et al. An estimation of the global volume of surgery: a modelling strategy based on available data. *Lancet* 372, 139-144 (2008).
2. Orser, B. A. Lifting the fog around anesthesia. *Sci. Am.* 296, 54-61 (2007).
3. Moller, J. T., et al. Long-term postoperative cognitive dysfunction in the elderly ISPOCD1 study. ISPOCD investigators. International Study of Post-Operative Cognitive Dysfunction. *Lancet* 351, 857-861 (1998).
4. Caza, N., Taha, R., Qi, Y. & Blaise, G. The effects of surgery and anesthesia on memory and cognition. *Prog Brain Res* 169, 409-422 (2008).
5. Krenk, L., Rasmussen, L. S. & Kehlet, H. New insights into the pathophysiology of postoperative cognitive dysfunction. *Acta Anaesthesiol Scand* 54, 951-956 (2010).
6. Bekker, A., et al. Does mild cognitive impairment increase the risk of developing postoperative cognitive dysfunction? *Am J Surg* 199, 782-788 (2010).
7. Hanning, C. D. Postoperative cognitive dysfunction. *Br. J. Anaesth.* 95, 82-87 (2005).
8. Bai, D., et al. Distinct functional and pharmacological properties of tonic and quantal inhibitory postsynaptic currents mediated by γ-aminobutyric acid A receptors in hippocampal neurons. *Mol Pharmacol* 59, 814-824 (2001).
9. Caraiscos, V. B., et al. Tonic inhibition in mouse hippocampal CA1 pyramidal neurons is mediated by α5 subunit-containing γ-aminobutyric acid type A receptors. *Proc. Natl. Acad. Sci. U.S.A* 101, 3662-3667 (2004).

10. Cheng, V. Y., et al. α5GABA$_A$ receptors mediate the amnestic but not sedative-hypnotic effects of the general anesthetic etomidate. *J. Neurosci.* 26, 3713-3720 (2006).
11. Martin, L. J., Oh, G. H. & Orser, B. A. Etomidate targets α5 γ-aminobutyric acid subtype A receptors to regulate synaptic plasticity and memory blockade. *Anesthesiology* 111, 1025-1035 (2009).
12. Collinson, N., et al. Enhanced learning and memory and altered GABAergic synaptic transmission in mice lacking the α5 subunit of the GABAA receptor. *J Neurosci.* 22, 5572 5580 (2002).
13. Chambers, M. S., et al. Identification of a novel, selective GABAA α5 receptor inverse agonist which enhances cognition. *J. Med. Chem.* 46, 2227-2240 (2003).
14. Caraiscos, V. B., et al. Selective enhancement of tonic GABAergic inhibition in murine hippocampal neurons by low concentrations of the volatile anesthetic isoflurane. *J. Neurosci.* 24, 8454-8458 (2004).
15. Jones, M. J., et al. Cognitive and functional competence after anaesthesia in patients aged over 60: controlled trial of general and regional anaesthesia for elective hip or knee replacement. *BMJ* 300, 1683-1687 (1990).
16. Ghoneim, M. M., et al. Comparison of psychologic and cognitive functions after general or regional anesthesia. *Anesthesiology* 69, 507-515 (1988).
17. Culley, D. J., Baxter, M., Yukhananov, R. & Crosby, G. The memory effects of general anesthesia persist for weeks in young and aged rats. *Anesth. Analg.* 96, 1004-1009 (2003).
18. Phillips-Bute, B., et al. Association of neurocognitive function and quality of life 1 year after coronary artery bypass graft (CABG) surgery. *Psychosom. Med.* 68, 369-375 (2006).
19. Newman, M. F., et al. Longitudinal assessment of neurocognitive function after coronary-artery bypass surgery. *N. Engl. J. Med.* 344, 395-402 (2001).
20. Hudetz, J. A., et al. Postoperative cognitive dysfunction in older patients with a history of alcohol abuse. *Anesthesiology* 106, 423-430 (2007).
21. Squire, L. R., Stark, C. E. & Clark, R. E. The medial temporal lobe. *Annu Rev Neurosci* 27, 279-306 (2004).
22. Zola, S. & Squire, L. The medial temporal lobe and the hippocampus. in *The Oxford Handbook of Memory* (eds. Tulving, E. & Craik, F.) 485-500 (Oxford University Press, New York, 2000).
23. Squire, L. R. & Bayley, P. J. The neuroscience of remote memory. *Curr Opin Neurobiol* 17, 185-196 (2007).
24. Wiig, K., Cooper, L. & Bear, M. Temporally graded retrograde amnesia following separate and combined lesions of the perirhinal cortex and fornix in the rat. in *Learning & memory*, Vol. 3 313-325 (Cold Spring Harbor, N.Y., 1996).
25. Saab, B. J., et al. Memory impairment after isoflurane can be prevented by pretreatment with the α5GABA$_A$ receptor inverse agonist L-655,708. *Anesthesiology* (in press).
26. Olsen, R. W. & Tobin, A. J. Molecular biology of GABAA receptors. *Faseb J* 4, 1469-1480 (1990).
27. Smith, G. B. & Olsen, R. W. Functional domains of GABAA receptors. *Trends Pharmacol Sci* 16, 162-168 (1995).
28. Martin, L. J., et al. α5GABA$_A$ receptor activity sets the threshold for long-term potentiation and constrains hippocampus-dependent memory. *J Neurosci* 30, 5269-5282 (2010).
29. Ju, Y. H., et al. Distinct properties of murine α5 γ-aminobutyric acid type a receptors revealed by biochemical fractionation and mass spectroscopy. *J Neurosci Res* 87, 1737-1747 (2009).
30. Xiang, Y. Y., et al. A GABAergic system in airway epithelium is essential for mucus overproduction in asthma. *Nat. Med.* 13, 862-867 (2007).
31. Bonin, R. P., Martin, L. J., MacDonald, J. F. & Orser, B. A. α5GABA$_A$ receptors regulate the intrinsic excitability of mouse hippocampal pyramidal neurons. *J Neurophysiol* 98, 2244-2254 (2007).
32. Cheng, V. Y., et al. Gabapentin increases a tonic inhibitory conductance in hippocampal pyramidal neurons. *Anesthesiology* 105, 325-333 (2006).
33. Yeung, J. Y., et al. Tonically activated GABAA receptors in hippocampal neurons are highaffinity, low-conductance sensors for extracellular GABA. *Mol. Pharmacol.* 63, 2-8 (2003).
34. McAdam, L. C., MacDonald, J. F. & Orser, B. A. Isobolographic analysis of the interactions between midazolam and propofol at GABAA receptors in embryonic mouse neurons. *Anesthesiology* 89, 1444-1454 (1998).
35. Macdonald, R. L. & Olsen, R. W. GABAA receptor channels. *Annu. Rev. Neurosci.* 17:569-602, 569-602 (1994).
36. Chebib, M. & Johnston, G. A. GABA-activated ligand gated ion channels: medicinal chemistry and molecular biology. *J Med. Chem* 43, 1427-1447 (2000).
37. Mody, I. Distinguishing between GABAA receptors responsible for tonic and phasic conductances. *Neurochem. Res.* 26, 907-913 (2001).
38. Farrant, M. & Nusser, Z. Variations on an inhibitory theme: phasic and tonic activation of GABAA receptors. *Nat. Rev. Neurosci.* 6, 215-229 (2005).
39. Soltesz, I. & Nusser, Z. Background inhibition to the fore. *Nature* 409, 24-25, 27 (2001).
40. Wu, Y., Wang, W. & Richerson, G. B. GABA transaminase inhibition induces spontaneous and enhances depolarization-evoked GABA efflux via reversal of the GABA transporter. *J Neurosci.* 21, 2630-2639 (2001).
41. Liu, Q. Y., Schaffner, A. E., Chang, Y. H., Maric, D. & Barker, J. L. Persistent activation of GABAA receptor/Cl-channels by astrocyte-derived GABA in cultured embryonic rat hippocampal neurons. *J. Neurophysiol.* 84, 1392-1403 (2000).
42. Glykys, J. & Mody, I. The main source of ambient GABA responsible for tonic inhibition in the mouse hippocampus. *J. Physiol* 582, 1163-1178 (2007).
43. Crestani, F., et al. Trace fear conditioning involves hippocampal α5 GABAA receptors. *Proc. Natl. Acad. Sci. U.S.A* 99, 8980-8985 (2002).
44. Brunig, I., Scotti, E., Sidler, C. & Fritschy, J. M. Intact sorting, targeting, and clustering of γ-aminobutyric acid A receptor subtypes in hippocampal neurons in vitro. *J Comp Neurol* 443, 43-55 (2002).
45. Savic, M. M., et al. Are GABAA receptors containing alpha5 subunits contributing to the sedative properties of benzodiazepine site agonists? *Neuropsychopharmacology* 33, 332-339 (2008).
46. O'Keefe, J. Hippocampus, theta, and spatial memory. *Curr Opin Neurobiol* 3, 917-924 (1993).
47. Buzsaki, G. Theta rhythm of navigation: link between path integration and landmark navigation, episodic and semantic memory. *Hippocampus* 15, 827-840 (2005).
48. Wiklund, A., et al. Object memory in young and aged mice after sevoflurane anaesthesia. *Neuroreport* 20, 1419-1423 (2009).

49. Greeson, J. M. Mindfulness Research Update: 2008. *Complement Health Pract Rev* 14, 10-18 (2009).
50. Goshen, I. & Yirmiya, R. The role of pro-inflamatory cytokines in memory processes and neural plasticity. in *Psychoneuroimmunology*, Vol. 1 (ed. Ader, R.) 337-377 (Elsevier Academic Press, London, 2007).
51. Serantes, R., et al. Interleukin-1β enhances GABAA receptor cell-surface expression by a phosphatidylinositol 3-kinase/Akt pathway: relevance to sepsis-associated encephalopathy. *J Biol Chem* 281, 14632-14643 (2006).
52. Pickering, M. & O'Connor, J. J. Pro-inflammatory cytokines and their effects in the dentate gyrus. *Prog Brain Res* 163, 339-354 (2007).
53. Cibelli, M., et al. Role of interleukin-1β in postoperative cognitive dysfunction. *Ann Neurol* 68, 360-368 (2010).
54. O'Neill, L. A. The interleukin-1 receptor/Toll-like receptor superfamily: 10 years of progress. *Immunol Rev* 226, 10-18 (2008).
55. Gabay, C., Lamacchia, C. & Palmer, G. IL-1 pathways in inflammation and human diseases. *Nat Rev Rheumatol* 6, 232-241 (2010).
56. O'Neill, L. A. & Greene, C. Signal transduction pathways activated by the IL-1 receptor family: ancient signaling machinery in mammals, insects, and plants. *J Leukoc Biol* 63, 650-657 (1998).
57. Dinarello, C. A. The role of the interleukin-1-receptor antagonist in blocking inflammation mediated by interleukin-1. *N Engl J Med* 343, 732-734 (2000).
58. Wan, Y., et al. Postoperative impairment of cognitive function in rats: a possible role for cytokine-mediated inflammation in the hippocampus. *Anesthesiology* 106, 436-443 (2007).
59. Rosczyk, H. A., Sparkman, N. L. & Johnson, R. W. Neuroinflammation and cognitive function in aged mice following minor surgery. *Exp Gerontol* 43, 840-846 (2008).
60. Cao, X. Z., et al. Postoperative cognitive deficits and neuroinflammation in the hippocampus triggered by surgical trauma are exacerbated in aged rats. *Prog Neuropsychopharmacol Biol Psychiatry* (in press).
61. Tsai, S. J., et al. Interleukin-1β (C-511T) genetic polymorphism is associated with cognitive performance in elderly males without dementia. *Neurobiol Aging* (2008).
62. Fleischmann, R. M., et al. Safety of extended treatment with anakinra in patients with rheumatoid arthritis. *Ann Rheum Dis* 65, 1006-1012 (2006).
63. Avital, A., et al. Impaired interleukin-1 signaling is associated with deficits in hippocampal memory processes and neural plasticity. *Hippocampus* 13, 826-834 (2003).
64. McAfoose, J. & Baune, B. T. Evidence for a cytokine model of cognitive function. *Neurosci Biobehav Rev* 33, 355-366 (2009).
65. Dawson, G. R., et al. An unverse agonist selective for α5 subunit-containing GABAA receptors enhances cognition. *J. Pharmacol. Exp. Ther.* 316, 1335-1345 (2006).
66. Sternfeld, F., et al. Selective, orally active γ-aminobutyric acidA α5 receptor inverse agonists as cognition enhancers. *J. Med. Chem.* 47, 2176-2179 (2004).
67. Nutt, D. J., Besson, M., Wilson, S. J., Dawson, G. R. & Lingford-Hughes, A. R. Blockade of alcohol's amnestic activity in humans by an alpha5 subtype benzodiazepine receptor inverse agonist. *Neuropharmacology* (2007).
68. Sun, H. S., et al. Suppression of hippocampal TRPM7 protein prevents delayed neuronal death in brain ischemia. *Nat Neurosci* 12, 1300-1307 (2009).
69. Terrando, N., et al. Tumor necrosis factor-α (TNF-α) provokes cytokine cascade to produce postoperative cognitive decline. (submitted).
70. Terrando, N., et al. The impact of IL-1 modulation on the development of lipopolysaccharideinduced cognitive dysfunction. *Crit Care* 14, R88 (2010).
71. Dutton, R. C., et al. The concentration of isoflurane required to suppress learning depends on the type of learning. *Anesthesiology* 94, 514-519 (2001).
72. Sonner, J. M., et al. Effect of isoflurane and other potent inhaled anesthetics on minimum alveolar concentration, learning, and the righting reflex in mice engineered to express alpha1 gamma-aminobutyric acid type A receptors unresponsive to isoflurane. *Anesthesiology* 106, 107-113 (2007).
73. Sonner, J. M., et al. Alpha 1 subunit-containing GABA type A receptors in forebrain contribute to the effect of inhaled anesthetics on conditioned fear. *Mol Pharmacol* 68, 61-68 (2005).
74. Fritschy, J. M., Johnson, D. K., Mohler, H. & Rudolph, U. Independent assembly and subcellular targeting of GABAA-receptor subtypes demonstrated in mouse hippocampal and olfactory neurons in vivo. *Neurosci. Lett.* 249, 99-102 (1998).
75. Semyanov, A., Walker, M. C. & Kullmann, D. M. GABA uptake regulates cortical excitability via cell type-specific tonic inhibition. *Nat. Neurosci.* 6, 484-490 (2003).
76. Nguyen, K. T., et al. Exposure to acute stress induces brain interleukin-1p protein in the rat. *J Neurosci* 18, 2239-2246 (1998).
77. Ban, E., Haour, F. & Lenstra, R. Brain interleukin 1 gene expression induced by peripheral lipopolysaccharide administration. *Cytokine* 4, 48-54 (1992).
78. Ostberg, J. R., Taylor, S. L., Baumann, H. & Repasky, E. A. Regulatory effects of fever-range whole-body hyperthermia on the LPS-induced acute inflammatory response. *J Leukoc Biol* 68, 815-820 (2000).
79. Heida, J. G., Moshe, S. L. & Pittman, Q. J. The role of interleukin-1β in febrile seizures. *Brain Dev* 31, 388-393 (2009).
80. Turrin, N. P., et al. Pro-inflammatory and anti-inflammatory cytokine mRNA induction in the periphery and brain following intraperitoneal administration of bacterial lipopolysaccharide. *Brain Res Bull* 54, 443-453 (2001).
81. Sparkman, N. L., Martin, L. A., Calvert, W. S. & Boehm, G. W. Effects of intraperitoneal lipopolysaccharide on Morris maze performance in year-old and 2-month-old female C57BL/6J mice. *Behav Brain Res* 159, 145-151 (2005).
82. Harry, L. E., et al. Comparison of the healing of open tibial fractures covered with either muscle or fasciocutaneous tissue in a murine model. *J Orthop Res* 26, 1238-1244 (2008).
83. Joo, D. T., et al. Blockade of AMPA receptors and volatile anesthetics: reduced anesthetic requirements in GluR2 null mutant mice for loss of the righting reflex and antinociception but not minimum alveolar concentration. *Anesthesiology* 94, 478-488 (2001).
84. Miller, L. G., Galpern, W. R., Dunlap, K., Dinarello, C. A. & Turner, T. J. Interleukin-1 augments γ-aminobutyric acid A receptor function in brain. *Mol Pharmacol* 39, 105-108 (1991).
85. Yu, B. & Shinnick-Gallagher, P. Interleukin-1β inhibits synaptic transmission and induces membrane hyperpolarization in amygdala neurons. *J Pharmacol Exp Ther* 271, 590-600 (1994).

86. Wang, S., Cheng, Q., Malik, S. & Yang, J. Interleukin-1β inhibits γ-aminobutyric acid type A (GABAA) receptor current in cultured hippocampal neurons. *J Pharmacol Exp Ther* 292, 497-504 (2000).
87. Zeise, M. L., Espinoza, J., Morales, P. & Nalli, A. Interleukin-1β does not increase synaptic inhibition in hippocampal CA3 pyramidal and dentate gyrus granule cells of the rat in vitro. *Brain Res* 768, 341-344 (1997).
88. Tang, R. B., Lee, B. H., Chung, R. L., Chen, S. J. & Wong, T. T. Interleukin-1β and tumor necrosis factor-α in cerebrospinal fluid of children with bacterial meningitis. *Childs Nerv Syst* 17, 453-456 (2001).
89. Stellwagen, D., Beattie, E. C., Seo, J. Y. & Malenka, R. C. Differential regulation of AMPA receptor and GABA receptor trafficking by tumor necrosis factor-α. *J Neurosci* 25, 3219-3228 (2005).
90. Sekiyama, K. D., Yoshiba, M. & Thomson, A. W. Circulating proinflammatory cytokines (IL-1β, TNF-α, and IL-6) and IL-1 receptor antagonist (IL-1Ra) in fulminant hepatic failure and acute hepatitis. *Clin Exp Immunol* 98, 71-77 (1994).
91. Hernandez-Rodriguez, J., et al. Tissue production of pro-inflammatory cytokines (IL 1β, TNFα and IL-6) correlates with the intensity of the systemic inflammatory response and with corticosteroid requirements in giant-cell arteritis. *Rheumatology (Oxford)* 43, 294-301 (2004).
92. Srinivasan, D., Yen, J. H., Joseph, D. J. & Friedman, W. Cell type-specific interleukin-1β signaling in the CNS. *J Neurosci* 24, 6482-6488 (2004).
93. Wang, S. H., Ostlund, S. B., Nader, K. & Balleine, B. W. Consolidation and reconsolidation of incentive learning in the amygdala. *J Neurosci* 25, 830-835 (2005).
94. Uusi-Oukari, M. & Korpi, E. R. Regulation of GABA (A) receptor subunit expression by pharmacological agents. *Pharmacol Rev* 62, 97-135.
95. Man, H. Y., et at Activation of PI3-kinase is required for AMPA receptor insertion during LTP of mEPSCs in cultured hippocampal neurons. *Neuron* 38, 611-624 (2003).
96. Wang, Q., et al. Control of synaptic strength, a novel function of Akt. *Neuron* 38, 915-928 (2003).
97. Jacob, T. C., Moss, S. J. & Jurd, R. GABAA receptor trafficking and its role in the dynamic modulation of neuronal inhibition. *Nat Rev Neurosci* 9, 331-343 (2008).
98. Moss, S. J. & Smart, T. G. Constructing inhibitory synapses. *Nat. Rev. Neurosci.* 2, 240-250 (2001).
99. Thomas-Crusells, J., Vieira, A., Saarma, M. & Rivera, C. A novel method for monitoring surface membrane trafficking on hippocampal acute slice preparation. *J Neurosci Methods* 125, 159-166 (2003).
100. Bhat, R., et al. Inhibitory role for GABA in autoimmune inflammation. *Proc Natl Acad Sci USA* 107, 2580-2585 (2010).
101. Roberts, D. S., et al. Egr3 stimulation of GABRA4 promoter activity as a mechanism for seizure-induced up-regulation of GABAA receptor α4 subunit expression. *Proc Natl Acad Sci USA* 102, 11894-11899 (2005).
102. Roberts, D. S., Hu, Y., Lund, I. V., Brooks-Kayal, A. R. & Russek, S. J. Brain-derived neurotrophic factor (BDNF)-induced synthesis of early growth response factor 3 (Egr3) controls the levels of type A GABA receptor α4 subunits in hippocampal neurons. *J Biol Chem* 281, 29431-29435 (2006).
103. Kellenberger, S., Malherbe, P. & Sigel, E. Function of the α1β2γ2S γ-aminobutyric acid type A receptor is modulated by protein kinase C via multiple phosphorylation sites. *J Biol Chem* 267, 25660-25663 (1992).
104. Connolly, C. N., et al. Cell surface stability of γ-aminobutyric acid type A receptors. Dependence on protein kinase C activity and subunit composition. *J Biol Chem* 274, 36565-36572 (1999).
105. Malenka, R. C. & Bear, M. F. LTP and LTD: an embarrassment of riches. *Neuron* 44, 5-21 (2004).
106. Squire, L. R. & Kandel, E. R. *Memory: from mind to molecules*, (Roberts & Company, Colorado, 2008.).
107. Nguyen, P. V. & Kandel, E. R. Brief θ-burst stimulation induces a transcription-dependent late phase of LTP requiring cAMP in area CA1 of the mouse hippocampus. *Learn Mem* 4, 230-243 (1997).
108. Turrigiano, G. Homeostatic signaling: the positive side of negative feedback *Curr Opin Neurobiol* 17, 318-324 (2007).
109. Bruel-Jungerman, E., Davis, S. & Laroche, S. Brain plasticity mechanisms and memory: a party of four. *Neuroscientist* 13, 492-505 (2007).
110. Bruel-Jungerman, E., Rampon, C. & Laroche, S. Adult hippocampal neurogenesis, synaptic plasticity and memory: facts and hypotheses. *Rev Neurosci* 18, 93-114 (2007).
111. Drapeau, E., Montaron, M. F., Aguerre, S. & Abrous, D. N. Learning-induced survival of new neurons depends on the cognitive status of aged rats. *J Neurosci* 27, 6037-6044 (2007).
112. England, M. R. The changes in bispectral index during a hypovolemic cardiac arrest. *Anesthesiology* 91, 1947-1949 (1999).
113. Honan, D. M., Breen, P. J., Boylan, J. F., McDonald, N. J. & Egan, T. D. Decrease in bispectral index preceding intraoperative hemodynamic crisis: evidence of acute alteration of propofol pharmacokinetics. *Anesthesiology* 97, 1303-1305 (2002).
114. Villacorta, J., et al. Perioperative cerebral ischaemia in cardiac surgery and BIS. *Anaesth Intensive Care* 33, 514-517 (2005).
115. Tallarida, R. J. Interactions between drugs and occupied receptors. *Pharmacol Ther* 113, 197-209 (2007).
116. Tallarida, R. J. An overview of drug combination analysis with isobolograms. *J Pharmacol Exp Ther* 319, 1-7 (2006).
117. Hein, A. M., et al. Sustained hippocampal IL-1β overexpression impairs contextual and spatial memory in transgenic mice. *Brain Behav Immun* 24, 243-253 (2010).
118. Rosi, S., et al. Accuracy of hippocampal network activity is disrupted by neuroinflammation: rescue by memantine. *Brain* 132, 2464-2477 (2009).
119. Kelley, J. M., Hughes, L. B. & Bridges, S. L., Jr. Does γ-aminobutyric acid (GABA) influence the development of chronic inflammation in rheumatoid arthritis? *J Neuroinflammation* 5, 1 (2008).
120. Sakai, T., Okada, H., Kise, M., Komatsu, T. & Yamamoto, S. γ-Aminobutyric acid (GABA) suppresses antigen-specific immune responses in ovalbumin γ(OVA)-immunized BALB/c mice. *Am J Immunol* 1, 101-105 (2005).

Example 3

Inflammation-Induced Memory Impairment is Mediated by an Increase in Tonic GABAergic Inhibition Acute systemic inflammation caused by a multitude of diseases, infections, and injuries leads to a constellation of symptoms that together are referred to as "sickness behavior"$_{1, 2}$. One prominent and disabling neurological symptom of sickness behavior is memory loss, as evidenced by impaired explicit recall in humans and deficiencies of performance in fear memory and object recognition tasks in laboratory animals$_3$. Inflammation also contributes to certain chronic neurodegenerative diseases that are characterized by memory loss, including Parkinson's disease, traumatic brain injury, multiple sclerosis, and even HIV-associated dementia[3-5].

Severe inflammation results in the production of multiple cytokines, including IL-1β, tumor necrosis factor-α (TNF-α) and interleukin-6 (IL-6)[1-3]. In particular, elevated levels of IL-1β strongly correlate with memory deficits. In patients with sepsis-associated encephalopathy, increased plasma levels of IL-1β have been correlated with cognitive deficits[6]. Also, elderly people with expression of a genetic variant of the IL-1β-converting enzyme that produces lower levels of IL-1β exhibit better cognitive performance than the general population. In laboratory animals, an increase in IL-1β in the hippocampus associated with medical and surgical inflammation is strongly correlated with memory deficits[3, 8]. Currently, no treatments are available to reverse IL-1β-dependent memory impairment. Directly blocking the membrane-bound type 1 IL-1 receptors that bind IL-1β or inhibiting the general inflammatory response are impractical because of the risk of infection and delayed wound healing[9]. Moreover, low basal levels of IL-1β play a physiological role and are essential for normal memory performance'. Thus, elucidating the downstream targets of IL-1β-activated signaling pathways that impair memory is crucial for the development of effective treatments.

Inflammation, and elevated levels of IL-1β modify multiple neurotransmitter systems; however, a causal role for a specific receptor in inflammation-induced cognitive dysfunction has not previously been demonstrated. Elevated levels of IL-1β predominantly impair hippocampus-dependent memory, possibly by enhancing inhibitory neurotransmission$_3$. However, in vitro studies have shown that IL-1β has contradictory and even opposing effects, either increasing or decreasing the function and expression of γ-aminobutyric acid (GABA) type A receptors (GABA$_A$Rs), depending on the experimental preparation[6, 10-14]. In the hippocampus, GABA$_A$Rs generate two distinct forms of inhibition: conventional fast inhibitory postsynaptic currents and a background tonic inhibitory conductance. The tonic inhibition is generated primarily by extrasynaptic GABA$_A$Rs that are activated by low ambient levels of GABA in a cell-specific manner[15, 16]. In CA1 principal cells of the hippocampus, tonic inhibition is generated by the a5 subunit-containing subtype of GABA$_A$Rs (α5GABA$_A$Rs)[17, 18]. Here, we tested the hypothesis that α5GABA$_A$Rs are critical downstream regulator in the pathogenesis of IL-1β-induced impairment of memory.

Materials and Methods
Experimental Animals

All experimental procedures were approved by the Animal Care Committee of the University of Toronto (Toronto, Ontario, Canada). The generation, genotyping, and characterization of α5GABAAR null-mutant (Gabra5−/−) mice has been previously described[41]. In all studies, the experimenter was blinded to the drug treatment and genotype of the mice.

Cell Culture

Cultures of embryonic hippocampal neurons were prepared from Swiss white mice (Charles River, Wilmington, Mass., USA) as previously described[18]. Cells were maintained in culture for 12 to 16 days before use.

Neuron-Microglia Co-Culture

Mixed microglial cultures were prepared from embryonic cerebral cortex of 15- or 16-day-old mice. Cells were cultured in glial culture media (MEM supplemented with 10% fetal bovine serum) on 60-mm dishes at 37° C. in a 5% $CO_2$ incubator; the medium was changed every 3 or 4 days. Once confluence was achieved, microglia was separated from the mixed glial culture (typically at 10-14 days) by gentle shaking (200 rpm for 2 h at 37° C.) and was then collected by centrifugation. The pellet was suspended in neurobasal medium and applied directly over cultured hippocampal neurons at 10-14 days in vitro. To induce microglial activation, primary microglia-enriched cultures were treated with LPS (100 ng ml$^{-1}$) overnight (12-15 h) before the electrophysiological recordings were obtained.

Whole Cell Voltage-Clamp Recordings in Cultured Neurons

Recordings were performed as previously described[18]. The extracellular solution contained (in mM): 140 NaCl, 2 $CaCl_2$, 1 $MgCl_2$, 5.4 KCl, 25 N-2-hydroxy-ethylpiperazine-N-2-ethanesulphonic acid (HEPES), 28 glucose (pH 7.4, 325-335 mOsm). In addition, 6-cyano-7-nitroquinoxaline-2,3-dione (CNQX, 10 pM) and (2R)-amino-5-phosphonovaleric acid (APV, 40 pM) were added to the extracellular solution to block ionotropic glutamate receptors, and tetrodotoxin (0.3 pM) was used to block voltage-dependent sodium channels. To record the tonic GABAergic current, 0.5 pM GABA was added to the extracellular solution and the GABA$_A$R competitive antagonist bicuculline (Bic, 100 pM) was applied to reveal the tonic current. The intracellular solution contained (in mM): 140 CsCl, 10 HEPES, 11 EGTA, 4 $K_2$ATP, 2 $MgCl_2$, 1 $CaCl_2$, and 2 TEA (pH 7.3 with CsOH, 285-295 mOsm). All cells were recorded at a holding potential of −60 mV.

Whole Cell Voltage-Clamp Recordings in Hippocampal Slices

Recordings were performed as previously described[29]. Hippocampal slices (350 pm) were prepared from male 3- to 4-week-old WT mice with a mixed genetic background (C57BL/6/SvEv129). Mice were injected with vehicle (0.1% bovine serum albumin, i.p.) or IL-1β (1 pg kg$^{-1}$, i.p.) 2-3 hours before sacrifice. To record the tonic GABAergic current, 5 pM GABA was added, and the GABA$_A$R competitive antagonist Bic (10 pM) was applied to reveal the tonic current. All cells were recorded at a holding potential of −60 mV.

Synaptic Plasticity in Hippocampal Slices

The long-term potentiation (LTP) of evoked field postsynaptic potentials (fPSPs) was studied using previously described methods[29]. Male 3- to 4-month-old WT or Gabra5−/−mice were injected with either LPS (125 pg kg$^{-1}$, i.p.) or vehicle control (physiological saline, i.p.), and hippocampal slices (350 pm) were prepared 3 h later. Baseline stimulation frequency was 0.05 Hz. LTP was induced in the slices with theta burst stimulation (TBS), which consisted of 10 stimulus trains at 5 Hz, with each train consisting of 4 pulses at 100 Hz. The fPSPs were monitored for 10 min before TBS and for 60 min after TBS.

Hippocampal Slice Cell Surface Biotinylation Assay

Cell surface biotinylation assay for α5 and α1 subunits of GABA$_A$Rs was performed as previously described[25]. Hippocampal slices (350 pm) from male 10- to 14-week-old C57BL/6 mice were treated with IL-1β (20 ng ml$^1$, 40 min). Anti-GABA$_A$R α1 and α5 antibodies were obtained from PhosphoSolutions (Aurora, Calif., USA).

Fear Conditioning

Pavlovian fear-conditioning tasks were used for behavioral analysis[29]. LPS (125 μg kg$^{-1}$, i.p., with physiological saline as the vehicle control) or IL-1β (1 μg kg$^{-1}$, i.p., with 0.1% bovine serum albumin as the vehicle control) was injected into male 3- to 4-month-old WT and Gabra5−/− mice 3 h before conditioning. The intensity of the electric footshock was 0.5 mA. For some mice, the inverse agonist L-655,708 (0.35 or 0.5 mg kg$^{-1}$, i.p.) or vehicle control (10% DMSO, i.p.) was injected 30 min before training. The movement of the mouse was monitored. The percentage of time that each mouse spent in a freezing position was determined using FreezeView software (Version 2.26, Actimetrics Inc, Wilmette, Ill., USA).

Statistical Analyses

Data are presented as mean±S.E.M. Student paired or unpaired t tests were used to compare pairs of data. For comparing three or more groups, one-way analysis of variance (ANOVA) followed by the Dunnett or Newman-Keuls post-hoc test was used. Cumulative distributions of the amplitude and frequency of mIPSCs were compared using the Kolmogorov-Smirnov test. Statistical significance was set at P<0.05.

Results

IL-1β Increases Tonic Inhibition Generated by α5GABA$_A$Rs

To determine whether IL-1β regulates α5GABA$_A$R activity, whole-cell currents were recorded from cultured hippocampal pyramidal neurons. The amplitude of the tonic inhibitory current generated by α5GABA$_A$Rs was studied by applying the GABA$_A$R antagonist bicuculline (Bic, 100 μM) and measuring the change in holding current, as previously described[15, 17]. FIG. 1 illustrates that IL-1β increases the tonic current generated by α5GABA$_A$Rs in cultured hippocampal neurons. In FIG. 1A, the tonic current was increased by exogenous IL-1β (20 ng ml$^{-1}$ for 20 min), as revealed by the GABA$_A$R competitive antagonist bicuculline (Bic, 100 μM) (left). The variance of the noise (root mean square deviation) was greater in the IL-1β-treated neurons (9.8±0.7 pA, n=22) than in vehicle-treated controls (7.5±0.4 pA, n=21) (right).  P=0.0049, Student t test. In FIG. 1B the concentration-dependent effects of IL-1β on the tonic current density are shown. n=13-22, one-way ANOVA $F_{4,84}$=7.13, P<0.0001, Dunnett post-hoc test, relative to control (Con).  P<0.01, *** P<0.001. Treatment with IL-β (20 ng ml$^{-1}$ for 20 min) increased the amplitude of the current by 45% (IL-13 1.6±0.1 pA pF$^{-1}$, n=22, versus control 1.1±0.1 pA pF$^{-1}$, n=21, P<0.001; FIGS. 1A and B) and also increased the variance of the baseline noise (FIG. 1A). The concentration-dependent increase in the tonic current by IL-1β is shown in FIG. 1B. Increasing the duration of IL-1β treatment to 3 h further increased the amplitude of the tonic current (IL-1β 60 ng ml$^{-1}$ for 3 h 2.0±0.3 pA pF$^{-1}$, n=6, versus control 1.2±0.2 pA pF$^{-1}$, n=6, P=0.026, Student t test), but no further increase was observed in neurons treated overnight (IL-1β for 12-15 h 1.3±0.6 pA pF$^{-1}$, n=21, versus control 0.8±0.08 pA pF$^{-1}$, n=12, P=0.0003, Student t test). To confirm that the IL-1β-enhanced tonic current was generated by α5GABA$_A$Rs, a benzodiazepine inverse agonist that preferentially inhibits this type of receptor (L-655,708, 20 nM) was applied[17, 19]. L-655,708 inhibited the tonic current by 66.1%±4.2% (n=11; FIG. 1C), an effect size that is consistent with the efficacy of L-655,708 for inhibition of α5GABA$_A$Rs[19]. FIG. 1C is a representative recording showing the tonic currents revealed by Bic (100 μM) or by the inverse agonist for α5GABA$_A$Rs, L-655,708 (20 nM). Interestingly, the pro-inflammatory cytokines TNF-α and IL-6 did not modify the tonic conductance in hippocampal neurons (FIG. S1). FIG. S1 illustrates that treatment with TNF-α and IL-6 does not affect the tonic current. The tonic current was not changed by treatment of the cultured hippocampal neurons for 20 min with TNF-α (A) and IL-6 (10 ng ml$^{-1}$) (B). n=10-14, one-way ANOVA $F_{2,36}$=0.05, P=0.95 for A; n=5, P=0.63, Student's t test for B. N.S.: non-significant result.

We next tested whether IL-1β increased the tonic current in neurons from genetically modified mice lacking α5GABA$_A$ Rs (Gabra5−/−). IL-1β increased the tonic current recorded in wild-type (WT) neurons but not in neurons isolated from Gabra5−/− mice (FIG. 1D), which confirmed that the α5GABA$_A$Rs are necessary to generate the IL-1β-sensitive tonic current. FIG. 1D illustrates that α5GABA$_A$Rs are necessary for the enhancing effects of IL-1β on the tonic current. n=8-13, * P=0.015, N.S.: non-significant result (P=0.39), Student t test.

To explore whether an increase in the endogenous production of IL-1β enhanced tonic inhibition, we prepared co-cultures of hippocampal neurons and microglia as described previously[20]. The co-cultures were treated overnight with an endotoxin (lipopolysaccharide [LPS] 100 ng ml$^{-1}$ for 12-15 h) to induce the production of IL-1β[20]. LPS treatment increased the amplitude of the tonic current in the co-cultured neurons (LPS 0.88±0.08 pA pF$^{-1}$, n=16, versus control 0.44±0.04 pA pF$^{-1}$, n=13, P<0.001). FIG. 1E illustrates that the tonic current was increased by treating neuron and microglia co-cultures with the endotoxin LPS (100 ng ml$^{-1}$, overnight) (left). IL-1ra: IL-1 receptor antagonist, 250 ng ml$^{-1}$, overnight. n=13-19, one-way ANOVA $F_{3,65}$=7.27, P=0.0003, Newman-Keuls post-hoc test  P<0.01, * P<0.001, compared with LPS. For neurons that were cultured alone (right): n=10-14, N.S.: non-significant result (P=0.92), Student t test. Here and in subsequent figures, error bars represent S.E.M. In neurons that were cultured alone, LPS did not alter the tonic current (FIG. 1E). To ensure that LPS increased the tonic current via activation of the IL-1 receptor by IL-1β, the co-cultures were treated with an IL-1 receptor antagonist (IL-1ra 250 ng ml$^{-1}$), which fully reversed the enhancement of the tonic current (FIG. 1E).

IL-1β Decreases Inhibitory Postsynaptic Currents

Figure 2:
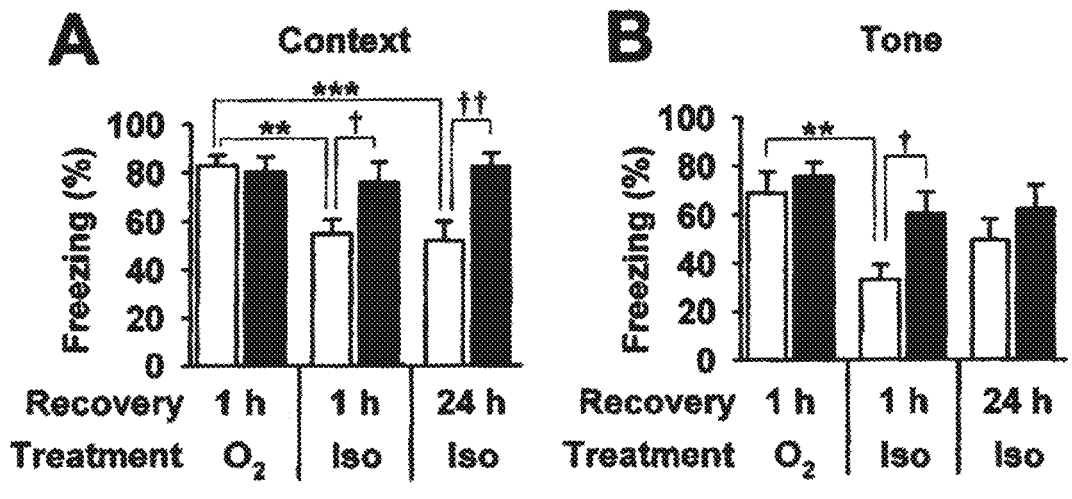
FIG. 2A illustrates freezing behaviour to the context studied 30 min after training in Example 1.
FIG. 2B illustrates freezing behavior to the audible cue at 90 min after training in Example 1.
FIG. 2C illustrates freezing behaviour to the context at 2 days after training in Example 1.
FIG. 2D illustrates freezing behaviour to the audible cue at 2 days after training in Example 1.
Figure 2:
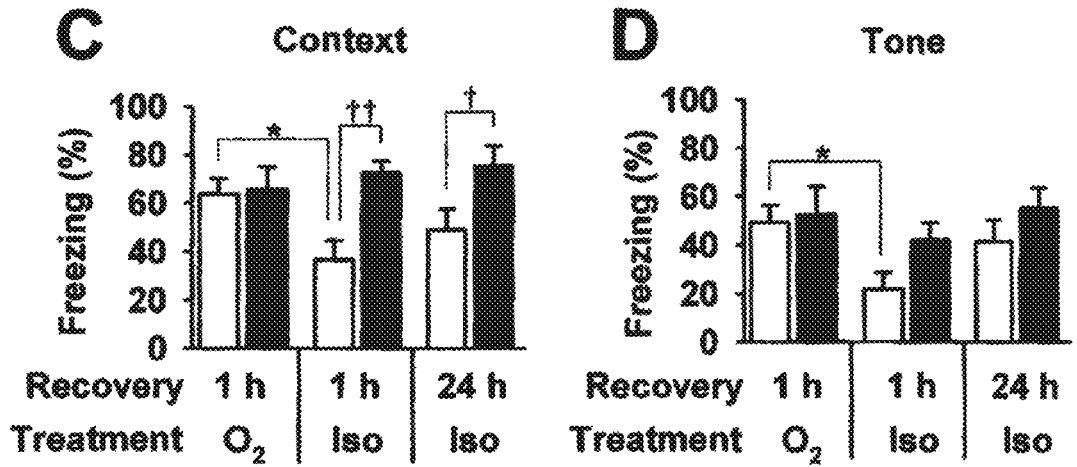

We next studied whether IL-1β modified inhibitory synaptic transmission by recording miniature inhibitory postsynaptic currents (mIPSCs) from cultured hippocampal neurons either before or after treatment with IL-1β (20 ng ml$^{-1}$). IL-1β modestly reduced synaptic inhibition, as described previously[14, 21]. The amplitude of the mIPSCs was reduced by 17.3%±3.1%, and the charge transfer was reduced by 22.2%±7.0% (FIGS. 2 A-C and Table 4). FIG. 2 illustrates that IL-1β decreases the amplitude of inhibitory synaptic currents in cultured hippocampal neurons. FIG. 2A illustrates that GABA$_A$R-mediated mIPSCs were inhibited by pre-treatment with IL-1β (20 ng ml$^{-1}$), and this effect could be blocked by IL-1ra (250 ng ml$^{-1}$). FIG. 2B traces were averaged from 314-474 individual mIPSCs. The cumulative amplitude and frequency distributions of mIPSCs in FIG. 2C show that the amplitude was inhibited by IL-1β; an effect abolished by IL-1ra (left). P<0.001 for control versus IL-1β, P=0.16 for control versus IL-1ra+IL-1β, Kolmogorov-Smirnov test. The frequency of mIPSCs was not affected by IL-1β (right). P=0.22 for control versus IL-1β, Kolmogorov-Smirnov test. To confirm that IL-1β reduced the mIPSCs by modifying the function of postsynaptic GABA$_A$Rs, whole-cell currents were evoked by applying exogenous GABA (10 μM, applied for 16 s). Under these experimental conditions, postsynaptic GABA$_A$Rs generate the fast component of the GABA-evoked current, whereas a combination of synaptic and extrasynaptic GABA$_A$Rs would generate the steady-state current[22-24]. Factors that inhibit postsynaptic GABA$_A$Rs primarily reduce the amplitude of the peak current. IL-1β (20 ng ml$_{-1}$) inhibited the peak current by 27.8%±2.2% (n=9, P<0.001), whereas the steady-state current was inhibited by 12.7%±1.5% (n=9, P=0.0004, Student t test) (FIG. 2D).

TABLE 4

The parameters of GABAergic mIPSCs measured before and after treatment of neurons with IL-1β (20 ng ml$^{-1}$) in the absence or presence of IL-1 receptor antagonist (IL-1ra, 250 ng ml$^{-1}$) (mean ± S.E.M.).

| | Amplitude (pA) | Frequency (Hz) | Rise time (ms) | Decay time (ms) | Area (pA · ms) |
|---|---|---|---|---|---|
| Control | 30.0 ± 2.8 (n = 6) | 4.5 ± 1.7 (n = 6) | 2.9 ± 0.3 (n = 6) | 16.3 ± 0.9 (n = 6) | 352.6 ± 38.0 (n = 6) |
| IL-1β | 24.7 ± 2.1** (n = 6) | 3.7 ± 2.3 (n = 6) | 2.4 ± 0.1 (n = 6) | 14.8 ± 1.1 (n = 6) | 279.0 ± 46.5* (n = 6) |
| IL-1ra + IL-1β | 30.0 ± 2.3 (n = 6) | 6.5 ± 4.4 (n = 6) | 2.6 ± 0.2 (n = 6) | 15.4 ± 0.8 (n = 6) | 372.7 ± 45.6 (n = 6) |

**P = 0.0041 for Amplitude.
*P = 0.029 for Area, Student's t test compared to control.

FIG. 2D illustrates that the peak response evoked by application of GABA (10 μM), which is generated by synaptic GABA$_A$Rs, was inhibited by pre-perfusion with IL-1β (20 ng ml$^{-1}$), and this effect could be blocked by IL-1ra (250 ng ml$^{-1}$). n=9, one-way ANOVA $F_{3,35}$=22.87, P<0.0001, Dunnett post-hoc test, compared with control *** P<0.001.

IL-1β Enhances Tonic Inhibition Via the p38 MAPK-Dependent Pathway

We next sought to identify the membrane receptor and the signaling pathways by which IL-1β increases tonic inhibition and reduces synaptic currents. IL-1ra (250 ng ml$^{-1}$) completely blocked both the increase in tonic current and the reduction of synaptic current by IL-1β (FIG. 2 and FIG. 3A). FIG. 3 illustrates that IL-1β modulates tonic and synaptic inhibitory currents through different signaling pathways. FIG. 3A illustrates that IL-1β-induced enhancement of tonic current was blocked by co-application of IL-1ra (250 ng ml$^{-1}$, 30 min) (left). n=11-22, one-way ANOVA $F_{3,64}$=7.92, P=0.0002, Dunnett post-hoc test, compared with control *** P<0.001. Treatment with an inhibitor of p38 MAPK, SB203, 580 (p38 Anta, 20 μM, 30 min) abolished the enhancing effects of IL-1β (20 ng ml$^{-1}$, 20 min) (right), n=10-14, one-way ANOVA $F_{3,48}$=4.85, P=0.0052, Newman-Keuls post-hoc test, compared with control * P<0.05. To identify the specific kinases that contribute to the IL-1β-dependent changes, neurons were treated with selective kinase inhibitors. SB203,580 (20 μM, 30 min), an inhibitor of p38 MAPK, completely blocked the IL-1β-induced increase in the tonic current (IL-1p+SB203,580 1.0±0.1 pA pF$^{-1}$, n=14, versus IL-1β 1.4±0.1 pA pF$_{-1}$, n=13, Newman-Keuls post hoc test P<0.05, one-way ANOVA $F_{3,48}$=4.85, P=0.0052) (FIG. 3A), whereas an inactive analog of SB203,580, SB202,474 (10 μM, 30 min), had no effect on the tonic current (FIG. S2A). FIG. S2 illustrates that JNK- and PI3K-dependent pathways do not contribute to IL-1β-induced enhancement of tonic current. The enhancing effects of IL-1β on the tonic current were not blocked by SB202, 474 (SB202, 10 mM, 30 min), an inactive analog of the p38 MAPK inhibitor SB203,580. n=9-11, one-way ANOVA F3.38=11.10, P<0.0001, Dunnett's post hoc compared to control  P<0.01 * P<0.001 (FIG. S2A). These results suggest that p38 MAPK mediates the IL-1β-induced increase in tonic current. Inhibitors of c-Jun N-terminal kinases (JNKs) (SP600,125, 1 μM, 30 min) and phosphatidylinositol 3-kinases (PI3Ks) (LY294,002, 20 μM, 30 min) had no effect on the IL-1β-induced increase in tonic current, which indicates that these kinases are not required for the action of IL-1β on tonic current (FIGS. S2 B and C). FIG. S2B illustrate the JNK antagonist SP600,125 (JNK Anta, 1 mM, 30 min). n=11-16, one-way ANOVA F2,39=14.42, P<0.0001, Dunnett's post hoc compared to control * P<0.001 and FIG. S2C illustrates the PI3K antagonist LY294,002 (PI3K Anta, 20 mM, 30 min). n=10-12, one-way ANOVA F2,32=11.13, P=0.0002, Dunnett's post hoc compared to control * P<0.001. Consistent with a preferential effect on extrasynaptic GABA$_A$Rs, SB203,580 had no effect on inhibition of the GABA-evoked peak current by IL-1β (FIG. 3B). FIG. 3B illustrates that the peak response evoked by application of GABA (10 μM) was inhibited by pre-perfusion with IL-1β (20 ng and this effect could be blocked by a PI3K inhibitor, wortmannin (WTM, 0.1 μM). The p38 MAPK inhibitor SB203,580 (20 μM) did not block the inhibitory effects of IL-1β on the evoked peak response. n=5-8, one-way ANOVA $F_{5,40}$=49.39, P<0.0001, Dunnett post-hoc test, compared with control * P<0.001. In contrast, the PI3K inhibitors wortmannin (0.1 μM) and LY294, 002 (20 μM) completely prevented IL-1β-dependent inhibition of the GABA-evoked peak current (FIG. 3B and FIG. S3), consistent with the observation that the PI3K pathway contributes to the IL-1β-dependent inhibition of postsynaptic currents. FIG. S3 illustrates that the PI3K inhibitor blocks the IL-1β-induced reduction of GABA-evoked peak currents. The inhibitory effects of IL-1β (20 ng ml$^{-1}$) on the peak current evoked by GABA (10 mM) were abolished by treating the neurons with the PI3K inhibitor LY294,002 (LY, 20 mM). LY294,002 alone had no effect on the GABA-evoked peak responses. n=6-11, one-way ANOVA $F_{3,37}$=85.41, P<0.0001, Dunnett's post hoc compared to control * P<0.001.

Next, to examine whether the IL-1β-induced enhancement of the tonic current was associated with an increase in the expression of α5GABA$_A$Rs on the surface of neurons, hippocampal slices were treated with IL-1β (20 ng ml$_{-1}$, 40 min), and quantitative Western blot analysis of the biotinylated protein was performed[25]. IL-1β consistently increased the levels of α5 subunits expressed on the surface of the neurons, to 183.3%±29.6% of vehicle-treated control slices (n=3, P=0.033, Student t test; FIG. 3C). FIG. 3C illustrates that the surface expression of the α5 subunit was increased in hippocampal slices that had been treated with IL-1β (20 ng ml$^{-1}$, 40 min). n=3, * P=0.033, Student t test. In contrast, IL-1β caused no increase in the surface expression of α1 subunits (FIG. 3D) contributing to postsynaptic GABA$_A$Rs[15, 16]. FIG. 3D illustrates that surface expression of the α1 subunit was not increased after IL-1β treatment (n=5). N.S.: non-significant result (P=0.15), Student t test.

Inflammation Attenuates Synaptic Plasticity in Hippocampal Slices from WT but not Gabra5−/− mice The experiments described above showed that IL-1β up-regulates α5GABA$_A$ R-mediated tonic inhibition. We next investigated whether the increased tonic inhibition altered an activity-dependent form of synaptic plasticity that is thought to contribute to learning and memory[26]. First, to confirm that IL-1β increased tonic inhibition in CA1 pyramidal neurons, whole-cell recordings were performed using ex vivo hippocampal slices obtained from WT mice that were treated with either IL-1β (1 μg kg$^{-1}$, i.p., 2-3 h before sacrifice) or vehicle (0.1% bovine serum albumin in PBS). A two-fold increase in tonic current was observed in slices from IL-1β-treated mice (44.9±9.4 pA, n=6) compared with vehicle-treated controls (20.3±5.6 pA, n=7, P=0.041, Student t test).

Figure 4:
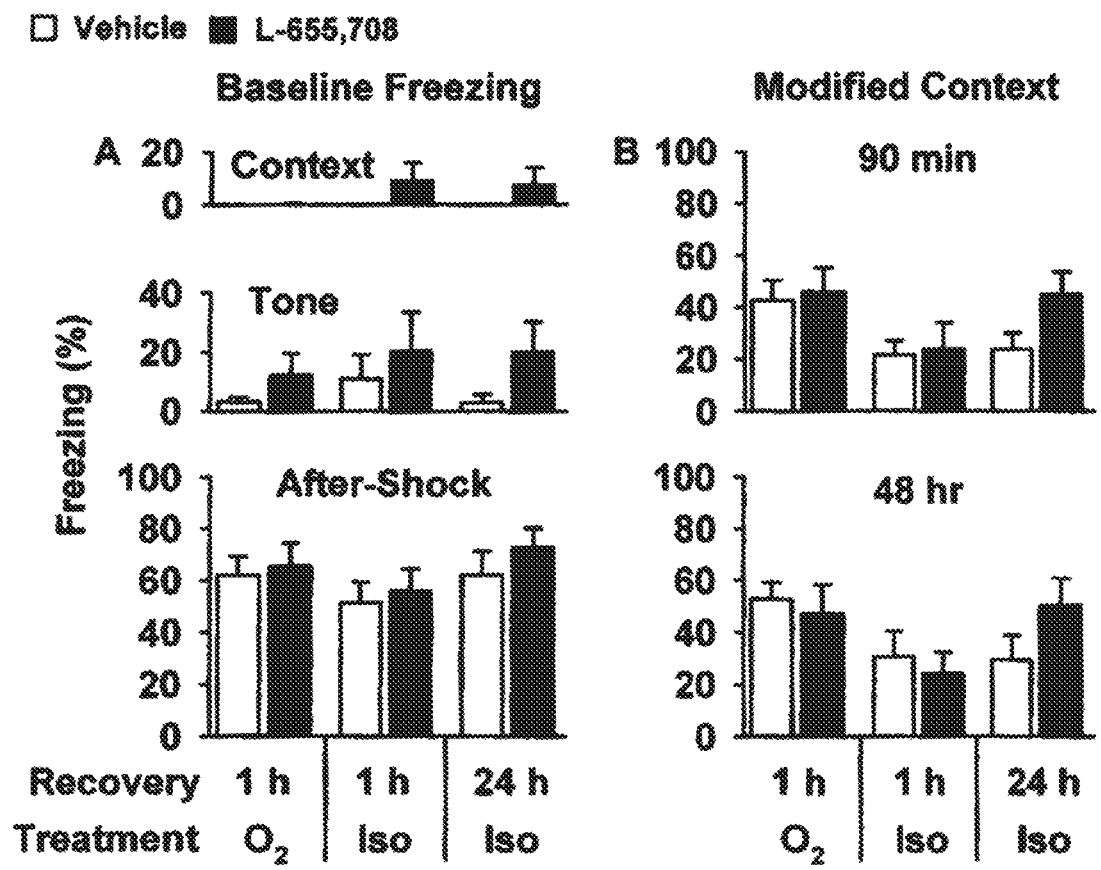
FIG. 4A illustrates the effect of isoflurane and L-655,708 on baseline freezing behavior, motor function and nociception in mice in Example 1.
FIG. 4B illustrates the effect of isoflurane and L-655,708 on freezing behavior in a modified context in Example 1.

To determine whether α5GABA$_A$Rs contribute to inflammation-induced alteration of synaptic plasticity, long-term potentiation (LTP) was studied in slices obtained from WT and Gabra5-/- mice treated with LPS (125 jtg kg$^{-1}$, i.p., slices obtained 3 h later). Field postsynaptic potentials (fPSPs) were recorded from the CA1 stratum radiatum before and after theta burst stimulation (TBS) of the Schaffer collateral pathway. FIG. 4 illustrates that LPS-induced inflammation impairs long-term potentiation in WT but not Gabra5-/- mice. FIG. 4A illustrates injection of LPS inhibited LTP in WT mice. LTP was 136.1%±14.9% (n=9) in the vehicle group and 113.1%±2.5% (n=10) after injection of LPS. ** P=0.0012, Student t test. The slope of the fPSPs was increased for at least 60 min after TBS in slices from vehicle-treated WT mice (slope 136.1%±5.6% of baseline, n=9; FIG. 4A). LPS treatment attenuated LTP in slices from WT mice (slope 113.1%±2.5% of baseline, n=10, P=0.0012, compared to slices from vehicle-treated mice; FIG. 4A). This inhibition of LTP was abolished by incubating the slices with IL-1ra (100 ng ml$^{-1}$ for 1 h before the recordings; FIGS. S4A-C). FIG. S4 illustrates that endogenous IL-1β release induced by injection of LPS inhibits long-term potentiation in slices from wild-type mice. FIG. S4A illustrates that long-term potentiation (LTP) was induced by theta burst stimulation (TBS) in wild-type (WT) mice. FIG. S4B illustrates that incubation of slices with IL-1ra (100 ng ml$^{-1}$) for 1 h abolished the LPS-induced impairment of LTP in WT mice. FIG. S4C illustrates quantified data for results shown in FIG. S4A. LTP was 136.1%±5.6% (n=9) for vehicle-treated control, 126.2%±3.9% (n=10) after LPS+IL-1ra treatment, and 113.1%±2.5% (n=10) for LPS alone. One-way ANOVA F$_{2,28}$=7.82, P=0.0022, Newman-Keuls' post hoc * P<0.05, ** P<0.01, compared to LPS. Importantly, in slices from Gabra5-/- mice, LPS did not impair synaptic plasticity (LPS slope 133.1%±4.3% of baseline, n=15, versus vehicle slope 135.4%±5.9% of baseline, n=13, P=0.76; FIG. 4B and FIGS. S4 D and E). FIG. 4B illustrates that injection of LPS did not affect LTP in Gabra5-/- mice. LTP was 135.4%±5.9% (n=13) in the vehicle group and 133.1%±4.3% (n=15) after injection of LPS. P=0.76, Student nest. FIGS. S4D and S4E illustrate that LTP in Gabra5-/- mice was not affected by injection of LPS.

IL-1β Impairs Learning and Memory in WT but not Gabra5-/- Mice

Figure 5:
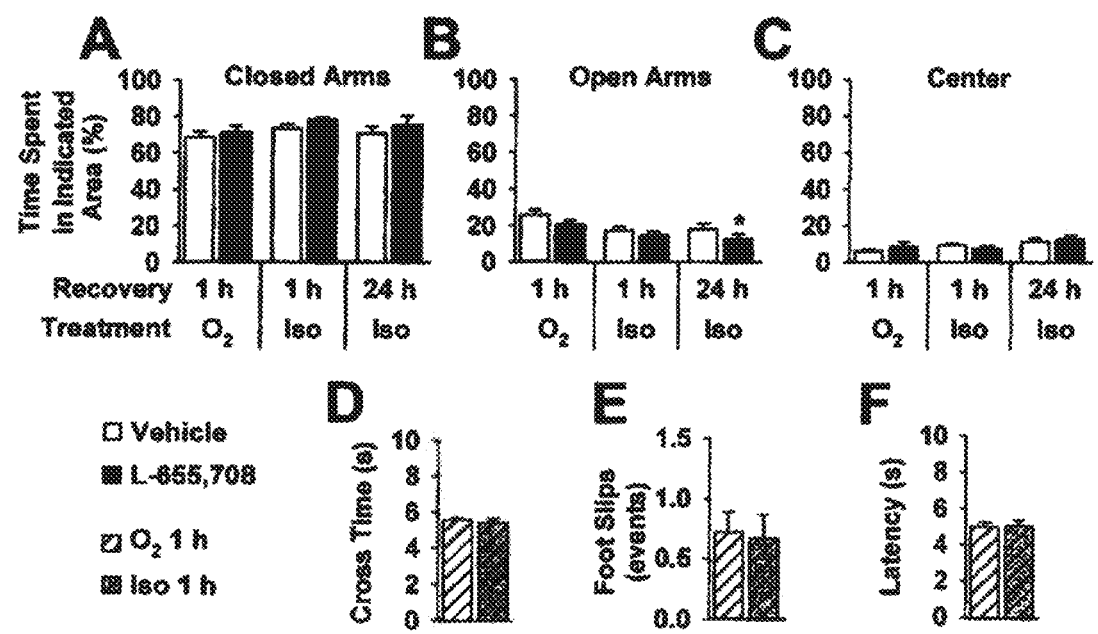
FIG. 5 A illustrates the effect of isoflurane according to the amount of time spent in the closed arms region of the elevated plus maze in Example 1.

The results presented above predict that IL-β impairs memory behavior through α5GABA$_A$R-dependent mechanisms. We tested this prediction using a well-validated model of aversive fear memory[27]. WT and Gabra5-/- mice were treated with IL-1β (1 μg kg$^{-1}$, i.p.) or vehicle (0.1% bovine serum albumin in PBS) 3 h before fear conditioning. Mice were trained to associate an electric footshock with the training context and an auditory tone. Contextual fear memory was measured 24 h after conditioning as the percentage of time spent freezing in the training context. IL-1β-treated WT mice showed impairment of contextual fear memory, as evidenced by lower freezing scores than vehicle-treated controls (FIG. 5A). In contrast, Gabra5-/- mice treated with IL-1β exhibited no such deficits (FIG. 5A). This impairment of memory did not result from a global disruption of cognitive processes, as cued fear memory, which does not depend on α5GABA$_A$R function[28, 29], was not disrupted. FIG. 5 illustrates that IL-1β-induced impairment of contextual fear memory is absent in Gabra5-/- mice and can be prevented by pharmacological inhibition of α5GABA$_A$Rs with L-655,708 in WT mice. Fear conditioning was performed 3 h after injection of IL-1β (1 μg kg$^{-1}$, i.p.). FIG. 5A illustrates that IL-1β reduced freezing scores for contextual fear memory in WT (left) but not Gabra5-/- (right) mice. n=14-16, ** P=0.0034, N.S.: non-significant result (P=0.67), Student t test. Freezing to the conditioned auditory tone was normal and unchanged by IL-1β treatment in both WT and Gabra5-/- mice (FIG. 5B). FIG. 5B illustrates that cued fear memory to a conditioned tone stimulus was not affected by IL-1β in either WT (left) or Gabra5-/- (right) mice. n=14-16, P=0.37 for WT mice, P=0.51 for Gabra5-/- mice, Student t test.

To probe whether systemic inflammation and increased production of endogenous cytokines also impair memory through activation of α5GABA$_A$Rs, WT and Gabra5-/- mice were treated with LPS. The WT mice, but not the Gabra5-/- mice, exhibited a reduction in contextual fear memory (FIG. S5). FIG. S5 illustrates that systemic inflammation induced by LPS (125 μg kg$^{-1}$, i.p.) impairs hippocampus-dependent memory in wild-type but not in Gabra5-/- mice. FIG. S5A illustrates that LPS reduced freezing scores for contextual fear memory in WT mice (left), but not in Gabra5-/- mice (right). n=14-15, * P=0.013, N.S. P=0.19, Student's t test. FIG. S5B illustrates that cued fear memory to a conditioned tone stimulus was not affected by LPS in WT (left) or Gabra5-/- mice (right). n=13-15, P=0.33 for WT, P=0.94 for Gabra5-/-, Student's t test. N.S.: non-significant result. Finally, we tested whether pharmacological inhibition of α5GABA$_A$R activity with the drug L-655,708 could prevent the IL-1β-induced memory deficits. Under baseline conditions, L-655,708 alone does not modify contextual fear memory in WT mice[29]. However, L-655,708 attenuated the IL-1β-induced contextual fear memory deficits in WT mice (FIG. 5C). FIG. 5C illustrates that L-655,708 restored freezing scores for contextual fear memory to control values when it was co-administered with IL-1β (left), and it did not affect freezing to a conditioned tone stimulus (right). n=11, * P=0.029, N.S.: non-significant result (P=0.34), Student t test.

Discussion

The goal of the study was to elucidate the mechanisms underlying the poorly understood association between inflammation and memory deficits. Our results show that activation of a subtype of GABA$_A$Rs plays a fundamental role in memory loss secondary to elevation in the levels of the cytokine IL-1β as well as LPS-induced systemic inflammation. In hippocampal pyramidal neurons, IL-1β enhances a tonic inhibitory conductance generated by α5GABA$_A$Rs. Moreover, selective reduction in α5GABA$_A$R activity, by either genetic or pharmacological strategies, reversed the inhibition of plasticity and improved memory performance.

The observation that IL-1β selectively up-regulates tonic inhibition but not synaptic inhibition in hippocampal neurons was unexpected. These results help to reconcile seemingly contradictory effects reported by others because IL-1β either up- or down-regulates the function and expression of GABA$_A$ receptors depending on the experimental conditions[6, 10-14]. Consistent with our results showing that IL-1β increases tonic inhibition, IL-1β also increases GABAergic inhibition in CA1 pyramidal neurons[10], GABA-mediated chloride uptake by synaptosomes[11], and the surface expression of GABA$_A$Rs in oocytes and neurons[6]. Similar to its effects on mIPSCs, IL-1β reduces inhibitory postsynaptic currents in cerebellar Purkinje neuronS[12], CA3 pyramidal neurons[13], and cultured hippocampal neurons[14]. The discordant effects of IL-1β on tonic and synaptic currents can likely be attributed to differences in the subunit composition of the underlying receptors[15, 16]. In the hippocampus, the tonic current is generated primarily by α5β2,3γ2 GABA$_A$Rs or α4,6β32,3δ GABA$_A$Rs, whereas α1-3β2,3γ2 GABA$_A$Rs generate postsynaptic currents[15, 16, 30]. The subunit composition of GABA$_A$Rs is critical to determining interactions with cytosolic anchoring and trafficking proteins and regulation by signaling cascades that are activated by IL-1β[16, 30]. Elucidating the signaling pathways that differentially regulate the trafficking of extrasynaptic versus synaptic GABA$_A$Rs by IL-1β in the hippocampus was beyond the scope of the current study but is worthy of future investigation.

The findings described above represent the first evidence of a direct link between increases tonic inhibition and thereby inhibits synaptic plasticity through p38 MAPK-dependent signaling cascades is supported by previous studies[31, 32]. Extrasynaptic α5GABA$_A$Rs regulate the threshold for the induction of synaptic plasticity in CA1 pyramidal neuronS[29] and reduce neuronal excitability via shunting inhibition[18]. Drugs that cause a marked increase in α5GABA$_A$ R activity cause profound memory blockade[28, 33]. Others have shown that recombinant human IL-1β significantly inhibits the induction of LTP in the hippocampus through p38 MAPK-dependent signaling pathways[32]. IL-1β also stimulates several additional signaling pathways, including JNKs and PI3Ks[34], and PI3K and Akt modify β2 subunit-containing GABAARs[6]. However, β2 subunit-containing synaptic receptors are unlikely to play a major role in the IL-1β-induced inhibition of LTP, given that the postsynaptic currents were reduced by IL-1β. IL-1β also influences several other key modulators of plasticity, including glutamate receptor signaling, intracellular calcium levels, and cholinergic neurotransmission; however, these receptor systems are unlikely to account for our current findings[5].

The characterization of the molecular mechanisms underlying inflammation-induced memory deficits could lead to the development of novel therapeutic approaches to a variety of neurological diseases. In particular, our current results have implications for the pathogenesis and treatment of several immune cognitive disorders. For example, after ischemic stroke in the forelimb motor cortex, tonic inhibition was increased in the pen-infarct regions, and inhibition of α5GABA$_A$Rs improved motor function[35]. The authors of that study attributed the increased tonic inhibition to decreased activity of GABA transporters. Our results suggest an additional potential mechanism, since inflammation occurring after ischemia[36] could increase the surface expression of extrasynaptic GABAARs in neurons. As such, inhibition of α5GABAAR might be a plausible and safe treatment strategy for such disorders. Inverse agonists that inhibit α5GABA$_A$Rs are generally well tolerated, because they lack the proconvulsant and anxiogenic properties of nonselective GABA$_A$R antagonists[37, 38], a result of the expression of α5GABA$_A$Rs being primarily restricted to the hippocampus[39]. Taken together, the above results will stimulate interest in the contribution of extrasynaptic GABA$_A$Rs to the cognitive deficits and organ dysfunction associated with a variety of diseases associated with an immunological response[2, 40].

Reference List for Example 3

1. Konsman J P, Parnet P, Dantzer R (2002) Cytokine-induced sickness behaviour: mechanisms and implications. *Trends Neurosci* 25:154-159.
2. Dantzer R, O'Connor J C, Freund G G, Johnson R W, Kelley K W (2008) From inflammation to sickness and depression: when the immune system subjugates the brain. *Nat Rev Neurosci* 9:46-56.
3. Yirmiya R, Goshen 1 (2011) Immune modulation of learning, memory, neural plasticity and neurogenesis. *Brain Behav Immun* 25:181-213.
4. Kipnis J, Derecki N C, Yang C, Scrable H (2008) Immunity and cognition: what do age-related dementia, HIV-dementia and 'chemo-brain' have in common? *Trends Immunol* 29:455-463.
5. Di Filippo M, Sarchielli P, Picconi B, Calabresi P (2008) Neuroinflammation and synaptic plasticity: theoretical basis for a novel, immune-centred, therapeutic approach to neurological disorders. *Trends Pharmacol Sci* 29:402-412.
6. Serantes R, et al. (2006) Interleukin-1â enhances GABAA receptor cell-surface expression by a phosphatidylinositol 3-kinase/Akt pathway: relevance to sepsis-associated encephalopathy. *J Biol Chem* 281:14632-14643.
7. Trompet S, et al. (2008) Genetic variation in the interleukin-la-converting enzyme associates with cognitive function. The PROSPER study. *Brain* 131:1069-1077.
8. Cibelli M, et al. (2010) Role of interleukin-la in postoperative cognitive dysfunction. *Ann Neurol* 68:360-368.
9. Fleischmann R M, et al. (2006) Safety of extended treatment with anakinra in patients with rheumatoid arthritis. *Ann Rheum Dis* 65:1006-1012.
10. Hellstrom I C, Danik M, Luheshi G N, Williams S (2005) Chronic LPS exposure produces changes in intrinsic membrane properties and a sustained IL-â-dependent increase in GABAergic inhibition in hippocampal CA1 pyramidal neurons. *Hippocampus* 15:656-664.
11. Miller L G, Galpern W R, Dunlap K, Dinarello C A, Turner T J (1991) Interleukin-1 augments ãaminobutyric acid A receptor function in brain. *Mol Pharmacol* 39:105-108.
12. Pringle A K, Gardner C R, Walker R J (1996) Reduction of cerebellar GABAA responses by interleukin-1 (IL-1) through an indomethacin insensitive mechanism. *Neuropharmacology* 35:147-152.
13. Zeise M L, Espinoza J, Morales P, Nalli A (1997) Interleukin-la does not increase synaptic inhibition in hippocampal CA3 pyramidal and dentate gyrus granule cells of the rat in vitro. *Brain Res* 768:341-344.
14. Wang S, Cheng Q, Malik S, Yang J (2000) Interleukin-1â inhibits ã-aminobutyric acid type A (GABAA) receptor current in cultured hippocampal neurons. *J Pharmacol Exp Ther* 292:497-504.
15. Glykys J, Mody I (2007) Activation of GABAA receptors: views from outside the synaptic cleft. *Neuron* 56:763-770.
16. Luscher B, Fuchs T, Kilpatrick C L (2011) GABAA receptor trafficking-mediated plasticity of inhibitory synapses. *Neuron* 70:385-409.
17. Caraiscos V B, et al. (2004) Tonic inhibition in mouse hippocampal CA1 pyramidal neurons is mediated by α5 subunit-containing ã-aminobutyric acid type A receptors. *Proc Natl Acad Sci USA* 101:3662-3667.
18. Bonin R P, Martin L I, MacDonald J F, Orser B A (2007) α5GABA$_A$ receptors regulate the intrinsic excitability of mouse hippocampal pyramidal neurons. *J Neurophysiol* 98:2244-2254.
19. Quirk K, et al. (1996) [3H]L-655,708, a novel ligand selective for the benzodiazepine site of GABAA receptors which contain the α5 subunit. *Neuropharmacology* 35:1331-1335.

20. Polazzi E, Contestabile A (2006) Overactivation of LPS-stimulated microglial cells by co-cultured neurons or neuron-conditioned medium. *J Neuroimmunol* 172:104-111.
21. Kawasaki Y, Zhang L, Cheng J K, Ji R R (2008) Cytokine mechanisms of central sensitization: distinct and overlapping role of interleukin-1â, interleukin-6, and tumor necrosis factor-a in regulating synaptic and neuronal activity in the superficial spinal cord. *J Neurosci* 28:5189-5194.
22. Banks M I, Pearce R A (2000) Kinetic differences between synaptic and extrasynaptic GABAA receptors in CA1 pyramidal cells. *J Neurosci* 20:937-948.
23. Yeung J Y, et al. (2003) Tonically activated GABAA receptors in hippocampal neurons are high-affinity, low-conductance sensors for extracellular GABA. *Mol Pharmacol* 63:2-8.
24. Bai D, et al. (2001) Distinct functional and pharmacological properties of tonic and quantal inhibitory postsynaptic currents mediated by y-aminobutyric acid A receptors in hippocampal neurons. Mol Pharmacol 59:814-824.
25. Abramian A M, et al. (2010) Protein kinase C phosphorylation regulates membrane insertion of GABAA receptor subtypes that mediate tonic inhibition. *J Biol Chem* 285:41795-41805.
26. Lynch M A (2004) Long-term potentiation and memory. *Physiol Rev* 84:87-136.
27. Wehner J M, Radcliffe R A (2004) Cued and contextual fear conditioning in mice. *Curr Protoc Neurosci, Unit* 8.5c.
28. Martin L I, Oh G H, Orser B A (2009) Etomidate targets α5 y-aminobutyric acid subtype A receptors to regulate synaptic plasticity and memory blockade. Anesthesiology 111:1025-1035.
29. Martin L J, et al. (2010) α5GABA$_A$ receptor activity sets the threshold for long-term potentiation and constrains hippocampus-dependent memory. *J Neurosci* 30:5269-5282.
30. Vithlani M, Terunuma M, Moss S J (2011) The dynamic modulation of GABAA receptor trafficking and its role in regulating the plasticity of inhibitory synapses. *Physiol Rev* 91:1009-1022.
31. Coogan A N, O'Neill L A, O'Connor J J (1999) The P38 mitogen-activated protein kinase inhibitor SB203580 antagonizes the inhibitory effects of interleukin-1â on long-term potentiation in the rat dentate gyrus in vitro. *Neuroscience* 93:57-69.
32. Kelly A, et al. (2003) Activation of p38 plays a pivotal role in the inhibitory effect of lipopolysaccharide and interleukin-la on long term potentiation in rat dentate gyrus. *J Biol Chem* 278:19453-19462.
33. Cheng V Y, et al. (2006) α5GABA$_A$ receptors mediate the amnestic but not sedative-hypnotic effects of the general anesthetic etomidate. *J Neurosci* 26:3713-3720.
34. O'Neill L A (2002) Signal transduction pathways activated by the IL-1 receptor/toll-like receptor superfamily. *Curr Top Microbiol Immunol* 270:47-61.
35. Clarkson A N, Huang B S, Macisaac S E, Mody I, Carmichael S T (2010) Reducing excessive GABA mediated tonic inhibition promotes functional recovery after stroke. *Nature* 468:305-309.
36. Denes A, Thornton P, Rothwell N J, Allan S M (2010) Inflammation and brain injury: acute cerebral ischaemia, peripheral and central inflammation. *Brain Behav Immun* 24:708-723.
37. Atack J R (2010) Preclinical and clinical pharmacology of the GABAA receptor a5 subtype-selective inverse agonist a5IA. *Pharmacol Ther* 125:11-26.
38. Biggio 0, et al. (1990) GABAergic and dopaminergic transmission in the rat cerebral cortex: effect of stress, anxiolytic and anxiogenic drugs. *Pharmacol Ther* 48:121-142.
39. Pirker S, Schwarzer C, Wieselthaler A, Sieghart W, Sperk G (2000) GAB A A receptors: immunocytochemical distribution of 13 subunits in the adult rat brain. *Neuroscience* 101:815-850.
40. Barnum C J, Tansey M G (2010) Modeling neuroinflammatory pathogenesis of Parkinson's disease. *Prog Brain Res* 184:113-132.
41. Collinson N, et al. (2002) Enhanced learning and memory and altered GABAergic synaptic transmission in mice lacking the α5 subunit of the GABAA receptor. *J Neurosci* 22:5572-5580.

Example 4

Inhibition of α5GABAA Receptors Restores Recognition Memory after General Anesthesia. Treatment for Memory Deficits in the Early Postoperative Period Introduction General anesthetics and benzodiazepines are routinely administered to millions of patients each year to allow them to tolerate surgery. Unfortunately, these neurodepressive drugs may cause cognitive deficits that persist much longer than would be expected on the basis of their pharmacokinetic properties. For example, up to 47% of elderly patients who have undergone anesthesia for noncardiac surgery exhibit cognitive deficits at the time of hospital discharge[1]. The duration of anesthesia has been shown to be an independent predictor of cognitive dysfunction in the early postoperative period[2]. Similarly, the risk of severe brain dysfunction, including delirium, increases in critically ill patients who receive benzodiazepines[3]. Such cognitive deficits are associated with poor long-term outcome, yet no specific treatments have been developed to date[4-5]. Consequently, a research priority is to understand the neurobiological basis of postanesthetic cognitive deficits, including the brain structures and types of memory that are susceptible to disturbance by anesthetics and the molecular mechanisms underlying these deficits.

γ-Aminobutyric acid (GABA) is the major inhibitory neurotransmitter in the brain, and GABA subtype A (GABA$_A$) receptors are principal targets for most inhaled anesthetics[6-7]. The prototypic volatile anesthetic isoflurane interacts with a putative binding cavity on the GABA$_A$ receptor, allosterically increasing its function[6]. In particular, increased activity of GABA$_A$ receptors containing the α5 subunit (α5GABA$_A$ receptors) is thought to contribute to acute, desirable memory blockade during anesthesia[8-9].

At the cellular level, both onset of and recovery from isoflurane modulation of GABA$_A$ receptors occur on a time scale of milliseconds to seconds[7]. In humans, the rate of uptake of isoflurane is rapid (onset 3 to 5 min)[10]. The elimination of isoflurane also occurs within minutes with an initial, fast, 5 min component and a slower 15 min component[11]. Similarly, in laboratory animals, 97% of the isoflurane is eliminated from the brain within 270 min[12]. Surprisingly, despite rapid elimination, isoflurane has been shown to cause anterograde and retrograde memory deficits that persist for days to months in laboratory animals[13-15].

Using a mouse model, we showed in Example 1 that isoflurane administered at 1 MAC for 1 h caused deficits in fear-associated learning and memory that lasted for at least 24 to 48 h[16]. These postanesthetic memory deficits were prevented by pretreating the mice with the drug L655,708 thirty minutes before administration of isoflurane[16]. L-655,708 is an imidazobenzodiazepine that acts at the benzodiazepine site of the $GABA_A$ receptor to reduce GABA affinity and to reduce the opening of the integral chloride channel[17-18]. The affinity of L-655,708 is 50-fold greater for $\alpha 5GABA_A$ receptors than for other receptor subtypes[17]. Thus, our results in Example 1 are interpreted as showing that preventing the activation of $\alpha 5GABA_A$ receptors during isoflurane anesthesia prevents memory deficits that persist for 24 to 48 hours.

The above results raise the following critical question: Can memory impairment that occurs after isoflurane has been eliminated be reversed by inhibiting $\alpha 5GABA_A$ receptors? It also remains to be determined whether isoflurane triggers downstream events that impair memory through processes initially requiring the interaction between isoflurane and $\alpha 5GABA_A$ receptors. The main aims of the current study were to determine whether isoflurane causes deficits in anterograde recognition memory and whether L-655,708, administered after isoflurane anesthesia restores memory to baseline levels. Additionally, we examined whether working memory and short-term memory were equally impaired after isoflurane and measured the time required for spontaneous recovery of recognition memory. To determine whether the expression of $\alpha 5GABA_A$ receptors is necessary for the development of memory deficits after isoflurane, we studied genetically modified mice lacking $\alpha 5GABA_A$ receptors (Gabra5−/− mice). Finally, to determine whether other volatile anesthetics also impair recognition memory, learning and memory were examined 24 h after exposure to sevoflurane.

Methods

Animal Model

Experiments were approved by the Animal Care Committee of the University of Toronto and complied with the guidelines of the Canadian Council on Animal Care. The Gabra5−/− mice were generated using a C57BL/6J and Sv129Ev background, as described previously[19]. Gabra5−/− mice breed normally, have a normal lifespan, and do not display an overt behavioral phenotype[19]. They exhibit normal motor coordination, with no evidence of compensatory changes in the expression of other GABAA receptor subunits[19]. Mice were housed in groups under standard conditions and were supplied with food and water ad libitum. A circadian cycle of 14 h light/10 h dark was maintained in the housing room, and all experiments were performed during the light phase. For all behavioral tests, age-matched 3- to 4-month-old male wild-type and Gabra5−/− mice were studied. To reduce variability in learning and memory performance caused by acute stress during the conditioning and testing phases of the study, each mouse was handled for at least 10 min daily for 5 days before the start of the behavioral experiments. Mice were randomly assigned to treatment groups, and the experimenter was blinded to the drug treatment of individual mice.

Anesthesia

Mice were randomly assigned to treatment with isoflurane (1.3%; 1 MAC) or vehicle gas (70% air, 30% $O_2$) for 1 h. For treatment, each mouse was placed in an airtight acrylic chamber (27 cm wide×10 cm deep×10 cm high) that had been preflushed with the anesthetic gas mixture or the vehicle gas, delivered at 1 L/min. The concentrations of isoflurane, $O_2$, and expired $CO_2$ in the chamber were continuously analyzed with a commercial gas analyzer (Datex Ohmeda, Mississauga, Ontario, Canada). To prevent hypothermia, the temperature of the chamber was maintained at 35° C. with a heating blanket, as previously described[16]. Following exposure to isoflurane or the vehicle gas, the mouse was removed from the chamber and was allowed to recover for 1 h under a heat lamp before being returned to its home cage. This anesthesia regimen is known not to cause hypoxia or hypothermia[16]. Behavioral testing was performed 24 or 72 h after discontinuation of treatment. At that point, motor function had fully recovered, and the sedative and analgesic actions of isoflurane had dissipated[16]. We have previously shown in Example 1 that the concentration of isoflurane in the brain at 24 h after anesthesia, as measured with gas chromatography, is undetectable or at trace levels (0.0095%)[16]. For experiments with sevoflurane, mice were treated with sevoflurane (2.3%; 1 MAC) or vehicle gas (70% air, 30% O2) for 1 h under the conditions described above.

Novel Object Recognition

In the current study, we used a mouse model to study the effects of the prototypic volatile anesthetic isoflurane on recognition memory. The object recognition assay relies on the natural preference of rodents to explore novel rather than familiar objects[20]. The test involves the training or sample phase, a retention delay, and the choice phase[20]. During the training phase, the mouse is allowed to explore two identical "sample" objects[20]. The mouse is returned to its home cage for a retention period and is then presented with one familiar, sample object and one novel object (the choice phase)[20]. Usually, mice will explore the novel object significantly more than the familiar object[20-21]. This bias toward novelty is interpreted as indicating "recognition" or recall of the familiar object. The length of the retention delay (the time between the sample and choice phases) can be varied to study the influence of increasing mnemonic demands on performance of the task[22-23]. Memory deficits after a short retention delay (1 min) suggest impairment of encoding, whereas memory deficits after a longer delay (1 h) implicate the processes of memory consolidation and/or retention.

In the current study, object recognition was assessed in a 20 cm×20 cm×30 cm opaque chamber in a dimly lit room. Movement and interaction with the test objects (interlocking building blocks or toy cars) was recorded with a video camera mounted above the chamber. Each mouse was habituated to the chamber for 15 min on the day before testing. Mice were randomly assigned to be trained with one pair of sample objects. Pilot studies were performed to confirm that there was no inherent preference for either of the objects. Additionally, the set of objects and the position of the familiar and novel objects in the test chamber were counterbalanced and randomized throughout the experiments. No external motivational factors, such as food deprivation or appetitive or aversive stimuli, were used. Mice were trained on the object recognition memory paradigm 24 or 72 h after exposure to isoflurane or vehicle gas (FIGS. 1A and 1B). FIG. 1 illustrates the timeline of experimental treatment in which wild-type and Gabra5−/− mice were trained on the object recognition paradigm 24 h after anesthesia. The mice were tested on the object recognition paradigm 1 min or 1 h after training to test working memory and short-term memory, respectively. A subset of mice was treated with L-655,708, 23.5 h after isoflurane and 10 before behavioural training. FIG. 1B illustrates that timeline of experimental treatment in which wild-type mice were tested 72 after isoflurane. Mice were treated with vehicle by injection 23.5 h after exposure to isoflurane or vehicle gas and 30 min before behavioral training. FIG. 1C illustrates the time of experimental treatment in which wild-type and Gabra5−/− mice received injections of L-655,708 or vehicle 10 min prior to anesthesia. Mice were trained and tested on the object recognition paradigm 24 h after anesthesia.

During the training phase, each mouse was placed in the chamber and allowed to explore the two identical sample objects for 10 min. After either 1 min (to test working memory) or 1 h (to test short-term memory), the mouse was reintroduced to the same context and was exposed to one familiar sample object and one novel object (FIG. 1A). All of the mouse's movements were video-recorded, and the time spent exploring each object was scored manually. Exploratory behavior was defined as sniffing, licking, or touching the object while facing it[21]. Learning was deemed to have taken place if the time spent with the novel object was greater than the time spent with the familiar object. Additionally, memory was assessed by measuring the proportion of total exploration time that was spent exploring the novel object and calculating a discrimination ratio, where the discrimination ratio was the time spent exploring the novel object divided by the total time spent exploring both objects[21]. Mice that spent a greater proportion of time with the novel object, as evidenced by a discrimination ratio greater than the chance value of 0.5, were deemed to have remembered the familiar object (i.e., the object to which they had previously been exposed). Typical discrimination ratios that indicate learning range from 0.61 to 0.72[21,24-26].

As previously described, animals that did not interact for a minimum of 1 s with each object during the test period were excluded[27-28]. Mice meeting this criteria included those treated with isoflurane+vehicle injection (n=2), vehicle gas+L-655,708 (0.7 mg/kg; n=2), and mice treated with isoflurane+L-655,708 (0.7 mg/kg; n=3). In addition, animals for which the discrimination ratio deviated from the mean discrimination ratio by 2 standard deviations or more were also excluded from the analysis[15]. In total, 2 animals were excluded during the analysis phase, one from the group that received vehicle gas plus vehicle injection and the other from the group that received isoflurane plus L-655,708 (0.7 mg/kg).

To determine whether the treatments affected locomotor activity or exploration, the total time spent exploring both objects was measured during the training phase. Several of the 247 potential videos were not available due to corrupt or unavailable files, these include videos in the following groups: WT control in the treatment experiment (n=1), isoflurane-treated in the treatment experiment (n=2), Gabra5−/− control (n=1), Gabra5−/− isoflurane-treated (n=1), Gabra5−/− treated with vehicle gas and L-655,708 (n=2), Gabra5−/− mice treated with isoflurane and L-655,708 (n=1), control group in the sevoflurane experiment (n=3) and sevoflurane-treated group (n=2).

Drug Treatment

Selective antagonists for α5GABA$_A$ receptors are currently not available; however, the inverse agonist L-655,708 preferentially decreases the activity of α5GABA$_A$ receptors. To ascribe to L-655,708 selective actions on α5GABA receptors, careful dose selection is important[17,29]. The doses of L-655,708 used in this study were selected on the basis of in vivo binding data, pharmacokinetic analyses, and previous memory studies[30-31]. In experiments to study reversal of memory deficits by L-655,708, doses of this agent (0.35 mg/kg or 0.70 mg/kg, i.p) or vehicle (90% saline, 10% dimethylsulfoxide [DMSO], i.p.) were administered 23.5 h after exposure to isoflurane or vehicle gas and 30 min before training in the object recognition paradigm (FIG. 1A,B). This time schedule was selected so that all mice in the treatment cohort would be studied 24 h after isoflurane anesthesia. In the prevention experiments, wild-type and Gabra5−/− mice were treated with L-655,708 (0.7 mg/kg) or vehicle (90% saline, 10% DMSO, i.p.) injection 10 min before administration of isoflurane, sevoflurane or vehicle gas (FIG. 1C). The 0.7 mg/kg dose administered 10 min before anesthesia has been studied previously, with no apparent effect on the potency of the anesthetic, as measured by the tail pinch assay,[16] and no generalized effects on fear-associated learning[32]. In previous studies, L-655,708 (0.7 mg/kg) caused 60% to 70% occupancy of α5GABA$_A$ receptors in vivo at 30 min after i.p. injection, with limited binding to other GABA$_A$ receptors[29,31]. To control for the effect of injection, control mice tested 1 min after training (working memory) or 72 h after anesthesia were given an injection of vehicle (90% saline, 10% DMSO, i.p.) 30 min before behavioral training.

Statistical Analysis

Results are presented as means±standard error of the mean (SEM). Within each group, we determined whether learning occurred by comparing the mean time spent with the novel object and the mean time spent with the familiar object using a Student t test. Differences in learning between groups were compared with a two-way analysis of variance (ANOVA) (L-655,708 dose×gas). Post hoc analyses, when required, were conducted with Tukey's Honestly Significant Difference (HSD) test. Statistical testing was performed with two statistical software packages: Number Crunching Statistical System Software, version 2007 (NCSS Inc., Kaysville, Utah, USA), and GraphPad Prism software, version 4.0 (GraphPad Software, San Diego, Calif., USA). A P value less than 0.05 was considered statistically significant.

Results

Working Memory and Short-Term Memory Performance 24 h after Isoflurane

Mice were treated with isoflurane or vehicle gas for 1 h and studied the following day. To determine whether isoflurane impaired both working memory and short-term recognition, mice were trained on the object recognition paradigm and tested 1 min or 1 h later, respectively. FIG. 2 illustrates normal working memory performance 24 h after isoflurane anesthesia. One day after isoflurane exposure, mice were trained on the object recognition paradigm and tested 1 min after training (FIG. 2A). FIG. 2A illustrates time spent with novel and familiar objects during testing. Both control (exposed to vehicle gas; n=10) and Isoflurane (exposed to 1 h, 1.3% isoflurane; n=10) mice demonstrated normal memory performance as they spent more time exploring the novel than the familiar object. Control mice (exposed to vehicle gas and a vehicle injection) demonstrated normal working memory, spending more time exploring the novel object than the familiar object (novel vs. familiar object, t=3.30, df=9, P=0.005; FIG. 2A). Isoflurane-treated mice also demonstrated normal working memory (novel vs. familiar object, t=2.64, df=9, P=0.013; FIG. 2A). FIG. 2B illustrates the discrimination ratios (time spent with novel object/time spent with both objects) of Control and Isoflurane-treated mice. The dotted line represents a chance level of interaction with the novel object (discrimination ratio=0.5). The discrimination ratios for working memory for control and isoflurane-treated groups were similar (0.68±0.05 vs. 0.67±0.04, t=0.026, df=18, P=0.979; FIG. 2B). FIG. 2C illustrates time spent exploring identical sample objects during training. Data are represented as mean±SEM. * denotes significance at P<0.05. Time spent exploring both sample objects during the training phase did not differ between the groups (45.21±8.05 s vs. 49.28±9.60 s, t=0.32, df=18, P=0.750; FIG. 2C).

FIG. 3 illustrates impaired short-term recognition memory 24 h after isoflurane anesthesia. One day after isoflurane exposure, mice were trained on the object recognition paradigm and tested 1 h later. FIG. 3A illustrates time spent with novel and familiar objects during testing. In testing of short-term recognition memory, control mice demonstrated evidence of learning as they spent more time exploring the novel object than the familiar object (novel vs. familiar object, t=4.00, df=30, P=0.0002; FIG. 3A). In contrast, isoflurane-treated mice failed to recognize the familiar object and exhibited no preference for the novel object (novel vs. familiar object, t=0.40, df=30, P=0.345; FIG. 3A). As such, control (exposed to vehicle gas; n=31) mice demonstrated normal memory performance as they spent more time exploring the novel than the familiar object, whereas isoflurane (exposed to 1 h, 1.3% isoflurane; n=31) mice spent equal an equal amount of time with each object and hence, impaired memory performance. FIG. 3B illustrates the discrimination ratios (time spent with novel object/ time spent with both objects) of control and isoflurane-treated mice. The dotted line represents a chance level of interaction with the novel object (discrimination ratio=0.5). The discrimination ratio for the isoflurane-treated group was lower than that for the control group and was similar to that predicted by chance (0.51±0.03 vs. 0.66±0.03, t=3.66, df=60, P=0.0005; FIG. 3B). FIG. 3C illustrates time spent exploring identical sample objects during training. Data are represented as mean±SEM. * denotes significance at P<0.05. The impairment of short-term memory performance could not be attributed to differences in exploratory behavior during the training phase (control 74.02±7.54 s vs. isoflurane 62.3±9.44 s, t=0.97, df=58, P=0.336; FIG. 3C).

L-655,708 Reverses Memory Deficits after Isoflurane

We next sought to determine whether short-term memory impairment detected 24 h after isoflurane was reversed by L-655,708. Mice were exposed to isoflurane, followed by L-655,708 (0.35 mg/kg or 0.7 mg/kg, i.p.) or vehicle administered 24 h after anesthesia and 30 min before behavioral training. Short-term memory was assessed 1 h after training. FIG. 4 illustrates that short-term memory deficits can be reversed by inhibition of α5GABA$_A$Rs 24 h after isoflurane anesthesia. Mice were trained on the object recognition paradigm 24 h after anesthesia and short-term memory was tested 1 h after training. Mice received either an injection of vehicle (10% DMSO) or the α5GABA$_A$R-selective inverse agonist L-655,708 (0.35 mg/kg, i.p.) 23.5 h after anesthesia and 30 min before behavioral training. Control=vehicle gas (30% O$_2$, 70% air, 1 h) and vehicle injection (n=31); Isoflurane=isoflurane (1.3%, 1 h) and vehicle injection (n=31); L-655,708=vehicle gas and L-655,708 (0.35 mg/kg, i.p.; n=10); Isoflurane+L-655,708=isoflurane (1.3%, 1 h) and L-655,708 (0.35 mg/kg, i.p.; n=11). FIG. 4A illustrates time spent with novel and familiar objects during testing. As described above, mice in the control group (vehicle gas+ vehicle injection) spent more time with the novel object than with the familiar object (t=4.00, df=30, P=0.0002; FIG. 4A). As shown in FIG. 3, mice exposed to isoflurane only (isoflurane+vehicle injection) exhibited memory deficits and spent a similar amount of time with the novel and familiar objects (t=0.400, df=30, P=0.346; FIG. 4A). FIG. 4B illustrates discrimination ratios (time spent with novel object/ time spent with both objects) of Control, L-655,708, and Isoflurane+L-655,708 groups demonstrate learning. The dotted line represents a chance level of interaction with the novel object (discrimination ratio=0.5). L-655,708 improved memory performance (effect of L-655,708 F$_{2,102=3.80}$, P=0.026; FIG. 4B). Specifically, L-655,708 restored normal memory performance in groups that were exposed to isoflurane (effect of isoflurane×L-655,708 F$_{2, 102}$=4.76, P=0.011; FIG. 4B). Low dose L-655,708 (0.35 mg/kg) increased the proportion of time that isoflurane-treated mice spent with the novel object (discrimination ratio, isoflurane+L-655,708, 0.68±0.03 vs. isoflurane+vehicle injection, 0.51±0.03, P<0.05, Tukey's HSD; FIG. 4B). Both control and isoflurane treated mice that received L-655,708 at 0.35 mg/kg learned the task and spent more time with the novel object than with the familiar object (control, novel vs. familiar object, t=3.53, df=9, P=0.003; isoflurane+low-dose L-655,708, novel vs. familiar object, t=4.85, df=10, P=0.0003; FIG. 4A). We also tested a higher dose of L-655,708 (0.7 mg/kg) on short-term memory. This higher dose of L-655,708 failed to reverse the memory deficit in isoflurane-treated mice (discrimination ratio, isoflurane+vehicle injection 0.54±0.04; isoflurane+high-dose L655,708 0.54±0.05) and both vehicle and L-655,708 injected groups that were exposed to isoflurane spent similar amounts of time spent with the novel and familiar objects (Isoflurane+vehicle injection, novel vs. familiar object, t=1.42, df=9, P=0.094; isoflurane+high dose L655,708, novel vs. familiar object, t=1.29, df=8, P=0.117). FIG. 4C illustrates time spent exploring identical sample objects during training. Data are represented as mean±SEM. * denotes significance at P<0.05. The memory performance could not be attributed to changes in exploratory behavior during training, as treatment with isoflurane and L-655,708 did not influence the amount of time that mice spent with both objects (effect of isoflurane, F$_{1,99}$=0.15, P=0.703; effect of L655,708, F$_{2,99}$=2.40, P=0.096; effect of isoflurane+L-655,708, F$_{2,99}$=2.07, P=0.132; FIG. 4C).

Short-Term Memory Performance 72 h after Isoflurane

To determine whether short-term memory deficits persisted beyond the first 24 h, mice were studied 72 h after isoflurane treatment. FIG. 5 illustrates normal recognition memory 72 h after isoflurane anesthesia. Mice were trained on the object recognition paradigm 72 h after anesthesia and short-term memory was tested 1 h after training. FIG. 5A illustrates time spent with novel and familiar objects during testing. Control (exposed to vehicle gas; n=10) and Isoflurane (exposed to 1 h, 1.3% isoflurane; n=10) mice demonstrated normal memory performance as they spent more time exploring the novel than the familiar object. At the 72 h time point, control and isoflurane-treated mice showed normal recognition memory, as evidenced by a preference for the novel object in both groups (control, novel vs. familiar object, t=2.86, df=9, P=0.009; isoflurane, novel vs. familiar object; t=2.45, df=9, P=0.018; FIG. 5A). FIG. 5B illustrates the discrimination ratios (time spent with novel object/time spent with both objects) of Control and Isoflurane-treated mice. The dotted line represents a chance level of interaction with the novel object (discrimination ratio=0.5). The discrimination ratios were similar between the two groups (control, 0.65±0.05 vs. isoflurane, 0.60±0.04; t=0.787, df=18, P=0.441; FIG. 5B), which indicates that learning and recognition memory recovered by 72 h after isoflurane treatment. FIG. 5C illustrates that time spent exploring identical sample objects during training. Data are represented as mean±SEM. * denotes significance at P<0.05. The normal memory performance at 72 h after anesthesia could not be attributed to differences in exploratory activity between groups as both control and isoflurane-treated mice spent a similar amount of time exploring both objects during the training phase (control, 45.92±9.44 s vs. isoflurane, 46.65±6.57 s; t=0.06, df=18, P=0.95; FIG. 5C).

Short-Term Memory Performance of Gabra5−/− Mice 24 h after Isoflurane

Figure 6:
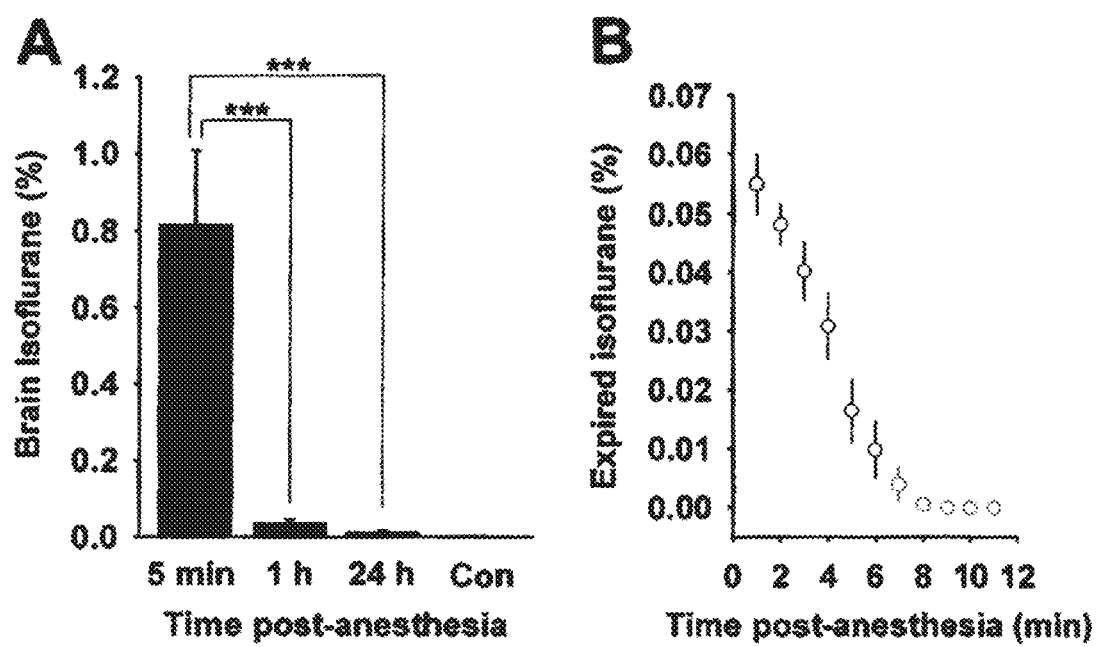
FIG. 6A illustrates the isoflurane pharmacokinetics in Example 1 by gas chomatographic quantification of isoflurane from whole mouse brain.
FIG. 6B illustrates the isoflurane pharmacokinetics in Example 1 by isoflurane clearance from expired gases.

Based on our previous study in Example 1, which showed that L-655,708 administered prior to anesthesia can prevent memory deficits and the results presented above, we predicted that mice lacking α5GABA$_A$ receptors would not exhibit postanesthesia memory deficits. To test this postulate, Gabra5−/− mice were trained and tested on the object recognition paradigm 24 h after anesthesia. FIG. 6 illustrates that α5GABA$_A$R null mutant mice exhibit no short-term recognition memory deficits 24 h after isoflurane anesthesia. Mice were trained on the object recognition paradigm 24 h after anesthesia and short-term memory was tested 1 h after training. Mice received either an injection of vehicle (10% DMSO) or the α5GABA$_A$ R-selective inverse agonist L-655,708 (0.70 mg/kg, i.p.) 10 min before gas exposure. Control=vehicle gas (30% O2, 70% air, 1 h) and vehicle injection (n=12); Isoflurane=isoflurane (1.3%, 1 h) and vehicle injection (n=12); L655,708=vehicle gas and L-655,708 (0.70 mg/kg, i.p.; n=12); Isoflurane+L-655,708=isoflurane (1.3%, 1 h) and L-655,708 (0.70 mg/kg, i.p.; n=11). FIG. 6A illustrates time spent with novel and familiar objects during testing. All groups all spent more time with the novel than the familiar object. The performance of control Gabra5−/− mice and control wild-type mice did not differ significantly (discrimination ratio 0.66±0.05 vs. 0.74±0.05; t=1.24, df=19, P=0.230). Control Gabra5−/− mice spent more time with the novel object than with the familiar object (novel vs. familiar object, t=2.56, df=11, P=0.013; FIG. 6A). As predicted, Gabra5−/− mice exposed to isoflurane also showed a preference for the novel object (novel vs. familiar object, t=2.51, df=11, P=0.015; FIG. 6A). FIG. 6B illustrates the discrimination ratios (time spent with novel object/time spent with both objects) of all groups demonstrate normal memory performance. The dotted line represents a chance level of interaction with the novel object (discrimination ratio=0.5). Isoflurane did not cause significant impairment of memory performance in Gabra5−/− mice at 24 h after anesthesia (discrimination ratio, control, 0.66±0.05; isoflurane, 0.62±0.05; effect of isoflurane, $F_{1,47}$=0.38, P=0.544; FIG. 6B). Gabra5−/− mice treated with L-655,708 (0.70 mg/kg) 10 min before exposure to isoflurane or vehicle gas also learned the task and preferred the novel object over the familiar object (L-655,708, novel vs. familiar object, t=2.10, df=11, P=0.030; Isoflurane+L-655,708, novel vs. familiar object, t=3.83, df=10, P=0.0016). L-655,708 did not affect the memory performance of Gabra5−/− mice exposed to vehicle gas or isoflurane (discrimination ratio, 0.64±0.05 vs. 0.62±0.05; effect of L-655,708, $F_{1,47}$=0.02, P=0.90; FIG. 6B). No significant interactions were observed (effect of isoflurane×L-655,708, $F_{1,46}$=0.02, P=0.41; FIG. 6B). FIG. 6C illustrates time spent exploring identical sample objects during training. Data are represented as mean±SEM. * denotes significance at P<0.05. Additionally, neither isoflurane nor L-655,708 influenced exploratory behavior during training (effect of isoflurane, $F_{1,43}$=0.04, P=0.851; effect of L-655,708, $F_{1,43}$=1.17, P=0.285; effect of isoflurane×L-655,708, $F_{1,43}$=0.66, P=0.423; FIG. 6C).

Prevention of Postanesthesia Memory Deficits

In Example 1 we have shown that L-655,708, administered before isoflurane, prevents memory deficits in the early postanesthetic period[16]. We also sought to determine whether the deficit in recognition memory could be prevented by administering L-655,708 before isoflurane as a positive control. L-655,708 (0.7 mg/kg) was injected and thirty minutes later, mice were exposed to isoflurane. FIG. 7 illustrates that short-term recognition memory deficits can be prevented by inhibition of α5GABA$_A$Rs prior to anesthesia. Mice were trained on the object recognition paradigm 24 h after anesthesia and short-term memory was tested 1 h after training. Mice received either an injection of vehicle (10% DMSO) or the α5GABA$_A$R-selective inverse agonist L-655,708 (0.70 mg/kg, i.p.) 10 min before gas exposure. Control=vehicle gas (30% O$_2$, 70% air, 1 h) and vehicle injection (n=9); Isoflurane=isoflurane (1.3%, 1 h) and vehicle injection (n=11); L-655,708=vehicle gas and L-655,708 (0.70 mg/kg, i.p.; n=10); Isoflurane+L-655,708=isoflurane (1.3%, 1 h) and L-655,708 (0.70 mg/kg, i.p.; n=9). FIG. 7A illustrates time spent with novel and familiar objects during testing. All groups all spent more time with the novel than the familiar object. FIG. 7B illustrates the discrimination ratio (time spent with novel object/time spent with both objects). The dotted line represents a chance level of interaction with the novel object (discrimination ratio=0.5). Memory performance was studied 24 h later using the object recognition paradigm. Control mice showed the predicted preference for the novel object (time spent with novel vs. familiar object, t=3.43, df=8, P=0.045, FIG. 7A; discrimination ratio 0.74±0.04, FIG. 7B). In contrast, mice exposed to isoflurane did not prefer the novel object (time spent with novel vs. familiar object, t=0.64, df=10, P=0.268), and the discrimination ratio was 0.53±0.05, similar to a chance level of interaction with the novel object (FIG. 7B). Again, isoflurane administered to wild-type mice 24 h before training impaired their performance in the object recognition task (effect of isoflurane, $F_{1,38}$=10.39, P=0.003; FIG. 7B). Mice treated with L-655,708 before exposure to vehicle gas showed normal learning and preference for the novel object (time spent with novel vs. familiar object, t=4.91, df=9, P=0.0004; FIG. 7A). Mice treated with L-655,708 before exposure to isoflurane preferred the novel object (time spent with novel vs. familiar object, t=2.48, df=8, P=0.019; FIG. 7A). L-655,708 alone did not significantly enhance or diminish discrimination ratios across any of the groups (effect of L-655,708, $F_{1,39}$=1.59, P=0.215; FIG. 7B). There was no significant interaction between L-655,708 and isoflurane ($F_{1,39}$=0.614, P=0.439; FIG. 7B) although the study may have been underpowered to detect a difference between these groups. FIG. 7C illustrate time spent exploring identical sample objects during training. Data are represented as mean±SEM. * denotes significance at P<0.05. Neither isoflurane nor L655,708 influenced the amount of time that mice spent with both objects during training (effect of isoflurane, $F_{1,38}$=1.43, P=0.240; effect of L-655,708, $F_{1,38}$=1.54, P=0.223; effect of isoflurane×L-655,708, $F_{1,38}$=0.10, P=0.752; FIG. 7C).

Short-Term Memory Performance 24 h after Sevoflurane

Finally, to determine whether the postanesthetic impairment in recognition memory was seen following exposure to other commonly used inhaled anesthetic, mice were treated with sevoflurane then trained on the object recognition task 24 h later. Control, vehicle-gas treated mice demonstrated normal memory performance and preferred the novel object (novel 33.92±5.03; familiar 20.03±3.03, t=5.00, df=9, P=0.0004). In contrast, sevoflurane-treated mice spent a similar amounts of time with the novel and familiar object and hence, did not learn the task (novel 15.41±2.25; familiar 13.13±1.95, t=1.07, df=9, P=0.157). The discrimination ratio for the sevoflurane-treated group was lower than that for the control group and was similar to that predicted by chance (sevoflurane 0.53±0.03 vs. control 0.63±0.02, t=2.22, df=18, P=0.039). Exploratory behavior during the training phase was not affected by exposure to sevoflurane (sevoflurane 23.45±3.88 s vs. control 36.46±4.77 s, t=2.14, df=13, P=0.052).

Discussion

The results of this study show that isoflurane caused deficits in short-term recognition memory but not working memory for at least 24 h in wild-type mice. A low dose of the α5GABA$_A$ receptor-selective inverse agonist, L-655,708, administered 24 h after isoflurane fully reversed short-term memory deficits. Changes in memory performance on the object recognition task could not be attributed to changes in exploratory activity as exposure to isoflurane or L-655,708 did not alter the time that mice spent exploring the objects, which indicated that all mice had equal opportunity to perceive and learn the characteristics of the objects. Short-term memory deficits resolved within 72 h. The expression of α5GABAA receptors was necessary for the isoflurane-induced deficits in recognition memory to occur, as Gabra5−/− mice exhibited no memory impairment. Finally, recognition memory deficits also occur 24 h after sevoflurane.

The most novel and important finding of this study is that a low dose of L-655,708 (0.35 mg/kg) administered 24 h after isoflurane completely reversed the deficit in recognition memory. This result was unexpected, given the widely believed mechanism by which volatile anesthetics block memory. The concentration-dependent suppression of memory during acute exposure to isoflurane has been attributed, at least in part, to increased activity of GABAA receptors[6-7, 33]. Isoflurane and other volatile anesthetics, including desflurane and sevoflurane, potentiate GABAA receptor function, and the resulting increase in chloride conductance reduces neuronal excitability[6]. In brain networks, such as the cornus ammonis 1 subfield of the hippocampus, the enhanced chloride conductance prevents the synaptic plasticity that subserves memory formation[32]. Once the anesthetic has been eliminated, it is assumed that GABAA receptor activity returns to baseline and memory recovers[7, 34]. However, in these experiments, memory performance was impaired 24 h after exposure to isoflurane, when the concentration of isoflurane in the brain has declined to the limits of detection (0.0095%)[16]. This low concentration of isoflurane is orders of magnitude less than the concentration (0.4%) required for memory blockade during anesthesia[35]. Taken together, the available data suggest that a simple interaction between isoflurane and GABAA receptors would not account for the memory deficits at 24 hours.

An analogous and surprising long-term effect of the intravenous anesthetic ketamine on cognitive function has been reported[36-37]. Ketamine is a noncompetitive antagonist of the N-methyl-D-aspartate subtype of glutamate receptors[38-39]. A single dose of ketamine causes long-lasting effects that persist after the drug has been eliminated, specifically a rapid and sustained reversal of depression that lasts for weeks to months[36, 40-41]. The sustained effect of ketamine involves the rapamycin intracellular signalling pathway, which increases synaptic signaling proteins and the number and function of synapses in the cortex[37].

Modulation of α5GABAA receptors by isoflurane plays a crucial role in initiating the memory deficits that were evident at 24 h, as genetic and pharmacological inhibition of these receptors prevented memory impairment. L-655,708, administered after isoflurane, may counteract an unrecognized increase in the function or expression of α5GABAA receptors that persists after anesthesia in the absence of isoflurane binding to the receptor. Alternatively, L-655,708 may cause a nonspecific compensatory enhancement of memory processes. The molecular mechanisms that are triggered during periods of high GABAergic activity during anesthesia, and cause α5GABA$_A$ receptor-dependent memory deficits, remain to be determined.

On the basis of the current study, we propose that inhibition of α5GABAA receptors is a plausible strategy for reversing memory deficits after general anesthesia in patients. Inverse agonists that preferentially target α5GABA$_A$ receptors lack the adverse effects that typify nonselective GABAA receptor antagonists, such as anxiogenesis and seizures[29, 42, 43]. Several human trials have studied this class of drugs[43, 44]. The inverse agonist α5IA, which is functionally selective for α5GABA$_A$ receptors, attenuated ethanol-induced impairment of word recall when administered before ethanol and was well tolerated by human volunteers[44]. Also, the α5GABAA receptor-selective inverse agonist RG1662 (Roche Pharmaceuticals, Basel, Switzerland) is currently undergoing phase 1 clinical trials for treatment of cognitive deficits in patients with Alzheimer disease. Our results suggest that the dose of inverse agonist must be selected carefully, as a high dose administered immediately before learning may actually impair memory performance. Higher doses of inverse agonist may exert agonist-like effects on non-α5GABAA receptors, thus increasing the activity of GABAA receptors[45].

The interaction times and discrimination ratios for object recognition measured under baseline, control conditions in the current study were comparable to those reported by others for rodents and nonhuman primates[46-48]. Also, the memory deficits observed in isoflurane-treated mice were consistent with a deficit in retrograde memory observed in mice treated with sevoflurane (2.6% for 2 h) and then conditioned with two object learning sessions$_{26}$. Notably, we observed that isoflurane impaired short-term recognition memory, whereas working memory remained intact. These results suggest that isoflurane spares the perception and encoding of information but disrupts consolidation of memory into long-term storage or memory retrieval. Our results predict that patients exposed to isoflurane could exhibit normal recall for immediate events that are accessible to working memory but might exhibit deficits in recall for events after a longer delay. Similar effects on working memory have been found after exposure to the benzodiazepines alprazolam and diazepam: object recognition was intact when rats were tested 10 min after training but impaired when they were tested 1 h after training[46].

The current study raises many additional important questions for future study. Although short-term memory deficits resolved spontaneously within 72 h, it will be critical to determine whether higher doses of isoflurane (due to higher concentrations and/or longer durations of treatment) prolong the memory deficit. Also, it must be determined whether factors that impair recognition memory performance, such as age and inflammation, exacerbate isoflurane-induced memory loss. Previous studies have shown that age exacerbates postanesthetic memory loss; for example, aged rats had impaired anterograde memory for up to 2 weeks after anesthesia, whereas adult rats were no longer impaired at that time point[49-50]. The object recognition task is a versatile experimental model to study such interactions, as it requires no appetitive or aversive reinforcement, and it has the potential for high throughput[21,51].

In summary, isoflurane impairs short-term memory but not working memory after anesthesia in an ethologically relevant paradigm. Furthermore, α5GABA$_A$ receptors are necessary for the development of postanesthetic memory deficits and are a potential therapeutic target for restoring memory after general anesthesia.

Reference List for Example 4

1. Rohan D, Buggy D J, Crowley S, Ling F K, Gallagher H, Regan C, Moriarty D C. Increased incidence of postoperative cognitive dysfunction 24 hr after minor surgery in the elderly. Can J Anaesth. 2005; 52(2):137-42.
2. Moller J T, Cluitmans P, Rasmussen L S, Houx P, Rasmussen H, Canet J, Rabbitt P, Jolles J, Larsen K, Hanning C D, Langeron O, Johnson T, Lauven P M, Kristensen P A, Biedler A, van Beem H, Fraidakis O, Silverstein J H, Beneken J E, Gravenstein J S. Long-term postoperative cognitive dysfunction in the elderly ISPOCD1 study. ISPOCD investigators. International Study of Post-Operative Cognitive Dysfunction. Lancet. 1998; 351(9106):857-61.
3. Girard T D, Pandharipande P P, Wesley E W. Delirium in the intensive care unit. Critical Care. 2008; 12(S3).
4. Price C C, Garvan C W, Monk T G. Type and severity of cognitive decline in older adults after noncardiac surgery. Anesthesiology. 2008; 108(1):8-17.
5. Steinmetz J, Christensen K B, Lund T, Lohse N, Rasmussen L S. Long-term consequences of postoperative cognitive dysfunction. Anesthesiology. 2009; 110(3):548-55.
6. Hemmings H C, Jr., Akabas M H, Goldstein P A, Trudell J R, Orser B A, Harrison N L. Emerging molecular mechanisms of general anesthetic action. Trends Pharmacol Sci. 2005; 26(10):503-10.
7. Caraiscos V B, Newell J G, You T, Elliott E M, Rosahl T W, Wafford K A, MacDonald J F, Orser B A. Selective enhancement of tonic GABAergic inhibition in murine hippocampal neurons by low concentrations of the volatile anesthetic isoflurane. J Neurosci. 2004; 24(39):8454-8.
8. Cheng V Y, Martin L J, Elliott E M, Kim J H, Mount H T, Taverna F A, Roder J C, MacDonald J F, Bhambri A, Collinson N, Wafford K A, Orser B A. Gt5GABAA receptors mediate the amnestic but not sedative-hypnotic effects of the general anesthetic etomidate. J Neurosci. 2006; 26(14):3713-20.
9. Martin L T, Oh G H, Orser B A. Etomidate targets α5 γ-aminobutyric acid subtype A receptors to regulate synaptic plasticity and memory blockade. Anesthesiology. 2009; 111(5):1025-35.
10. Hendrickx J F A, Dishart M K, De Wolf A M. Isoflurane and desflurane uptake during liver resection and transplantation. Anes Analg. 2003; 96(2):356-62.
11. Lu C C, Tsai C S, Hu OYP, Chen R M, Chen T L, Ho S T. Pharmacokinetics of isoflurane in human blood. Pharmacology. 2008; 81(4):344-9.
12. Strum D P, Johnson B H, Eger E I, 2nd. Elimination of anesthetics from rabbit brain. Science. 1986; 234(4783):1586-8.
13. Culley D J, Baxter M, Yukhananov R, Crosby G. The memory effects of general anesthesia persist for weeks in young and aged rats. Anesth Analg. 2003; 96(4):1004-9, table.
14. Culley D J, Baxter M G, Yukhananov R, Crosby G. Long-term impairment of acquisition of a spatial memory task following isoflurane-nitrous oxide anesthesia in rats. Anesthesiology. 2004; 100(2):309-14.
15. Palanisamy A, Baxter M G, Keel P K, Xie Z C, Crosby G, Culley D J. Rats exposed to isoflurane in utero during early gestation are behaviorally abnormal as adults. Anesthesiology. 2011; 114(3):521-8.
16. Saab B J, MacLean A J B, Kanisek M, Zurek A A, Martin L J, Roder J C, Orser B A. Short-term memory impairment after isoflurane in mice is prevented by the α5 gamma-aminobutyric acid type a receptor inverse agonist 1-655,708. Anesthesiology. 2010; 113(5):1061-71.
17. Quirk K, Blurton P, Fletcher S, Leeson P, Tang F, Melillo D, Ragan C I, McKernan R M. [3H]L-655,708, a novel ligand selective for the benzodiazepine site of GABAA receptors which contain the α5 subunit. Neuropharmacology. 1996; 35(9-10):1331-5.
18. Johnston G A. GABAA receptor pharmacology. Pharmacol Ther. 1996; 69(3):173-98.
19. Collinson N, Kuenzi F M, Jarolimek W, Maubach K A, Cothliff R, Sur C, Smith A, Otu F M, Howell O, Atack J R, McKernan R M, Seabrook G R, Dawson G R, Whiting P J, Rosahl T W. Enhanced learning and memory and altered GABAergic synaptic transmission in mice lacking the α5 subunit of the GABAA receptor. J Neurosci. 2002; 22(13):5572-80.
20. Ennaceur A, Delacour J. A new one-trial test for neurobiological studies of memory in rats. 1: Behavioral data. Behav Brain Res. 1988; 31(1):47-59.
21. Bevins R A, Besheer J. Object recognition in rats and mice: a one-trial non-matching-to-sample learning task to study recognition memory. Nat Protoc. 2006; 1(3):1306-11.
22. Jessberger S, Clark R E, Broadbent N J, Clemenson Jr G D, Consiglio A, Lie D C, Squire L R, Gage F H. Dentate gyms-specific knockdown of adult neurogenesis impairs spatial and object recognition memory in adult rats. Learn Mem. 2009; 16(2):147-54.
23. Ennaceur A, Meliani K. Effects of physostigmine and scopolamine on rats' performances in object-recognition and radial-maze tests. Psychopharm. 1992; 109(3):321-30.
24. Clarke J R, Cammarota M, Gruart A, Izquierdo I, Delgado-Garcia J M. Plastic modifications induced by object recognition memory processing. Proc Natl Acad Sci USA. 2010; 107(6):2652-7.
25. Miller S, Yasuda M, Coats J K, Jones Y, Martone M E, Mayford M. Disruption of dendritic translation of CaMKIIα impairs stabilization of synaptic plasticity and memory consolidation. Neuron. 2002; 36(3):507-19.
26. Wiklund A, Granon S, Faure P, Sundman E, Changeux J P, Eriksson L I. Object memory in young and aged mice after sevoflurane anaesthesia. Neuroreport. 2009; 20(16):1419-23.
27. Capsoni S, Giannotta S, Stebel M, Garcia A A, De Rosa R, Villetti G, Imbimbo B P, Pietra C, Cattaneo A. Ganstigmine and donepezil improve neurodegeneration in AD11 antinerve growth factor transgenic mice. Am J Alzheimers Dis Other Demen. 2004; 19(3):153-60.
28. Bertaina-Anglade V, Enjuanes E, Morillon D, la Rochelle C D. The object recognition task in rats and mice: A simple and rapid model in safety pharmacology to detect amnesic properties of a new chemical entity. J Pharmacol Toxicol Methods. 2006; 54(2):99-105.
29. Atack J R, Bayley P J, Seabrook G R, Wafford K A, McKernan R M, Dawson G R. L-655,708 enhances cognition in rats but is not proconvulsant at a dose selective for α5-containing GABA(A) receptors. Neuropharmacology. 2006; 51(6):1023-9.
30. Chambers M S, Atack J R, Broughton H B, Collinson N, Cook S, Dawson G R, Hobbs S C, Marshall G, Maubach K A, Pillai G V, Reeve A J, MacLeod A M. Identification of a novel, selective GABAA α5 receptor inverse agonist which enhances cognition. J Med Chem. 2003; 46(11): 2227-40.

31. Atack J R, Pike A, Clarke A, Cook S M, Sohal B, McKernan R, Dawson G. Rat pharmacokinetics and pharmacodynamics of a sustained release formulation of the GABAA α5-selective compound L-655,708. Drug Metab Dispos. 2006.

32. Martin L I, Zurek A A, MacDonald J F, Roder J C, Jackson M F, Orser B A. α5GABA$_A$ receptor activity sets the threshold for long-term potentiation and constrains hippocampus-dependent memory. J Neurosci. 2010; 30(15):5269-82.

33. Dutton R C, Maurer A J, Sonner J M, Fanselow M S, Laster M J, Eger E L The concentration of isoflurane required to suppress learning depends on the type of learning. Anesthesiology. 2001; 94(3):514-9.

34. Bai D, Pennefather P S, MacDonald J F, Orser B A. The general anesthetic propofol slows deactivation and desensitization of GABAA receptors. J Neumsci. 1999; 19(24): 10635-46.

35. Alkire M T, Gorski L A. Relative amnesic potency of five inhalational anesthetics follows the Meyer-Overton rule. Anesthesiology. 2004; 101(2):417-29.

36. DiazGranados N, Ibrahim L A, Brutsche N E, Ameli R, Henter I D, Luckenbaugh D A, Machado-Vieira R, Zarate C A. Rapid resolution of suicidal ideation after a single infusion of an N-Methyl-D-Aspartate antagonist in patients with treatment-resistant major depressive disorder. J Clin Psychiatry. 2010; 71(12):1605-11.

37. Li N X, Lee B, Liu R T, Banasr M, Dwyer J M, Iwata M, Li X Y, Aghajanian G, Duman R S. mTOR-Dependent synapse formation underlies the rapid antidepressant effects of NMDA antagonists. Science. 2010; 329(5994): 959-64.

38. MacDonald J F, Miljkovic Z, Pennefather P. Use-dependent block of excitatory amino acid currents in cultured neurons by ketamine. J NeurophysioL 1987; 58(2):251-66.

39. Orser B A, Pennefather P S, MacDonald J F. Multiple mechanisms of ketamine blockade of N-methyl-D-aspartate receptors. Anesthesiology. 1997; 86(4):903-17.

40. aan het Rot M, Collins K A, Murrough J W, Perez A M, Reich D L, Charney D S, Mathew S J. Safety and efficacy of repeated-dose intravenous ketamine for treatment-resistant depression. Biol Psychiatry. 2010; 67(2):139-45.

41. Price R B, Nock M K, Charney D S, Mathew S J. Effects of intravenous ketamine on explicit and implicit measures of suicidality in treatment-resistant depression. Biol Psychiatry. 2009; 66(5):522-6.

42. Ballard T M, Knoflach F, Prinssen E, Borroni E, Vivian J A, Basile J, Gasser R, Moreau J L, Wettstein J G, Buettelmann B, Knust H, Thomas A W, Trube G, Hernandez M C. RO4938581, a novel cognitive enhancer acting at GABAA α5 subunit-containing receptors. Psychopharmacology. 2009; 202(1-3):207-23.

43. Wallace T L, Ballard T M, Pouzet B, Riedel W J, Wettstein J G. Drug targets for cognitive enhancement in neuropsychiatric disorders. Pharmacol Biochem Behav. 2011; 99(2): 130-45.

44. Nutt D J, Besson M, Wilson S J, Dawson G R, Lingfofti-Hughes A R. Blockade of alcohol's amnestic activity in humans by an α5 subtype benzodiazepine receptor inverse agonist. Neuropharmacology. 2007.

45. Savic M M, Huang S, Fulanuller R, Clayton T, Huck S, Obradovic D I, Ugresic N D, Sieghart W, Bokonjic D R, Cook J M. Are GABAA receptors containing α5 subunits contributing to the sedative properties of benzodiazepine site agonists? Neuropsychopharmacology. 2008; 33(2): 332-9.

46. Bertaina-Anglade V, Enjuanes E, Morillon D, Drieu la Rochelle C. The object recognition task in rats and mice: A simple and rapid model in safety pharmacology to detect amnesic properties of a new chemical entity. J Pharmacol Toxicol Methods. 2006; 54(2):99-105.

47. Mishkin M, Delacour J. Analysis of short-term visual memory in monkey. J Exp Psychol Anim Behav Process. 1975; 1(4):326-34.

48. Mahut H, Zolamorgan S, Moss M. Hippocampal resections impair associative learning and recognition memory in the monkey. J Neurosci. 1982; 2(9):1214-29.

49. Crosby C, Culley D J, Baxter M G, Yukhananov R, Crosby G. Spatial memory performance 2 weeks after general anesthesia in adult rats. Anesth Analg. 2005; 101(5):1389-92.

50. Culley D J, Baxter M G, Crosby C A, Yukhananov R, Crosby G. Impaired acquisition of spatial memory 2 weeks after isoflurane and isoflurane-nitrous oxide anesthesia in aged rats. Anesth Analg. 2004; 99(5):1393-7.

51. Ennaceur A. One-trial object recognition in rats and mice: Methodological and theoretical issues. Behav Brain Res. 2010; 215(2):244-54.

Example 5

Figure 46:
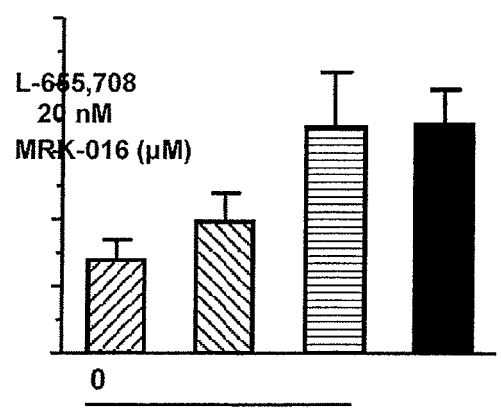
FIG. 46 illustrates the examination of the effects of L-655,708 on the tonic current evoked by an application of GABA in the absence or presence of the inverse agonist MRK-016 in Example 5.

MRK-016, an Inverse Agonist that has Different Structural Properties than L-655,708 Blocks the Tonic Inhibitory Current in Hippocampal Neurons from Mice We examined the effects of L-655,708 on the tonic current evoked by an application of GABA (0.5 µM). The amplitude of the GABA-evoked tonic current, measured in the absence or presence of MRK-016, is shown in FIG. 46. MRK-016 is a GABA$_A$ receptor inverse agonist selective for the α5-subtype (EC50=3 nM) having the following, chemical name: 3-(1,1-Dimethylethyl)-7-(5-methyl-3-isoxazolyl)-2-[(1-methyl-1H-1,2,4-triazol-5-yl)methoxy]-pyrazolo[1,5-d][1, 2,4]triazine and the following chemical structure:

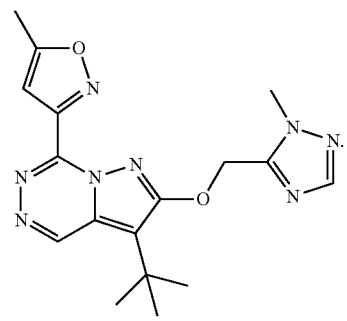 [SMILES: Cc1cc(-c2nncc3c(C(C)(C)C)c(OCc4ncnn4C)nn23)no1]

Note that similar to L-655,708 (20 nM), MRK-016 inhibited the tonic current (n=3-6 cells) as evidenced by the change in holding current. The tonic current indicated by 100% represents the change in holding current that was measured in the presence of non-selective GABA$_A$ receptor antagonist bicuculline (100 um). This change in holding current reflects the inhibition of all GABA$_A$ receptors.

Example 6

Figure 47:
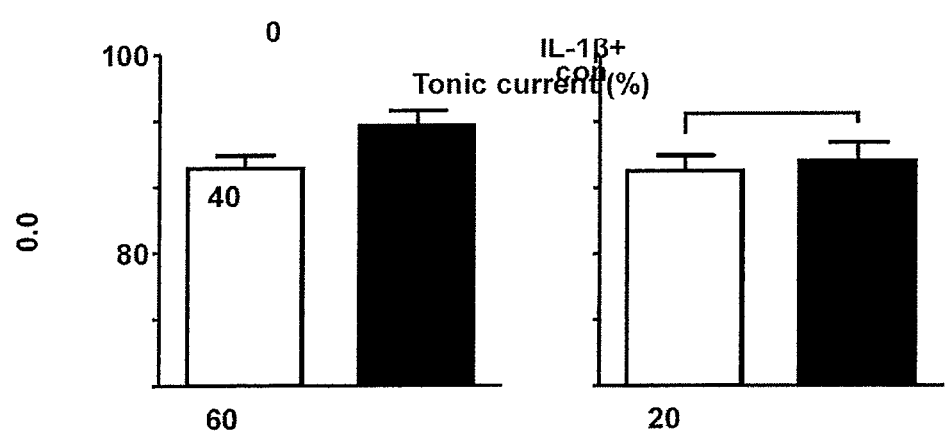
FIG. 47 illustrates the reversal of IL-1β-induced impairment of contextual fear memory by pharmacological inhibition of α5GABA$_A$ receptors by the inverse agonist MRK-016 in Example 6.

A Second Inverse Agonist that Preferentially Targets α5GABA$_A$ Receptors but has Different Structural Properties than L-655,708 (MRK-016) Reverses Memory Deficits Associated with Inflammation We have determined that IL-1β-induced impairment of contextual fear memory can be reversed by pharmacological inhibition of α5GABA$_A$ receptors by the inverse agonist MRK-016. Fear conditioning was performed 3 h after injection of IL-1β (1 μg kg$^{-1}$, i.p.) in both wild-type (WT) and α5GABA$_A$ receptor knock out (Gabra5−/−) mice. Mice were trained to associate a context (contextual fear) and a tone (cued fear) with an aversive electric footshock. 24 h after conditioning each mouse was placed in the training context, and contextual fear memory was measured as the percentage of time spent freezing. Cued fear memory was measured 48 h after training as the percentage of time spent freezing to the conditioned auditory tone in a novel context. As shown in FIG. 47, MRK-016 restored freezing scores for contextual fear memory to control values when it was co-administered with IL-1β (left), and it did not affect freezing to a conditioned tone stimulus (right). n=8-9, * P=0.048, N.S.: non-significant result, P=0.72, Student's t test.

Example 7

Figure 48:
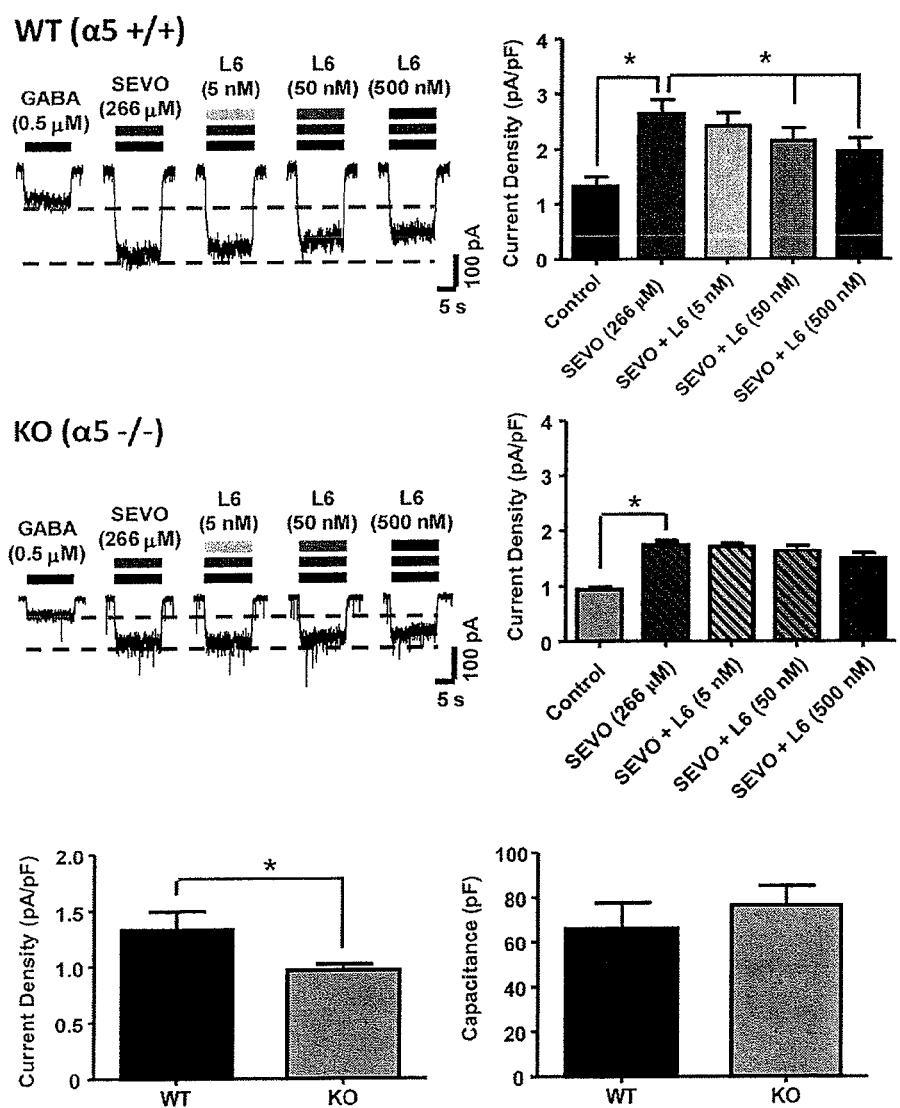
FIG. 48 illustrates the reversal of the anesthetic-induced increase in tonic inhibitory conductance generated by GABAA receptors by the inverse agonist L-655,708 in Example 7.

The Inverse Agonist L-655,708 Reverses the Anesthetic-Induced Increase in Tonic Inhibitory Conductance Generated by GABA$_A$ Receptors GABA$_A$ receptors in the hippocampus generate a tonic inhibitory conductance that is highly sensitive to anesthetics. Our in vitro electrophysiological data illustrated in FIG. 48 show that the α5GABA$_A$ receptor inverse agonist, L-655,708 reverses enhancement of the tonic current by the inhaled anaesthetics isoflurane and desflurane. Currents were recorded from cultured fetal hippocampal neurons from mice.

While the foregoing provides a detailed description of preferred embodiments of the present invention, it is to be understood that this description is illustrative only of the principles of the invention and not limitative.

The invention claimed is:

1. A method for attenuating and/or treating a persistent memory deficit, comprising administering a benzodiazepine site inverse agonist, wherein the memory deficit is induced by inflammation and/or administration of an anesthetic selected from the group consisting of isoflurane, sevoflurane, desflurane, etomidate and propofol.

2. The method of claim 1, wherein the memory deficit is short-term memory loss.

3. The method of claim 1, wherein the memory deficit is long-term memory loss.

4. The method of claim 1, wherein the inverse agonist is selected from the group consisting of L-655,708, MRK-016, Ru493851, α5IA, pyridazines, TB-21007, PWZ-029, and combinations thereof.

5. The method of claim 4, wherein the inverse agonist is selected from the group consisting of L-655,708, MRK-016 and combinations thereof.

6. The method of claim 1, wherein the memory deficit is induced by administration of the anesthetic.

7. The method of claim 1, wherein the memory deficit is induced by inflammation.

8. The method of claim 1, wherein the inverse agonist agent reduces inflammation- and/or surgery-induced increases in IL-1β expression and/or activity.

9. The method of claim 1, where the inverse agonist is administered before the memory deficit is induced.

10. The method of claim 9, wherein the inverse agonist is further administered during and/or after the memory deficit is induced.

11. The method of claim 1, where the inverse agonist is administered while the memory deficit is induced.

12. The method of claim 1, where the inverse agonist is administered after the memory deficit is induced.

13. The method of claim 12, wherein the inverse agonist is further administered before and/or while the memory deficit is being induced.

14. The method of claim 1, wherein the inverse agonist preferentially targets α5GABA$_A$ receptors.

15. The method of claim 1, wherein the persistent memory deficit is a memory deficit that persists for 24 hours or more after administration of the anesthetic.

16. The method of claim 1, carried out on an immature subject.

17. A method for attenuating a persistent memory deficit induced by an anesthetic in a subject to be treated with the anesthetic, the method comprising administering a benzodiazepine site inverse agonist prior to or with the anesthetic to prevent the anesthesia-induced memory deficit, wherein the subject is at risk for a post-anesthetic cognitive deficit and wherein the anesthetic is selected from the group consisting of isoflurane, sevoflurane, desflurane, etomidate and propofol.

18. The method of claim 17, wherein the subject is being anesthetized for surgery.

19. The method of claim 17, wherein the inverse agonist is administered 30 minutes before the anesthetic.

20. The method of claim 17, wherein the method further comprises administering the inverse agonist after administration of the anesthetic.

21. The method of claim 20, wherein the inverse agonist is administered within 72 hours of the anesthetic.

22. The method of claim 17, wherein the inverse agonist preferentially targets α5GABA$_A$ receptors.

23. The method of claim 17, wherein the persistent memory deficit persists for 24 hours or more after administration of the anesthetic.

24. The method of claim 17, wherein the subject is immature.

25. A method for treating a persistent memory deficit induced by an anesthetic in a subject having been treated with the anesthetic, the method comprising administering a benzodiazepine site inverse agonist to treat the anesthesia-induced memory deficit, wherein the subject is experiencing a post-anesthetic cognitive deficit and wherein the anesthetic is selected from the group consisting of isoflurane, sevoflurane, desflurane, etomidate and propofol.

26. The method of claim 25, wherein the subject was anesthetized for surgery.

27. The method of claim 25, wherein the inverse agonist is administered within 72 hours of the anesthetic.

28. The method of claim 25, wherein the inverse agonist preferentially targets α5GABA$_A$ receptors.

29. The method of claim 25, wherein the persistent memory deficit persists for 24 hours or more after administration of the anesthetic.

30. The method of claim 25, wherein the subject is immature.

\* \* \* \* \*